(12) United States Patent
Baker et al.

(10) Patent No.: US 7,718,157 B1
(45) Date of Patent: May 18, 2010

(54) TARGETED LIPID PARTICLES

(76) Inventors: Terence Seward Baker, The Mayes, 4 Gatson Lane, Wraysbury, Slains, Middlesex (GB) TW19 5JF; Andrew Neil Charles Weir, 7 Willow Drive, Twyferd, Berkshire (GB) RG10 9DD; Catherine Fiona Catterall, Courtway, Dukes Close, Gerrards Cross, Buckinghamshire (GB) SL9 7LH; Michael Anthony William Eaton, Nethercore, Chinnor Road, Aston Rowant, Oxfordshire (GB) OX9 5SH; Timothy John Norman, 14 Mohwell Terrace, Aylesbury Road, Great Missenden, Buckinghamshire (GB) HP16 9AU; David Parker, University of Durham, South Road, Durham (GB) DH1 3LE ( * ) Notice: Subject to any disclaimer, the term of this patent is extended or adjusted under 35 U.S.C. 154(b) by 2006 days.

(21) Appl. No.: 10/049,670

(22) PCT Filed: Aug. 16, 2000

(86) PCT No.: PCT/GB00/03170

§ 371 (c)(1),
(2), (4) Date: Nov. 22, 2002

(87) PCT Pub. No.: WO01/12154

PCT Pub. Date: Feb. 22, 2001

(30) Foreign Application Priority Data

Aug. 16, 1999 (GB) ................................. 9919338.5

(51) Int. Cl.
*C01B 31/02* (2006.01)
*C09C 1/48* (2006.01)
(52) U.S. Cl. ...................................................... 423/450
(58) Field of Classification Search .................. 423/450
See application file for complete search history.

(56) References Cited

FOREIGN PATENT DOCUMENTS

| WO | 98/16240 A1 | 4/1998 |
|---|---|---|
| WO | WO 99 52858 | 10/1999 |
| WO | WO 00 64858 | 11/2000 |

OTHER PUBLICATIONS

Fuhrhop et al, *Chemistry and Physics of Lipids*, 43:193-213 (1987).
Christoph H. Hagemeier et al., "Insight into the mechanism of biological methanol activation based on the crystal structure of the methanol-cobalamin methyltransferase complex", PNAS, Dec. 12, 2006, 103(50): 18917-18922.

*Primary Examiner*—Deborah D Carr
(74) *Attorney, Agent, or Firm*—Sughrue Mion, PLLC

(57) ABSTRACT

Targeted lipids and lipid particles are described which are assemblies of multipolar lipids, targeting molecules such as antibodies and polyanions. The lipids are of particular use for the delivery of bioactive substances such as nucleic acids to cells in vitro and especially in vivo.

23 Claims, 7 Drawing Sheets

TARGETED LIPID PARTICLES

Figure 1:
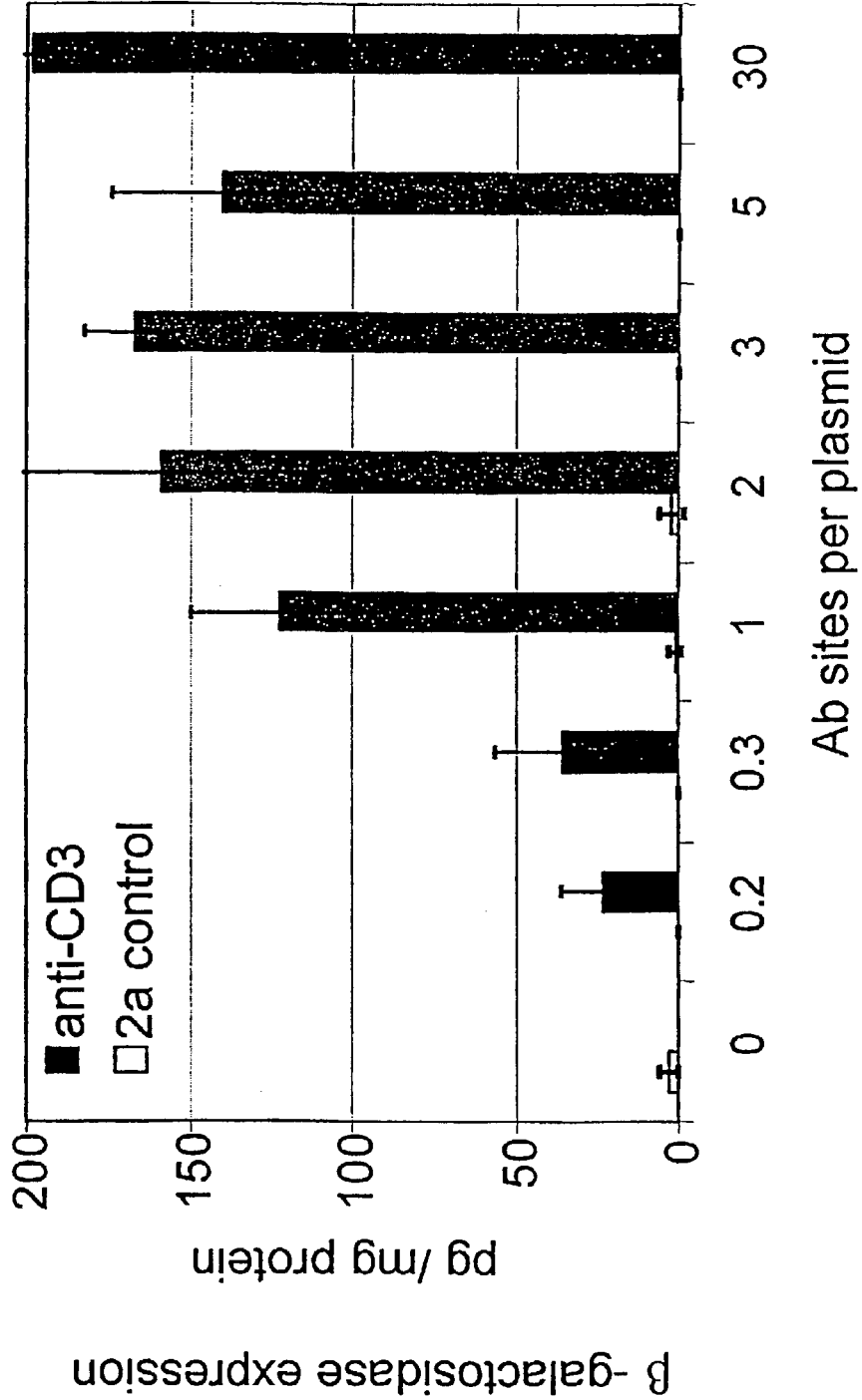
Figure 2:
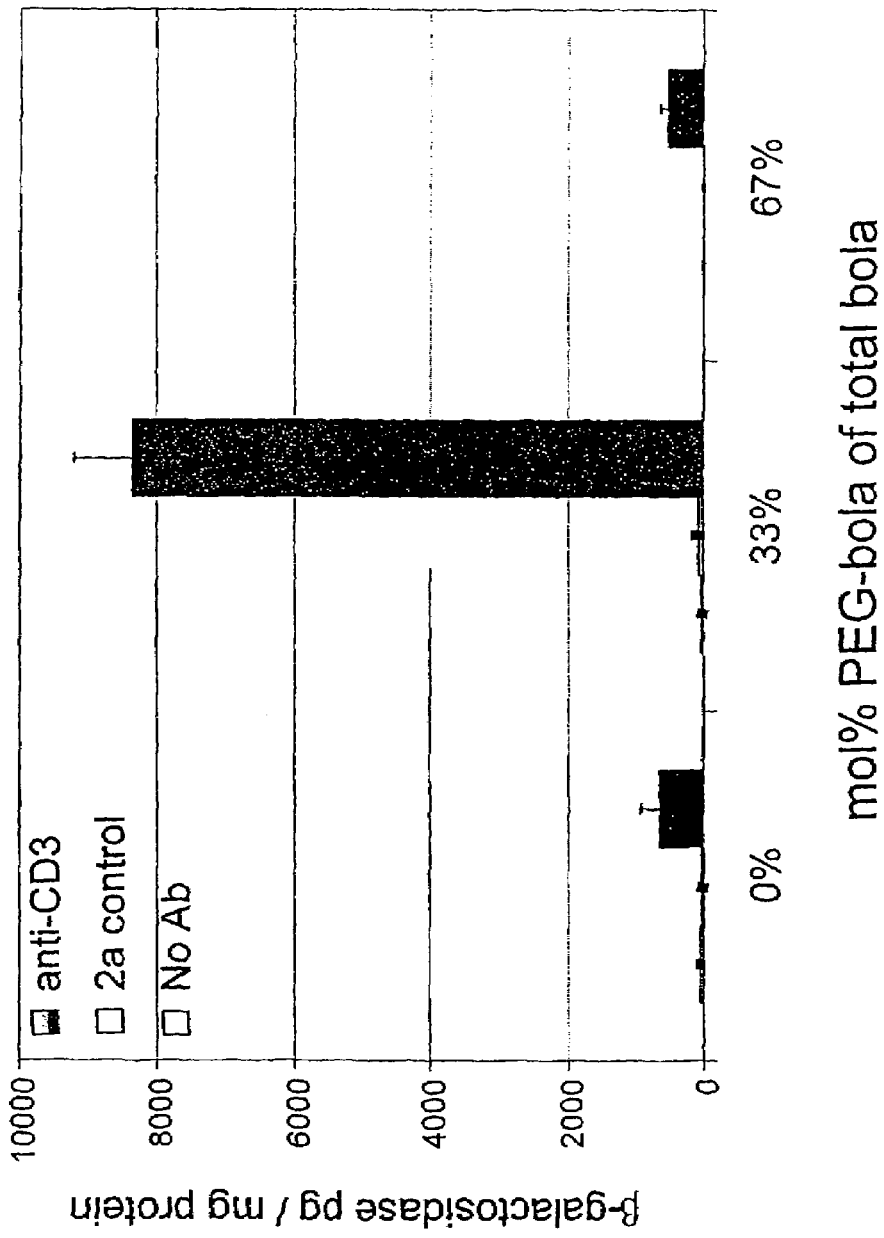
Figure 3:
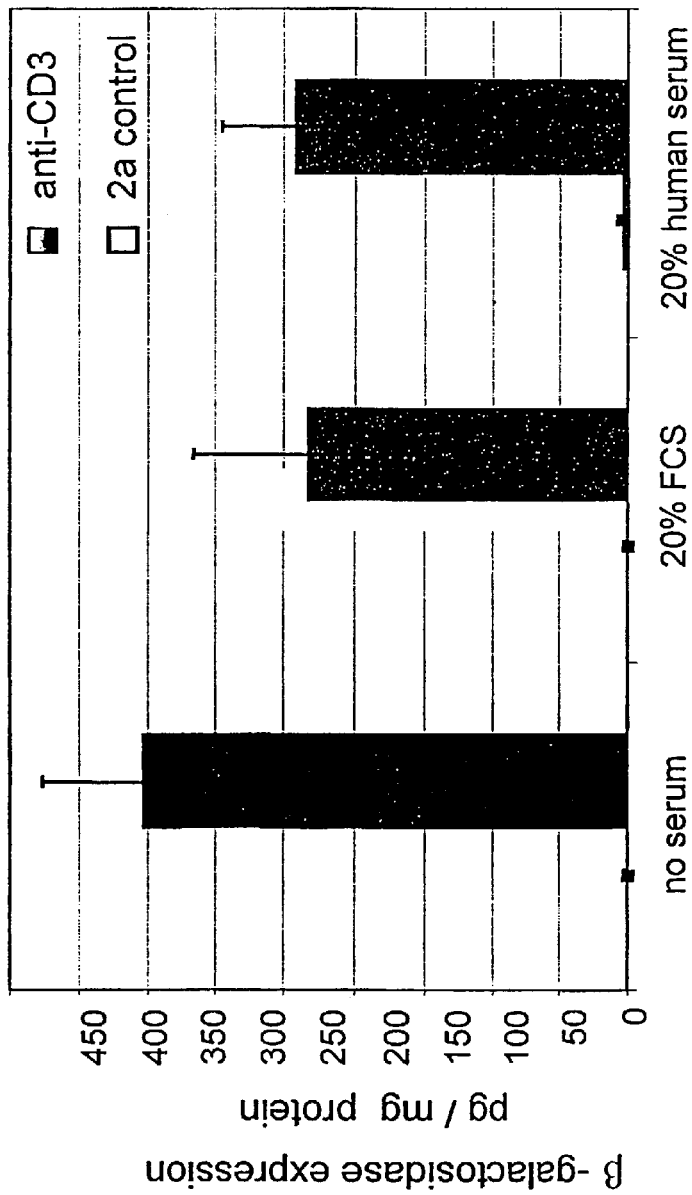
Figure 4:
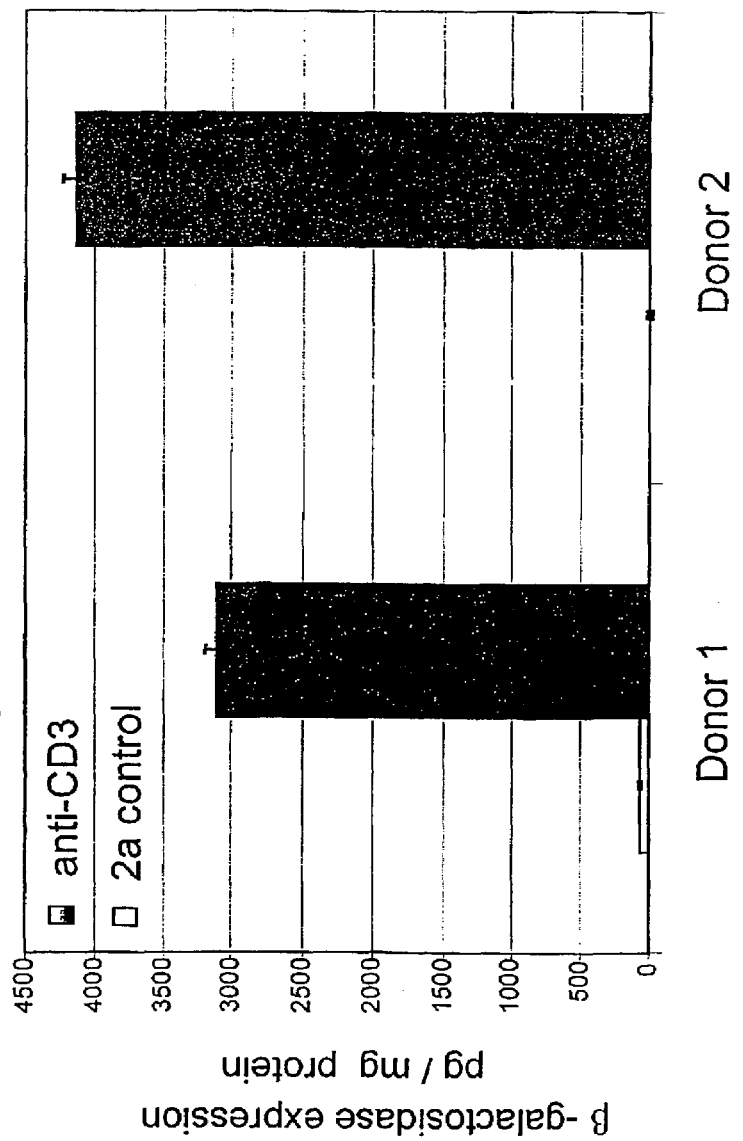

This application is a 371 of PCT/GB00/03170, filed Aug. 16, 2000. The disclosure of which is incorporated herein by reference.

This invention relates to targeted lipid particles, to targeted lipids and to their use as delivery agents.

To be effective, many pharmaceutical agents need to be efficiently delivered to the cytoplasm of a eukaryotic cell. For many low molecular weight compounds of low to moderate polarity this is not a problem since such molecules can pass directly through the plasma membrane of the cell and into the cytoplasm. Direct passage is not available to other compounds of greater polarity or high molecular weight and these generally enter the cell by receptor mediated endocytosis or phagocytosis. These mechanisms are not efficient however for all sizes and types of molecule. In particular, large, polyanionic compounds are not readily taken up by cells when delivered in aqueous solution.

One general solution to this problem is to couple any poorly transported pharmaceutical agent to a carrier which itself is readily taken up into the cytoplasm of a cell. This is not always satisfactory however, since coupling to the carrier may have an undesirable effect on the metabolism and/or antigenicity of the pharmaceutical agent and/or it may be difficult to recover the desired biological activity from the resulting conjugate once inside the cell.

An alternative solution is to formulate the pharmaceutical agent with a delivery vehicle which is soluble in aqueous solutions but which can also mimic naturally occurring cell membrane constituents. This encourages fusion of the vehicle with a cell membrane and subsequent delivery of any associated pharmaceutical agent to the cytoplasm.

Amphiphilic lipids have frequently been used for this purpose. These typically have a hydrophobic backbone composed of one or more hydrocarbons and a hydrophilic polar head group containing one or more ionisable groups, to facilitate the transport of macromolecules to and across the plasma membrane of cells and into the cytoplasm. The polarity of the head group may be controlled by the selection of the number and/or type of ionisable groups to achieve a range of negatively charged (anionic), neutral or positively charged (cationic) lipids.

For the delivery of polyanions it is generally advantageous to use cationic lipids. The advent of gene therapy and the need to deliver anionic molecules such as nucleic acids to mammalian cells has provided much impetus to the development of this class of lipids. First generation compounds include those with a monocation head group such as N-[1(2,3-dioleyloxy)propyl]-N,N,N-trimethylammonium chloride [DOTMA; Felgner, P L and Ringold, G M, Nature, 337 387-388 (1989)], 1,2-dimyristyloxypropyl-3-dimethylhydroxyethylammonium bromide [DMRIE; Zabner, J et al J. Biol. Chem, 270, 18997-19007 (1995)] and 3β[N-($N^1$,$N^1$-dimethylaminoethane)carbamoyl]cholesterol [DC-Chol; Farhood, H et al. Biochim. Biophys. Acta. 111, 239-246 (1992)] and those with a polycation head group such as dioctadecylamidoglycylspermine [DOGS; Behr, J-P, et al, Proc. Natl. Acad. Sci. 86, 6982-6986 (1989)].

In an effort to improve the properties of these early compounds for in vivo delivery of polyanions many more cationic lipids have been developed in which the nature and size of the hydrophobic backbone and/or the cationic head group have been varied (see for example International Patent Specifications Nos. WO95/21931, WO96/10038, WO96/17823, WO96/18273, WO96/25508, WO96/26179, WO96/41606, WO97/18185, WO97/25339, WO97/30170 and WO97/31934).

A major problem with cationic lipids is that when mixed with polyanions they form amorphous complexes that bind non-specifically to cells. This makes this class of lipids inefficient for in vivo use, particularly where it is desired to selectively deliver a pharmaceutical agent to specific target cells.

We have overcome this problem with a new class of targeted particles based on multipolar lipids. The particles are easily formed from a mixture of components, including polycationic hydrophilic lipids, antibodies or other targeting molcules, and the polyanion to be delivered. The particles are small and are stable to physiological salt and pH conditions. Advantageously they are capable of efficiently transporting nucleic acids and other polyanions to targeted cells in the presence of serum. When used in vivo the targeted particles advantageously generate little or no harmful side-effects when compared with other conventional cationic lipid delivery agents.

Thus according to one aspect of the invention we provide a targeted lipid particle comprising an assembly of one or more different multipolar lipids, polyanions and targeting molecules.

In general each particle according to the invention contains multipolar lipid molecules, each of which is non-covalently associated with its neighbours and any polyanion present. Each targeting molecule similarly may be present as part of this non-covalent assembly or in one convenient arrangement may be covalently attached to a multipolar lipid or where present other component of the particle. More than one type of multipolar lipid, polyanion and/or targeting molecule may be present in each particle. Additional molecules may also be optionally present as part of each non-covalent assembly, including for example co-lipids and extraneous materials for delivery to a target as more particularly described below. Each particle of the invention is a discrete structure and non-liposomal in character.

Each multipolar lipid in the particle according to the invention comprises a lipid with two or more covalently attached polar atoms or groups. By "polar atom or group" is meant any atom or group which is or contains one or more cationic or anionic centres and/or which is capable of being solvated by water. The same, or mixtures of such atoms or groups may be present on each lipid. In general, each multipolar lipid will contain at least one cationic centre capable of interacting with the polyanion(s) in the particle.

The multipolar lipid may in particular comprise a lipid covalently linked to two or more polar groups selected from oligocations and hydrophilic hydrocarbons as more particularly described hereinafter. In one particular class, the multipolar lipid is a bipolar lipid. Particular examples of such lipids include those wherein the lipid is covalently attached to an oligocation and a hydrophilic hydrocarbon and is for example covalently linked HH-LP-OC (where HH, LP and OC are the abbreviations used herein for hydrophilic hydrocarbon, lipid and oligocation respectively).

As explained above, the targeting molecule may be present in the particle either non-covalently associated with or covalently linked to a multipolar lipid or other component. Particular examples of covalently linked targeting molecules include for example TM-HH-LP-OC (where TM is the abbreviation used herein for targeting molecule), TM-HH-LP, TM-LP-OC, TM-HH-OC, TM-LP, TM-OC or TM-HH.

Additional molecules which may optionally be present in the particle include for example one or more of LP-OC, HH-LP, HH-OC, LP, HH and co-lipids. In these, and the targeted forms just described, each targeting and other element may where appropriate be directly linked, or where desired indirectly linked to each other via a spacer group. Covalently linked elements may be obtained by coupling together individual elements using standard chemical coupling techniques and appropriate functional groups present in the starting materials. Such reactions are described generally and in more detail hereinafter in relation to particular classes of compounds for use in the invention but can be readily adapted to provide any desired covalently linked combination of targeting molecule, hydrophilic hydrocarbon, lipid and oligocation.

As used herein the term "targeting molecule" or abbreviation "TM" is each intended to mean a member of a complementary binding pair, the other member of the pair being present in a mammalian, e.g. human, or other animal, insect, microbial or plant host either attached to a cell membrane or other cell surface or in soluble form and present intracellularly and/or extracellularly. Thus in general the targeting molecule may be a peptide, including a glycopeptide, a polypeptide, protein, including a glycoprotein or phosphoprotein, a carbohydrate, glycolipid, phospholipid, oligonucleotide, polynucleotide or other organic molecule, e.g. a vitamin, which can specifically bind to a receptor, ligand, antigen or other naturally occurring or synthetic organic molecule.

The binding affinity of the targeting molecule for the other member of the complementary pair will be at least $10^{-5}$M, preferably $10^{-7}$M and greater, e.g. around $10^{-8}$M to around $10^{-12}$M. Preferably the targeting molecule will be selective for the other member of the pair and it will not cross-react although absolute specificity is not essential. Advantageously the interaction of the targeting molecule with its ligand leads to delivery of the polyanion and any other assembled extraneous material to the cell interior.

Antibodies and antigen-binding fragments and derivatives thereof as more particularly defined hereinafter form one particular class of suitable targeting molecules. Advantageously the antibody, fragment or derivative is an internalising antibody, fragment or derivative.

Other examples of suitable targeting molecules include antibody mimetic molecules produced by combinatorial or other synthetic means; interferons, for example interferons α, β and γ; tumour necrosis factors α and β; interleukins, for example interleukins 1 to 15; chemokines, for example MIP-1α, MIP-1β and RANTES; growth factors, for example PDGF, VEGF, EGF, TGFα, TBFβ, GM-CSF, G-CSF, M-CSF, FGF, IGF, bombesins, thrombopoietin, erythropoietin, oncostatin and endothelin 1; peptide hormones, for example LH, FSH, TRH, TSH, ACTH, CRH, PRH, MRH, MSH, glucagon and prolactin; transferrin; lactoferrin; angiotensin; histamine; insulin; lectins; tissue inhibitor or metalloproteinases, for example TIMP-1, TIMP-2 and TIMP-3; apolipoproteins, for example apolipoprotein E; kinins; and vitamins, for example folic acid and vitamin B12. Fragments and other synthetic analogues of these molecules may be used, where these retain or have the appropriate selective binding action. It will be appreciated that the above list is not exhaustive and may be extended to include other naturally occurring binding molecules, including for example the complementary binding partner, or a binding fragment thereof, of each of those mentioned, for example the PDGF receptor, the VEGF receptor and so on.

Similarly, adhesion moelcules and their binding partners or binding fragments thereof may be used in the invention as targeting molecules. Particular examples include VLA-4, VMAC-1, fibronectin, LFA-1, MAC-1, ICAM-1, ICAM-2, Lewis X, GMP-140, ELAM-1, S-Lewis X, fibrinogen, GPIIb/IIIa, CD28, B7, CD40, CD402L, CD4, laminin, VLA-1, VLA-2, VLA-3 and VLA-6.

Other examples of suitable targeting molecules include monosaccharides and oligosaccharides such as galactose, lactose and mannose.

The term "hydrophilic hydrocarbon" and the abbreviation "HH" is each used herein to mean any hydrocarbon containing one, two or more groups capable of being solvated by water. The hydrophilic hydrocarbon may thus be any aliphatic, heteroaliphatic, cycloaliphatic, polycycloaliphatic, heterocycloaliphatic or polyheterocycloaliphatic group, for example as described more particularly hereinafter in relation to the compounds of formula (1) [as being linked to the group $R^1$] or to the compounds of formula (1a) [as being the group $R^7$].

As used herein the term "lipid" or the abbreviation "LP" is each used herein to mean one or more optionally substituted straight or branched aliphatic or heteroaliphatic chains each containing a minimum of ten up to a maximum or around one hundred chain-linked atoms. Suitable lipids include those $R^1$ and $R^6$ hydrocarbon chains described in compounds of formulae (1) and (1a) below.

Co-lipids which may optionally be present as additional molecules in the particles according to the invention include acyclic and cyclic saturated or unsaturated lipids of natural or synthetic origin. Particular classes or co-lipids include for example glycerides, phospholipids, steroids, e.g. chlolesterol, and derivatives thereof.

The term "oligocation" or the abbreviation "OC" is each used herein to mean any molecule containing two or more cationic centres. Each cationic centre may be provided by one or more heteroatoms capable of retaining a positive charge at a pH in the range from around pH2.0 to around pH10.0. In practice whether a heteroatom will retain a positive charge in this pH range will depend on the nature and number of any other atoms or groups attached to it. Thus particular examples of suitable cationic centres include primary, secondary, tertiary and quaternary amino groups, sulphonium and phosphonium groups.

The number of cationic centres may be varied as desired depending on the intended use of the particle of the invention. At least two centres will be present, but three, four, five, six, seven, eight or more may be optionally incorporated. More than one type of centre may be present, for example mixtures of amino groups may be accommodated, and/or sulphonium and/or phosphonium groups.

In one general preference each cationic centre is an amino group. Particularly useful amino groups include primary, secondary and/or tertiary amino groups. The number of cationic centres in the oligocation will preferably be from three to eight.

In operation, each particle according to the invention can be used to deliver the assembled polyanion, together with any other optional extraneous material forming part of the assembly, to a desired target as more particularly described hereinafter. The extraneous compound may be any organic compound ranging in size from a low molecular weight molecule through to a macromolecule. Extraneous complexes include for example complexed metal and other ions. Mixtures of compounds and/or complexes may be present in each particle. In one generally preferred class each extraneous compound or complex may be polyanionic.

The polyanion and any extraneous compound or complex may be in particular a bioactive substance. Each bioactive substance may be for example a pharmacologically active agent, including an endosomolytic agent, a diagnostic agent or any agent able to modify the genotype and/of phenotype of a cell. Particular examples of such substances include bioactive proteins, peptides, polysaccharides, nucleic acids including synthetic polynucleotides, oligonucleotides and derivatives thereof, lipids, glycolipids, lipoproteins, lipopolysaccharides and viral, bacterial, protozoal, cellular or tissue fractions.

Particular polyanions in the particle include nucleic acids, for example single, double or triple stranded, circular or supercoiled DNA or RNA and hybrids, e.g. chimeroplasts and derivatives thereof. Where desired the DNA may be part of a structure such as a plasmid.

Each cationic centre will in general be separated from any other centre by spacer groups arranged to link the centres in a linear (straight and/or branched) or cyclic fashion. The overall effect may be an oligocation which has a straight and/or branched linear structure, a cyclic structure, or a mixture of straight and/or branched linear and cyclic structures. More than one type of spacer group may be present in an oligocation. Where desired a spacer group may form a terminal group on the oligocation, acting as a substituent on a cationic centre rather than a group connecting centres together. Each spacer group will in general be non-ionic and contain at least one carbon atom. Suitable groups include optionally substituted aliphatic, cycloaliphatic, heteroaliphatic, heterocycloaliphatic, aromatic or heteroaromatic groups. Particular examples of such groups include those generally and specifically described below in relation to the group $R^2$ in compounds of formulae (1) and (1a) where this does not contain a cationic centre.

One particularly useful class of particles according to the invention is that wherein the targeting molecule component is an antibody or an antigen-binding fragment thereof.

The antibody will in general be capable of selectively binding to an antigen. Clearly the nature of the antigen is not crucial providing that it is accessible to the antibody. Thus the antigen may be any cell-associated antigen, for example a cell surface antigen such as a T-cell, endothelial cell or tumour cell marker, or it may be a soluble antigen. Particular examples of cell surface antigens include adhesion molecules, for example integrins such as β1 integrins, e.g. VLA-4, E-selectin, P-selectin or L-selection, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8 or IL-12, viral antigens, for example respiratory syncytial virus or cytomegalovirus antigens, immunoglobulins, such as IgE, interferons such as interferon-α, interferon-β or interferon-γ, tumour necrosis factor-α, tumour necrosis factor-β, colony stimulating factors such as G-CSF or GM-CSF, and platelet derived growth factors such as PDGF-α, and PDGF-β and where appropriate receptors thereof.

The antibody will comprise at least a variable region domain. The variable region domain may be of any size or amino acid composition and will generally comprise at least one hypervariable amino acid sequence responsible for antigen binding embedded in a framework sequence. In general terms the variable (V) region domain may be any suitable arrangement of immunoglobulin heavy ($V_H$) and/or light ($V_L$) chain variable domains. Thus for example the V region domain may be monomeric and be a $V_H$ or $V_L$ domain where these are capable of independently binding antigen with acceptable affinity. Alternatively the V region domain may be dimeric and contain $V_H$-$V_H$, $V_H$-$V_L$, or $V_L$-$V_L$, dimers in which the $V_H$ and $V_L$ chains are non-covalently associated (abbreviated hereinafter as $F_v$). Where desired, however, the chains may be covalently coupled either directly, for example via a disulphide bond between the two variable domains, or through a linker, for example a peptide linker, to form a single chain domain (abbreviated hereinafter as $scF_v$).

The variable region domain may be any naturally occurring variable domain or an engineered version thereof. By engineered version is meant a variable region domain which has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody.

The variable region domain may be covalently attached at a C-terminal amino acid to at least one other antibody domain or a fragment thereof. Thus, for example where a $V_H$ domain is present in the variable region domain this may be linked to an immunoglobulin $C_H1$ domain or a fragment thereof. Similarly a $V_L$ domain may be linked to a $C_K$ domain or a fragment thereof. In this way for example the antibody may be a Fab fragment wherein the antigen binding domain contains associated $V_H$ and $V_L$ domains covalently linked at their C-termini to a CH1 and $C_K$ domain respectively. The CH1 domain may be extended with further amino acids, for example to provide a hinge region domain as found in a Fab' fragment, or to provide further domains, such as antibody CH2 and CH3 domains.

Antibodies for use in the invention may in general be monoclonal [prepared by conventional immunisation and cell fusion procedures] or in the case of fragments derived therefrom using any suitable standard chemical e.g. reduction or enzymatic cleavage and/or digestion techniques, for example by treatment with pepsin.

Alternatively, the antibody may be a recombinant or engineered antibody obtained by the use of recombinant DNA techniques involving the manipulation and re-expression of DNA encoding antibody variable and/or constant regions. Such DNA is known and/or is readily available from DNA libraries including for example phage-antibody libraries [see Chiswell, D J and McCafferty, J. Tibtech. 10 80-84 (1992)] or where desired can be synthesised. Standard molecular biology and/or chemistry procedures may be used to sequence and manipulate the DNA, for example, to introduce codons to create cysteine residues, to modify, add or delete other amino acids or domains as desired.

From here, one or more replicable expression vectors containing the DNA may be prepared and used to transform an appropriate cell line, e.g. a non-producing myeloma cell line, such as a mouse NSO line or a bacterial, e.g. *E. coli* line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al [Molecular Cloning, Cold Spring Harbor Laboratory, New York, 1989]; DNA sequencing can be performed as described in Sanger et al [PNAS 74, 5463, (1977)] and the Amersham International plc sequencing handbook; and site directed mutagenesis can be carried out according to the method of Kramer et al [Nucl. Acids Res. 12, 9441, (1984)] and the Anglian Biotechnology Ltd handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews [ed. Tombs, M P, 10, Chapter 1, 1992, Intercept, Andover, UK] and in International Patent Specification No. WO 91/09967.

In one preferred particle according to the invention the antibody targeting molecule is covalently attached to one or more of the other components of the particle. Particularly useful covalently linked molecules of these types are TM-HH-LP-OC, TM-LP-OC and TM-LP where TM represents the antibody or an antigen binding fragment thereof as just described. In these and any other antibody-linked components the antibody or fragment may be attached to the remainder of the molecule through any available amino acid sidechain, terminal amino acid or, where present, carbohydrate functional group located in the antibody or fragment, always provided of course that this does not adversely affect the binding properties and eventual usefulness of the molecule. Particular functional groups include for example any free amino, imino, thiol, hydroxyl, carboxyl or aldehyde group. Attachment of the antibody and any other component may be achieved via such groups and an appropriate functional group in the other component using standard chemical procedures. Thus for example when it is desired to use a thiol group in the antibody or fragment as the point of attachment this may be achieved through reaction with a thiol reactive group present in the other component. Examples of such groups include an α-halocarboxylic acid or ester, e.g. iodoacetamide, an imide, e.g. maleimide, a vinyl sulphone, or a disulphide. These and other suitable linking procedures are generally and more particularly described in International Patent Specifications Nos. WO 93/06231, WO 92/22583, WO 90/091195 and WO 89/01476.

Particularly useful antibody targeting molecules in particles of the invention include Fab' fragments and scF$_v$ fragments covalently linked at the C-terminus to at least one other antibody domain, especially a hinge region domain, as described above. In these the fragment is preferably covalently linked to a HH-LP-OC, LP-OC or LP component. The linkage may especially be through a thiol group present in the fragment, especially in a hinge region domain. For this purpose the hinge region domain may be engineered to contain one reactive thiol group only by using the recombinant DNA techniques described above to create, modify or delete cysteine residues in the fragment.

Particularly useful hydrophilic hydrocarbon, lipid, and oligocation components for use in particles according to the invention are those wherein all three components are covalently linked in the sequence HH-LP-OC. A particularly useful group of these has the formula (1):

(1)

wherein $R^1$ is a hydrocarbon chain optionally substituted by one or more hydrophilic hydrocarbons each containing one, two or more atoms or groups capable of being solvated by water, provided that at least one hydrocarbon chain is substituted by at least one hydrophilic hydrocarbon and each hydrophilic hydrocarbon is attached to the hydrocarbon chain to achieve at least a ten atom spacing along the chain between the hydrophilic hydrocarbon and the group -(L$^1$)$_n$-OC;

m is an integer from 1 to 6;

L$^1$ is a linker atom or group;

OC is an oligocation;

n is zero or the integer 1;

and the salts, solvates and hydrates thereof.

Oligocations in compounds of formula (1) include groups of formula —[—C(R$^2$)(R$^3$)(R$^4$)] in which R$^2$ is a hydrogen atom or an optionally substituted aliphatic, cycloaliphatic, heteroaliphatic, heterocycloaliphatic, aromatic or heteroaromatic group optionally containing one or more cationic centres, and R$^3$ and R$^4$ which may be the same or different is each an optionally substituted aliphatic, cycloaliphatic, heteroaliphatic, heterocycloaliphatic, aromatic or heteroaromatic group containing one or more cationic centres, or R$^3$ and R$^4$ together with the carbon atom to which they are attached form a cycloaliphatic, heterocycloaliphatic, aromatic or heteroaromatic group containing two or more cationic centres.

In the group —C(R$^2$)(R$^3$)(R$^4$), the optionally substituted aliphatic, cycloaliphatic, heteroaliphatic, heterocycloaliphatic, aromatic or heteroaromatic group represented by R$^2$, R$^3$ and R$^4$ may each be an optionally substituted C$_{1-30}$ aliphatic, C$_{3-10}$ cycloaliphatic, C$_{1-30}$ heteroaliphatic, C$_{3-10}$ heterocycloaliphatic, C$_{6-12}$ aromatic or C$_{1-9}$ heteroaromatic group, each containing where appropriate one or more cationic centres. Each cationic centre may be one or more heteroatoms capable of retaining a positive charge as described in more detail above in relation to the term "oligocation".

Particular examples of optionally substituted aliphatic groups include optionally substituted C$_{1-10}$ aliphatic chains such as optionally substituted straight or branched C$_{1-6}$ alkylene, C$_{2-6}$ alkenylene or C$_{2-6}$ alkynylene chains.

Heteroaliphatic groups include the aliphatic chains just described but with each chain additionally containing one, two, three or four heteroatoms or heteroatom-containing groups. Particularly heteroatoms or groups include atoms or groups L$^2$ where L$^2$ is as defined below for L$^1$ when L$^1$ is a linker atom or group. Each L$^2$ atom or group may interrupt the aliphatic chain, or may be positioned at its terminal carbon atom.

Particular examples of aliphatic groups include optionally substituted —CH$_2$—, —CH$_2$CH$_2$—, —CH(CH$_3$)—, —C(CH$_3$)$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$) CH$_2$—, —C(CH$_3$)$_2$CH$_2$—, —(CH$_2$)$_4$CH$_2$—, —(CH$_2$)$_5$ CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$ CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups L$^2$ to form an optionally substituted heteroaliphatic group. Particular examples include optionally substituted —L$^2$CH$_2$—, —CH$_2$L$^2$CH$_2$—, —L$^2$(CH$_2$)$_2$—, —CH$_2$L$^2$(CH$_2$)$_2$—, —(CH$_2$)$_2$L$^2$CH$_2$—, —L$^2$(CH$_2$)$_3$— and —(CH$_2$)$_2$L$^2$ (CH$_2$)$_2$— chains. The optional substituents which may be present on aliphatic or heteroaliphatic groups include one, two, three or more substituents selected from halogen atoms, e.g. fluorine, chlorine, bromine or iodine atoms, or hydroxyl, C$_{1-6}$alkoxy, e.g. methoxy or ethoxy, haloC$_{1-6}$alkoxy, e.g. halomethoxy or haloethoxy such as difluoromethoxy or trifluoromethoxy, thiol, or C$_{1-6}$alkylthio e.g. methylthio or ethylthio. Particular examples of substituted groups include those specific chains just described substituted by one, two, three or more halogen atoms such as fluorine atoms, for example chains of the type —CH(CF$_3$)—, —C(CF$_3$)$_2$—, —CH$_2$CH(CF$_3$)—, —CH$_2$C(CF$_3$)$_2$—, —CH(CF$_3$)— and —C(CF$_3$)$_2$CH$_2$—.

Optionally substituted cycloaliphatic groups represented by R$^2$, R$^3$ or R$^4$ include optionally substituted C$_{3-10}$ cycloaliphatic groups. Particular examples include optionally substituted C$_{3-10}$cycloalkylene, e.g. C$_{3-7}$cycloalkylene, C$_{3-10}$cycloalkenylene e.g. C$_{3-7}$cycloalkenylene or C$_{3-10}$cycloalkynylene e.g. C$_{3-7}$cycloalkynylene groups.

Particular examples of cycloaliphatic groups include optionally substituted cyclopropylene, cyclobutylene, cyclopentylene, cyclohexylene, cycloheptylene, 2-cyclobuten-1-ylene, 2-cyclopenten-1-ylene and 3-cyclopenten-1-ylene groups.

Optionally substituted heterocycloaliphatic groups represented by R$^2$, R$^3$ or R$^4$ include the optionally substituted cycloaliphatic groups just described but with each group additionally containing one, two, three or four heteroatoms or heteroatom-containing groups L$^2$ as just defined.

The optional substituents which may be present on the cycloaliphatic or heterocycloaliphatic groups include one, two, three or more substituents selected from halogen atoms C$_{1-6}$alkyl, e.g. methyl or ethyl, haloC$_{1-6}$alkyl, e.g. halomethyl or haloethyl such as difluoromethyl or trifluoromethyl, hydroxyl, C$_{1-6}$alkoxy, e.g. methoxy or ethoxy, haloC$_{1-6}$ alkoxy, e.g. halomethoxy or haloethoxy such as difluoromethoxy or trifluoromethoxy, thiol, or C$_{1-6}$alkylthio e.g. methylthio or ethylthio groups.

Optionally substituted aromatic groups represented by R$^2$, R$^3$ or R$^4$ include for example monocyclic C$_{6-12}$ aromatic groups, such as optionally substituted phenylene.

Optionally substituted heteroaromatic groups include for example optionally substituted monocyclic C$_{1-9}$ heteroaromatic groups containing for example one, two, three or four heteroatoms selected from oxygen, sulphur or nitrogen atoms. Monocyclic heteroaromatic groups include for example five- or six-membered heteroaromatic groups containing one, two, three or four heteroatoms selected from oxygen, sulphur or nitrogen atoms.

Optional substituents which may be present on the aromatic or heteroaromatic groups include one, two, three or more substituents selected from those just described in relation to cycloaliphatic and heterocycloaliphatic groups.

When L$^1$ is present in compounds of formula (1) as a linker atom or group it may be any multivalent atom or group. Particular examples of suitable linker atoms or groups include those of formula -(Alk$^1$)$_r$(X$^1$)$_s$(Alk$^2$)$_t$- where X$^1$ is an —O— or —S— atom or a —C(O)—, —C(O)O—, —C(S)—, —S(O), —S(O)$_2$— —N(R$^5$)—, [where R$^5$ is a hydrogen atom, straight or branched alkyl group such as a methyl or ethyl group or an -Alk$^1$X$^1$— chain], —CON(R$^5$)—, —OC(O)N(R$^5$)—, —CSN(R$^5$)—, —N(R$^5$)CO—, N(R$^5$)C(O)O—, —N(R$^5$)CS—, —S(O)N(R$^5$)—, —S(O)$_2$N(R$^5$)—, —N(R$^5$)S(O)—, —N(R$^5$)S(O)$_2$—, —N(R$^5$)CON(R$^5$)—, or —N(R$^5$)SO$_2$N(R$^5$)— group [where any of these groups contains two R$^5$ substituents these may be the same or different]; Alk$^1$ and Alk$^2$ which may be the same or different is each an optionally substituted straight or branched C$_{1-10}$alkylene, C$_{2-10}$alkenylene or C$_{2-10}$alkynylene chain optionally interrupted or terminated by one or more, e.g. one, two or three, carbocyclic or heterocarbocyclic groups and/or heteroatoms or heteroatom containing groups X$^1$ as just defined, and r, s, and t, which may be the same or different, is each zero or the integer 1, provided that when one of r, s or t is zero at least one of the remainder is the integer 1.

Carbocyclic groups which may interrupt the groups Alk$^1$ and Alk$^2$ include for example optionally substituted C$_{4-8}$cycloalkyl, e.g. optionally substituted cyclopentyl or cyclohexyl groups, or optionally substituted C$_{4-8}$cycloalkenyl. e.g. optionally substituted cyclopentenyl or cyclohexenyl groups. Heterocarbocyclic groups include for example carbocyclic groups of the types just mentioned containing one or more heteroatoms or heteroatom-containing groups X$^1$ as defined above. Optional substituents which may be present on the chains represented by Alk$^1$ and Alk$^2$ and the carbocyclic or heterocarbocyclic groups which can interrupt or terminate them include one, two or three substituents selected from halogen atoms, e.g. fluorine, chlorine, bromine or iodine atoms or C$_{1-3}$alkyl, e.g. methyl or ethyl, or C$_{1-3}$alkoxy e.g. methoxy or ethoxy groups.

It will be appreciated that the linker atom or group will be at least divalent in the instance where one R$^1$ group is attached to it. Where it is desired to attach more than one hydrocarbon chain to the linker the latter will need to be selected with an appropriate valency and this will generally mean that at least one of Alk$^1$ or Alk$^2$ will need to be present in the linker in a branched form and with the requisite number of X$^1$ atoms or groups to achieve the desired coupling.

Particular examples of linker groups represented by L$^1$ include groups of formula —X$^1$Alk$^2$- where X$^1$ is as defined above and Alk$^2$ is an optionally substituted —CH$_2$—, —(CH$_2$)$_2$—, —(CH$_2$)$_3$—, —(CH$_2$)$_4$—, —(CH$_2$)$_5$— or —(CH$_2$)$_6$— chain; groups of formula [X$^1$]$_2$Alk$^1$X$^1$Alk$^2$ where Alk$^1$ is a —CH$_2$CH< group and X$^1$ and Alk$^2$ are as just defined or a group of formula [X$^1$]$_2$Alk$^1$Alk$^2$ where X$^1$, Alk$^1$ and Alk$^2$ are as just defined.

Each hydrocarbon chain as represented by R$^1$ in compounds of formula (1) may be a C$_{10}$ up to about a C$_{60}$ hydrocarbon chain, for example a C$_{16}$ to C$_{60}$ hydrocarbon chain such as a C$_{18}$ to C$_{48}$ hydrocarbon chain.

In particular, the chain may be an optionally substituted C$_{10-60}$ aliphatic chain such as an optionally substituted straight or branched C$_{10-60}$alkylene, C$_{10-60}$alkenylene or C$_{10-60}$alkynylene chain. Optional substituents which may be present on such chains include one or more halogen atoms, e.g. fluorine, chlorine, bromine or iodine atoms, or halo C$_{1-6}$alkyl, e.g. —CF$_3$ groups. Where desired each alkylene, alkenylene or alkynylene chain may be interrupted by one or more oxygen or sulphur atoms or optionally substituted C$_{5-7}$cycloalkyl, e.g. cyclopentyl or cyclohexyl, C$_{5-7}$cycloalkenyl, e.g. cyclopentenyl or cyclohexenyl, —C(O)—, —C(S)—, —C(O)N(R$^5$)—, —C(S)N(R$^5$)—, —N(R$^5$)C(O)—, —N(R$^5$)C(S)—, —C(O)O—, —C(O)S—, —OC(O)N(R$^5$)—, —S(O)—, —S(O$_2$)—, —S(O)N(R$^5$)—, —S(O)$_2$N(R$^5$)—, —N(R$^5$)S(O)—, —N(R$^5$)S(O)$_2$—, —N(R$^5$)C(O)N(R$^5$)—, —N(R$^5$)C(S)N(R$^5$)—, —N(R$^5$)S(O)N(R$^5$)— or —N(R$^5$)S(O)$_2$N(R$^5$)— groups. Optional substituents which may be present on cycloalkyl or cycloalkenyl groups of this type include one or more halogen atoms or haloalkyl groups as just described. It will be appreciated that when the aliphatic chain is an alkenylene or alkynylene chain it may have more than one unsaturated group.

Each hydrophilic hydrocarbon attached to the group R$^1$ may be an aliphatic, heteroaliphatic, cycloaliphatic, polycycloaliphatic, heterocycloaliphatic or polyheterocycloaliphatic group. Particular examples of aliphatic groups include alkyl, alkenyl or alkynyl groups. Cycloaliphatic groups include cycloalkyl or cycloalkenyl groups. Polycycloaliphatic groups include two or more cycloalkyl or cycloalkenyl groups either joined directly or indirectly through a linker atom or group, for example a linker atom or group L$^2$ where L$^2$ is an atom or group as described above for the group L$^1$. Each of these aliphatic, cycloaliphatic or polycycloaliphatic groups may be optionally interrupted by one or more heteroatoms or heteroatom-containing groups, for example of the type described above in relation to the group $L^1$ to yield heteroaliphatic, heterocycloaliphatic or polyheterocycloaliphatic hydrocarbon groups.

Each hydrophilic hydrocarbon contains one, two or more atoms or groups capable of being solvated by water. Examples of such groups include oxygen atoms (—O—) or oxygen-containing groups. Oxygen atoms may form part of a heteroaliphatic, heterocycloaliphatic or polycycloheteroaliphatic group as just described. Oxygen-containing groups may be substituents present on the various hydrocarbons just mentioned and include for example hydroxyl, amide and alkoxy groups such as methoxy or ethoxy groups. In general the number of groups capable of being solvated by water in each hydrocarbon will range from two to around two hundred.

Particular examples of suitable hydrophilic hydrocarbons include polyols. Suitable polyols include naturally occurring polyols such as sugars and derivatives thereof, and synthetic polyols. Particular sugars include mono- and oligosaccharides. Sugar derivatives include glycosides in which a non-ionic aliphatic or heteroaliphatic group (for example of the type described herein) is joined to a sugar by a glycosidic linkage. Monosaccharides include for example open-chain or cyclic compounds containing three to eight, e.g. five or six, carbon atoms and at least two hydroxyl substituents. Oligosaccharides include for example at least two monosaccharides as just defined linked together by a glycosidic or other linkage. More than one type of monosaccharide may be present to yield a homo- or heterooligosaccharide.

Alternatively the hydrophilic hydrocarbon may be a polyether, for example a poly(alkylene oxide) and derivatives thereof, such as poly(ethylene oxide), poly(propylene oxide) or methoxy poly(ethylene oxide), a poly(oxyalkylated alcohol) or a poly(alkenylene alcohol) or poly(alkynylene alcohol) such as poly(vinyl alcohol). The hydrocarbons may in general be straight or branched. Where desired co-polymers of these hydrocarbons may be used.

Each hydrophilic hydrocarbon may be linked directly or indirectly to a hydrocarbon chain represented by $R^1$. For indirect linkage a linker atom or group may be employed, for example an atom or group $L^3$ where $L^3$ is as defined above as for the linker atom or group $L^1$. Where the group $L^3$ is multivalent, for example when it is a branched alkylene chain containing more than one $X^1$ atom or group, more than one hydrophilic hydrocarbon may be attached to it.

A particularly useful group of compounds of formula (1) has the formula (1a):

(1a)

wherein OC, $L^1$, m and n are as defined for formula (1);

$R^6$ is a hydrocarbon chain;

$L^3$ is a linker atom or group;

$R^7$ is a hydrophilic hydrocarbon containing two or more atoms or groups capable of being solvated by water;

q is zero or an integer from one to six;

p is an integer from one to six;

and the salts, solvates and hydrates thereof, provided that each $R^7$ or $L^3$ group, when present, is attached to a group $R^6$ to achieve at least a ten atom spacing along $R^6$ between $R^7$ or $L^3$ and the group $-(L^1)_n$-OC.

In the compounds of formula (1a) the hydrocarbon chain represented by $R^6$ may be a $C_{10}$ up to about a $C_{60}$ hydrocarbon chain as generally and more particularly described above in relation to the group $R^1$. The hydrophilic hydrocarbon $R^7$ may similarly be a hydrophilic hydrocarbon as described previously in relation to the group $R^1$. The group $L^3$ may be a linker atom or group as just defined.

In the compounds of formulae (1) and (1a) the oligocation OC is preferably —C($R^2$)($R^3$)($R^4$) In these groups $R^2$ is preferably a hydrogen atom, and $R^3$ and $R^4$ is each preferably a group -$Sp^1$[W$Sp^2$]$_b$W$Sp^3$ or -$Sp^1$[W$Sp^2$]$_b$WH in which $Sp^1$, $Sp^2$ and $Sp^3$, which may be the same or different, is each a spacer group, W is a cationic centre as defined herein and b is zero or an integer from one to six. The spacer groups $Sp^1$, $Sp^2$ and $Sp^3$ may be any optionally substituted aliphatic, cycloaliphatic, heteroaliphatic, heterocycloaliphatic, aromatic or heteroaromatic group as described above for the group $R^2$ where this does not contain a cationic centre.

In particular groups of this type, the cationic centre W is preferably a —NH— group. $Sp^1$, $Sp^2$ and $Sp^3$, which may be the same or different, is each preferably an optionally substituted $C_{1-6}$alkylene chain. b is preferably an integer from one to three.

Particularly useful oligocations include those of formula —CH[$Sp^1$NH$Sp^2$NH$_2$]$_2$, —CH[$Sp^1$NH$Sp^2$NH$Sp^2$NH$_2$]$_2$ or —CH[$Sp^1$NH$Sp^2$NH$Sp^2$NHCH$_3$]$_2$ where each $Sp^1$ and $Sp^2$ group is the same or different and is an optionally substituted $C_{1-6}$alkylene chain, particularly wherein $Sp^1$ is —CH$_2$— and each $Sp^2$ is —(CH$_2$)$_3$— or —(CH$_2$)$_4$—.

In general in the compounds of formulae (1) and (1a) m is preferably an integer 2 or, especially, an integer 1. Each hydrocarbon chain, for example as represented by $R^1$ and $R^6$ in formulae (1) and (1a) respectively, is preferably linear and in particular is a linear, optionally substituted $C_{16-38}$alkylene chain. Optionally substituted $C_{18-30}$alkylene chains are particularly useful.

In general each $R^1$ group is preferably linked indirectly to the oligocation through a linker atom or group. The linker atom or group may be for example an atom or group $L^1$ as defined herein and thus in the compounds of formulae (1) and (1a) for example n is preferably the integer 1.

Preferred linkers include those of formula —$X^1$Alk$^2$- or —[$X^1$]$_2$Alk$^1$$X^1$Alk$^2$- where $X^1$, Alk$^1$ and Alk$^2$ are as defined previously. Particularly useful linkers of these types are those wherein Alk$^2$ is a —(CH$_2$)$_4$—, —(CH$_2$)$_5$— or, especially, —(CH$_2$)$_6$— chain. $X^1$ in these linkers is preferably a —CONH— group. Alk$^1$ when present is preferably a —CH$_2$—CH— chain.

Each hydrophilic hydrocarbon in the compounds of formulae (1) and (1a) is preferably attached to the terminal carbon atom of the hydrocarbon chain $R^1$ distal to the chain carbon atom attached to the oligocation. Preferably the hydrophilic hydrocarbon and hydrocarbon chain are indirectly linked through a linker atom or group. Thus in one particular preference in compounds of formula (1a) q is the integer 1 and p is the integer 1 or 2.

In compounds of this type and in general the group $L^3$ may preferably be an atom or group —$X^1$—, —$X^1$Alk$^1$$X^1$— or [$X^1$Alk$^1$]$_x$$X^1$Alk$^2$$X^1$—. Particularly useful $L^3$ groups include —NHCO—, —CONH—, —CONH(CH$_2$)$_2$NHCO—, or —[CONH(CH$_2$)$_2$—]$_2$NCO(CH$_2$)$_2$CONH— groups.

In general, the hydrophilic hydrocarbon, for example as represented by $R^7$ in formula (1a) is preferably a synthetic polyol, a naturally occurring polyol such as mono- or disaccharide, or a poly(alkylene oxide) as defined herein. In particular $R^7$ may be a poly(alkylene oxide) or a derivative thereof, especially a poly(ethylene oxide).

When linked to a targeting molecule, the compounds of formula (1) provide a group of targeted bipolar lipids which are particularly useful components of particles according to the invention. Such lipids form a further feature of the invention and we thus provide a targeted bipolar lipid comprising a compound of formula (1) as hereinbefore defined linked to one or more targeting molecules. In general the targeting molecule is preferably covalently linked to the compound of formula (1). The linkage point may be at any position in the compound of formula (1) provided that this does not adversely affect the binding and/or assembly properties of the bipolar lipids. The linkage may be achieved through appropriate functional groups in the targeting molecule and compound of formula (1) as described herein.

A particular useful subset of targeted bipolar lipids according to the invention is that wherein the targeting molecule is covalently linked to the group $R^1$ in compounds of formula (1). Thus in a further aspect of the invention we provide a targeted bipolar lipid of formula (2):

$$[TM]_u\text{-}(L^4)_v\text{-}[R^1]_m\text{-}(L^1)_n\text{-}OC \qquad (2)$$

wherein TM, $R^1$, m, $L^1$, n, and OC are as defined previously, u is an integer 1 or 2, $L^4$ is a linker atom or group and v is zero or the integer 1.

Linker atoms or groups represented by $L^4$ include those atoms or groups described above in relation to $L^1$.

As indicated above each TM in compounds of formula (2) may be attached to any part of each $R^1$ group, but in one preferred arrangement the TM is attached to the hydrophilic hydrocarbon portion of $R^1$ to provide a compound of formula (2a):

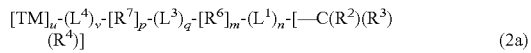

$$[TM]_u\text{-}(L^4)_v\text{-}[R^7]_p\text{-}(L^3)_q\text{-}[R^6]_m\text{-}(L^1)_n\text{-}[-C(R^2)(R^3)(R^4)] \qquad (2a)$$

wherein TM, u, $L^4$, v, $R^7$, p, $L^3$, q, $R^6$, m, $L^1$, n, $R^2$, $R^3$ and $R^4$ are as defined previously.

In general in the targeted bipolar lipids of this aspect of the invention the targeting molecule or TM [in compounds of formulae (2) or (2a)] is preferably an antibody or an antigen binding fragment or derivative thereof as defined herein.

One targeting molecule or TM is preferably present in each molecule. Thus u in compounds of formulae (2) and (2a) is preferably the integer 1.

When the targeting molecule or TM is indirectly linked to the remainder of the molecule through the linker $L^4$ (i.e. v is the integer 1) the latter may be an atom or group -(Alk$^1$)$_r$-(X$^1$)$_s$(Alk$^2$)$_t$- as generally and particularly described above. Particularly useful $L^4$ groups include —NHCO(Alk$^2$)$_t$- groups [where the aminocarbonyl group is attached to $R^1$ or $R^7$], especially

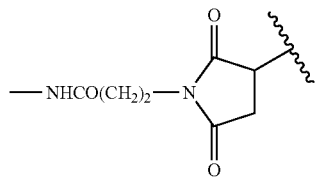

—NHCO(CH$_2$)$_2$—N groups.

It will be appreciated that the meanings and preferences expressed in relation to the various groups in compounds of formulae (1) and (1a) apply equally well to those same groups when present in compounds of formulae (2) and (2a).

The compounds of formulae (1), (1a), (2) and (2a) may generally be prepared by coupling appropriately functionalised starting materials in a predetermined order. Standard chemical coupling techniques may be employed utilising starting materials containing one or more reactive functional groups such as acids, thioacids, anhydrides, acid halides, esters, imides, aldehydes, ketones and amines. Illustrative reactions are described in detail in the Examples hereinafter for the preparation of a number of compounds of formulae (1), (1a), (2) and (2a) and these may be readily adapted using different starting materials to provide covalently linked hydrophilic hydrocarbons, lipids, oligocations and targeting molecules.

Thus in one general approach a homo- or heterobifunctional hydrocarbon chain may first be coupled to a hydrophilic hydrocarbon or oligocation and the resulting product coupled as necessary to the remaining component to provide for example a component HH-LP-OC.

The homo- or heterobifunctional hydrocarbon chain may be any hydrocarbon chain described herein containing two different reactive functional groups of the types just described. Particularly useful groups include acids and thioacids and reactive derivatives thereof, and amines. These can be used to participate in acylation or thioacylation reactions to couple the hydrocarbon chain to an amine or acid as appropriate in any suitable hydrophilic hydrocarbon and/or cationic head.

Acylation or thioacylation may be achieved using standard conditions for reactions of this type. Thus, for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a temperature from around ambient temperature to the reflux temperature, optionally in the presence of a base such as an amine, e.g. triethylamine, or a cyclic amine, such as 1,8-diazabicyclo[5.4.0]undec-7-ene pyridine, dimethylaminopyridine, or N-methylmorpholine.

Where an acid is used the acylation may additionally be performed in the presence of a condensing agent, for example a diimide such as 1-(3-dimethylaminopropyl)-3-ethylcarbodiimide or N,N'-dicyclohexylcarbodi-imide, advantageously in the presence of a catalyst such as a N-hydroxy compound e.g. a N-hydroxytriazole such as 1-hydroxybenzotriazole or a N-hydroxyimide such as N-hydroxysuccinimide. Alternatively, the acid may be reacted with a chloroformate, for example ethylchloroformate, prior to reaction with the amine.

In the heterobifunctional hydrocarbon chain one of the reactive functional groups may need to be in a protected form prior to any coupling reaction to avoid its unwanted participation in the reaction. Similarly other functional groups when present in the hydrocarbon chain, or the intermediates used to generate the hydrophilic hydrocarbon and/or the cationic head may need to be in a protected form before these reagents can be used. Conventional protecting groups may be used in accordance with standard practice [see, for example, Green, T. W. in "Protective Groups in Organic Synthesis", John Wiley & Sons, 1991 and the Examples hereinafter].

Suitable heterobifunctional hydrocarbon chains are either known, readily available materials or may be obtained by synthesis using conventional techniques for example as described in the Examples hereinafter. Thus generally a heterobifunctional hydrocarbon chain of any desired length may be synthesised in one or more reactions using appropriately functionalised shorter chains. Thus in one example a shorter chain aldehyde may be reacted with a shorter chain phosphonium salt to yield a longer chain olefin of the desired length. In this particular example the reaction may be carried out in the presence of a base, for example an organometallic base such as an organolithium compound, a hydride such as sodium or potassium hydride or an alkoxide such as a sodium alkoxide e.g. sodium methoxide. The reaction may be performed in a suitable solvent, for example a polar aprotic solvent such as an alkyl sulphoxide, e.g. dimethylsulphoxide at a low temperature, for example around 0° C. The starting aldehyde and phosphonium salt may be obtained from known starting alcohols and halides respectively using conventional procedures. Where desired, the olefin obtained above may be hydrogenated using hydrogen and a catalyst, for example Pearlman's catalyst, to yield the corresponding saturated hydrocarbon chain.

Where it is desired to obtain hydrocarbon chains containing one or more heteroatoms or heteroatom-containing groups these may be synthesised from smaller chains containing functional groups which can be chemically coupled, for example by acylation or thioacylation as generally described above.

Suitable functionalised hydrophilic hydrocarbons or oligocations for coupling to the heterobifunctional hydrocarbon chain and/or targeting molecule are either readily available or may be synthesised from known materials by conventional methods for example as described in the Examples hereinafter.

Where desired, the properties of the particle of the invention may be altered by varying the nature of the components and their relative proportions. Thus for example a particularly useful particle according to the invention comprises a targeting molecule (TM), hydrophilic hydrocarbon (HH), lipid (LP) and oligocation (OC) covalently linked in the sequence TM-HH-LP-OC. Such particles may contain one or more other co-lipid and in particular are present, especially when TM is a large molecular weight molecule such as an antibody or fragment or derivative thereof, such that the percentage of TM-HH-LP-OC in the particle is in the range 0.01 to 4 mol % of the total lipid content of the particle.

Particularly useful particles of these types are those containing a TM-HH-LP-OC component, a first HH-LP-OC component and optionally a second HH-LP-OC component in which the hydrophilic hydrocarbon differs from that present in the first component and is a polyether as generally and particularly described herein. Particles of these types in which an additional lipid component, such as a co-lipid, LP or LP-OC is present are especially useful. In these particles the TM-HH-LP-OC component is preferably a compound of formulae (2) or (2a) as herein described. Where desired a co-lipid may additionally be present in these particles.

When in use each particle according to the invention will in general be assembled with one or more multipolar lipids, targeting molecules, polyanions and any additional components such as co-lipids in a weight ratio of around 0.1:1 to around 100:1, for example around 1:1 to around 50:1, e.g. 20:1 to multipolar lipid, targeting molecule and any additional components to polyanion. The particles may be formed as liquids, by initially mixing the targeting, multipolar lipid and any additional components with the polyanion advantageously in an aqueous solvent using conventional procedures. Where desired the solvent may be removed, for example by lyophilisation, to obtain a solid lipid complex.

The particles according to the invention may be put to any in vitro, ex vivo or in vivo use depending on the nature of the polyanion and any extraneous compounds and/or complexes assembled with them. Where the polyanion and/or extraneous material is a pharmaceutical agent the particle is of use as a targeted delivery agent in medicine and the invention extends to a method of treatment of a human or animal subject, the method comprising administering to the subject an effective amount of a particle described above, the products described herein for use as a medicament and the use of the products described herein in the preparation of a medicament for treating conditions described hereinafter.

In particular in this aspect of the invention the particle may be associated with one or more nucleic acids as described previously. The exact amount of particle to be used will depend on the age and condition of the patient, the nature of the disease or disorder and the route of administration, but may be determined using conventional means, for example by extrapolation of animal experiment derived data. In particular, for ex vivo use the number of transfected effector cells required may be established by ex vivo transfection and re-introduction into an animal model of a range of effector cell numbers. Similarly the quantity required for in vivo use may be established in animals using a range of concentrations of polyanion or extraneous material.

The particle according to the invention may be useful in the treatment of a number of diseases or disorders. Such diseases or disorders may include those described under the general headings of infectious diseases, e.g. HIV infection; inflammatory disease/autoimmunity e.g. rheumatoid arthritis, osteoarthritis, inflammatory bowel disease; cancer; allergic/atopic diseases e.g. asthma, eczema; congenital e.g. cystic fibrosis, sickle cell anaemia; dermatologic, e.g. psoriasis; neurologic, e.g. multiple sclerosis; transplants e.g. organ transplant rejection, graft-versus-host disease; metabolic/idiopathic disease e.g. diabetes.

The lipid particles according to the invention may be formulated with other materials such as one or more pharmaceutically acceptable carriers, excipients or diluents and the invention extends to such compositions. The compositions may take any other supermolecular form suitable for oral, buccal, parenteral, nasal, topical or rectal administration, or a form suitable for administration by inhalation or insufflation.

For oral administration, the compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The particles of the invention may be formulated for parenteral administration by injection, including bolus injection or infusion or particle mediated injection. Formulations for injection may be presented in unit dosage form, e.g. in glass ampoule or multi dose containers, e.g. glass vials or a device containing a compressed gas such as helium for particle mediated administration. The compositions for bolus injection or infusion may take such forms as suspensions, solutions or emulsions in oily or aqueous vehicles, and may contain formulatory agents such as suspending, stabilising, preserving and/or dispersing agents. Alternatively, the complex may be in powder form for constitution with a suitable vehicle, e.g. sterile pyrogen-free water, before use. For particle mediated administration the complex may be coated on particles such as microscopic gold particles.

In addition to the formulations described above, the particles may also be formulated as a depot preparation. Such long acting formulations may be administered by implantation or by intramuscular injection.

For nasal administration or administration by inhalation, the particles may be conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The particles may, if desired, be presented in a pack or dispenser device which may contain one or more unit dosage forms containing the active ingredient. The pack or dispensing device may be accompanied by instructions for administration.

The quantity of particle required for any particular application will to a large extent depend on the nature of the polyanion and/or extraneous material being delivered. Another important factor will include whether the particle is intended for in vitro or in vivo use. If the latter, the route of administration and particular formulation chosen as well as factors such as the age and condition of the subject will govern the quantity of particle used. In general however up to around 50 mg of particle can be used for every kilogram of body weight.

The following Examples illustrate the invention. These have been divided into sections for ease of understanding as follows:

SECTION 1

This describes the preparation of various bipolar lipids for use in the particles of the invention. The section is divided into:

Intermediates
 Section
B. Polyamine Intermediates
C. Disugar Intermediates
D. Long Chain Amino Acid Syntheses
E. Lipid Polyamines
F. Glycolipid Syntheses
G. Two Lipid Chain Syntheses Lipids
 Section
H. Carbohydrate Lipid Tetramines and Hexamines
I. PEG Lipids Compounds are referred to throughout the text by their Section numbering B1, B2, B3 . . . etc.

SECTION 2

This describes the preparation of functionalised lipids suitable for the attachment of a targeting molecule.

SECTION 3

This describes the preparation of targeted bipolar lipids according to the invention.

SECTION 4

This describes the preparation of particles of the invention and their use as delivery agents.

Throughout the Examples the following abbreviations are used:

| | |
|---|---|
| BOC | t-butoxycarbonyl; |
| DCM | dichloromethane; |
| EDC | 1-(3-dimethylaminopropyl)-3-ethylcarbodiimide; |
| TFA | trifluoroacetic acid; |
| LDA | lithium diisopropylamide; |
| PDC | pyridinium dichromate; |
| DBU | 1,8-diazabicyclo[5.4.0]un-dec-7-ene; |
| CBZ | benzyloxycarbonyl; |
| PEG | poly(ethyleneglycol); |
| THF | tetrahydrofuran; |
| DMF | dimethylformamide; |
| DMSO | dimethylsulphoxide; |
| HOBt | 1-hydroxybenzotriazole; |
| DMAP | 4-dimethylaminopyridine, |
| NHS | N-hydroxysuccinimide; |
| MAL | maleimide; |
| Me | CH$_3$; |
| Bn | benzyl; |
| Ph | phenyl; |
| tlc | thin layer chromatography |
| Ar | aryl; |
| Ac | acetate; |

SECTION 1

B. POLYAMINE INTERMEDIATES

This section contains the syntheses of:

BOC PROTECTED TETRAMINE (B8) N-(t-Butyloxycarbonyl)-N-(t-butyloxycarbonylaminobutyl)-2-[t-butyloxycarbonylaminobutyl(t-butyloxycarbonyl)aminomethyl]octane-1,8-diamine

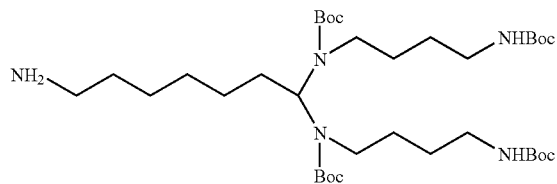

BOC PROTECTED HEXAMINE (B16) 11-Aminohexyl-4,9,13,18-tetrakis(t-butyloxy-carbonyl)-4,9,13,18-tetraazaeicosane-1,21-diamine

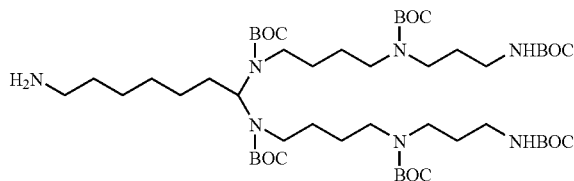

BOC PROTECTED DIMETHYLATED HEXAMINE (B21) N-[Methyl(t-butyloxycarbonyl)aminopropyl(t-butyloxy-carbonyl)aminobutyl(t-butyloxycarbonyl)]-2-[methyl(t-butyloxycarbonyl)aminopropyl(t-butyloxycarbonyl)-amino butyl(t-butyloxycarbonyl)aminomethyl]-1,8-octanediamine

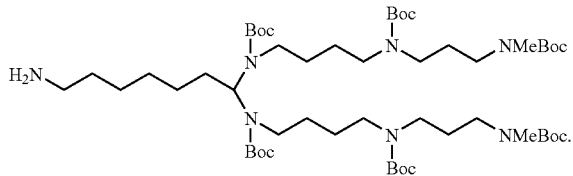

BOC PROTECTED TETRAMINE (B1) 1-Benzyloxy-6-chlorohexane.

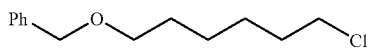

To a stirred solution of 6-chloro-1-hexanol (15.0 g, 0.110 mol) and benzyl bromide (18.8 g, 0.110 mol) in dry THF (200 ml) at room temperature under argon was slowly added (over 30 min.) sodium hydride powder (2.899 g, 0.121 mol). The solution was left overnight and the solids filtered off. The solvent was removed under reduced pressure, the residues taken up into dichloromethane (100 ml) and washed (2×20 ml water). The solution was dried over $MgSO_4$ and the solvent removed to yield an orange oil which was subsequently distilled (160° C., 0.5 mBar) to yield the title compound (17.5 g, 70%) as a colourless oil. $C_{13}H_{19}OCl$ requires 226. Found DCI: $MNH_4^+$, 244. δH ($CDCl_3$) 1.49 (4H, m, $(CH_2)_2(CH_2)_2Cl$), 1.70 (2H, p, $CH_2CH_2O$), 1.83 (2H, t, $CH_2CH_2Cl$), 3.54, 3.56 (4H, 2×t, $CH_2CH_2O$, $CH_2Cl$), 4.56 (2H, s, $CH_2Ph$), 7.40 (5H, m, Ph). δC ($CDCl_3$) 25.3 (1C, $CH_2(CH_2)_2Cl$), 26.4 (1C, $CH_2(CH_2)_3Cl$), 29.3 (1C, $CH_2(CH_2)_2O$), 32.3 (1C, $CH_2CH_2Cl$), 44.8 (1C, $CH_2Cl$), 69.9, 72.6 (2C, $CH_2O$), 127.2 (1C, $CH(CH_2)_2C$), 127.3 (2C, CHC), 128.1 (2C, CHCHC), 138.4 (1C, $CCH_2O$).

(B2) Diethyl 2-(benzyloxyhexyl)malonate

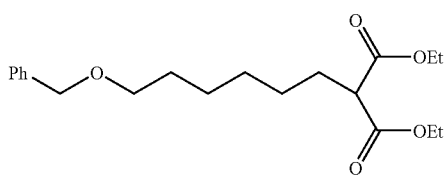

To sodium metal (1.32 g, 0.0573 mol) dissolved in dry ethanol (150 ml) under argon at room temperature was added diethyl malonate (14.13 g, 0.088 mol) over a period of 10 minutes and the solution left for 2 hours. B1 (10.0 g, 0.044 mol) was then added dropwise over 2 hours and this solution heated at reflux overnight. Excess salts were quenched by the addition of 50 ml of water and the total solvent volume reduced to 50-100 ml. Diethyl ether (100 ml) and water (50 ml) were added and the aqueous layer extracted 3 times with diethyl ether. The organic fractions were combined, dried ($K_2CO_3$), and the solvent removed to yield the crude product as a yellow oil. Distillation of the oil (0.5 mBar, 220° C.) gave the title compound (10.52 g, 68%) as a colourless viscous oil. δH ($CDCl_3$) 1.32 (6H, t, Me), 1.43 (6H, br s, $(CH_2)_3CH_2CH$), 1.69 (2H, p, $CH_2CH_2O$), 1.99 (2H, q, $CH_2CH$), 3.39 (1H, t, CH), 3.53 (2H, t, $CH_2OCH_2Ph$), 4.25, 4.28 (4H, 2×q, $OCH_2Me$), 4.57 (2H, s, $CH_2Ph$), 7.3-7.4 (5H, m, Ph). δC ($CDCl_3$) 13.9 (2C, Me), 25.7 (1C, $CH_2(CH_2)_2CH$), 27.1 (1C, $CH_2(CH_2)_2O$), 28.5 (1C, $CH_2CH_2CH$), 28.9 (1C, $CH_2CH_2O$), 29.5 (1C, $CH_2CH$), 51.8 ($CHCO_2Et$), 61.0 (2C, $OCH_2Me$), 70.1, 72.7 (2C, $CH_2OCH_2$), 127.3 (1C, CH$(CH)_2C$), 127.4 (2C, CHC), 128.1 (2C, CHCHC), 138.5 (1C, $CCH_2O$) 169.3 (2C, $CO_2$).

(B3) N,N'-bis(Aminobutyl)-2-(benzyloxyhexyl)malonamide

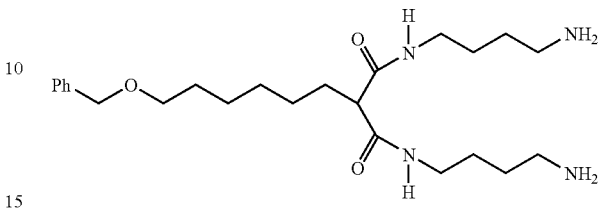

To a large excess of 1,4-diaminobutane (85 g, 0.964 mol) at 90° C. under argon was slowly added (over 2 hours) B2 (10.50 g, 0.030 mol). The solution was heated at 90° C. overnight and the excess diamine distilled off under reduced pressure (0.1 mBar, 28° C.) to quantitatively yield the title compound as a pale yellow low melting point solid. $C_{24}H_{42}N_4O_3$ requires 434. Found DCI: $M^++1$ 435. I.R. 1664 $cm^{-1}$ ($CO_2$). δH ($CDCl_3$) 1.15-1.40 (10H, br m, $(CH_2)_3CH_2CH$, $NH_2$), 1.40-1.60 (10H, br m, $(CH_2)_2CH_2NH_2$, $CH_2CH_2O$), 1.76 (2H, q, $CH_2CH$), 2.63 (4H, t, $CH_2NH_2$), 2.93 (2H, t, $CH_2CH$), 3.16 (4H, q, $CH_2NH$), 3.37 (2H, t, $CH_2OCH_2Ph$), 4.42 (2H, s, $CH_2Ph$), 7.26 (5H, m, Ph), 7.61 (2H, t, CONH). δC ($CDCl_3$) 25.7 (1C, $CH_2(CH_2)_2CH$), 26.6 (2C, $CH_2CH_2NH_2$), 28.8, 29.4 (2C, $CH_2CH_2CH$, $CH_2CH_2O$), 30.6 (2C, $CH_2CH_2NH$), 32.7 (1C, $CH_2CH$), 39.0 (2C, $CH_2NHCO$), 41.4 (2C, $CH_2NH_2$), 54.7 (1C, CHCO), 70.1, 72.6 (2C, $CH_2OCH_2$), 127.2 (1C, CH$(CH)_2C$), 127.3 (2C, CHC), 128.0 (2C, CHCHC), 138.5 (1C, $CCH_2O$), 171.0 (2C, CONH).

(B4) N,N'-bis(Aminobutyl)-2-benzyloxyhexyl-1,3-propanediamine

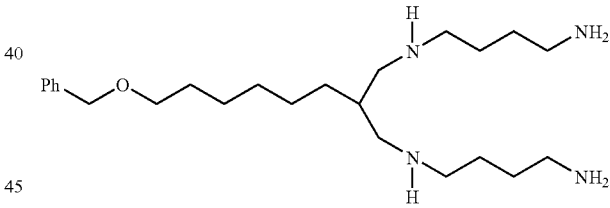

To B3 (0.430 g, 0.989 mmol) under argon was added an excess (25 ml) of 1.0 M $BH_3$-THF, and the solution heated at 85° C. overnight. Excess borane was slowly quenched with methanol (10 ml) and the solvents removed under reduced pressure. The residues were taken up into 0.1 M HCl (100 ml), heated at 60° C. for 1 hour, and the solvent removed under reduced pressure. The residues were entrained with methanol (4×20 ml), and the tetraamine hydrochloride salt taken up into water (30 ml). The solution was basified to pH~14 with sodium hydroxide and exhaustively extracted with dichloromethane. The organic fractions were combined, dried ($K_2CO_3$), and the solvent removed to yield the title compound (0.352 g, 88%) as a pale yellow oil I gum. $C_{24}H_{46}N_4O$ requires 406. Found DCI: $M^++1$, 407. δH ($CDCl_3$) 1.0-1.6 (25H, br m, CH$(CH_2)_5$, NH, $NH_2$, $(CH_2)_2CH_2NH_2$), 2.2-2.6 (12H, br m, $CH_2N$), 3.28 (2H, t, $CH_2OCH_2Ph$), 4.31 (2H, s, $CH_2Ph$), 7.14 (5H, m, Ph). δC ($CDCl_3$) 25.3 (1C, $CH_2CH_2CH$), 26.2 (1C, $CH_2(CH_2)_2CH$), 26.6 (2C, $CH_2CH_2NH_2$), 28.9 (2C, $CH_2(CH_2)_2CH_2$), 30.7 (3C, $CH_2CH_2NH$, $CH_2CH_2O$), 37.6 (1C, CH), 41.2 (2C, $CH_2NH_2$), 49.3 (2C, $(CH_2)_3CH_2NH$), 53.5 (2C, $CHCH_2NH$), 69.5, 71.9 (2C, CH$_2$OCH$_2$), 126.5 (1C, CH(CH)$_2$C), 126.6 (2C, CHC), 127.4 (2C, CHCHC), 137.8 (1C, CCH$_2$O).

(B5) N,N'-bis(t-Butyloxycarbonyl)-N-[2-t-butyloxycarbonyl-aminobutyl(t-butyloxycarbonyl)aminomethyl]benzyloxyoctyl-1,4-diaminobutane.

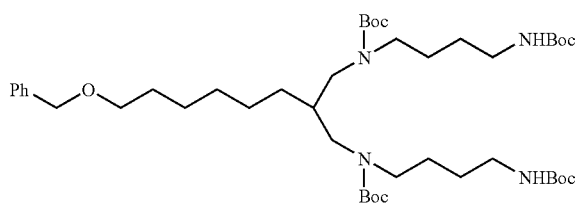

B4 (10 g, 24.6 mmol) was dissolved in aqueous sodium hydroxide (100 ml, 2M). To this solution was added t-butyldicarbonate (27 g, 123.3 mmol) portionwise with stirring at room temperature. The reaction was stirred overnight, water added and the aqueous phase extracted with ethyl acetate. The combined organic extracts were washed with water, brine, dried & evaporated to give the crude product. Chromatography (silica—20% ethyl acetate in hexane) gave the title compound as a glass (11 g, 55%). C$_{44}$H$_{78}$N$_4$O$_9$ requires 806. Found DCI: M$^+$+1, 807.8. δH (CDCl$_3$) 7.74 (5H, m, ArH), 4.49 (2H, s, CH$_2$Ar), 3.45 (2H, t, CH$_2$OCH$_2$Ph), 2.9-3.3 (12H, m, CH$_2$N), 1.95 (1H, brm, CH$_2$CH(CH$_2$)$_2$), 1.2-1.7 (52H, m, CH$_2$).

(B6) 8-[t-Butyloxycarbonylaminobutyl(t-butyloxycarbonyl)amino]-7-[t-butyloxycarbonylaminobutyl(t-butyloxy-carbonyl)aminomethyl]octanol

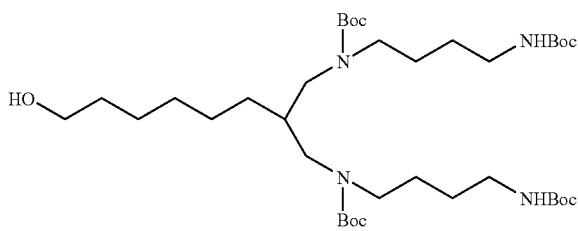

To B5 (11 g) in methanol (70 ml) under argon was added palladium on carbon catalyst (1 g). The stirred suspension was put under a hydrogen atmosphere for two days at atmospheric pressure and room temperature. The mixture was filtered through Celite which was washed with dichloromethane. Evaporation yielded the title compound (9.67 g, 87%) which was used for the next stage without purification.

(B7) 8-[t-Butyloxycarbonylaminobutyl(t-butyloxycarbonyl)amino]-7-[t-butyloxycarbonylaminobutyl(t-butyloxy-carbonyl)aminomethyl]octyl methanesulphonate

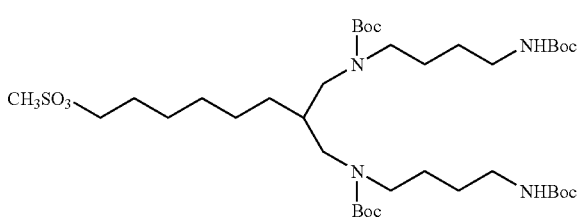

Methanesulphonyl chloride (1.25 ml, 16.21 mmol) was added to a stirred solution of B6 (9.67 g, 13.5 mmol) in dry dichloromethane (100 ml) containing triethylamine (2.82 ml, 20.26 mmol) at 0° C. The flask was stirred at 0° C. for 1 hr, then overnight at room temperature. The solvent was removed and the residue chromatographed (silica—50% ethyl acetate in hexane) to yield the title compound (8.5 g, 79%. C$_{38}$H$_{74}$N$_4$O$_{11}$S requires 794. Found DCI: M$^+$+1, 795.6. δH (CDCl$_3$) 3.45 (2H, t, CH$_2$O), 2.9-3.3 (12H, m, CH$_2$N), 2.99 (3H, s, MeS), 1.95 (1H, brm, CH$_2$CH(CH$_2$)$_2$), 1.2-1.8 (50H, m, CH$_2$).

(B8) N-(t-Butyloxycarbonyl)-N-(t-butyloxycarbonylaminobutyl)-2-[t-butyloxycarbonylaminobutyl(t-butyloxycarbonyl)aminomethyl]octane-1,8-diamine

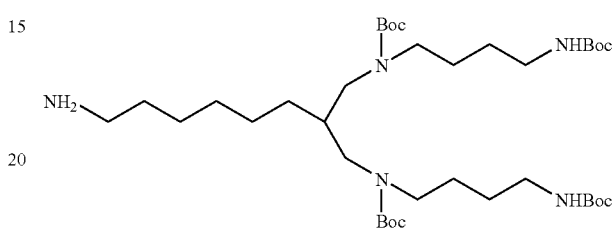

Sodium azide (2.05 g, 31.6 mmol) was added to a stirred solution of B7 (8.36 g, 10.53 mmol) in dry DMF (35 ml) at room temperature. The reaction was stirred for 48 hr and water added. The aqueous solution was extracted with ethyl acetate. The organic phase was washed with brine, dried (MgSO$_4$) and evaporated to dryness. The product was chromatographed (silica—up to 50% ethyl acetate in hexane) and the resulting azide was dissolved in methanol (100 ml) under argon and palladium on charcoal added. The atmosphere was changed to hydrogen and the reaction stirred overnight. The catalyst was filtered off and the product chromatographed (silica—up to 20% methanol in dichloromethane containing triethylamine to yield the title compound (45 g). C$_{37}$N$_{73}$N$_5$O$_8$ requires 715.55. Found DCI: M$^+$+1, 716.7. δH (CDCl$_3$) 4.71 (2H, br, NHBoc), 2.95-3.3 (12H, m, CH$_2$N), 2.85 (2H, br, NH$_2$), 2.75 (2H, t, CH$_2$NH$_2$), 1.95 (1H, brm, CH$_2$CH(CH$_2$)$_2$), 1.2-1.7 (54H, m, CH$_2$).

BOC PROTECTED HEXAMINE SYNTHESIS (B9) N,N'-bis(p-Methoxyphenylsulphonyl)-N-{2-[-methoxyphenylsulphonylaminobutyl(p-methoxyphenylsulphonyl)aminomethyl]benzyloxyoctyl}-1,4-butane-diamine

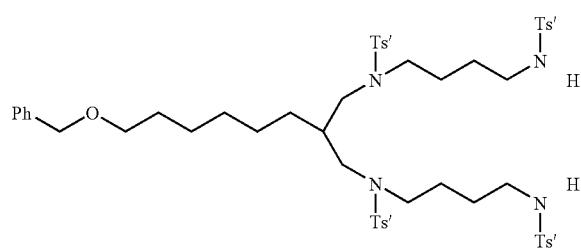

To B4 (301 mg, 0.740 mmol) and triethylamine (749 mg, 7.40 mmol) in dry THF (30 ml) under argon at −50° C. was slowly added p-methoxybenzenesulphonyl chloride (627 mg, 3.03 mmol). The solution was allowed to slowly warm to room temperature and left overnight. The product (tlc r.f. 0.7, 2% methanol in dichloromethane) was purified by gradient alumina column chromatography (0-2% methanol in dichloromethane) to yield the title compound (610 mg, 76%) as a colourless gum/solid. δH (CDCl$_3$) 1.15-1.70 (18H, br m, (CH$_2$)$_5$CH$_2$O, (CH$_2$)$_2$CH$_2$NH), 2.00 (1H, t, CH), 2.75-3.15 (12H, br m, CH$_2$N), 3.45 (2H, t, CH$_2$OCH$_2$Ph), 3.81, 3.84 (12H, 2×s, OMe), 4.47 (2H, s, CH$_2$Ph), 5.25 (2H, t, NH), 6.92, 6.97 (8H, 2×d, CHCSO$_2$), 7.29 (5H, m, Ph), 7.69, 7.75 (8H, 2×d, CHCOMe). δC (CDCl$_3$) 25.2-26.2 (5C, CH(CH$_2$)$_5$), 29.2, 29.3 (4C, (CH$_2$)$_2$CH$_2$NH), 36.0 (1C, CH), 42.1 (2C, CH$_2$NH), 48.8 (2C, (CH$_2$)$_3$CH$_2$NH), 51.2 (2C, CHCH$_2$N), 55.2 (4C, OMe), 70.0, 72.3 (2C, CH$_2$OCH$_2$), 113.8, 114.0 (8C, CHCSO$_2$), 127.0, 127.2, 127.9 (5C, Ph), 128.7, 128.9 (8C, CHCOMe), 129.8, 131.0 (4C, CSO$_2$), 138.2 (1C, CCH$_2$O), 162.3, 162.5 (4C, COMe).

(B10) 11-Benzyloxyhexyl-4,9,13,18-tetrakis(p-toluene-sulphonyl)-4,9,13,18-tetraazaeicosane-1,21-dinitrile

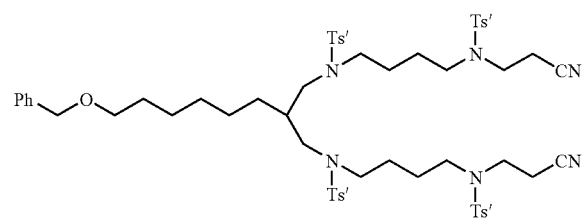

To B9 (588 mg, 0.541 mmol) and mesh potassium carbonate (523 mg, 3.784 mmol) in 20 ml of dry DMF under argon was added freshly distilled acrylonitrile (95 mg, 1.787 mmol) and the reaction left stirring at room temperature for 3-4 days. T.l.c. (alumina 2% MeOH in CH$_2$Cl$_2$) indicated the presence of two compounds r.f 0.9 and 0.8, later shown to be the desired di-nitrile and the mono-nitrile respectively. Gradient alumina column chromatography (as for B9) yielded the title compound as a colourless gum/solid in 52% (337 mg) yield. C$_{58}$H$_{76}$N$_6$O$_{13}$S$_4$ requires 1193 Found ES+: MNa$^+$ 1216. δH (CDCl$_3$) 1.15-1.40 (8H, br m, CH(CH$_2$)$_4$), 1.40-1.70 (10H, br, (CH$_2$)$_2$CH$_2$N, CH$_2$CH$_2$O), 2.02 (1H, t, CH), 2.63 (4H, t, CH$_2$CN), 2.80-3.16 (12H, br m, CH$_2$N), 3.24 (4H, t CNCH$_2$CH$_2$N), 3.47 (2H, t, CH$_2$OCH$_2$Ph), 3.81, 3.82 (12H, 2×s, OMe), 4.46 (2H, s, CH$_2$Ph), 6.95, 6.96 (8H, 2×d, CHCSO$_2$), 7.29 (5H, m, Ph), 7.69, 7.70 (8H, 2×d, CHCOMe). δC (CDCl$_3$) 18.9 (2C, CH$_2$CN), 25.3-28.3 (5C, CH(CH$_2$)$_5$), 29.6, 29.7 (4C, (CH$_2$)$_2$CH$_2$N), 36.4 (1C, CH), 44.5 (2C, CNCH$_2$CH$_2$), 48.7 (2C, CH$_2$N(CH$_2$)$_2$CN), 49.0 (2C, CH$_2$NCH$_2$CH), 51.5 (2C, CHCH$_2$N), 55.5 (4C, OMe), 70.3, 72.7 (2C, CH$_2$OCH$_2$), 114.2, 114.4 (8C, CHCSO$_2$), 117.7 (2C, CN), 127.3, 127.5, 128.2 (5C, Ph), 129.2 (8C, CHCOMe), 129.5, 130.2 (4C, CSO$_2$), 138.5 (1C, CCH$_2$O), 162.7, 163.0 (4C, COMe).

(B11) 11-Benzyloxyhexyl-4,9,13,18-tetrakis(p-toluene-sulphonyl)-4,9,13,18-tetraazaeicosane-1,21-diamine

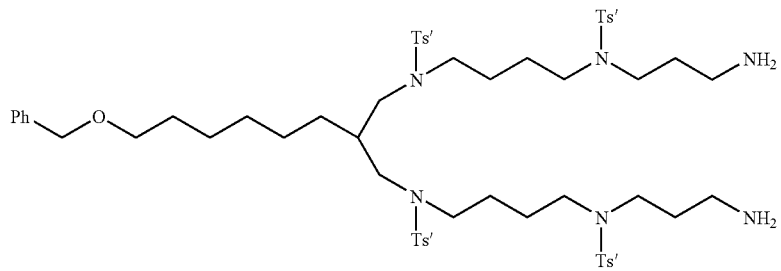

To B10 (337 mg, 0.282 mmol) under argon was added an excess (30 ml) of 1.0 M BH$_3$-THF, and the solution heated at 85° C. overnight. Excess borane was slowly quenched with methanol (10 ml) and the solvents removed under reduced pressure. The residues were taken up into 0.1 M HCl (100 ml), heated at 60° C. for 1 hour, and the solvent removed under reduced pressure. The residues were entrained with methanol (4×20 ml), and the hydrochloride salt taken up into water (30 ml). The solution was basified to pH>14 with sodium hydroxide and exhaustively extracted with dichloromethane. The organic fractions were combined, dried (K$_2$CO$_3$), and the solvent removed to yield the title compound (285 mg, 84%) as a colourless gum/solid. C$_{58}$H$_{84}$N$_6$O$_{13}$S$_4$ requires 1201. Found ES+: MH$^+$ 1202. δH (CDCl$_3$) 1.2-1.7 (26H, br m, CH(CH$_2$)$_5$, CH$_2$(CH$_2$)$_2$CH$_2$N, CH$_2$CH$_2$NH$_2$), 2.20 (1H, t, CH), 2.70 (4H, t, CH$_2$NH$_2$), 2.85-3.35 (16H, br m, CH$_2$N), 3.50 (2H, t, CH$_2$OCH$_2$Ph), 3.86, 3.88 (12H, 2×s, OMe), 4.52 (2H, s, CH$_2$Ph), 6.99, 7.02 (8H, 2×d, CHCSO$_2$), 7.75, 7.76 (8H, 2×d, CHCOMe). δC (CDCl$_3$) 25.1-26.2 (5C, CH(CH$_2$)$_5$), 29.4, 29.6 (4C, CH$_2$(CH$_2$)$_2$CH$_2$N), 32.0 (2C, CH$_2$CH$_2$NH$_2$), 36.2 (1C, CH), 38.8 (2C, CH$_2$NH$_2$), 45.9 (2C, CH$_2$(CH$_2$)$_2$NH$_2$), 47.7 (2C, CH$_2$N(CH$_2$)$_3$NH$_2$), 48.7 (2C, CHCH$_2$NCH$_2$), 51.1 (2C, CHCH$_2$N), 55.3 (4C, OMe), 70.1, 72.5 (2C, CH$_2$OCH$_2$), 113.9, 114.0 (8C, CHCSO$_2$), 127.1, 127.3, 128.0 (5C, Ph), 128.8, 129.0 (8C, CHCOMe), 130.2, 130.7 (4C, CSO$_2$), 138.5 (1C, CCH$_2$O), 162.4, 162.5 (4C, COMe).

(B12) 8-(Aminopropylaminobutylamino)-7-(aminopropylaminobutylaminomethyl)octanol

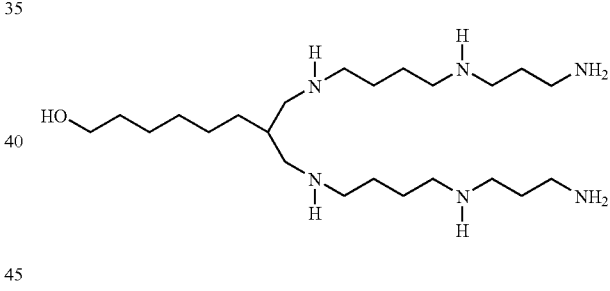

To B11 (743 mg, 0.618 mmol) in THF (30 ml) and ethanol (2 ml) at −78° C. was condensed liquid ammonia (75 ml). To this was then added 300 mg of lithium metal (turned blue), and the solution stirred for 2 hours. The solution was then allowed to slowly warm to room temperature overnight, boiling off the ammonia as it did. Ethanol (2 ml) followed by water (70 ml) were added to the now yellow solution and the organic solvents removed under reduced pressure. The pH of the remaining aqueous solution was lowered to 2 (concentrated HCl), washed (4×20 ml) with diethyl ether, and basified to pH 10-12 (NaOH). The solvent was removed to yield the title compound in the presence of a large excess of salts. This material was used for the next step without purification.

(B13) 8-[t-Butyloxycarbonylaminopropyl(t-butyloxycarbonyl)aminobutyl (t-butyloxycarbonyl)amino]-7-[t-butyloxycarbonylaminopropyl(t-butyloxycarbonyl)aminobutyl (t-butyloxycarbonyl)aminomethyl]octanol

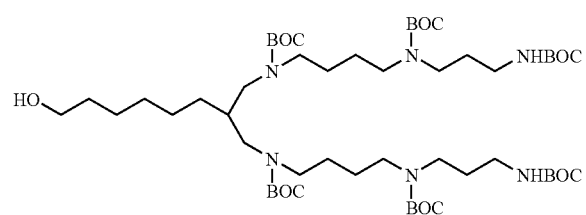

To B12 dissolved in methanol (5 ml) was added 10 equivalents of ditertbutyl dicarbonate (1.349 g, 6.183 mmol) and the solution left overnight. The solvent was removed, the residues taken up into water (20 ml), and extracted with dichloromethane (5×30 ml). The organic fractions were combined, dried (K$_2$CO$_3$), and the solvent removed to yield a pale yellow gum. Purification required alumina column chromatography (0-3% methanol in dichloromethane) to yield the desired BOC protected title compound (alumina tlc r.f. 0.7, 5% methanol in dichloromethane) as a colourless gum (281 mg, 44%). C$_{53}$H$_{102}$N$_6$O$_{13}$ requires 1031. Found ES+: MH$^+$ 1032, ES−: M$^-$ 1031, MCl$^-$ 1066. δH (CDCl$_3$) 1.1-2.0 (77H, br m, C(Me)$_3$, CH(CH$_2$)$_5$, CH$_2$(CH$_2$)$_2$CH$_2$N, CH$_2$CH$_2$NH), 2.7-3.4 (20H, br, CH$_2$N), 3.53 (2H, t, CH$_2$O), 5.26, 5.45 (2H, br, NHBOC). δC (CDCl$_3$) partial 43.5, 46.5, 48.9 (10C, CH$_2$N), 62.1 (1C, CH$_2$OH), 78.5, 79.1 (6C, C(Me)$_3$), 155.3, 155.7 (6C, CO).

(B14) 8-[t-Butyloxycarbonylaminopropyl(t-butyloxycarbonyl)aminobutyl (t-butyloxycarbonyl)amino]-7-[t-butyloxycarbonylaminopropyl(t-butyloxycarbonyl)aminobutyl (t-butyloxycarbonyl)aminomethyl]octyl methanesulphonate

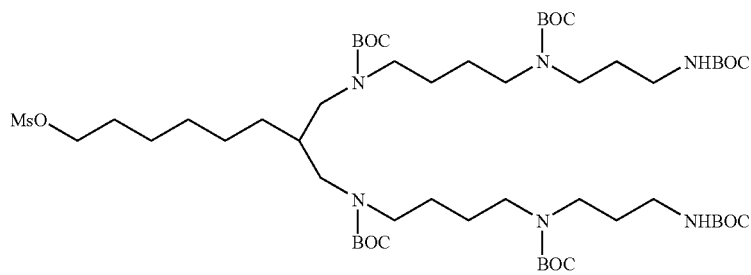

To B13 (555 mg, 0.538 mmol) and triethylamine (163 mg, 1.614 mmol) in dry dichloromethane (20 ml) at −20° C. under argon was added mesyl chloride (124 mg, 1.076 mmol) dropwise in dichloromethane (5 ml) over a period of 30 minutes. The solution was allowed to warm to room temperature and left overnight. The solvent was removed to quantitatively yield the title compound, tlc r.f. 0.35 (5% methanol in dichloromethane on alumina). δH (CDCl$_3$) 1.1-2.0 (77H, br m, C(Me)$_3$, CH(CH$_2$)$_5$, CH$_2$(CH$_2$)$_2$CH$_2$N, CH$_2$CH$_2$NH), 2.7-3.4 (20H, br, CH$_2$N), 3.01 (3H, s, MeS), 4.18 (2H, t, CH$_2$O), 5.26, 5.45 (2H, br, NHBOC). δC (CDCl$_3$) partial 38.4 (MeS), 43.5, 46.5, 48.9 (10C, CH$_2$N), 69.3 (C, CH$_2$O) 78.5, 79.1 (6C, C(Me)$_3$), 155.3, 155.7 (6C, CO).

(B15) 11-Azidohexyl-N,N',4,9,13,18-hexa(t-butyloxycarbonyl)-4,9,13,18-tetraaza-1,21-eicosanediamine

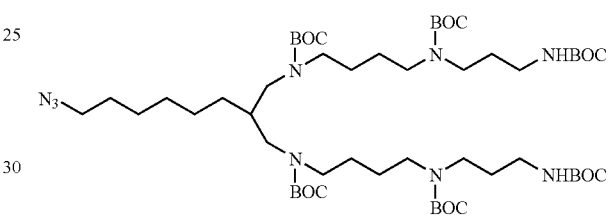

To the crude mesylate B14 in dry DMF (15 ml) under argon was added excess sodium azide (600 mg) and the solution/suspension stirred overnight. The volume was reduced to approximately 5 ml and added to 70 ml of water. This aqueous phase was extracted with ethyl acetate (10×30 ml) and the organics combined, dried (MgSO$_4$) and the solvent removed to yield the title compound as a pale yellow gum (570 mg, 100%). I.R. 2095 cm$^{-1}$ (N$_3$). C$_{53}$H$_{101}$N$_9$O$_{12}$ requires 1056. Found ES+: MH$^+$ 1057, MNa$^+$ 1079. δH (CDCl$_3$) 1.1-2.0 (77H, br m, C(Me)$_3$, CH(CH$_2$)$_5$, CH$_2$(CH$_2$)$_2$CH$_2$N, CH$_2$CH$_2$NH), 2.7-3.4 (20H, br, CH$_2$N), 3.31 (2H, t, CH$_2$N$_3$), 5.26, 5.45 (2H, br, NHBOC). δC (CDCl$_3$) partial 43.5, 46.5, 48.9 (10C, CH$_2$N), 51.3 (1C, CH$_2$N$_3$), 78.5, 79.1 (6C, C(Me)$_3$), 155.3, 155.7 (6C, CO).

(B16) 11-Aminohexyl-4,9,13,18-tetrakis(t-butyloxycarbonyl)-4,9,13,18-tetraazaeicosane-1,21-diamine

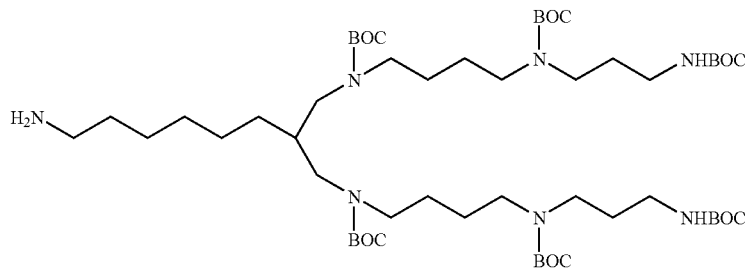

To B15 (134 mg, 0.127 mmol) in methanol (15 ml) was added 10% Pd/C (40 mg) and the suspension stirred overnight under an atmosphere of hydrogen. Removal of the catalyst by filtration through Celite followed by removal of the solvent gave the desired title compound as a colourless gum in quantitative yield (131 mg). $C_{53}H_{103}N_7O_{12}$ requires 1030. Found ES+: $MH^+$ 1031, $MHNa^{2+}$ 527. $\delta H$ (CDCl$_3$) 1.1-2.0 (79H, br m, NH$_2$, C(Me)$_3$, CH(CH$_2$)$_5$, CH$_2$(CH$_2$)$_2$CH$_2$N, CH$_2$CH$_2$NH), 2.7-3.4 (22H, br, CH$_2$N), 5.26, 5.45 (2H, br, NHBOC). $\delta C$ (CDCl$_3$) partial 39.8 (1C, CH$_2$NH$_2$), 43.5, 46.5, 48.9 (10C, CH$_2$N), 78.5, 79.1 (6C, C(Me)$_3$), 155.3, 155.7 (6C, CO).

BOC PROTECTED DIMETHYLATED HEXAMINE
(B17) N,N'-bis(t-Butyloxycarbonylaminopropanoylaminobutyl)-2-(benzyloxyhexyl)malonamide

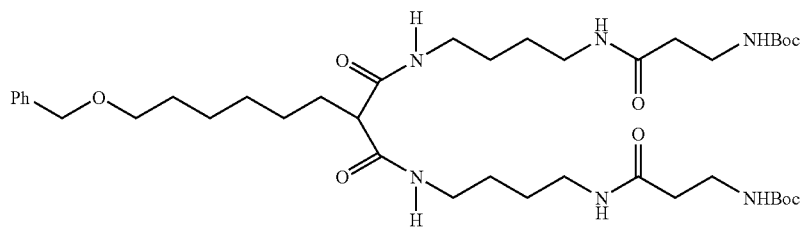

To a solution of BOC-β-alanine (2.5 g, 13.22 mmol) in dry dichloromethane (20 ml) was added N-methylmorpholine (1.6 ml, 14.55 mmol) followed by N-hydroxysuccinimide (91.67 g, 14.55 mmol). The flask was left stirring at 20° C. for 5 mins under argon before adding EDC (2.79 g, 14.55 mmol). The reaction was stirred overnight. Tlc showed that all the acid had been converted to the active ester. A solution of the B3 (2.86 g, 6.61 mmol) and triethylamine (4.6 ml, 33.05 mmol) in dichloromethane was added and the reaction stirred for 1 h. A precipitate formed. The product was purified by chromatography (silica—5-10% methanol in dichloromethane) to give the title compound as a glass (2.31 g, 46%). The product on Tlc is green when sprayed with ninhydrin and contains bis-BOC-1,4-diaminobutane, an impurity in the starting material. $C_{40}H_{60}N_6O_9$ requires 776.5. Found ES: $M^++1$ 777.6. $\delta H$ (CDCl$_3$) 7.31 (5H, m, PhCH$_2$O), 4.47 (2H, s, PhCH$_2$O), 3.45 (2H, t, PhCH$_2$OCH$_2$), 3.4-3.1 (12H, dm, CH$_2$N), 3.02 (1H, t, CHR$_3$), 2.34 (4H, t, COCH$_2$), 1.9-1.2 (26H, m, CH$_2$+Me).

(B18) 13-Benzyloxyhexyl-2,6,11,15,20,24-hexa(t-butyloxycarbonyl)-2,6,11,15,20,24-hexaazapentacosane

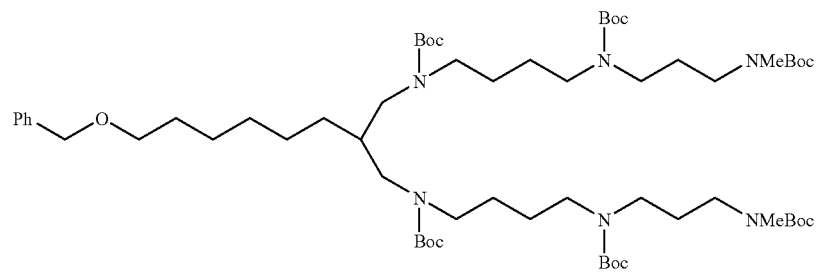

B17 (15.36 g, 15.36 mmol) was suspended in THF (240 ml) and borane methylsulphide complex (10M, 32 ml, 320 mmol) in THF (50 ml) added dropwise. Hydrogen was evolved and the tetraamide dissolved over 1 hr. The reaction was refluxed for 48 hr and carefully quenched with methanol. Solvent was removed in vacuo and hydrochloric acid added (6M, 100 ml). The reaction was refluxed for 1 hr at 60° C. and the hydrochloric acid removed in vacuo. The product was entrained in methanol and the solvent removed. The residue was dissolved in methanol containing 20% water and basified with solid sodium hydroxide and tert-butyl dicarbonate (32.7 g, 150 mmol) was added whilst maintaining the pH at 12. The basic solution was extracted with ethyl acetate, washed with brine, dried (MgSO$_4$) and evaporated to dryness. The residue was columned on silica (33% ethyl acetate in hexane) to give the title compound as an oil. $C_{60}H_{106}N_6O_{13}$ requires 1142. δH (CDCl$_3$) 7.31 (5H, m, PhCH$_2$O), 4.48 (2H, s, PhCH$_2$O), 3.44 (2H, t, PhCH$_2$OCH$_2$), 3.4-3.1 (20H, m, CH$_2$N), 3.02 (1H, t, CHR$_3$), 2.82 (6H, s, NMe), 1.9-1.2 (76H, m, CH$_2$+Me).

(B19)  8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl] octanol

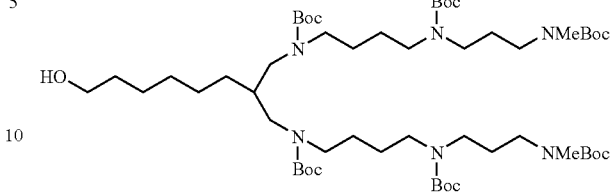

B18 (10.23 g, 89.6 mmol) was dissolved in t-butanol (100 ml) to which was added Raney nickel (8 ml) under argon. The atmosphere was changed to hydrogen and the reaction stirred for 48 hr. The Raney nickel was removed by filtration (glass fibre) and the product purified by chromatography on silica (50-75% ethyl acetate in hexane) to yield the title compound (6.75 g, 70%). $C_{55}H_{106}N_6O_{13}$ requires 1058.8. Found ES: MNa$^+$ 1081.8. δH (CDCl$_3$). 3.62 (2H, t, HOCH$_2$), 3.3-3.0 (20+1H, m, CH$_2$N+CHR$_3$), 2.84 (6H, s, NMe), 1.9-1.2 (76H, m, CH$_2$+Me).

(B20)  8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl] octyl methanesulphonate

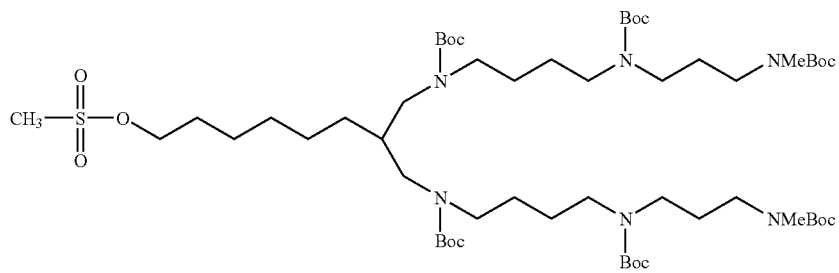

B19 (6.75 g, 6.54 mmol) was dissolved in dichloromethane (40 ml) containing triethylamine (1.2 ml) at 0° C. Methane sulphonyl chloride (0.6 ml, 7.8 mmol) was added in dichloromethane (10 ml) under argon. After 2 hr Tlc showed complete reaction (silica, 66% ethyl acetate in hexane). The title compound was evaporated to dryness and used in the next step without further purification. $C_{56}H_{108}N_6O_{15}S$ requires 1136.76. Found ES: M$^+$+1 1138.0 δH (CDCl$_3$). 4.21 (2H, t, HOCH$_2$), 3.3-3.0 (20+1H, m, CH$_2$N+CHR$_3$), 2.84 (6H, s, NMe), 2.99 (3H, s, SMe), 1.9-1.2 (76H, m, CH$_2$+Me.

(21)  13-Aminohexyl-2,6,11,15,20,24-hexakis(t-butyloxycarbonyl)-2,6,11,15,20,24-hexaazaeicosane

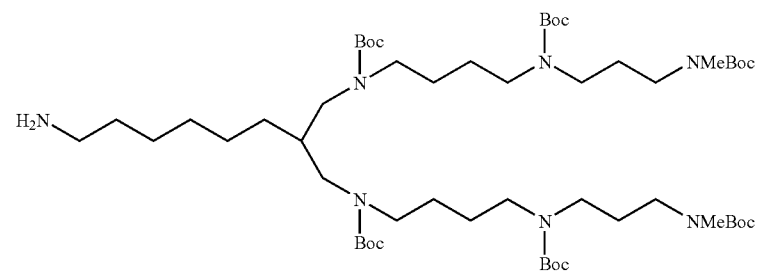

B20 (6.7 g, 6.5 mmol) was dissolved in DMF with heating, cooled and sodium azide (2.5 g) added portionwise. After 24 hr stirring the reaction was poured into brine (1l) and extracted with ethyl acetate. The organic phase was washed with water, dried and evaporated to dryness. This material was used for the reduction without purification. The crude azide was dissolved in t-butanol (50 ml) and 10% palladium on carbon (2 g) added under argon. The atmosphere was changed to hydrogen and the reaction stirred for 48 hr. The catalyst was removed and the product evaporated to dryness. The product was purified by chromatography (silica saturated with triethylamine, 1-10% methanol in DCM containing 0.1% triethylamine) to yield the title compound (3 g) as a glassy solid. $C_{55}H_{107}N_7O_{12}$ requires 1057.8. Found ES: M$^+$+1 1058.7 δH (CDCl$_3$). 3.3-2.9 (20+1H, m, CH$_2$N+ CHR$_3$), 2.83 (6H, s, NMe), 2.72 (2H, t, NH$_2$CH$_2$), 1.9-1.1 (76H, m, CH$_2$+Me).

C. DISUGAR INTERMEDIATES

This section contains the synthesis of the following:

(C4) N,N'-bis(Peracetylglucuronylaminoethyl)succinamic acid

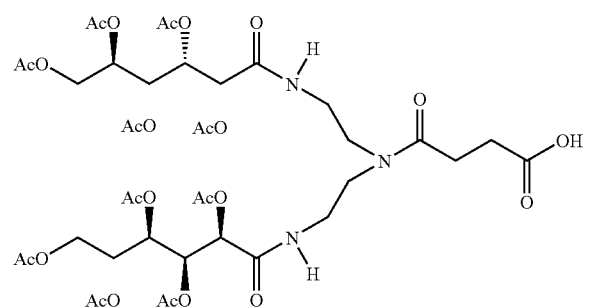

(C1) bis(Glucuronylaminoethyl)amine

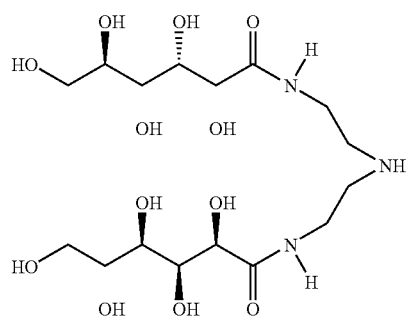

To a solution of d-gluconolactone (10.000 g, 56.14 mmol) in dry methanol (200 ml) under argon was added diethylenetriamine (2.825 g, 27.38 mmol) and the reaction stirred at room temperature overnight resulting in the formation of white precipitates. The solvent was removed from the resulting suspension giving a quantitative yield of the title compound as a pure white solid. $C_{16}H_{33}N_3O_{12}$ requires 459.2. Found ES$^+$: MH$^+$, 460.2. $δ_H$ (D$_2$O) 2.79 (4H, t, CH$_2$NHCH$_2$), 3.40 (4H, dt, CH$_2$NHCO), 3.6-3.9 (8H, m, CHOH), 4.09 (2H, d, CH$_2$OH), 4.33 (2H, d, CH$_2$OH).

(C2) N,N'-bis(Glucuronylaminoethyl)-O-t-butylcarbamate

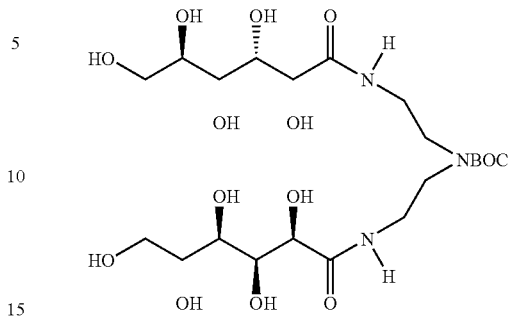

To C1 (7.000 g, 15.23 mmol) dissolved in methanol (235 ml) and water (90 ml) were added di-tert-butyl dicarbonate (3.990 g, 18.28 mmol) and triethylamine (1.542 g, 15.23 mmol) and the reaction stirred overnight at room temperature. The solvent was removed to quantitatively yield the BOC protected title compound which was used crude in the next synthetic step. $C_{20}H_{37}N_3O_{15}$ requires 559.2. Found ES$^+$: MH$^+$, 560.4. $δ_H$ (D$_2$O) 1.47 (9H, s, C(Me)$_3$), 3.3-3.6 (8H, br, CH$_2$N), 3.6-3.8 (8H, m, CHOH), 4.09 (2H, br s, CH$_2$OH), 4.30 (2H, d, CH$_2$OH).

(C3) N,N'-bis(Peracetylglucuronylaminoethyl)-O-t-butylcarbamate

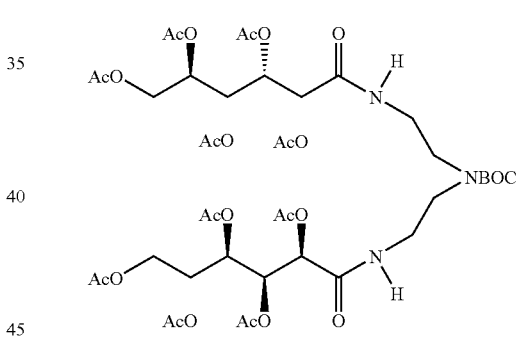

To a solution of crude C2 (15.23 mmol) in dry pyridine (50 ml) at 0° C. under argon was slowly added acetic anhydride (120 ml) and the solution allowed to warm to room temperature overnight. The majority of the solvent was removed and to the residues was added water (100 ml) and ethyl acetate (150 ml). The organic layer was separated off and the remaining aqueous layer extracted with more ethyl acetate (5×50 ml). The organics were combined, washed (1×citric acid, 4×water) and dried (MgSO$_4$) to yield on removal of the solvent a pale yellow gum. Gradient silica column chromatography (80% ethyl acetate in hexane to ethyl acetate) yielded the desired polyacetylated title compound (13.1 g, 88% as a white solid. $C_{41}H_{61}N_3O_{24}$ requires 979.4. Found ES$^+$: MNa$^+$, 1002.4. $δ_H$ (CDCl$_3$) 1.45 (9H, s, C(Me)$_3$), 2.02, 2.03, 2.04, 2.06, 2.09 (30H, 5×s, MeCO), 3.34 (8H, br, CH$_2$N), 4.10, 4.31 (4H, 2×dd, CH$_2$OAc), 5.06 (2H, m, CHOAc), 5.23 (2H, br, CHOAc), 5.45 (2H, q, CHOAc), 5.61 (2H, t, CHOAc), 6.61, 7.18 (2H, 2×br, NHCO).

(C4) N,N'-bis(Peracetylglucuronylaminoethyl)succinamic acid

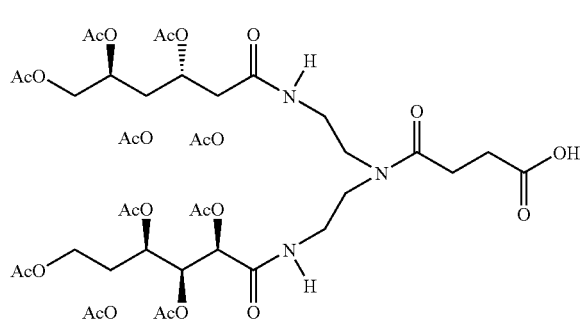

To C3 (3.000 g, 3.06 mmol) was added 1:1 trifluoroacetic acid: dichloromethane (15 ml) and the solution left at room temperature for 15 minutes. The solvent was removed and the residues dissolved in dry dichloromethane (40 ml). To this solution was added succinic anhydride (613 mg, 6.12 mmol) and triethylamine (1.549 g, 15.31 mmol) and the reaction stirred overnight at room temperature under argon. The solvent was removed, the residues taken up into dichloromethane (100 ml) and 1M aqueous HCl (50 ml) added. The solution was rapidly stirred for 5 hours, the aqueous layer removed, and the remaining organic layer washed (3×water). This was then dried (MgSO$_4$) and the solvent removed to yield the title compound as a white solid (2.945 g, 98%). $C_{40}H_{57}N_3O_{25}$ requires 979.3 Found ES$^+$: MH$^+$, 980.2, MNa$^+$, 1002.2, ES$^-$ (M—H$^+$)$^-$ 978.2. $\delta_H$ (CDCl$_3$) 2.03-2.23 (30H, 10×s, Me), 2.4-2.8 (4H, m, CH$_2$CO), 3.3-3.9 (8H, brm, CH$_2$N), 4.11 (2H, m, CH$_2$OAc), 4.35 (2H, dt, CH$_2$OAc), 5.09 (2H, 2×q, CHCH$_2$OAc), 5.18 (1H, d, CHCO), 5.27 (1H, d, CHCO), 5.44, 5.46, 5.58, 5.59 (4H, 4×t, CHOAc), 7.07, 7.15 (2H, 2×t, CONH).

D. LONG CHAIN AMINOACIDS

This section contains the syntheses of:
C$_{24}$ AMINOACID (D6) 24-Aminotetracosanoic acid

C$_{18}$ AMINOACID (D10) 18-Aminooctadecanoic acid

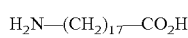

C$_{20}$ REDUCED BIXIN AMINOACID
(D15) N-Aminoethyl-4,8,13,17-tetramethyl-1,20-dodecanamoic acid trifluoroacetate salt

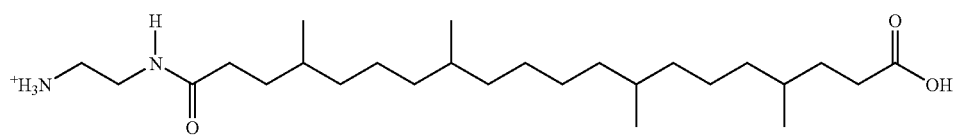

C24 AMINOACID CONTAINING MID-CHAIN AMIDE
(D18) 12-(Aminododecanoylamino)dodecanoic acid

(D19) 24-(Benzyloxycarbonylamino)tetracosanoic acid

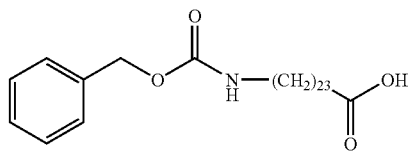

C$_{24}$ AMINOACID
(D1) 12-Aminododecanol hydrochloride

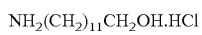

12-Aminododecanoic acid (21.52 g, 100 mmol) was suspended in 100 ml THF and borane THF complex (500 mmol, 1M solution) added. The reaction was left overnight and carefully quenched with methanol before evaporation to small bulk. The residue was suspended in 1M HCl (500 ml) and heated at 40° C. for 1 hr and left overnight. The white solid was filtered off and washed with cold 1M HCl. The product was recrystallised from 1M HCl, filtered off and dried over P$_2$O$_5$ in vacuo to yield the title compound (18.70 g, 79%). Mp 120° C. softens, 169° C. liquid. $C_{12}H_{28}N_1O_1Cl.1/5$ H$_2$O requires C: 59.70%, H: 11.86%, N: 5.80%. Found: C: 59.65%, H: 11.82%, N: 5.76%. $C_{12}H_{27}N_1O_1$ requires 201. Found ES+: MH$^+$ 202.1 (100%). $\delta_H$ (CD$_3$CO$_2$D) 3.64 (2H, t, CH$_2$O), 3.06 (2H, t, NCH$_2$), 1.73 (2H, m, CH$_2$CH$_2$O), 1.57 (2H, m, NCH$_2$CH$_2$), 1.2-1.5 (16H, m, CH2).

(D2) 12-(Dibenzylamino)dodecanol

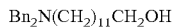

D1 (15 g, 63.2 mmol) was suspended in a mixture of dichloromethane (150 ml) and saturated sodium carbonate in water (150 ml). Benzyl bromide (189.6 mmol, 33.7 g, 23.5 ml) was added slowly. The suspension cleared and reaction was complete after 4 hr, aqueous ammonia (0.880, 30 ml) was added & the reaction left overnight. The organic layer was dried (MgSO$_4$) and evaporated to dryness. The product was stirred vigorously in refluxing hexane. The flask was left at –20° C. when crystals of the title compound slowly appeared. The crystals (Mp 45° C.) were collected by filtration (18.03 g, 75%). $C_{26}H_{39}N_1O_1$ requires C: 81.84%, H: 10.30%, N: 3.67%. Found: C: 81.64%, H: 10.24%, N: 3.54%. $C_{26}H_{39}N_1O_1$ requires 381. Found ES+: MH$^+$ 382 (100%). $\delta_H$ (CDCl$_3$) 7.1-7.6 (10H, m, Ar), 3.64 (2H, t, CH$_2$O), 3.56 (4H, s, ArCH$_2$), 2.41 (2H, t, NCH2), 1.1-1.8 (22H, dm, CH2).

(D3) 12-(Dibenzylamino)dodecanal

To a solution of anhydrous DMSO (30 mmol, 2.13 ml) in dichloromethane (200 ml) at –78° C. was added carefully oxalyl chloride (2.6 ml, 30 mmol) in dichloromethane (60 ml). After 15 mins D1 (10 g, 26 mmol) was added in dichloromethane (60 ml) and the reaction stirred for 20 mins at –78° C. Triethylamine (28 ml) was added dropwise to the cold reaction. A precipitate formed and after 15 mins the reaction was allowed to reach room temperature. Water (100 ml) was added to the reaction which was extracted with dichloromethane. The organic layers were washed with water, dried (MgSO$_4$) and evaporated to dryness. The residue was chromatographed (SiO$_2$, hexane—10% ethyl acetate in hexane) to give the title compound as an oil (7.97 g, 80%). This compound is unstable and should be used on the day of preparation.

I.R. 1725 cm$^{-1}$ (COH). C$_{26}$H$_{37}$NO requires 379.29. Found ES+: MH$^+$ 380.29. $\delta_H$ (CDCl$_3$) 1.32 (14H, br, (CH$_2$)$_7$(CH$_2$)$_2$N), 1.61 (4H, 2×p, CH$_2$CH$_2$N, CH$_2$CH$_2$CO), 2.43, 2.44 (4H, 2×t, CH$_2$N, CH$_2$CO), 3.60 (4H, s, CH$_2$Ph), 7.2-7.5 (10H, m, Ph), 9.78 (1H, t, COH). d$_C$ (CDCl$_3$) 22.0, 26.9, 27.1, 29.0, 29.3, 29.4, 29.5 (9C, (CH$_2$)$_9$CH$_2$N), 43.8 (1C, CH$_2$COH), 53.3 (1C, CH$_2$N), 58.2 (2C, CH$_2$Ph), 126.6 (2C, CH(CH)$_2$C), 128.0 (4C, CHC), 128.6 (4C, CHCHC), 140.0 (2C, CCH$_2$N), 202.3 (1C, COH).

(D4) 11-(Carboxyundecyl)triphenylphosphonium bromide

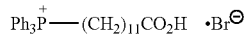

To 12-bromododecanoic acid (3.000 g, 10.7 mmol) suspended in acetonitrile (12 ml) was slowly added triphenylphosphine (2.818 g, 10.7 mmol). The reaction was heated at 100° C. (no condenser with argon blowing over the flask until the reaction was a fusion, then maintained at 100° C. (with condenser) for 24 hrs. The warm residues were dissolved in acetonitrile (18 ml) and added dropwise to rapidly stirred cold (dry ice) diethyl ether. The white precipitate formed was then filtered off and the title compound dried (5.353 g, 92%). Mp 110-112° C. C$_{30}$H$_{38}$O$_2$PBr requires C: 66.54%, H: 7.07%. Found: C: 66.42%, H: 7.10%. $\delta$p (CDCl$_3$) 24.3 (s). $\delta_H$ (CDCl$_3$) 1.05-1.30 (12H, br, (CH$_2$)$_6$(CH$_2$)$_2$CO$_2$H), 1.53 (6H, br, (CH$_2$)$_2$CH$_2$P, CH$_2$CH$_2$CO$_2$H), 2.28 (2H, t, CH$_2$CO$_2$), 3.55 (2H, br, CH$_2$P), 7.6-7.8 (15H, m, Ph). d$_C$(CDCl$_3$) 22.1, 22.3, 22.8, 24.5, 28.8, 28.9, 30.0, 30.2 (10C, (CH$_2$)$_{10}$CO$_2$H), 34.2 (1C, CH$_2$P), 117.3, 118.7 (3C, CP), 130.3, 130.5 (6C, CHCHCP), 133.3, 133.5 (6C, CHCP), 134.9 (3C, CH(CH)$_2$CP), 177.4 (1C, CO$_2$H).

(D5) 24-(Dibenzylamino)-12-tetracosenoic acid

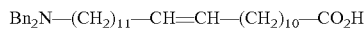

The phosphonium salt D4 (13.52 g, 25 mmol) was dissolved in dry DMSO (40 ml) under argon at ~0° C. (no DMSO solidification). 2.2 Equivalents of 2.0M LDA. (25 ml) were added, the solution turning orange. The reaction was left at 0° C. for ½ hour, and to the now dark orange solution was added a solution of D3 (7.97 g, 21 mmol) in dry THF (30 ml). The solution was maintained at 0° C. for 4 hours then added to 2M HCl (50 ml). The aqueous layer was extracted with dichloromethane, the fractions combined, dried (MgSO$_4$) and the solvent removed to yield the crude material as a pale yellow gum. Silica column chromatography (30-100% ethyl acetate in hexane) yielded the title compound (6.20 g, 53%), as a pale yellow gum. C$_{38}$H$_{59}$NO$_2$ requires 561.46. Found ES+: MH$^+$ 562.3, ES−: (M−H$^+$)$^-$ 560.55. $\delta_H$ (CDCl$_3$) 1.26 (30H, br, (CH$_2$)$_8$CH$_2$CH═CHCH$_2$(CH$_2$)$_7$), 1.42-1.72 (4H, m, CH$_2$CH$_2$CO$_2$H, CH$_2$CH$_2$N), 2.02 (4H, d×t, CH$_2$CH═CHCH$_2$), 2.34 (2H, t, CH$_2$CO$_2$H), 2.46 (2H, t, CH$_2$N), 3.65 (4H, s, CH$_2$Ph), 5.36 (2H, t, CH═CH), 7.2-7.4 (10H, m, Ph). $\delta_C$ (CDCl$_3$) 25.0, 26.4, 27.2, 29.3, 29.6 (19C, (CH$_2$)$_{10}$CH═CH(CH$_2$)$_9$), 34.5 (1C, CH$_2$CO$_2$H), 52.9 (1C, CH$_2$N), 57.7 (2C, CH$_2$Ph), 127.0 (2C, CH(CH)$_2$C, 128.2 (4C, CHC), 129.1 (4C, CHCHC), 129.9 (2C, CH═CH), 138.6 (2C, CCH$_2$N), 179.2 (1C, CO$_2$H).

(D6) 24-Aminotetracosanoic acid

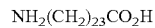

D5 (6.2 g) under an atmosphere of hydrogen was heated at 60° C. (to avoid the monobenzyl product) overnight in glacial acetic acid using Pearlman's catalyst (10% w/w). The reaction was filtered through glass fibre and evaporated to dryness. The title compound was crystallised from acetic acid/ether (4.2 g, 100%) and subjected to high vacuum to remove traces of acetic acid. Mp 151-155° C. C$_{24}$H$_{49}$NO$_2$.0.75 MeCO$_2$H requires C: 71.44%, H: 12.23%, N: 3.27%. Found: C: 71.43%, H: 12.15%, N: 3.26%. C$_{24}$H$_{49}$NO$_2$ requires 383.38. Found ES+: MH$^+$ 384.29 $\delta_H$ (CD$_3$OD+TFA) 1.32 (38H, br, (CH$_2$)$_{19}$(CH$_2$)$_2$NH$_2$), 1.65 (4H, br, CH$_2$CH$_2$NH$_2$, CH$_2$CH$_2$CO$_2$H), 2.33 (2H, t, CH$_2$CO$_2$H), 2.74 (2H, m, CH$_2$NH$_2$). $\delta_C$ (CD$_3$OD+TFA) partial 33.8 (1C, CH$_2$CO$_2$H), 35.3 (1C, CH$_2$NH$_2$).

C$_{18}$ AMINOACID (D7) 6-(Dibenzylamino)-1-hexanol

Benzyl bromide (61 ml, 511 mmol) was added to a stirred solution of 6-amino-1-hexanol (20 g, 170 mmol) and triethylamine (142 ml, 1.02 mol) in acetonitrile (500 ml) at room temperature for two days. The acetonitrile solution was concentrated to 100 ml and diluted with water. The aqueous phase was extracted with ethyl acetate, washed with brine, dried (MgSO$_4$) and evaporated to dryness to yield an orange oil. The product was chromatographed on silica (hexane—50% ethyl acetate/hexane) to yield the title compound as a colourless oil (25 g, 50%). $\delta_H$ (CDCl$_3$) 7.23-7.39 (10H, m, (ArH), 3.59 (6H, t+ds, CH$_2$OH+ArCH$_2$), 2.42 (2H, t, CH$_2$N), 1.47-1.56 (4H, m, CH$_2$CH$_2$NH$_2$+CH$_2$CH$_2$OH), 1.24-1.32 (4H, m, 2×CH$_2$).

(D8) 6-(Dibenzylamino)hexanal

To a stirred solution of DMSO (20 mmol, 1.41 ml) in dichloromethane (100 ml) at −78° C. was carefully added oxalyl chloride (1.7 ml, 20 mmol) in dichloromethane (30 ml). After 15 mins D7 (5 g, 16.83 mmol) was added in dichloromethane (30 ml) maintaining the temperature at −78° C. The reaction was stirred for 20 mins and triethylamine (14 ml) added dropwise. A precipitate formed, after 15 mins the reaction was allowed to reach room temperature. Water (100 ml) was added to the reaction which was extracted with dichloromethane. The organic layers were washed with water, dried (MgSO$_4$) and evaporated to dryness. The residue was chromatographed (SiO$_2$, hexane −20% ethyl acetate in hexane) to give the title compound as an oil (4.10 g, 83%). C$_{20}$H$_{25}$NO requires C: 81.31%, H: 8.53%, N: 4.74%. Found: C: 81.00%, H: 8.49%, N: 4.63%. C$_{20}$H$_{25}$NO requires 295. Found ES+: MH$^+$ 296 $\delta_H$(CDCl$_3$) 9.71 (1H, s, CHO), 7.2-7.5 (10H, m, ArH,), 3.57 (4H, s, ArCH$_2$), 2.3-2.5 (4H, dt, CH$_2$), 1.2-1.7 (6H, dm, CH$_2$).

(D9) 18-(Dibenzylamino)-12-octadecenoic acid

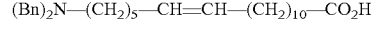

D4 (1.082 g, 2 mmol) was dissolved in dry DMSO (5 ml) under argon at ~0° C. (no DMSO solidification). 2.2 equivalents of 2.0M LDA (4 ml) was added, the solution turning orange. The reaction was left at 0° C. for ½ hour, and to the now dark orange solution was added a solution of D8 (0.7 g, 2 mmol) in dry THF (10 ml). The solution was maintained at 0° C. for 4 hours then added to 2M HCl (50 ml). The aqueous layer was extracted with ethyl acetate, the fractions combined, dried (MgSO$_4$) and the solvent removed to yield the crude material as a pale yellow gum. Silica column chromatography (30% ethyl acetate in hexane or 5% methanol in dichloromethane) yielded the title compound (453 mg, 53%), as a low melting (Mp 21° C.) white solid. $C_{32}H_{47}NO_2$ requires C: 80.45%, H: 9.92%, N: 2.93%. Found: C: 80.20%, H: 9.92%, N: 2.74%. $C_{38}H_{59}NO_2$ requires 477. Found ES+: $MH^+$ 478. $\delta_H$ (CDCl$_3$) 8.6-9.2 (1H, vbr, (CO$_2$H), 7.39-7.21 (10H, m, ArH), 5.37-5.29 (2H, m, trans HC=CH), 3.63 (4H, s, PhCH$_2$), 2.48-2.43 (2H, t, NCH$_2$), 2.36-2.31 (2H, t, CH$_2$CO$_2$H), 2.01-1.97 (2H, t, CH$_2$CH=CH), 1.66-1.55 (4H, m, CH$_2$), 1.29-1.24 (18H, m, CH$_2$).

(D10) 18-Aminooctadecanoic acid

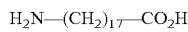

D8 (13 g) under an atmosphere of hydrogen was heated at 60° C. overnight in glacial acetic acid with Pearlman's catalyst (10% w/w). The reaction was filtered hot through glass fibre and evaporated to dryness. The product was crystallised from acetic acid/ether (8.2 g, 100%). The title compound was subjected to high vacuum to remove traces of acetic acid. Mp 162-163° C. $C_{24}H_{49}NO_2.0.25H_2O$ requires C: 71.12%, H: 12.43%, N: 4.61%. Found: C: 71.20%, H: 12.35%, N: 4.49%. $C_{24}H_{49}NO_2$ requires 299. Found ES+: $MH^+$ 300. $d_H$ (CD$_3$CO$_2$D) 3.06 (2H, t, CH$_2$NH$_2$), 2.38 (2H, t, CH$_2$CO$_2$H), 1.63-1.73 (4H, m, CH$_2$CH$_2$CO$_2$H+CH$_2$CH$_2$NH$_2$), 1.33 (26H, m, CH$_2$).

$C_{20}$ REDUCED BIXIN AMINOACID (D11) Hydrogen Methyl 4,8,13,17-tetramethyl-1,20-dodecanedioate

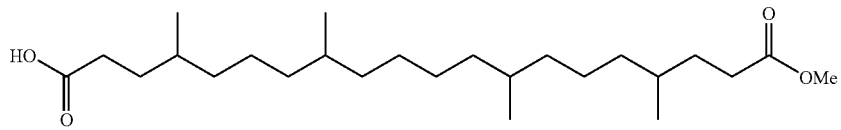

A suspension of bixin (9.959 g, 24.59 mmol) was stirred overnight in methanol (200 ml) in the presence of a hydrogen atmosphere and 10% Pd/C catalyst (1 g). The catalyst and solvent were removed to yield an opaque yellow viscous oil, silica tlc r.f. 0.4 (25% ethyl acetate in hexane) purified by gradient (20-35% ethyl acetate in hexane) silica chromatography to yield the title compound as a very pale yellow clear viscous oil (7.181 g, 71%). I.R. 1710 cm$^{-1}$ (CO$_2$H), 1743 cm$^{-1}$ (CO$_2$Me). $C_{24}H_{48}O_4$ requires 412.36. Found ES+: $MNa^+$ 435.38. $\delta_H$ (CDCl$_3$) 0.85-1.0 (12H, m, CHMe), 1.0-1.8 (28H, br, CH$_2$, CHCH$_3$), 2.35 (4H, m, CH$_2$CO), 3.70 (3H, s, OMe)

(D12) N-aminoethyl-O-t-Butylcarbamate

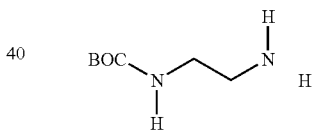

BOC-ON (16.4 g, 0.066 mmol) was added to a stirred mixture of ethylenediamine (13.4 ml, 0.2 mmol) and triethylamine (28 ml, 0.2 mmol) at room temperature under argon and left overnight. Ethyl acetate was added and the product extracted into potassium dihydrogen orthophosphate solution. The extracts were combined and basified to pH12 with sodium hydroxide. The aqueous basic solution was extracted with ethyl acetate, the combined organic phases washed with brine, dried and evaporated to dryness to yield the title compound which analysed without further purification. Yield 6.4 g. $C_7H_{16}N_2O_2$ requires 160. Found ES+: $MH^+$ 161. $\delta_H$ (CDCl$_3$) 5.12 (1H, br, CONH), 3.19 (2H, dt, OCONHCH$_2$), 2.93 (2H, s, NH$_2$), 2.82 (2H, t, CH$_2$N), 1.42 (9H, s, Me).

(D13) Methyl N-(t-butyloxycarbonylaminoethyl)-4,8,13,17-tetramethyl-1,20-dodecanamoate

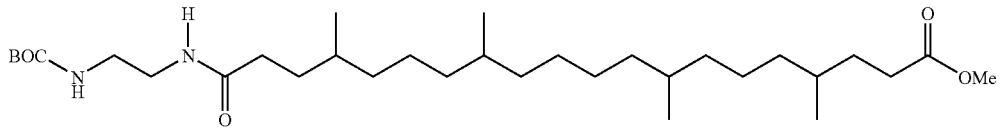

To D11 (7.181 g, 17.4 mmol) in dry dichloromethane (50 ml) under argon was added triethylamine (1.761 g, 17.4 mmol), EDC (5.171 g, 17.4 mmol) and N-hydroxysuccinimide (2.002 g, 17.4 mmol). The solution was left for three hours, during which time the formation of the slower moving NHS active ester was followed by silica tlc (r.f. 0.25, 25% ethyl acetate in hexane). Once complete ester formation was achieved, D12 (3.067 g, 19.1 mmol) was added in dichloromethane (20 ml) and the reaction left 48 hrs. Purification on silica (50% ethyl acetate in hexane) yielded the title compound (4.285 g, 44%), silica tlc r.f. 0.15 (25% ethyl acetate in hexane). $C_{32}H_{62}N_2O_5$ requires 554.47. Found ES+: MH+ 555.48, MNa+ 557.41. $\delta_H$ (CDCl$_3$) 0.7-0.9 (12H, m, CHMe), 0.8-1.8 (28H, br m, CHMe, CH$_2$), 1.41 (9H, s, C(Me)$_3$), 2.15 (2H, d×t, CH$_2$CONH), 2.27 (2H, m, CH$_2$CO$_2$Me), 3.15-3.35 (4H, m, CH$_2$NH), 3.63 (3H, s, OMe), 5.33 (1H, t, NHCO$_2$), 6.65 (1H, t, NHCO). $\delta_C$ (CDCl$_3$) 19.1, 19.5, 24.2, 27.3, 28.2, 31.7, 32.2, 32.6, 34.3, 37.0 (25C, CH$_2$, CHMe, C(CH$_3$)$_3$), 40.2, 40.4 (2C, CH$_2$N), 51.2 (1C, OMe), 79.2 (1C, C(Me)$_3$), 156.8 (1C, NHCO$_2$), 174.2, 174.4 (2C, CO$_2$Me, CONH).

(D14) N-(t-Butyloxycarbonylaminoethyl)-4,8,13,17-tetramethyl-1,20-dodecanamoic acid

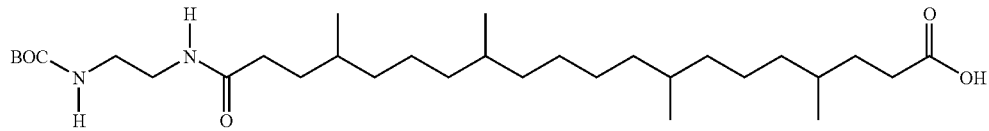

To D13 (4.285 g, 7.722 mmol) in methanol (35 ml) was added a suspension/solution of lithium hydroxide (3.239 g, 77.22 mmol) in water (10 ml). This was stirred for 2 hours then poured into 10% citric acid solution and extracted with ethyl acetate. These organic fractions were combined, washed with water and the solvent removed to yield the title compound. With dichloromethane:methanol:water 6:1:1 on silica the tlc of D13 and D14 have R$_f$ of 0.35 and 0.05 respectively. $C_{31}H_{60}N_2O_5$ requires 540.45. Found ES+: MH+ 541.48, MNa+ 563.45. $\delta_H$ (CDCl$_3$) 0.85-1.0 (12H, m, Me), 1.0-1.8 (28H, br m, CH$_2$, CH), 1.46 (9H, s, C(Me)$_3$), 2.20 (2H, m, CH$_2$CONH), 2.36 (2H, m, CH$_2$CO$_2$), 3.15-3.45 (4H, m, CH$_2$N), 5.16 (1H, t, NHCO$_2$), 6.55 (1H, t, NHCO). $\delta_C$ (CDCl$_3$) 19.3, 19.7, 24.2, 27.2, 28.3, 31.8, 32.3, 32.6, 34.4, 36.9 (25C, CH$_2$, CHMe, C(CH$_3$)$_3$), 40.0, 40.6 (2C, CH$_2$N), 79.6 (1C, C(Me)$_3$), 157.0 (1C, NHCO$_2$), 174.5 (1C, CONH), 179.5 (1C, CO$_2$H).

(D15) N-Aminoethyl-4,8,13,17-tetramethyl-1,20-dodecanamoic acid trifluoroacetate salt D14 was taken up into 96% TFA and left for 30 minutes. The solvent was removed to give the amino acid as a viscous oil which after silica chromatography (15% methanol in dichloromethane+0.1% acetic acid) gave the title compound as a colourless solid/gum, silica tlc r.f. 0.25, ninhydrin +ve (6:1 dichloromethane:methanol). The yield for the two steps D14 to D15 was 2.044 g, 60%. $C_{26}H_{52}N_2O_3$ requires 440.40. Found ES+: MH+ 441.36. $\delta_H$ (CD$_3$OD) 0.95-1.1 (12H, m, Me), 1.1-1.9 (28H, br m, CH, CH$_2$), 2.38 (4H, m, CH$_2$CO), 3.20 (2H, t, CH$_2$NH$_3^+$), 3.60 (2H, t, CH$_2$NHCO), $\delta_C$ (CD$_3$OD) 20.1, 20.5, 22.0, 25.6, 28.6, 33.6, 33.8, 34.0, 35.0, 38.4, 38.6 (22C, CH, CH$_2$, Me), 40.9 (2C, CH$_2$N), 177.9 (1C, CONH), 179.4 (1C, CO$_2$H).

C24 AMINOACID CONTAINING MID-CHAIN AMIDE
(D16) 12-(t-Butyloxycarbonylamino)dodecanoic acid

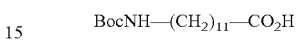

12-Aminododecanoic acid (2.15 g, 10 mmol) was dissolved in 1M NaOH (50 ml) at 50° C. BOC anhydride (2.33 g, 10 mmol) was added to the reaction which was stirred for 30 mins. The reaction was poured into stirred 10% citric acid (100 ml) and the white solid filtered off. The solid was washed with citric acid, water and dried in vacuo. The product was dissolved in ether and filtered before evaporating to dryness. The title compound was crystallised from hexane (2.33 g, 74%). Mp 72-76° C. $C_{17}H_{33}NO_4$ requires C: 64.73%, H: 10.55%, N: 4.44%. Found: C: 64.78%, H: 10.58%, N: 4.41%. $C_{24}H_{49}NO_2$ requires 315. Found ES+: MH+ 316. $\delta_H$ (CDCl$_3$) 3.08 (2H, t, CH$_2$NH$_2$), 2.33 (2H, t, CH$_2$CO$_2$H), 1.6 (2H, m, CH$_2$CH$_2$NH$_2$), 1.44 (11H, s+m, CH$_2$CH$_2$CO$_2$H+Boc), 1.26 (14H, m, CH$_2$).

(D17) 12-(t-Butyloxycarbonylaminododecanoylamino) dodecanoic acid

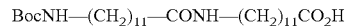

To D16 (1.59 g, 5.05 mmol) in stirred dichloromethane (20 ml) was added DBU (0.755 ml, 5.05 mmol), followed by N-hydroxysuccinimide (0.581 g, 5.05 mmol) and EDC (0.968 g, 5.05 mmol). The reaction was left overnight to go to completion. Chloroform (30 ml) containing 12-aminododecanoic acid (1.087 g, 5.05 mmol) and DBU (1.51 ml, 10.1 mmol) was added. After 3 hours the reaction was poured into 10% citric acid (100 ml) and extracted with dichloromethane (3×50 ml). The organic phases were dried (MgSO$_4$) and evaporated to dryness. The solid residue was triturated with refluxing hexane & dissolved in refluxing ethyl acetate. The solution was filtered hot and allowed to crystallise to yield the title compound (2.33 g, 90%). Mp 85-87° C. $C_{29}H_{56}N_2O_5$ requires 512. Found ES+: MH+ 513. $\delta_H$ (CDCl$_3$) 5.74 (1H,

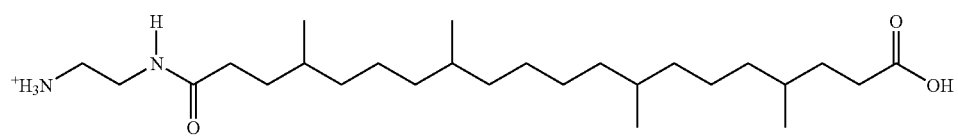

brt, CONH), 4.57 (1H, br, CONH), 3.0-3.3 (2×2 H, q+m, CH$_2$NH), 2.30 (2H, t, CH$_2$CO), 2.15 (2H, t, CH$_2$CO), 1.60 (4H, m, CH$_2$), 1.2-1.5 (9+32H, m, CH$_2$).

(D18) 12-(Aminododecanoylamino)dodecanoic acid

96% TFA (4% water, 7 ml) was added to D17 (2.3 g, 4.5 mmol) and the resulting solution stirred for 30 min. The reaction was evaporated to dryness and azeotroped with toluene/methanol before submitting to high vacuum. The title compound was recrystallised from ether containing acetic acid as a white solid (2.12 g). Mp 66-68° C. C$_{24}$H$_{48}$N$_2$O$_3$ requires 412. Found ES+: MH$^+$ 413. $\delta_H$ (CD$_3$CO$_2$D) 3.26 (2H, t, CH$_2$NH), 3.09 (2H, t, CH$_2$NH), 2.38 (2H, t, CH$_2$CO), 2.28 (2H, t, CH$_2$CO), 1.5-1.9 (4H, m, CH$_2$CH$_2$NH), 1.5-1.25 (32H, m, CH$_2$).

(D19) 24-(Benzyloxycarbonylamino)tetracosanoic acid

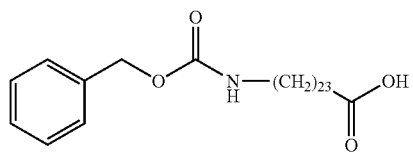

To D6 (0.500 g, 1.30 mmol) and DBU (794 mg, 5.21 mmol) in refluxing methanol (100 ml) was added neat benzylchloroformate and the reaction refluxed for 3 hours until complete conversion of D6 to either the protected amino acid D19 or its methyl ester was observed. The solvent was removed and the residues taken up into dioxane (60 ml) and water (2 ml) and lithium hydroxide (1 g) added. The reaction was then refluxed for 2 hours until hydrolysis of the methyl ester derivative to D19 was complete. The solvent was removed, the residues suspended in 1M HCl (100 ml) and extracted with hot ethyl acetate (300 ml). The hot ethyl acetate was dried (MgSO$_4$) and the solvent volume reduced to 40 ml. The solution/suspension was left at −10° C. for 1 hour, allowed to warm to room temperature and the resulting white precipitates filtered off and dried under vacuum to yield the title compound (585 mg, 87%). M.Pt 102-104° C. C$_{32}$H$_{55}$NO$_4$ requires 517.4. Found ES$^-$: MCl$^-$, 552.6. $\delta_H$ (d$_6$ DMSO), 1.32 (38H, s, (CH$_2$)$_{19}$(CH$_2$)$_2$N), 1.52 (2H, p, CH$_2$CH$_2$CO$_2$H), 1.65 (2H, p, CH$_2$CH$_2$NH), 2.35 (2H, t, CH$_2$CO$_2$H), 3.18 (2H, t, CH$_2$N), 5.14 (2H, s, CH$_2$Ph), 7.35 (5H, m, Ph).

E. LIPID POLYAMINE INTERMEDIATES

This section contains the synthesis of:

(E2) N-{8-[t-Butyloxycarbonylaminobutyl(t-butyloxycarbonyl)amino]-7-[t-butyloxycarbonylaminobutyl(t-butyloxycarbonyl)aminomethyl]octyl}-23-aminotetracosanamide

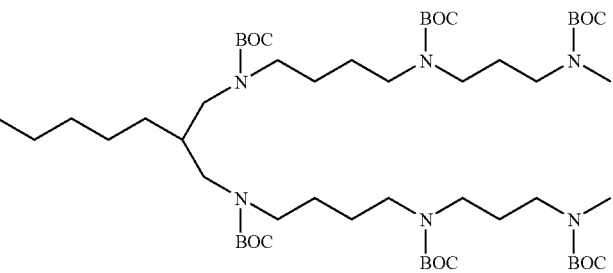

(E4) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-23-aminotetracosanamide

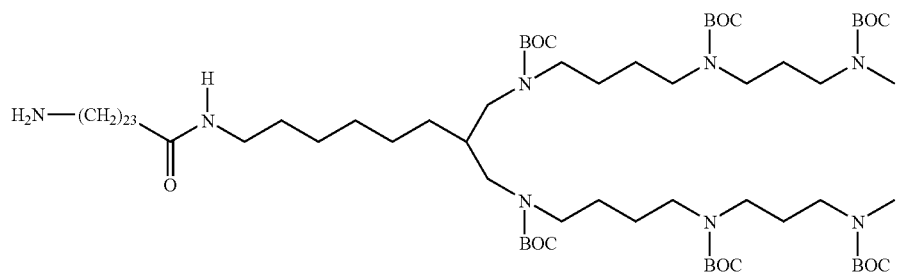

(E8)

(E1) N-{8-[t-Butyloxycarbonylaminobutyl(t-butyloxycarbonyl)amino]-7-[t-butyloxycarbonylaminobutyl(t-butyloxycarbonyl)aminomethyl]octyl}-23-benzyloxycarbonylamino)tetracosanamide

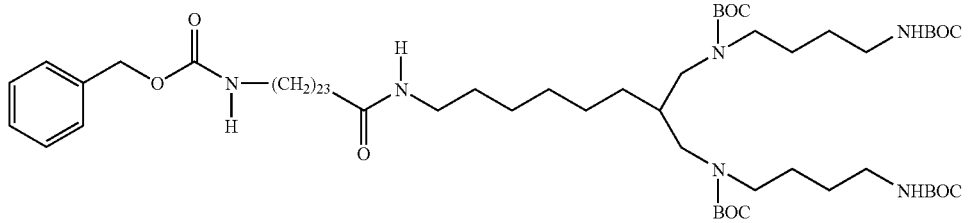

D19 (448 mg, 0.865 mmol), EDC hydrochloride (249 mg, 1.30 mmol), N-hydroxysuccinimide (149 mg, 1.30 mmol) and DBU (263 mg, 1.73 mmol) were dissolved in anhydrous dichloromethane (10 ml) and activated ester formation left overnight at room temperature under argon. B8 (589 mg, 0.82 mmol) was added and the reaction left for a further five hours. The solvent was removed and the residues purified by gradient silica column chromatography (40-60% ethyl acetate in hexane) to yield the title compound as a colourless glass (887 mg, 88%). $C_{69}H_{126}N_6O_{11}$ requires 1214.9. Found ES$^+$: MH$^+$, 1215.9. $\delta_H$ (CDCl$_3$) 1.24 (48H, br, (CH$_2$)$_{20}$(CH$_2$)$_2$N, (CH$_2$)$_4$CH), 1.43 (48H, br, Me, CH$_2$CH$_2$N), 2.03 (1H, br, CH), 2.18 (2H, t, CH$_2$CO), 3.00-3.35 (16H, brm, CH$_2$N), 4.4-4.6 (3H, br, NHCO$_2$), 5.09 (2H, s, CH$_2$O), 5.90 (1H, br, CONH), 7.34 (5H, m, Ph).

(E2) N-{8-[t-Butyloxycarbonylaminobutyl(t-butyloxycarbonyl)amino]-7-[t-butyloxycarbonylaminobutyl(t-butyloxycarbonyl)aminomethyl]octyl}-23-aminotetracosanamide

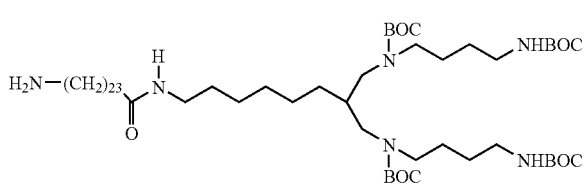

To E1 (877 mg) dissolved in tert-butanol (60 ml) was added Pearlmans catalyst (500 mg), ammonium formate (3 g) and Raney nickel (approximately 1 ml). The reaction was heated at 45° C. overnight and to maintain a hydrogen atmosphere the reaction was fitted with a bubbler. The catalysts were filtered off and the solvent removed to give a colourless gum which was purified by silica column chromatography (10% methanol in dichloromethane+0.1% triethylamine) to yield the title compound as a colourless glass/solid (744 mg, 95%). $C_{61}H_{120}N_6O_9$ requires 1080.9. Found ES$^+$: MH$^+$, 1082.1, ES$^-$: MCl$^-$, 1116.1. $\delta_H$ (CDCl$_3$) 1.24 (46H, br, (CH$_2$)$_{19}$(CH$_2$)$_2$CO), 1.42 (50H, br, Me, CH$_2$CH$_2$N, CH$_2$CH$_2$CO), 1.95 (1H, br, CH), 2.14 (2H, t, CH$_2$CO), 2.95 (2H, t, CH$_2$NH$_2$), 3.0-3.3 (14H, m, CH$_2$N), 4.69 (2H, br, NHCO$_2$), 5.64 (1H, t, NHCO).

(E3) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-23-(benzyloxycarbonylamino)tetracosanamide D19 (580 mg, 1.12 mmol), EDC hydrochloride (429 mg, 2.24 mmol), N-hydroxysuccinimide (193 mg, 1.68 mmol) and DBU (341 mg, 2.24 mmol) were dissolved in anhydrous dichloromethane (30 ml) and activated ester formation left overnight at room temperature under argon. B21 (1.186 g, 1.12 mmol) in anhydrous dichloromethane (20 ml) was added and the reaction left for a further five hours. The solvent was removed and the residues purified by gradient silica column chromatography (40-60% ethyl acetate in hexane) to yield the title compound as a colourless glass (1.261 g, 72%). $C_{87}H_{160}N_8O_{15}$ requires 1557.2. Found ES$^+$: MH$^+$, 1558.3. $\delta_H$ (CDCl$_3$) 1.24 (46H, (CH$_2$)$_{19}$(CH$_2$)$_{19}$(CH$_2$)$_2$CO, (CH$_2$)$_4$CH), 1.4-1.8 (72H, br+m, (Me)$_3$C, CH$_2$CH$_2$CO, CH$_2$CH$_2$N), 2.03 (1H, br, CH), 2.21 (2H, t, CH$_2$CO), 2.83 (6H, s, MeN), 3.0-3.35 (24H, m, CH$_2$N), 4.73 (1H, br, NHCO$_2$), 5.3 (2H, s, CH$_2$O), 6.08 (1H, br, NHCO), 7.34 (5H, m, Ph).

(E4) N-{8-[Methyl(t-butyloxycarbonyl)aminopropyl(t-butyloxycarbonyl)aminobutyl(t-butyloxycarbonyl)amino-7-[methyl(t-butyloxycarbonyl)aminopropyl(t-butyloxycarbonyl)-aminobutyl(t-butyloxycarbonyl)aminomethyl]octyl}-23-aminotetracosanamide

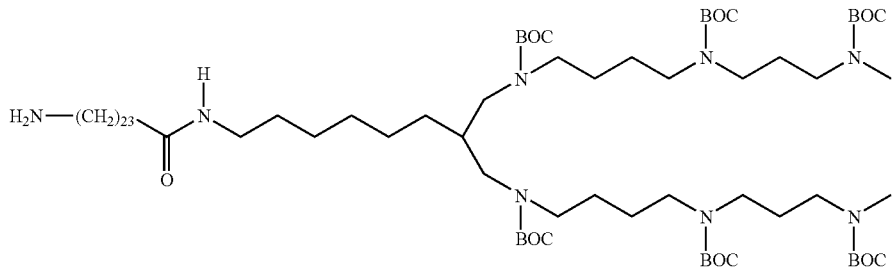

To E3 (1.260 g) dissolved in tert-butanol (60 ml) was added Pearlmans catalyst (500 mg), ammonium formate (3 g) and Raney nickel (approximately 1 ml). The reaction was heated at 45° C. overnight and to maintain a hydrogen atmosphere the reaction was fitted with a bubbler. The catalysts were filtered off and the solvent removed to give a colourless gum which was purified by silica column chromatography (10% methanol in dichloromethane+0.1% triethylamine) to yield the title compound as a colourless glass/solid (1.088 g, 94%). $C_{79}H_{154}N_8O_{13}$ requires 1423.2. Found $ES^+$: $MH^+$, 1424.3 $\delta_H$ (CDCl$_3$) 1.24 (48H, (CH$_2$)$_{20}$CH$_2$CO, (CH$_2$)$_4$CH), 1.43 (70H, br+m, (Me)$_3$C, CH$_2$CH$_2$N), 1.95 (1H, br, CH), 2.14 (2H, t, CH$_2$CO), 2.80 (2H, t, CH$_2$NH$_2$), 2.83 (6H, s, NMe), 3.0-3.35 (22H, m, CH$_2$N), 5.65 (1H, br, CONH).

(E5) 36-Chlorohexatriaconta-12,24-dienoic acid

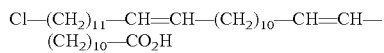

To a rapidly stirring suspension of silica (200 ml) and 50% dichloromethane in hexane (200 ml) was slowly added tosic acid (2 g) in water (6 ml). The suspension was stirred for 10 minutes and used to pack a column. After washing the column with 50% dichloromethane in hexane 35-Chloro-1-(1,3-dioxalan-2-yl)pentatriaconta-12,24-diene (4.04 g) was loaded and eluted over 2 hours with 50% dichloromethane in hexane to give the aldehyde 2.5264 g, 66% as a white waxy solid. To PDC (3.792 g, 10.080 mmol) in anhydrous DMF (30 ml) was added the aldehyde (2.5264 g, 4.582 mmol) in anhydrous DMF (30 ml) and the reaction stirred at ambient temperature under argon for 2 days. The reaction was poured into water (500 ml), extracted with hexane and the combined hexane fractions washed with water (3×150 ml). The solution was dried (MgSO$_4$), and the solvent removed to yield a brown oil which was purified by silica gradient chromatography eluting with 10-20% ethyl acetate in hexane to give the title compound as a white waxy solid, 1.528 g, 50%. $C_{36}H_{67}O_2Cl$ requires 566.6. Found $ES^-$: $(M-H^+)^-$, 565.6. $\delta_H$ (CDCl$_3$) 1.27 (46H, br, Cl(CH$_2$)$_2$(CH$_2$)$_8$CH$_2$CH=CHCH$_2$(CH$_2$)$_8$CH$_2$CH=CHCH$_2$(CH$_2$)$_7$), 1.63 (2H, p, CH$_2$CH$_2$CO$_2$H), 1.76 (2H, p, CH$_2$CH$_2$Cl), 2.01 (8H, m, CH$_2$CH=), 2.34 (2H, t, CH$_2$CO$_2$H), 3.52 (2H, t, CH$_2$Cl), 5.34 (4H, m, CH=CH).

(E6) 36-Azidohexatriaconta-12,24-dienoic acid

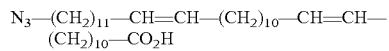

To E5 (1.528 g, 2.693 mmol) in anhydrous DMF (70 ml) was added sodium azide (1.226 g, 18.851 mmol) and the reaction heated for 5 days at 50° C. under argon. The solvent was reduced to almost dryness and the residues taken up into water (150 ml) and ethyl acetate (150 ml). The aqueous layer was further extracted with ethyl acetate (4×150 ml), the fractions combined, washed (2×150 ml water), dried (MgSO$_4$) and the solvent removed to quantitatively yield the title compound as a pale yellow waxy solid 1.465 g, 95%. $C_{36}H_{67}O_2N_3$ requires 573.5. Found $ES^-$: $(M-H^+)$, 572.6. $d_H$ (CDCl$_3$) 1.27 (46H, br, N$_3$(CH$_2$)$_2$(CH$_2$)$_8$ CH$_2$CH=CHCH$_2$(CH$_2$)$_8$CH$_2$CH=CHCH$_2$(CH$_2$)$_7$), 1.63 (4H, m, CH$_2$CH$_2$N3), CH$_2$H$_2$CO$_2$H), 2.02 (8H, m, CH$_2$CH=), 2.34 (2H, t, CH$_2$CO), 3.35 (2H, t, CH$_2$N$_3$), 5.35 (4H, m, CH=CH).

(E7) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-36-azidohexatriaconta-12,24-dienamide

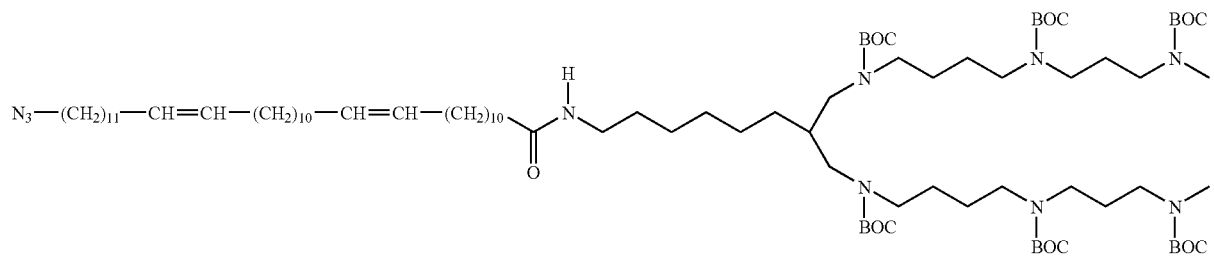

To E6 (299 mg, 0.521 mmol) in anhydrous dichloromethane (10 ml) were added EDC hydrochloride (200 mg, 1.043 mmol), N-hydroxysuccinimide (90 mg, 0.782 mmol) and the reaction left for 4 hours at room temperature. To the reaction were then added B21 (607 mg, 0.573 mmol) and triethylamine (211 mg, 2.085 mmol) in anhydrous dichloromethane (10 ml). The reaction was left for a further 3 hours and the solvent removed. The residues were purified by gradient silica chromatography eluting with 30-60% ethyl acetate in hexane to yield the title compound as a colourless viscous oil, 720 mg, 86%. $C_{91}H_{172}N_{10}O_{13}$ requires 1613.3. Found ES$^+$: MH$^+$, 1614.3, MH$_2^{2+}$, 807.9. $\delta_H$ (CDCl$_3$) 1.27 (54H, br, N$_3$(CH$_2$)$_2$(CH$_2$)$_8$CH$_2$CH=CHCH$_2$(CH$_2$)$_8$CH$_2$CH=CHCH$_2$(CH$_2$)$_7$), (CH$_2$)$_4$CH), 1.35-1.80 (72H, m, (Me)$_3$C, CH$_2$CH$_2$N$_3$, CH$_2$CH$_2$CO, CH$_2$CH$_2$N), 2.00 (8H, m, CH$_2$CH=), 2.05 (1H, br, CH), 2.23 (2H, t, CH$_2$CO), 2.84 (6H, s, NMe), 2.95-3.35 (22H, m, CH$_2$N), 3.25 (2H, t, CH$_2$N$_3$), 5.34 (4H, m, CH=CH), 6.12 (1H, br, CONH).

(E8) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-36-aminohexatriacontanamide

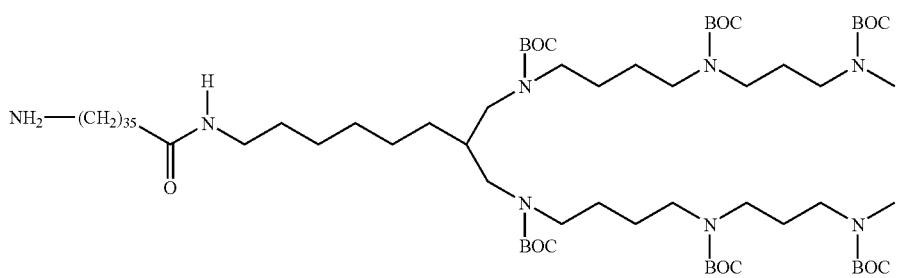

To E7 (184 mg) dissolved in tert-butanol at 40° C. was added Pd/C (50 mg) and the atmosphere changed to hydrogen. The hydrogenation was heated at 40° C. for 3 days, the catalyst filtered off and the solvent removed. The residues were purified by silica chromatography eluting initially with 100:10:0 CH$_2$Cl$_2$:MeOH:NH$_4$OH to remove faster running impurities then with 100:10:1 to remove the title compound as a colourless gum, 61 mg, 34%. $C_{91}H_{178}N_8O_{13}$ requires 1591.3. Found ES$^+$: MH$^+$, 1592.3. $\delta_H$ (CDCl$_3$) 1.24 (72H, br, H$_2$N(CH$_2$)$_2$(CH$_2$)$_{32}$, CONH(CH$_2$)$_2$(CH$_2$)$_4$), 1.44 (66H, br, (Me)$_3$C, CH$_2$CH$_2$N), 1.72 (4H, p, NCH$_2$CH$_2$CH$_2$N), 1.98 (1H, br, CH), 2.14 (2H, t, CH$_2$CO), 2.67 (2H, t, CH$_2$NH$_2$), 2.83 (6H, s, NMe), 2.95-3.30 (22H, m, NCH$_2$), 5.62 (1H, br, CONH(CH$_2$)$_6$CH).

F. GLYCOAMINOLIPID SYNTHESES

This section contains the syntheses of:

(F4) 18-(Peracetylglucuronylamino)octadecanoic acid

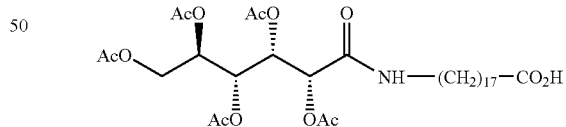

(F5) N-(Peracetylglucuronylaminoethyl)-4,8,13,17-tetramethyldodecanamic acid

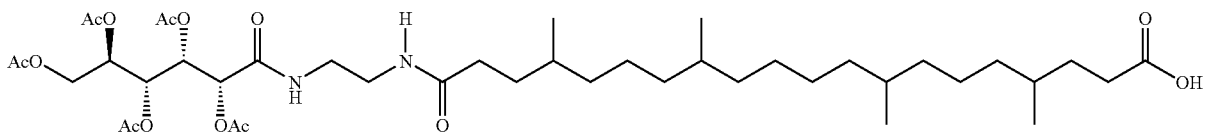

(F6) (12-(Peracetylglucuronylaminododecanoylamino)dodecanoic acid

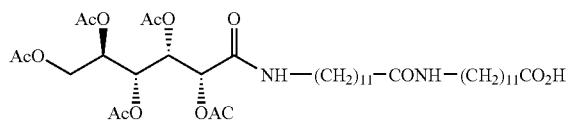

(F8) (12-(Peracetylglucuronylamino)dodecanoic acid

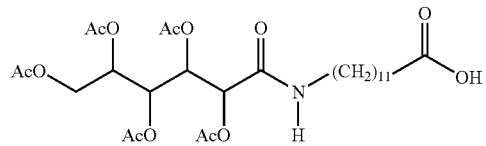

$C_{24}$ GLYCOAMINOLIPID
(F1) 24-(Glucuronylamino)tetracosanoic acid

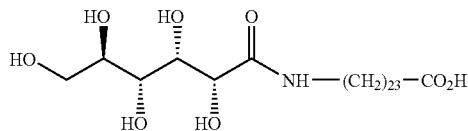

A suspension of D6 (792 mg, 2.064 mmol), d-gluconolactone (1.839 g, 10.32 mmol) and DBU (4.2 g, 30.9 mmol) in dry methanol (90 ml) were heated at 60° C. for approximately 10 minutes until all solids had dissolved. The solution was left at room temperature overnight, then the solvent removed. The residues were taken up into water (5 ml) and acidified to pH 1 with 1M HCl to precipitate out the desired compound. This was filtered off and dried to yield the title compound as a white solid (765 mg, 66%). Silica tlf $R_f$ 0.35, ninhydrin negative (1:1:1 methanol:acetic acid:dichloromethane). I.R. 1581 cm$^{-1}$ ($CO_2^-$), 1639 cm$^{-1}$ (CONH. $\delta_H$ (DMSO) 1.32 (42H, br, $(CH_2)_{21}CH_2CO_2H$), 2.27 (2H, t, $CH_2CO_2H$), 3.15 (2H, m, $CH_2N$), 3.3-3.8 (4H, m, CHOH), 4.0-4.1 (2H, m, $CH_2O$).
(F2) 24-(Peracetylglucuronylamino)tetracosanoic acid

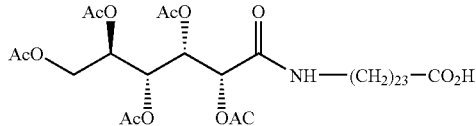

To F1 (765 mg, 1.362 mmol) dissolved in dry pyridine (20 ml) was added acetic anhydride (20 ml). The solution was stirred under argon overnight and water (50 ml) added slowly. The solution was extracted with dichloromethane and the dichloromethane then washed with HCl pH 3 (2×20 ml) and water (5×30 ml). The organics were dried (MgSO$_4$) and the solvent removed to yield the title compound as a white solid (940 mg, 89%). Alumina tlc $R_f$ 0.15 (15% methanol in dichloromethane). $C_{40}H_{69}NO_{13}$ requires 771.48. Found ES+: MH$^+$ 772.07, MNa$^+$ 794.25. ES-: (M-H$^+$)$^-$ 770.65. $\delta_H$ (CDCl$_3$) 1.26 (38H, br, $(CH_2)_{19}(CH_2)_2CO_2H$), 1.64 (4H, m, $CH_2CH_2CO_2H$, $CH_2CH_2NH$), 2.07, 2.11, 2.13, 2.21 (15H, s, MeCO), 2.35 (2H, t, $CH_2CO_2H$), 3.24 (2H, m, $CH_2NH$), 4.30 (2H, 2×d×d, $CH_2OAc$), 5.05 (1H, q, CH(OAc)$CH_2OAc$), 5.32 (1H, d, CH(OAc)CONH), 5.46 (1H, t, CH(OAc)CH(OAc) $CH_2OAc$), 5.70 (1H, t, CH(OAc)CH(OAc)CONH), 6.42 (1H, t, NH). $\delta_C$ (CDCl$_3$) 20.4, 24.5, 26.6, 28.8-29.5 (26C, $(CH_2)_{21}CH_2CO_2H$, MeCO), 33.8 (1C, $CH_2CO_2H$), 39.3 (1C, $CH_2NH$), 61.3 (1C, $CH_2OAc$), 68.5, 68.9, 69.1, 71.5 (4C, CHOAc), 165.8 (1C, CONH), 160.0, 169.5, 169.7, 170.4 (5C, MeCO), 178.6 (1C, $CO_2H$).

$C_{18}$ GLYCOLIPID
(F3) 18-(Glucuronylamino)octadecanoic acid

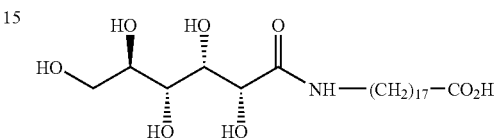

To a suspension of D10 (850 mg, 2.8 mmol) in methanol (100 ml) at 50° C. was added DBU (1.27 g, 8.4 mmol) When the aminoacid had dissolved d-gluconolactone (748 mg, 4.2 mmol) was added. After 3 hrs no ninhydrin positive material was seen on tlc and the reaction was evaporated to dryness. Cold 0.5 M HCl was added and the resulting buff precipitate filtered off, washed with water and dried in vacuo to yield the title compound which was used without further purification.
(F4) 18-(Peracetylglucuronylamino)octadecanoic acid

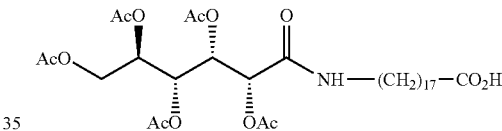

Crude F3 was dissolved in 50 ml 20% acetic anhydride in pyridine containing DMAP (100 mg). The reaction was left overnight, water added (10 ml) with cooling and evaporated to dryness. Dilute hydrochloric acid (50 ml, 0.5M) was added and the aqueous phase extracted with ethyl acetate. The organic phase was dried (MgSO$_4$ and evaporated to dryness to give a brown tar. This material was dissolved in dichloromethane and chromatographed (Silica eluted with ethyl acetate in hexane (30% to 50%), all containing 0.1% acetic acid. Solvent removal yielded the title compound as a white solid (826 mg, 49% 2 steps). $C_{34}H_{56}NO_{13}$ requires C: 59.46%, H: 8.22%, N: 2.04%. Found: C: 59.24%, H: 8.35%, N: 1.97%. $C_{24}H_{49}NO_2$ requires 687. Found ES+: MH$^+$ 688. $\delta_H$ (CD$_3$CO$_2$D) 6.10 (1H, brt, CONH, 5.70 (1H, t, CH (OAc) CH(OAc)CONH), 5.45 (1H, t, CH(OAc)CH(OAc)CH—(OAc)CONH), 5.30 (1H, m, CH(OAc)CONH), 5.05 (1H, m AcOCH$_2$(OAc)CH), 4.31 (1H, dd[J$_1$=4 Hz, J$_2$=12 Hz] AcOCH$_2$(OAc), 4.13 (1H, dd[J$_1$=6 Hz, J$_2$=12 Hz] AcOCH$_2$ (OAc), 3.22 (2H, M, NCH$_2$), 2.33 (2H, t, CH$_2$CO$_2$H), 2.0-2.25 (15H, 5×s, acetate), 1.61 (2H, t, NCH$_2$CH$_2$), 1.45 (1H, t, CH$_2$CH$_2$CO$_2$H), 1.25 (26H, s, CH$_2$).

REDUCED BIXIN GLYCOLIPID
(F5) N-(Peracetylglucuronylaminoethyl)-4,8,13,17-tetramethyldodecanamic acid

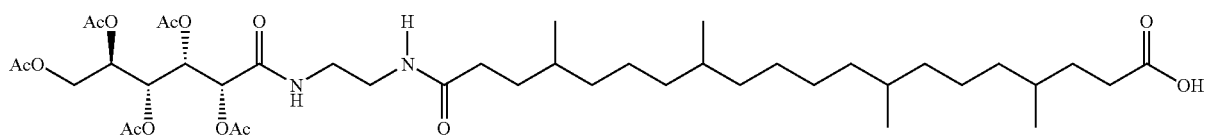

D15 (4.91 g, 11.1 mmol) was dissolved in methanol (50 ml) containing DBU (5.02 ml, 33.6 mmol). ∂-Gluconolactone (2.4 g, 13.3 mmol) was added to the stirred solution, which was left at room temperature for 5 hrs. The reaction was evaporated to dryness and 10% cold citric acid added (50 ml). The precipitant was kept cold whilst it was filtered off and washed with cold water. The step can be slow. The solid was dried in vacuo then dissolved in pyridine and dried by evaporation of solvent. The residue was dissolved in pyridine (100 ml) containing acetic anhydride (20 ml) and DMAP (200 mg) and left stirring overnight. Water was added (30 ml) with cooling and the reaction evaporated to dryness. The resulting black tar was chromatographed (silica, 30% ethyl acetate in hexane containing 0.1% acetic acid) to yield the title compound as a glassy solid (1.83 g, 20%). $C_{42}H_{72}N_2O_{14}$ requires 828. Found ES+: MH+ 829. $d_H$ ($CD_3CO_2D$) 7.1 (1H, brt, CONH), 6.17 (1H, brt, CONH), 5.60 (1H, t, CH(OAc)CH (OAc)CONH), 5.41 (1H, t, CH(OAc)CH (OAc)CH(OAc) CONH), 5.24 (1H, m, CH(OAc)CONH), 5.02 (1H, m, AcOCH$_2$(OAc)CH), 4.29 (1H, dd[$J_1$=4 Hz, $J_2$=12 Hz] AcOCH$_2$(OAc), 4.11 (1H, dd[$J_1$=6 Hz, $J_2$=12 Hz] AcOCH$_2$ (OAc), 3.2-3.62 (4H, m, NCH$_2$), 2.33-0.8 (57H, mm, CH$_2$ & CH$_3$).

C24 AMIDE CONTAINING GLYCOLIPID (F6) (12-(Peracetylglucuronylaminododecanoylamino) dodecanoic acid

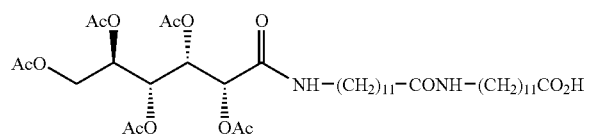

D18 (2.12 g, 5.1 mmol) was dissolved in methanol (50 ml) containing DBU (2.3 ml, 15.3 mmol). d-gluconolactone (1.09 g, 6.12 mmol) was added to the stirred solution, which was left at room temperature for 3 hrs. The reaction was evaporated to dryness & 10% cold citric acid added (50 ml). The precipitant was kept cold whilst it was filtered off and washed with cold water. This step can be slow. The solid was dried in vacuo then dissolved in pyridine and dried by evaporation of solvent. The residue was dissolved in pyridine (100 ml) containing acetic anhydride (20 ml) & DMAP (200 mg) and left stirring overnight. Water was added (30 ml) with cooling and the reaction evaporated to dryness. Dilute hydrochloric acid (1M, 100 ml) was added and the aqueous phase extracted with dichloromethane, dried and evaporated to dryness. The resulting black tar was chromatographed (silica, 5% methanol in dichloromethane) to yield the title compound as a glass (2.44 g, 53%). $C_{40}H_{68}N_2O_{14}$ requires 800. Found ES+: MH+ 801. $\delta_H$ (CDCl$_3$) 7.1 (1H, brt, CONH), 5.68 (1H, br, CONH), 5.66 (1H, t, CH(OAc)CH(OAc)CONH), 5.43 (1H, t, CH(OAc)CH(OAc)CH(OAc)CONH), 5.29 (1H, m, CH(OAc) CONH), 5.04 (1H, m, AcOCH$_2$(OAc)CH), 4.33 (1H, dd[$J_1$=4 Hz, $J_2$=12 Hz] AcOCH$_2$(OAc), 4.15 (1H, dd[$J_1$=6 Hz, $J_2$=12 Hz] AcOCH$_2$(OAc), 3.27-3.18 (4H, m, NCH$_2$), 2.33 (2H, t, CH$_2$CO), 2.19-2.04 (2H+15H, t+5s, CH$_2$CO+acetates), 1.6-1.1 (36H, tm, CH$_2$).

(F7) 12-(Glucuronylamino)dodecanoic acid

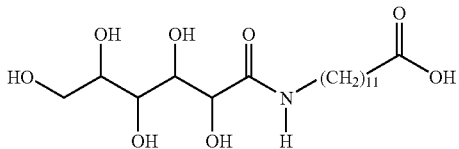

To a solution of d-gluconolactone (1.654 g, 9.288 mmol) in dry methanol (50 ml) under argon was added 12-aminolauric acid (2.000 g, 9.288 mmol) in dry methanol (50 ml), followed by dry triethylamine (9.398 g, 92.88 mmol). The solution/suspension was heated at 80° C. for two hours until all solids dissolved then left at room temperature overnight. Removal of the solvent yielded the desired product as a white insoluble powder, a suspension of which was washed in water (100 ml) at 90° C. for two hours. Filtration and subsequent drying under vacuum yielded the title compound (3.817 g, 83%) as a pure white solid. I.R. 1561 cm$^{-1}$ ($CO_2^-$), 1626 cm$^{-1}$ (CONH, $CO_2^-$). $\delta_H$(CD$_3$OD) 1.0-1.7 (18H, br m, (CH$_2$)$_9$CH$_2$CO$_2$), 2.11 (2H, t, CH$_2$CO$_2$), 3.20 (2H, t, CH$_2$N), 3.5-3.9 (4H, m, CH$_2$OH), 4.05, 4.25 (2H, 2×br, CH$_2$OH). $d_C$(CD$_3$OD) 11.6, 29.4, 32.0 (9C, (CH$_2$)$_9$CH$_2$CO$_2$), 41.0, 42.5 (2C, CH$_2$NH, CH$_2$CO$_2$), 66.0 (1C, CH$_2$OH), 73.7, 74.4, 75.6, 76.8 (4C, CHOH).

(F8) 12-(Peracetylglucuronylamino)dodecanoic acid

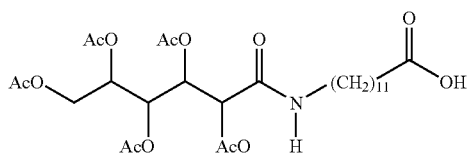

To F7 (1.739 g, 3.515 mmol) dissolved in dry pyridine (10 ml) under argon was added acetic anhydride (10 ml). The solution was left overnight at room temperature and water (10 ml) slowly added to decompose any anhydride. The solution was extracted exhaustively with dichloromethane and this organic fraction washed (4×20 ml HCl, pH3, and 4×20 ml water), dried (MgSO$_4$) and the solvent removed to quantitatively yield the title compound as a pale yellow solid/gum, alumina tlc r.f. 0.1 (10% methanol in dichloromethane). $C_{28}H_{45}NO_{13}$ requires 603.29. Found ES+: MH+ 604.31, ES−: (M−H+)$^-$ 602.37. $\delta_H$(CDCl$_3$) 1.08 (15H, br, Me), 1.27, 1.42 (4H, 2×m, (CH$_2$)$_2$(CH$_2$)$_4$CO$_2$H), 1.75-2.05 (14H, br, (CH$_2$)$_4$ (CH$_2$)$_2$(CH$_2$)$_3$CO$_2$H), 2.14 (2H, m, CH$_2$CO$_2$H), 3.00 (2H, m, CH$_2$NH), 3.90-4.15 (2H, br, CH$_2$O), 4.90, 5.11, 5.26, 5.48 (4H, 4×br, CHO), 6.95 (1H, NHCO). $\delta_C$(CDCl$_3$) 19.6, 19.9 (5C, Me), 24.1, 26.1, 28.3, 28.5, 28.6, 28.7, 28.8, 33.3 (9C, (CH$_2$)$_9$CH$_2$CO$_2$H), 38.9 (1C, CH$_2$CO$_2$H), 53.1 (1C, CH$_2$N), 60.8 (1C, CH$_2$O), 68.1, 68.4, 68.7, 71.3 (4C, CHO), 165.8 (1C, CONH), 168.6, 169.1, 169.2, 169.9, 170.0 (5C, COMe), 176.7 (1C, CO$_2$H).

G. TWO LIPID CHAIN SYNTHESES

This section contains the synthesis of:

(G4)(RS)-N-{1-[8-aminobutylamino-7-aminobutylaminomethyl)octylaminocarbonyl)-2-(peracetylglucuronylaminotetracosanoylamino)ethyl)-24-(peracetylglucuronylamino)tetracosanamide tetra(trifluoroacetate) salt

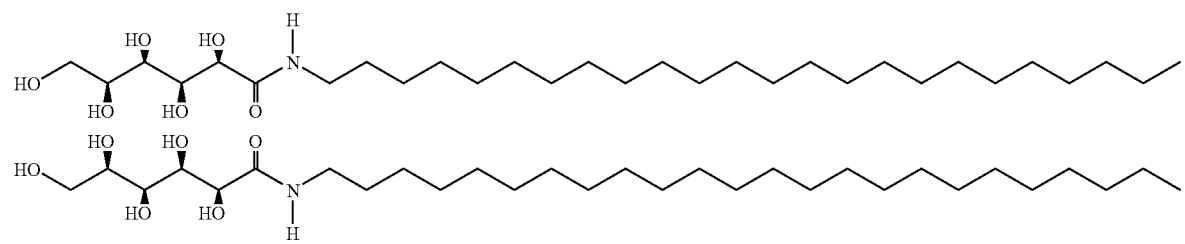

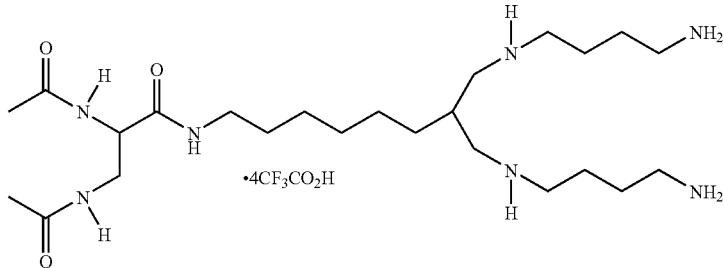

(G1) (RS)-2,3-bis(Peracetylglucuronylaminotetracosanoylamino)propanoic acid

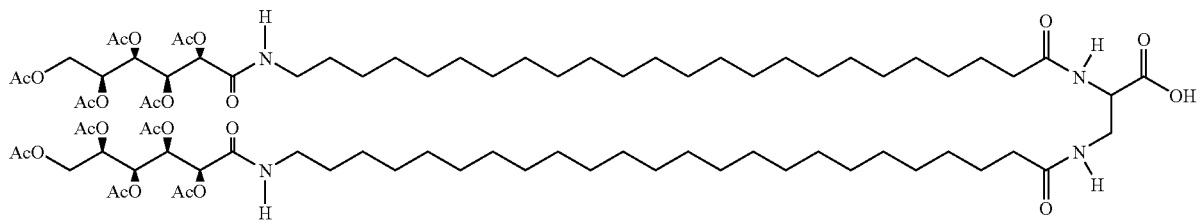

To F2 (250 mg, 0.324 mmol) dissolved in anhydrous dichloromethane (10 ml) were added EDC hydrochloride (68 mg, 0.356 mmol) and N-hydroxysuccinimide (41 mg, 0.356 mmol) and the reaction left overnight under argon at room temperature. To this was added a solution of 2,3 diaminopropionic acid hydrochloride (228 mg, 0.162 mmol) and DBU (148 mg, 0.972 mmol) and the reaction stirred rapidly overnight. The solvent was removed and the residues taken up into hot water (20 ml). The solution was allowed to cool and acidified to pH 1 with 1M HCl. The resulting precipitate was filtered off, washed with water and dried under vacuum to yield the title compound as a buff coloured precipitate (249 mg, 92%). $C_{83}H_{142}N_4O_{26}$ requires 1611.0. Found ES$^+$: MNa$^+$, 1633.4, MH$^+$, 1611.6, ES$^-$ (M–H$^+$)$^-$ 1609.6. $\delta_H$ (CDCl$_3$) 1.24 (76H, br, (CH$_2$)$_{19}$(CH$_2$)$_2$CO), 1.46 (4H, p, CH$_2$CH$_2$CO), 1.62 (4H, br, CH$_2$CH$_2$N), 2.04-2.19 (30H, m, MeCO), 2.24 (4H, m, CH$_2$CO), 3.23 (4H, m, CH$_2$N), 3.45, 3.85 (2H, 2×m, CHCH$_2$N), 4.12, 4.31 (4H, 2×m, CH$_2$OAc), 4.38 (1H, m, CHCO$_2$), 5.04 (2H, q, CHOAcCH$_2$OAc), 5.28 (2H, d, CHOAcCONH), 5.43, 5.66 (4H, 2×t, (CHOAc)$_2$CHOAcCH$_2$OAc), 6.09 (2H, t, CONH(CH$_2$)$_{23}$), 6.65 (1H, t, CH$_2$NHCO(CH$_2$)$_{23}$), 7.76 (1H, d, CONHCHCO$_2$H).

(G2) (RS)-N-(1-{8-[t-butyloxycarbonylaminobutyl(t-butyloxycarbonyl)amino]-7-[t-butyloxycarbonylaminobutyl(t-butyloxycarbonyl)aminomethyl]octylaminocarbonyl}-2-(peracetylglucuronylaminotetracosanoylamino)ethyl)-24-(peracetylglucuronylamino)tetracosanamide

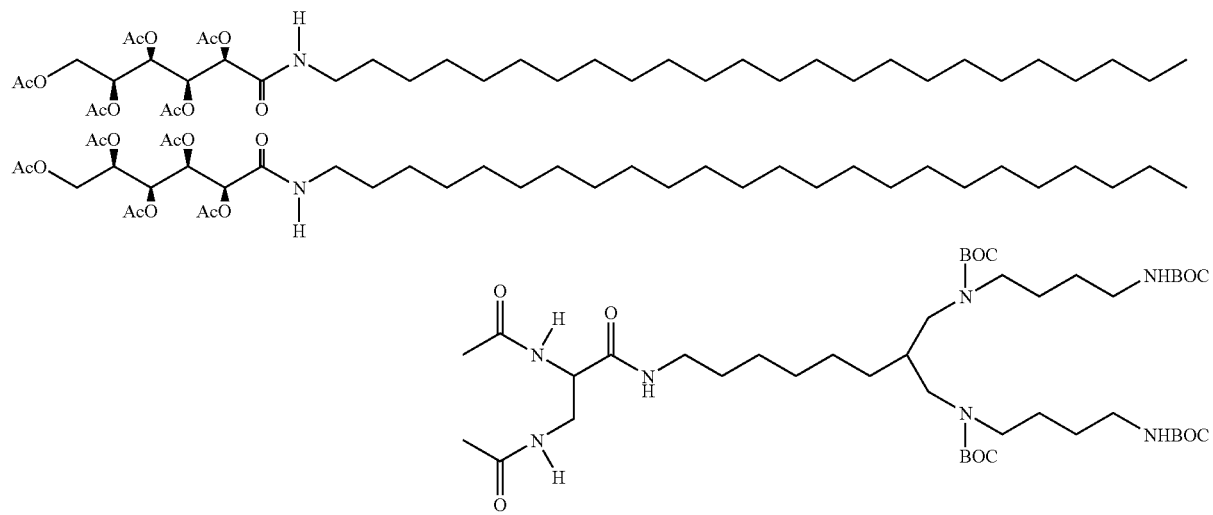

To G1 (240 mg, 0.149 mmol) in anhydrous dichloromethane (20 ml) were added EDC hydrochloride (40 mg, 0.208 mmol) and N-hydroxysuccinimide (19 mg, 0.164 mmol) and the reaction left overnight under argon at room temperature. To this was added B8 (112 mg, 0.156 mmol) and triethylamine (90 mg, 0.893 mmol) and the reaction left for a further five hours. The solvent was removed and the residues purified by silica column chromatography (80% ethyl acetate in hexane) to yield the title compound (163 mg, 47%) as a colourless solid. $C_{120}H_{213}N_9O_{33}$ requires 2308.5. Found ES$^+$: MHNa$^{2+}$, 1167.5, MNa$_2^{2+}$, 1177.5. $\delta_H$ (CDCl$_3$) 1.24 (84H, br, (CH$_2$)$_{19}$(CH$_2$)$_2$CO, (CH$_2$)$_4$CH), 1.43 (54H, m, CH$_2$CH$_2$N, C(Me)$_3$, CH$_2$CH$_2$CO), 2.0 (1H, br, CH), 2.0-2.3 (30H, m, MeCO), 2.24 (4H, m, CH$_2$CO), 2.95-3.35 (18H, m, CH$_2$N), 3.45-3.80 (2H, m, CHCH$_2$N), 4.1-4.35 (4H, m, CH$_2$OAc), 4.40 (1H, m, CHCH$_2$N), 5.03 (2H, q, CHOAcCH$_2$OAc), 5.16 (2H, d, CHOAcCO), 5.44, 5.54 (4H, 2×t, (CHOAc)$_2$CHOAcCO), 6.10 (3H, br, CHCONH, NHCOCHOAc), 7.45, 7.60 (2H, 2×br, CONHCHCH$_2$NHCO).

(G3) (RS)-N-(1-(8-[t-butyloxycarbonylaminobutyl(t-butyloxycarbonyl)amino]-7-[t-butyloxycarbonylaminobutyl(t-butyloxycarbonyl)aminomethyl]octylaminocarbonyl}-2-(glucuronylaminotetracosanoylamino)ethyl)-24-(glucuronylamino)tetracosanamide

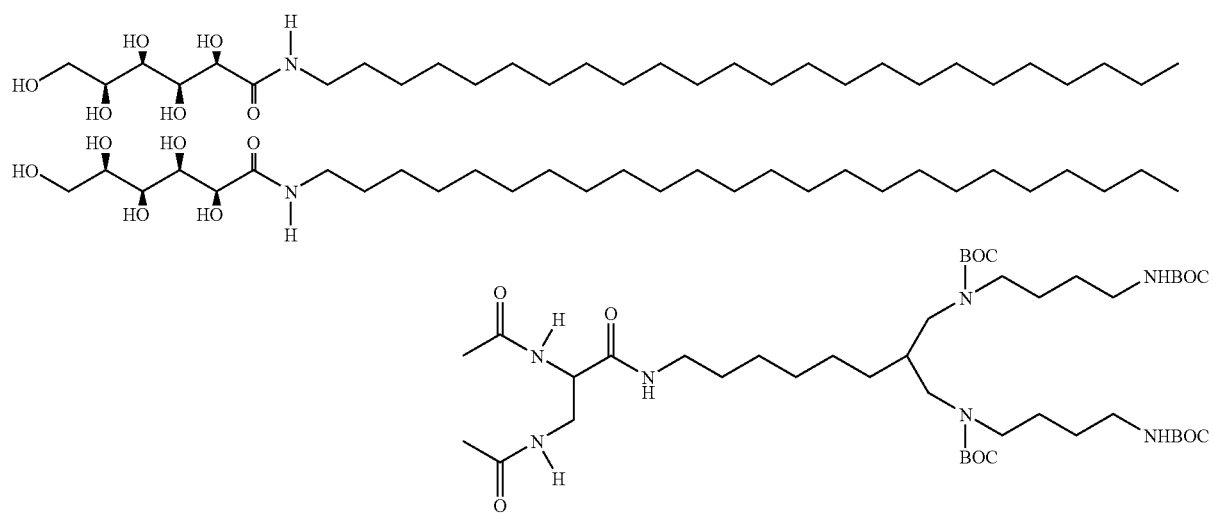

To G2 (163 mg) dissolved in methanol (30 ml) was added concentrated ammonium hydroxide until the solution started to become cloudy (approximately 3 ml). The reaction was left for three hours but had not given total deacetylation and was precipitating out of solution. The solvent was removed, the residues taken up into 2:1 dichloromethane:methanol (60 ml) with heating and concentrated ammonium hydroxide added until the solution started to become cloudy (approx 10 ml). The reaction was left for a further six hours and the solvents removed to yield the title compound as an off white solid too insoluble for analysis and used crude in the next step.

(G4) (RS)-N-{1-[8-aminobutylamino-7-(aminobutylaminomethyl)octylaminocarbonyl)-2-(peracetylglucuronylaminotetracosanoylamino)ethyl}-24-(peracetylglucuronylamino)tetracosanamide tetra(trifluoroacetate) salt

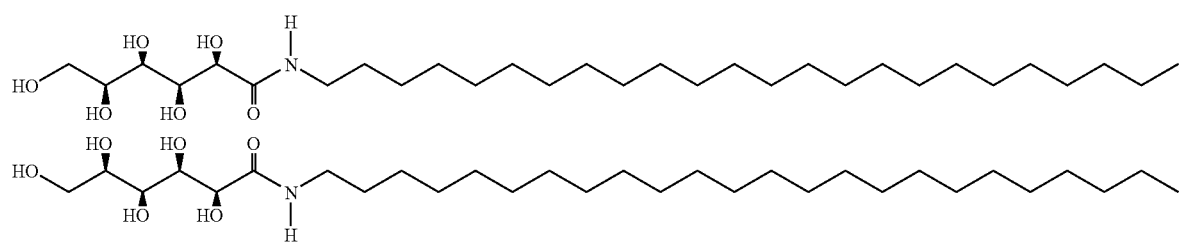

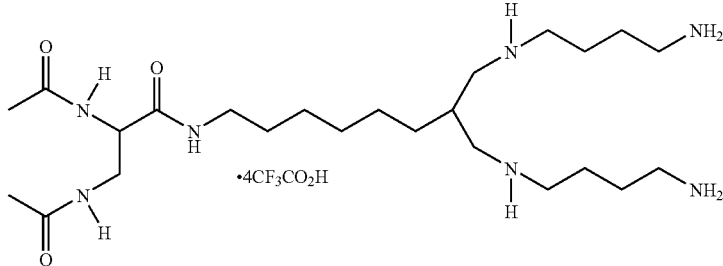

G3 (120 mg) was dissolved in 96:4 trifluoroacetic acid: dichloromethane (8 ml) and left for 20 minutes at room temperature. The solvent was removed, the residues taken up into water, filtered (0.45 mm polypropylene) and freeze dried to give the title compound as a pale yellow solid (126 mg). $C_{80}H_{161}N_9O_{15}$ requires 1488.2. Found ES$^+$: $MH_2^{2+}$, 745.4, MH$^+$, 1489.3. $\delta_H$ (D$_2$O) 1.7-2.25 (94H, br, (CH$_2$)$_{21}$CH$_2$CO, (CH$_2$)$_5$CH), 2.38 (8H, br, NCH$_2$(CH$_2$)$_2$CH$_2$N), 2.80 (5H, br, CH, CH$_2$CO), 3.65-3.95 (18H, m, NCH$_2$), 4.11 (2H, br, CHCH$_2$NH), 4.2-4.5 (8H, m, CHOH), 4.6 (1H, m, COCHNH), 4.7, 4.85 (4H, 2×br, CH$_2$OH).

H. SYNTHESES OF PROTECTED & UNPROTECTED CARBOHYDRATE LIPID TETRAMINES AND HEXAMINES

This section contains the syntheses of:

CARBOHYDRATE LIPID TETRAMINES (H3) N-[8-(aminobutylamino)-7-(aminobutylaminomethyl) octyl]-24-(glucuronylamino)tetracosanamide tetra(trifluoroacetate) salt

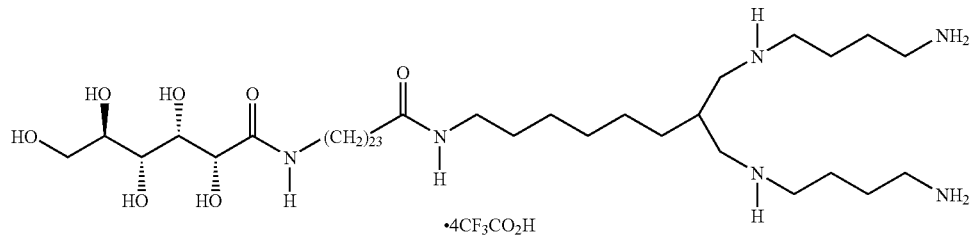

(H6) N-[8-(Aminobutylamino)-7-(aminobutylaminomethyl) octyl]-18-(glucuronylamino)octadecanamide tetra(trifluoroacetate) salt

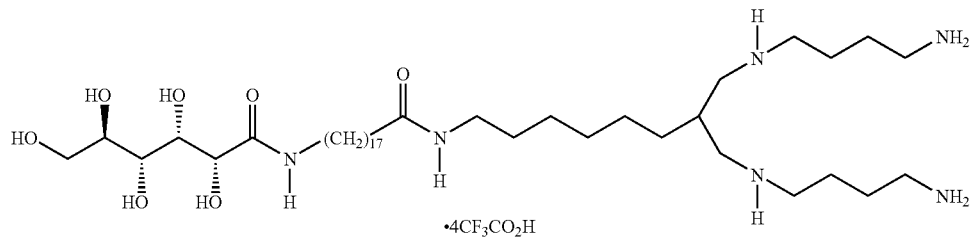

(H12) N-[8-Aminobutylamino-7-(Aminobutylamin-o-methyl)octyl]-18-(glucuronylaminododecanoylamino)dodecanamide tetra(trifluoroacetate) salt

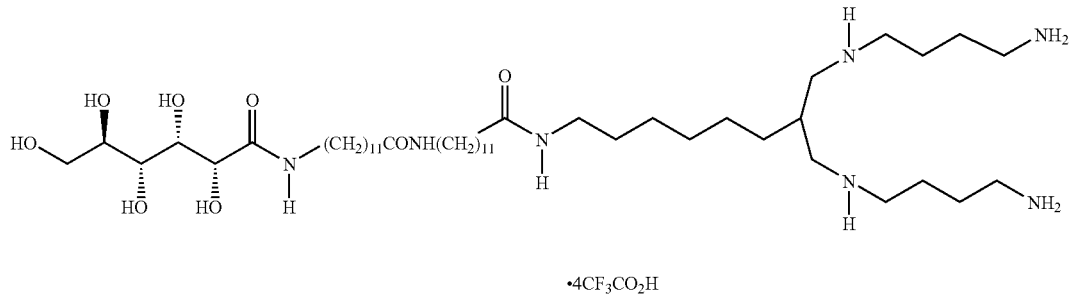

(H9) N-[8-(aminobutylamino)-7-(aminobutylaminomethyl)
octyl]-N'-(glucuronylaminoethyl)-4,8,13,17-tetramethyl-
1,20-docosadiamide tetra(trifluoroacetate) salt
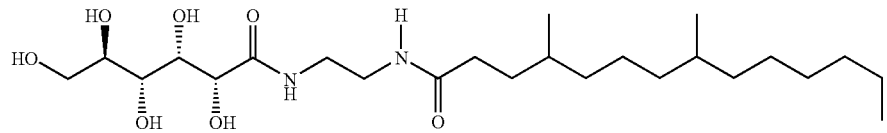
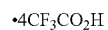
•4CF₃CO₂H
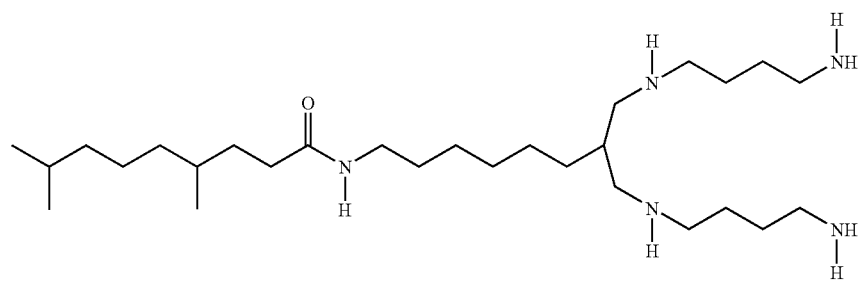
(H15) N-[8-(aminobutylamino)-7-(aminobutylaminom-
ethyl)octylaminocarbonyltricosanyl]-N',N'-bis(glucuro-
nylaminoethyl)succinamide tetra(trifluoroacetate) salt
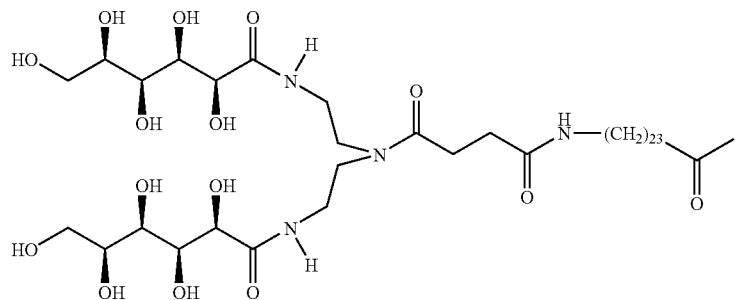
•4CF₃CO₂H
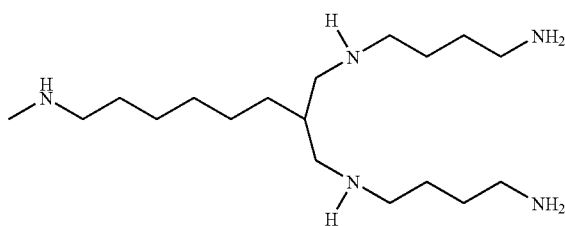

CARBOHYDRATE LIPID HEXAMINES (H18) N-[8-(Aminopropylaminobutylamino)-7-(aminopropylaminobutylaminomethyl)octyl]-24-(glucuronylamino)tetracoanamide. hexa(trifluoroacetate) salt

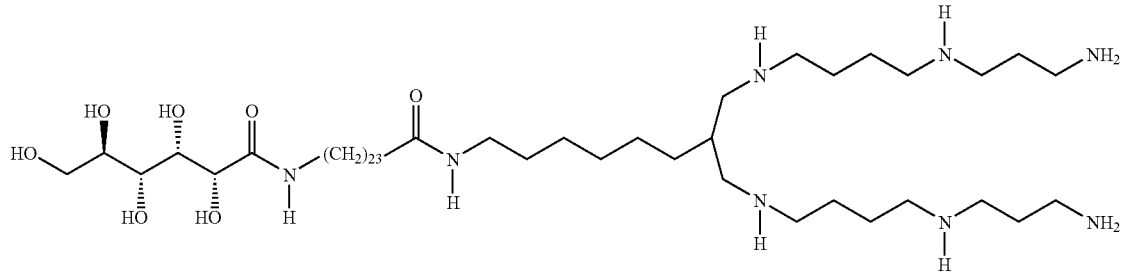

(H21) N-[8-(aminopropylaminobutylamino)-7-(aminopropylaminobutylaminomethyl)octyl]-18-(glucuronylamino)octadecanamide. hexa(trifluoroacetate) salt

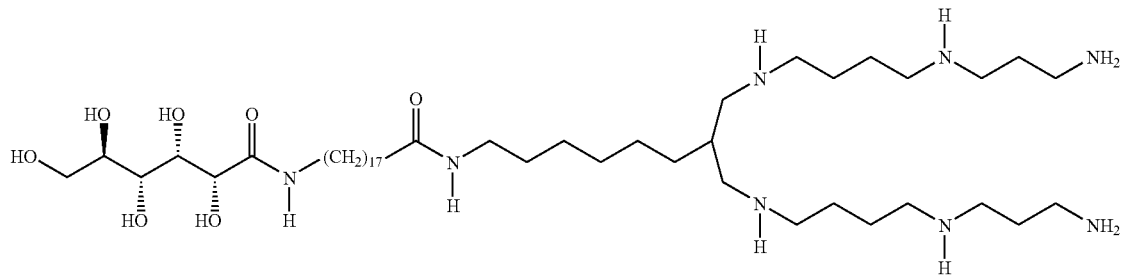

(H24) N-[8-(aminopropylaminobutylamino)-7-(aminopropylaminobutylaminomethyl)octyl]-N'-(glucuronylaminoethyl)-4,8,13,17-tetramethyl-1,20-docosadiamide hexa(trifluoroacetate) salt

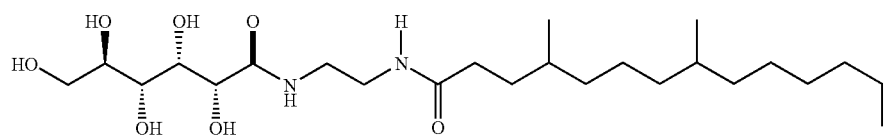

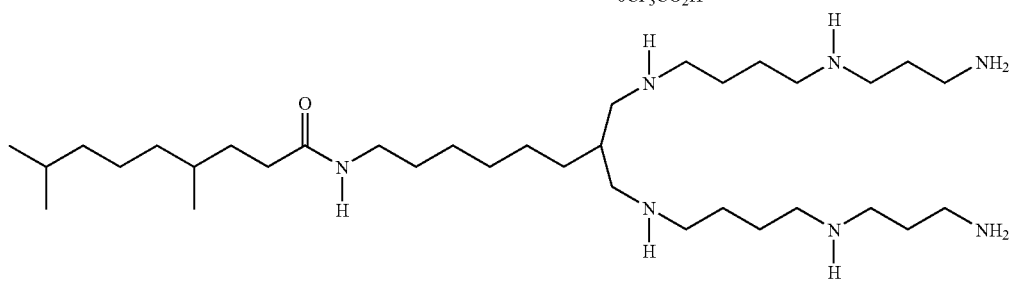

(H27) N-[8-(Aminopropylaminobutylamino)-7-(aminopropylbutylaminomethyl)octyl]-12-(glucuronylamino)dodecanoylamino)dodecanamidehexa(trifluoroacetate) salt

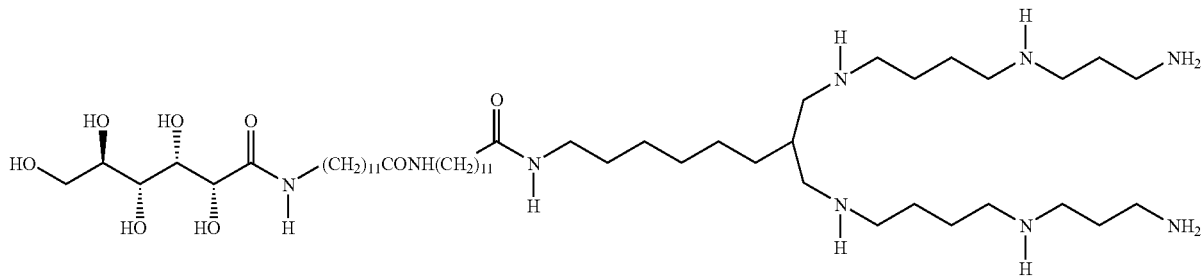

(H20) N-[8-(Methylaminopropylaminobutylamino)-7-(methylaminopropylaminobutylaminomethyl)octylaminocarbonyl tricosanyl}-N',N'-bis(glucuronylaminoethyl)succinamide

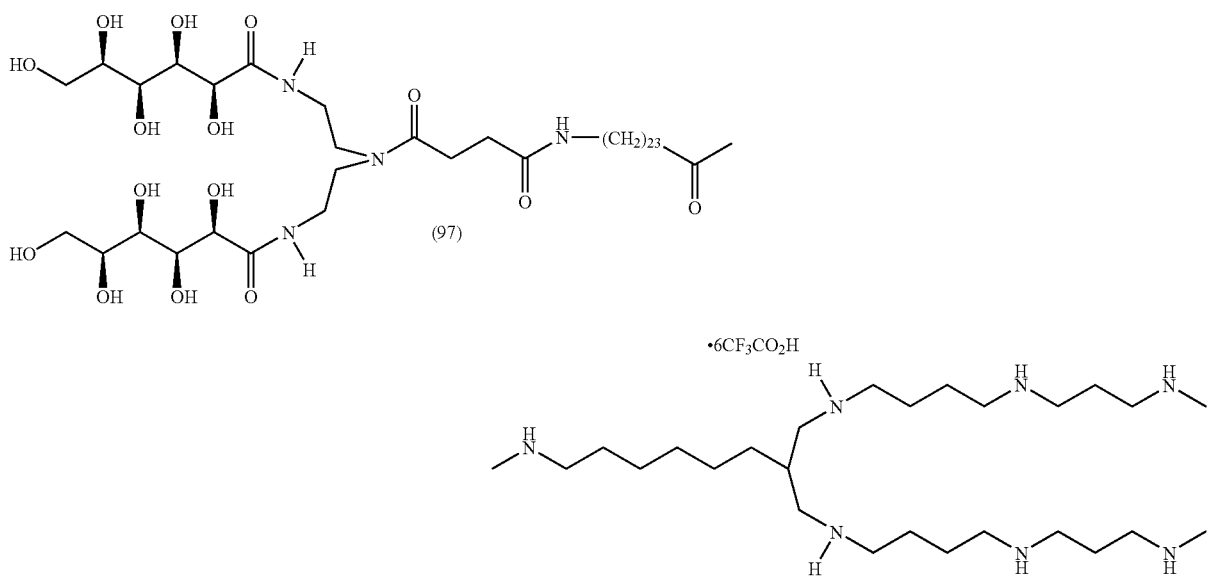

(H33) N-[8-(methylaminopropylaminobutylamino)-7-(methylaminopropylaminobutylaminomethyl)octyl]-24-(glucuronylamino)tetracosanamide

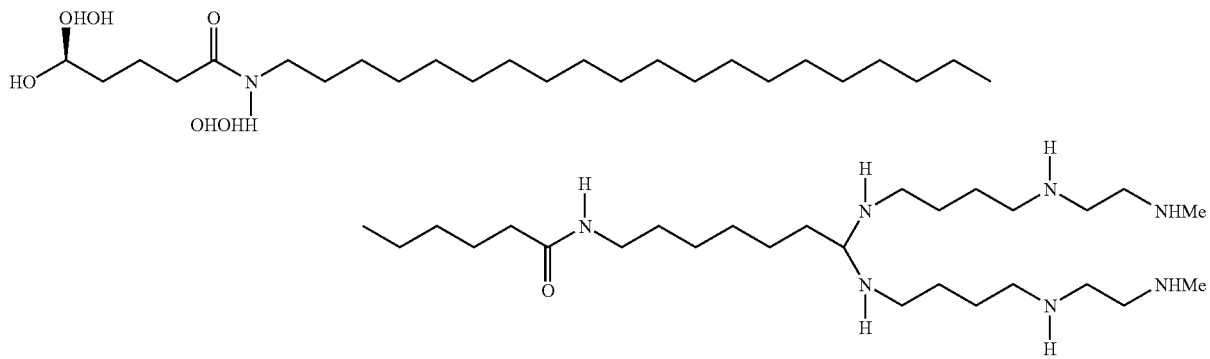

(H36) N-[8-(Methylaminopropylaminobutylamino)-7-(methylaminopropylaminobutylaminomethyl)octyl]-24-(glucuronylaminododecanoylamino)tetracosanamide

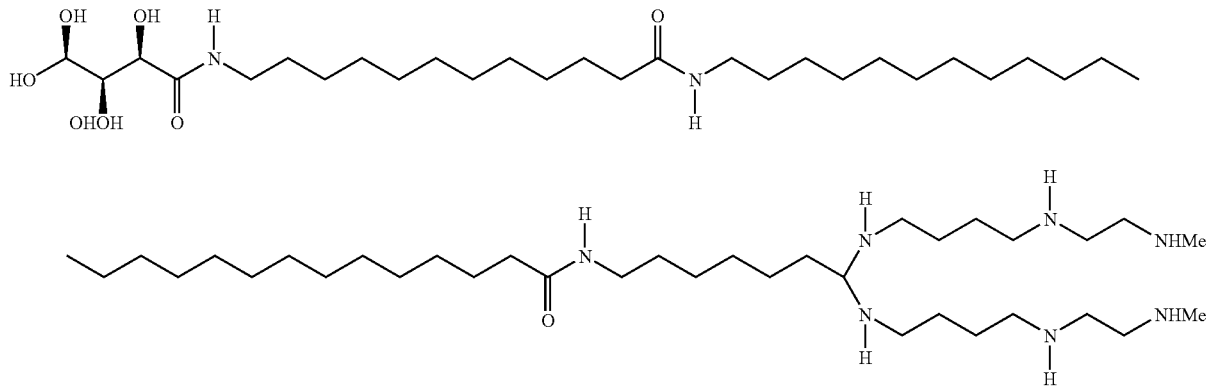

(H38)

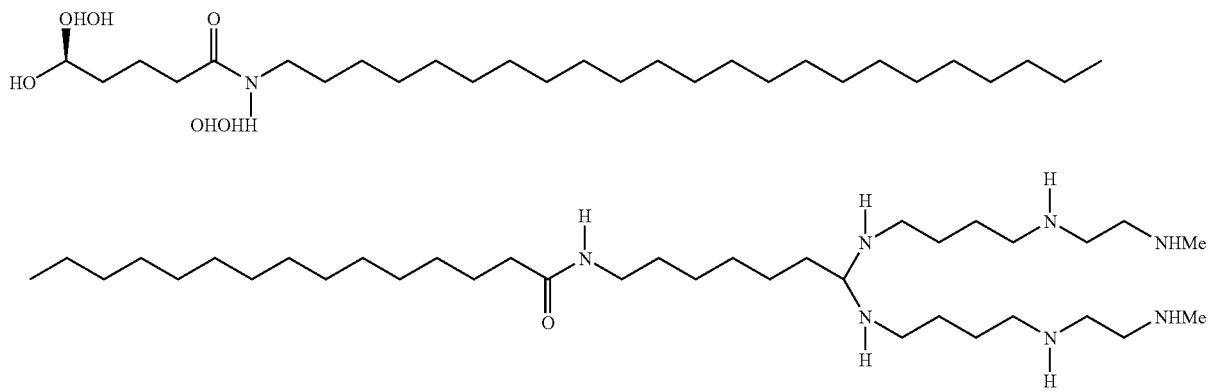

CARBOHYDRATE LIPID TETRAMINES

C24 tetramine (H1) N-{8-[t-Butyloxycarbonylaminobutyl(t-butyloxycarbonyl)amino]-7-[t-Butyloxycarbonylaminobutyl(t-butyloxycarbonyl)aminomethyl]octyl}-24-(peracetylglucuronylamino)tetracosanamide

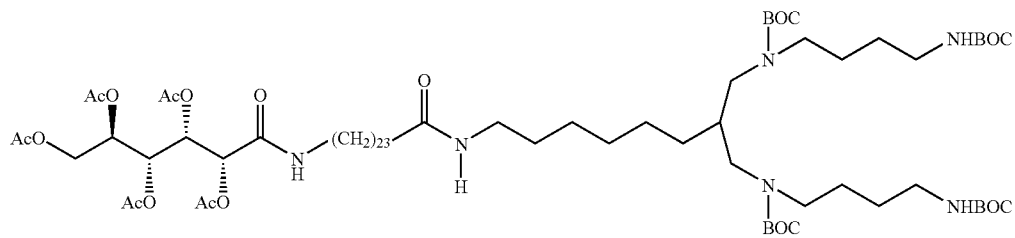

N-Methylmorpholine (0.12 ml, 1.1 mmol) was added to a stirred solution of F2 (0.771 mg, 1 mmol) in dry dichloromethane (10 ml) at room temperature under argon. After a few minutes N-hydroxysuccinimide (127 mg, 1.1 mmol) was added followed by EDC (270 mg, 1.4 mmol), the reaction was stirred overnight (tlc showed conversion to the active ester). A solution of B8 (860 mg, 1.3 mmol) and triethylamine (0.7 ml, 5.5 mmol) in dry dichloromethane (5 ml) was added dropwise and stirring continued for two hours. Tlc showed the active ester had been converted to a slower moving product (silica—60% ethyl acetate in hexane). The solvent was removed and the product chromatographed (silica—60% ethyl acetate in hexane) to yield the title compound (1.25 g, 70%). $C_{77}H_{140}N_6O_{20}.H_2O$ requires C: 62.53%, H: 9.54%, N: 5.61%, Found: C: 62.53%, H: 9.52%, N: 5.69%. $C_{77}H_{140}N_6O_{20}$ requires 1469. Found ES+: MH+ 1470. $\delta_H$ (CDCl$_3$) 6.07 (1H, brt, CONH), 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m, AcOCH$_2$(OAc)CH), 4.31 (1H), dd[J$_1$=4 Hz, J$_2$=12 Hz] AcOCH$_2$(OAc), 4.13 (1H, dd[J$_1$=6 Hz, J$_2$=12 Hz] AcOCH$_2$(OAc), 2.9-3.4 (16H, m, NCH$_2$), 2.0-2.3 (17H, m, CH$_2$CO), 1.2-1.7 (96H, dm, CH$_2$), (H2) N-{8-[t-Butyloxycarbonylaminobutyl(t-butyloxycarbonyl)-amino]-7-[t-Butyloxycarbonylaminobutyl(t-butyloxycarbonyl)aminomethyl]octyl}-24-(glucuronylamino)tetracosanamide

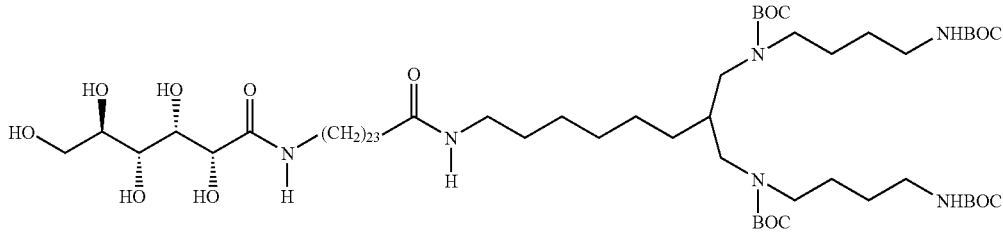

A solution of potassium carbonate (431 mg, 3.12 mmol) in water (2 ml) was added dropwise to a stirred solution of H1 (905 mg, 0.61 mmol) in methanol (15 ml) at room temperature. The flask was stirred for 20 min whereupon tlc showed no starting material was present. Water was added and the precipitate filtered, washed and dried. The product was purified by chromatography (silica—15% methanol in dichloromethane) to yield the title compound (445 mg, 57%). $C_{67}H_{130}N_6O_{15}$ requires 1259. Found ES+: MH+ 1260. $\delta_H$ (CD$_3$OD) 3.6-4.2 (6H, m, sugar), 3.0-3.4 (16H, m, CH$_2$N), 2.15 (3H, t, CH$_2$CO), 2.05 (1H, m, CH$_2$CH(CH$_2$)$_2$), 1.2-1.7 (96H, m, CH$_2$), (H3) N-[8-(aminobutylamino)-7-(aminobutylaminomethyl)octyl]-24-(glucuronylamino)tetracosanamide tetra(trifluoroacetate) salt

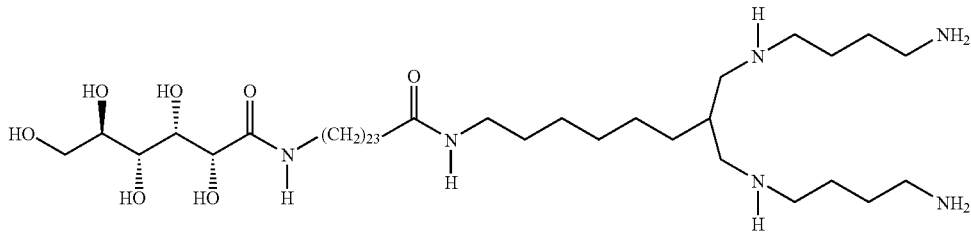

•4CF$_3$CO$_2$H

A solution of the H2 (445 mg, 0.353 mmol) in 96% TFA (4% water) was stirred for 30 mins at room temperature. The TFA was removed under vacuum, and traces removed by evaporation of water. The title compound was obtained as a colourless solid by lyophilisation. 400 mg, 86%. $C_{55}H_{102}N_6O_{15}F_{12}$.1.6H$_2$O requires C: 46.95%, H: 7.34%, N: 5.76%. Found: C: 46.99%, H: 7.17%, N: 5.82%. The free base $C_{47}H_{98}N_6O_7$ requires 858.7. Found ES+: MH+ 859.7. $\delta_H$ (CD$_3$OD) 3.6-4.2 (6H, m, sugar), 3.0-3.4 (16H, m, CH$_2$N), 2.0-2.2 (2H, t, CH$_2$CO), 1.2-1.7 (96H, m, CH$_2$).

C18 Tetramine (H4) N-{8-[t-Butyloxycarbonylaminobutyl(t-butyloxycarbonyl)amino]-7-[t-Butyloxycarbonylaminobutyl(t-butyloxycarbonyl)aminomethyl]octyl}-18-(peracetylglucuronylamino)octadecanamide

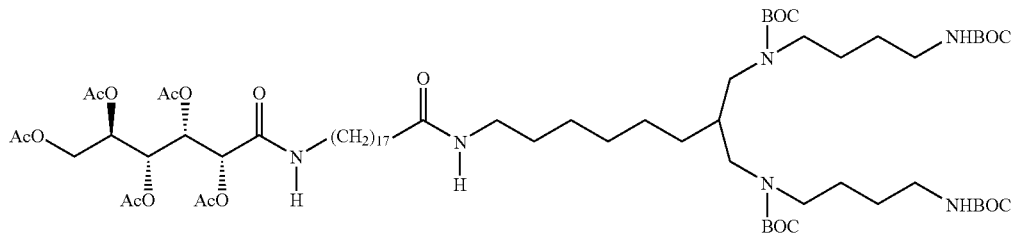

N-Methylmorpholine (0.12 ml, 1.1 mmol) was added to a stirred solution of F4 (687 mg, 1 mmol) in dry dichloromethane (20 ml) at room temperature under argon. A few minutes later N-hydroxysuccinimide (127 mg, 1.1 mmol) was added followed by EDC (270 mg, 1.4 mmol), the reaction was stirred overnight (tlc showed conversion to the active ester). A solution of B8 (394 mg, 0.55 mmol) and triethylamine (0.35 ml, 5.5 mmol) in dry dichloromethane (4 ml) was added dropwise and stirring continued for two hours. Tlc showed the active ester had been converted to a slower moving product (silica—60% ethyl acetate in hexane). The solvent was removed and the product chromatographed (silica—60% to 80% ethyl acetate in hexane) to yield the title compound (533 mg, 80%). $C_{61}H_{128}N_6O_{15}.2/3H_2O$ requires C: 61.01%, H: 9.33%, N: 6.01%. Found: C: 61.05%, H: 9.32%, N: 5.87%. $C_{61}H_{128}N_6O_{20}$ requires 1384.9. Found ES+: MH$^+$ 1386.3. $\delta_H$ (CDCl$_3$) 6.07 (1H, brt, CONH), 5.85 (1H, br, CONH), 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m AcOCH$_2$(OAc)CH), 4.65 (2H, br, 2×NH), 4.31 (1H, dd [J$_1$=4 Hz, J$_2$=12 Hz] AcOCH$_2$(OAc), 4.13 (1H, dd[J$_1$=6 Hz, J$_2$=12 Hz] AcOCH$_2$(OAc), 2.9-3.4 (16H, m, NCH$_2$), 2.0-2.3 (17H, m, MeCO+CH$_2$CO), 1.2-1.7 (84H, dm, CH$_2$).

(H5) N-{8-[t-Butyloxycarbonylaminobutyl(t-butyloxycarbonyl)amino]-7-[t-Butyloxycarbonylaminobutyl(t-butyloxycarbonyl)aminomethyl]octyl}-18-(glucuronylamino)octadecanamide

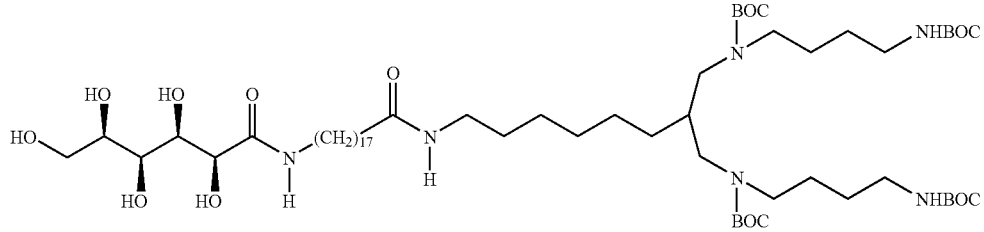

A solution of potassium carbonate (207 mg, 1.5 mmol) in water (1 ml) was added dropwise to a stirred solution of H4 (415 mg, 0.3 mmol) in methanol (12 ml) at room temperature. The flask was stirred for 30 mins whereupon tlc showed no starting material was present. Amberlite CG50 (4 g wet) was added and the resin filtered, washed with methanol and dried. The product was purified by chromatography (silica—10% methanol in dichloromethane) to yield the title compound (190 mg, 54%). $C_{61}H_{118}N_6O_{15}.3/5H_2O$ requires C: 61.75%, H: 10.13%, N: 7.081%. Found: C: 61.755%, H: 10.06%, N: 6.95%. $C_{61}H_{118}N_6O_{15}$ requires 1174.9. Found ES+: MH$^+$1176.0. $\delta_H$ (CD$_3$OD) 3.6-4.2 (6H, m, sugar), 3.0-3.4 (16H, m, CH$_2$N), 2.15 (2H, t, CH$_2$CO), 2.06 (1H, m, CH$_2$CH(CH$_2$)$_2$), 1.2-1.7 (84H, m, CH$_2$).

(H6) N-[8-(Aminobutylamino)-7-(aminobutylaminomethyl) octyl]-18-(glucuronylamino)octadecanamide tetra(trifluoroacetate) salt

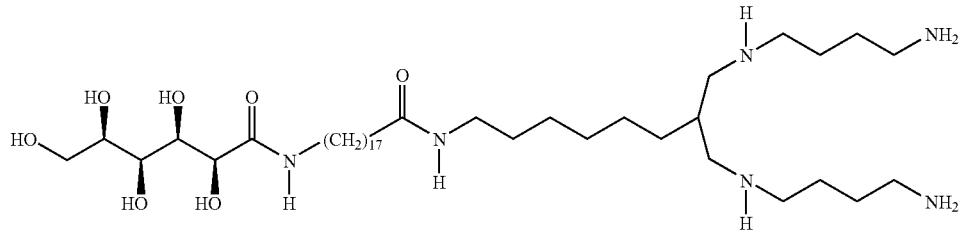

4CF$_3$CO$_2$H

A solution of H5 (190 mg, 0.16 mmol) in 96% TFA (4% water) was stirred for 30 mins at room temperature. The TFA was removed under vacuum, and traces removed by evaporation of water. The title compound was obtained as a colourless hygroscopic solid (190 mg, 95%) by lyophilisation. C$_{49}$H$_{90}$N$_6$O$_{15}$F$_{12}$.2H$_2$O (Mwtanhydrous=1230) requires C: 46.95%, H: 7.34%, N: 5.76%. Found: C: 46.99%, H: 7.17%, N: 5.82%. The free base C$_{41}$H$_{86}$N$_6$O$_7$ requires 774. Found ES+: MH$^+$ 775. $\delta_H$(CD$_3$OD) 3.6-4.25 (6H, m, sugar), 2.9-3.4 (16H, m, CH$_2$N), 2.15 (2H, t, CH$_2$CO), 2.23 (1H, m, CH$_2$CH(CH$_2$)$_2$), 1.2-1.9 (84H, m, CH$_2$).

Bixin Tetramine (H7) N-{8-[t-Butyloxycarbonylaminobutyl(t-butyloxycarbonyl)amino]-7-[t-butyloxycarbonylaminobutyl(t-butyloxycarbonyl)aminomethyl]octyl}-N'-(peracetylglucuronylaminoethyl)-4,8,13,17-tetramethyl-1,20-docosadiamide

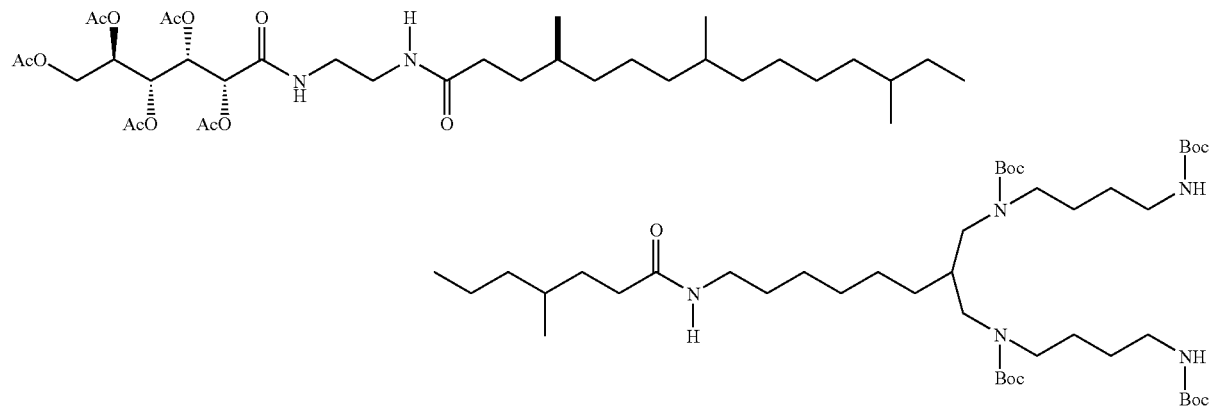

N-Methylmorpholine (0.16 ml, 1.47 mmol) was added to a stirred solution of F5 (1.04 g, 1.33 mmol) in dry dichloromethane (20 ml) at room temperature under argon. A few minutes later N-hydroxysuccinimide (170 mg, 1.47 mmol) was added followed by EDC (282 mg, 1.47 mmol), the reaction was stirred overnight (tlc showed conversion to the active ester). A solution of B8 (520 mg, 1.45 mmol) and triethylamine (0.46 ml, 3.35 mmol) in dry dichloromethane (10 ml) was added dropwise and stirring continued for two hours. Tlc showed the active ester had been converted to a slower moving product (silica—60% ethyl acetate in hexane). The solvent was removed and the product chromatographed (silica—5% methanol in dichloromethane) to yield the title compound (810 mg, 60%). C$_{79}$H$_{143}$N$_7$O$_{21}$ requires C: 62.14%, H: 9.44%, N: 6.42%. Found: C: 61.76%, H: 9.42%, N: 6.35%. C$_{79}$H$_{143}$N$_7$O$_{21}$ requires 1526. Found ES+: MH$^+$ 1527.1. $\delta_H$ (CDCl$_3$) 7.15 (1H, br, CONH), 6.47 (1H, br, CONH), 5.95 (1H, br, CONH), 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m, AcOCH$_2$(OAc)CH), 4.65 (2H, br, 2×NH), 4.31 (1H, dd[J$_1$=4 Hz, J$_2$=12 Hz] AcOCH$_2$(OAc), 4.13 (1H, dd[J$_1$=6 Hz, J$_2$=12 Hz] AcOCH$_2$(OAc), 4.70 (2H, br, CONH), 2.9-3.5 (18 H, m, NCH$_2$), 2.0-2.3 (21H, m, MeCO+CH$_2$CO), 1.0-1.7 (82H, dm, CH$_2$), 0.8-0.9 (12H, 4×s, Me).

(H8) N-{8-[t-Butyloxycarbonylaminobutyl(t-butyloxycarbonyl)amino]-7-[t-butyloxycarbonylaminobutyl(t-butyloxycarbonyl)aminomethyl]octyl}-N'-(glucuronylaminoethyl)-4,8,13,17-tetramethyl-1,20-docosadiamide

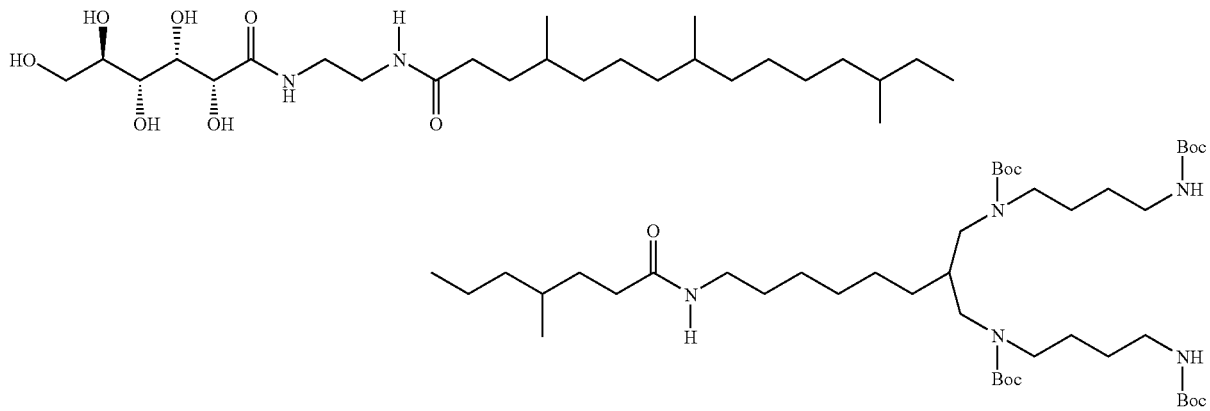

A solution of potassium carbonate (372 mg, 2.7 mmol) in water (1 ml) was added dropwise to a stirred solution of H7 (790 mg, 0.52 mmol) in methanol (12 ml) at room temperature. The flask was stirred for 30 min whereupon tlc showed no starting material was present. Amberlite® CG50 (5 g wet) was added and the resin filtered, washed with methanol & dried. The product was purified by chromatography (silica—10%-20% methanol in dichloromethane) to yield the title compound (230 mg, 72%). $C_{69}H_{133}N_7O_{16}$ requires 1315.9. Found ES+: MH$^+$ 1317.0. $\delta_H$ (CD$_3$OD) 3.6-4.3 (6H, m, sugar), 3.0-3.4 (18H, m, CH$_2$N), 2.0-2.3 (6H, m, CH$_2$CO), 1.0-1.7 (81H, m, alkane, 0.8-1.0 (12H, 4×s, Me).

(H9) N-[8-(aminobutylamino)-7-(aminobutylaminomethyl)octyl]-N'-(glucuronylaminoethyl)-4,8,13,17-tetramethyl-1,20-docosadiamide tetra(trifluoroacetate) salt

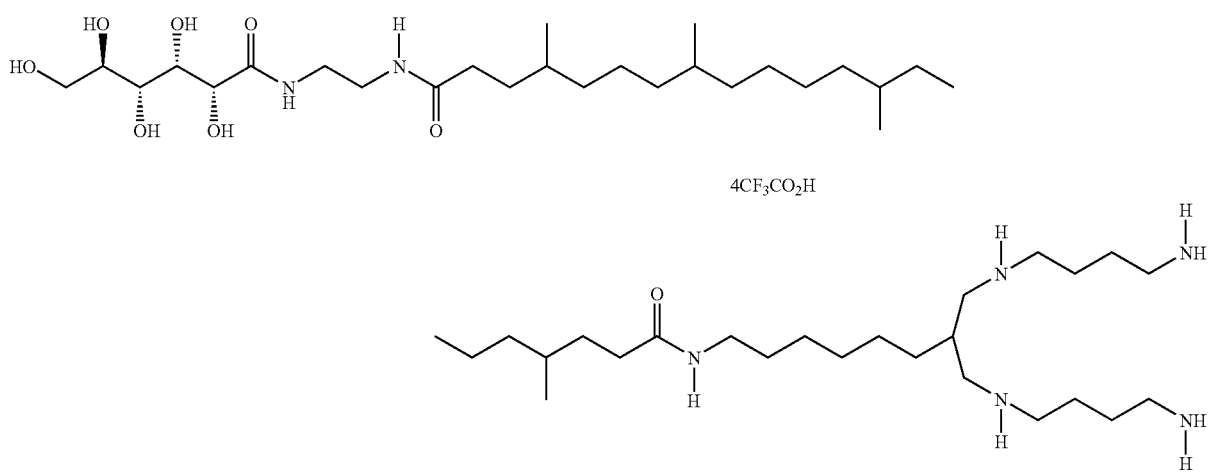

A solution of H8 (180 mg, 0.137 mmol) in 96% TFA (4% water) was stirred for 30 min at room temperature. The TFA was removed under vacuum, and traces removed by evaporation of water. The title compound was obtained as to a colourless hygroscopic solid (170 mg, 91%) by lyophilisation. The free base $C_{49}H_{101}N_7O_8$ requires 915.8 (salt $C_{57}H_{105}F_{12}N_7O_{16}$=1371). Found ES+: MH$^+$ 917.1. $\delta_H$ (CD$_3$OD) 3.6-4.25 (1+1+4H, 3×m, sugar), 2.9-3.4 (4+8+4H, 3×m, CH$_2$N), 2.1-2.35 (5H, m, CH$_2$CO+CH$_2$CH(CH$_2$)$_2$), 1.0-2.0 (44H, m, alkane), 0.8-1.0 (12H, 4×s, Me).

C24 Amide Tetramine (H10) N-{8-[t-Butyloxycarbonylaminobutyl(t-butyloxycarbonyl)amino]-7-[t-butyloxycarbonylaminobutyl(t-butyloxycarbonyl)aminomethyl]octyl}-12-(peracetylglucuronylaminododecanoylamino)dodecanamide

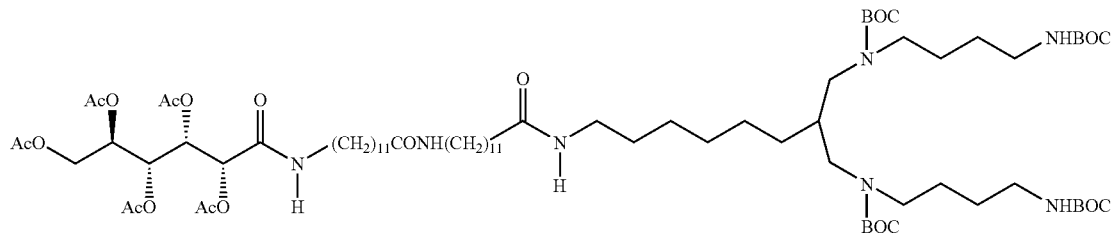

DBU (0.05 ml, 0.36 mmol) was added to a stirred suspension of F6 (264 mg, 0.33 mmol) in dry dichloromethane (4 ml) at room temperature under argon. After a few minutes N-hydroxysuccinimide (38 mg, 0.33 mmol) was added followed by EDC (63 mg, 0.33 mmol), the reaction was stirred overnight (tlc showed conversion to the active ester). A solution of B8 (260 mg, 0.36 mmol) and DBU (0.1 ml, 0.66 mmol) in dry dichloromethane (4 ml) was added dropwise and stirring continued for two hours. Tlc showed the active ester had been converted to a slower moving product (silica—60% ethyl acetate in hexane). The solvent was removed and the product chromatographed (silica—2% to 5% methanol in dichloromethane) to yield the title compound (376 mg, 76%). $C_{77}H_{139}N_7O_{21}$ requires 1498.0. Found ES+: MH+ 1499.0

$\delta_H$ (CDCl$_3$) 6.15 (1H, brt, CONH), 5.92 (1H, br, CONH), 5.75 (1H, br, CONH), 4.7 (2H, br, 2×CONH) 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m AcOCH$_2$(OAc)CH), 4.31 (1H, dd[J$_1$=4 Hz, J$_2$=12 Hz] AcOCH$_2$(OAc), 4.13 (1H, dd[J$_1$=6 Hz, J$_2$=12 Hz] AcOCH$_2$(OAc), 3.0-3.3 (20H, m, NCH$_2$), 2.0-2.3 (18H, m, MeCO+CH$_2$CO+CH$_2$CH(CH$_2$)$_2$), 1.2-1.7 (90H, dm, CH$_2$+Me).

(H11) N-{8-[t-Butyloxycarbonylaminobutyl(t-butyloxycarbonyl)amino]-7-[t-butyloxycarbonylaminobutyl(t-butyloxycarbonyl)aminomethyl]octyl}-12-(glucuronylaminododecanoylamino)dodecanamide

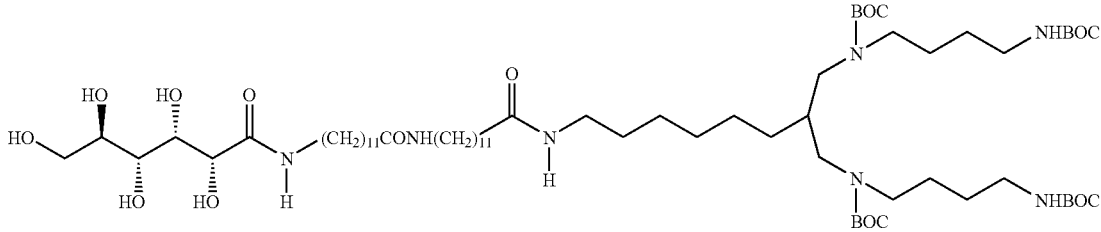

Ammonia solution (20 ml, 0.880) was added to a stirred solution of H10 (370 mg, 0.25 mmol) in methanol (20 ml) at room temperature. The flask was stirred for 30 min and evaporated to dryness. The white solid was suspended in water, filtered off and dried. The product was chromatographed (Reverse phase silica, Merck-Lichroprep eluted with dichloromethane/methanol/water [2:6:1]). The product was evaporated to dryness and triturated with ether. High vacuum yielded the title compound (234 mg) as a white solid. $C_{67}H_{129}N_7O_{16}$ requires 1287.9. Found ES+: MH+ 1288.9. $\delta_H$ (CD$_3$OD) 3.6-4.2 (6H, m, sugar), 3.0-3.4 (18H, m, CH$_2$N), 2.15 (4H, t, CH$_2$CO), 2.06 (1H, m, CH$_2$CH(CH$_2$)$_2$, 1.2-1.7 (90H, m, CH$_2$+Me).

(H12) N-[8-(Aminobutylamino)-7-(aminobutylaminomethyl)octyl]-12-(glucuronylaminododecanoylamino) dodecanamide tetra(trifluoroacetate) salt

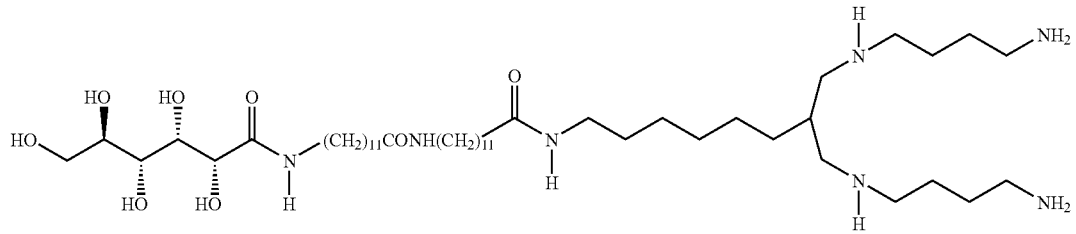

A solution of H11 (260 mg, 0.18 mmol) in 96% TFA (6 ml, 4% water) was stirred for 30 min at room temperature. The TFA was removed under vacuum, and traces removed by evaporation of toluene/water. The compound was subjected to high vacuum overnight, dissolved in water (5 ml) and filtered through a 0.45 μM (Whatman PP) filter The compound was converted to a colourless solid by lyophilisation. The lyophilised hygroscopic solid was triturated with ether and dried in vacuo to yield the title compound (287 mg, 100%). $C_{47}H_{97}N_7O_8 \cdot C_8H_4O_8.F_{12}$ 3.25$H_2O$ (Mwt anhydrous=1344.4) requires C: 47.09%, H: 7.72%, N: 6.99%. Found: C: 49.14%, H: 7.57%, N: 7.29%. The free base $C_{47}H_{97}N_7O_8$ requires 887.7. Found ES+: $MH^+$ 888.7. $\delta_H$ ($D_2O$) 3.6-4.25 (6H, m, sugar), 2.9-3.4 (18H, m, $CH_2H$), 2.15 (4H, dt, $CH_2CO$, 2.23 (1H, m, $CH_2CH(CH_2)_2$), 1.2-1.9 (54H, m, $CH_2$).

DISUGAR TETRAMINES (H13) N-{8-[t-Butyloxycarbonylaminobutyl(t-butyloxycarbonyl)amino]-7-[t-butyloxycarbonylaminobutyl(t-butyloxycarbonyl)aminomethyl]octylaminocarbonyltricosanyl}-N',N'-bis(peracetylglucuronylaminoethyl) succinamide C4 (259 mg, 0.254 mmol), EDC hydrochloride (101 mg, 0.528 mmol) and N-hydroxysuccinimide (46 mg, 0.396 mmol) were dissolved in anhydrous dichloromethane (20 ml) and activated ester formation left at room temperature for two hours under argon. To the solution was added E2 (300 mg, 0.277 mmol) and triethylamine (80 mg, 0.792 mmol) and the reaction left overnight at room temperature under argon. The solvents were removed, and the resulting residues purified by gradient silica column chromatography (3-7% methanol in dichloromethane) to yield the title compound as a colourless solid (350 mg, 65%). $C_{101}H_{175}N_9O_{33}$ requires 2042.2. Found ES+: $MH^+$, 2043.4, $MNa^+$, 2065.5, $MK^+$, 2081.4. $\delta_H$ ($CDCl_3$) 1.24 (48H, br, $(CH_2)_{20}CH_2)CO$, $(CH_2)_4CH$), 1.43 (48H, br, $(Me)_3C$, $CH_2CH_2N$), 2.03-2.23 (30H, 10×s, MeCO), 2.19 (2H, t, $(CH_2)_{22}CH_2CO$), 2.3-2.8 (4H, brm, $(CH_2)_2CO$), 3.0-3.4 (24H, brm, $CH_2N$), 4.10 (2H, m, $CH_2OAc$), 4.31 (2H, m, $CH_2OAc$), 4.65 (2H, br, $NHCO_2$), 5.05 (2H, m, $CHCH_2OAc$), 5.21, 5.25 (2H, 2×d, CHCON), 5.44, 5.66 (4H, 2×m, $(CHOAc)_2CHOAcCH_2OAc$), 5.75 (1H, br, $(CH_2)_{23}CONH$), 6.48 (1H, br, $(CH_2)_2CONH$), 7.21, 7.70 (2H, 2×t, $N(CH_2CH_2NHCO)_2$).

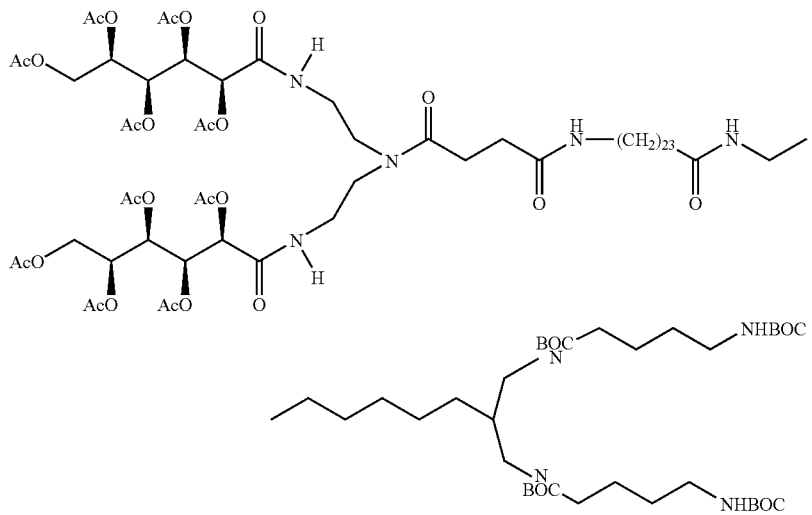

(H14) N-{8-[t-Butyloxycarbonylaminobutyl(t-butyloxycarbonyl)amino]-7-[t-butyloxycarbonylaminobutyl(t-butyloxycarbonyl)aminomethyl]octylaminocarbonyltricosanyl}-N',N'-bis(glucuronylaminoethyl)succinamide

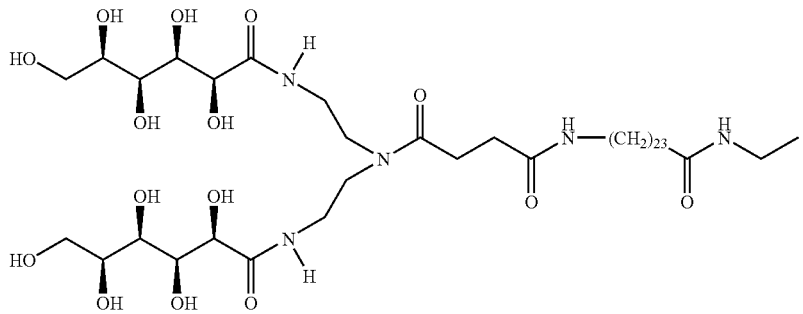

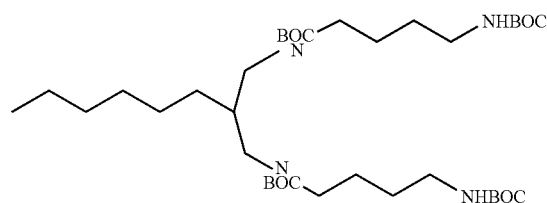

To H13 (349 mg) in methanol (20 ml) was added concentrated ammonium hydroxide (5 ml). The cloudy solution/suspension was rapidly stirred for two hours whereupon the solvent was removed and the resulting residues purified by reverse phase silica chromatography eluting with 2:6:1 dichloromethane:methanol:water to yield the title compound as a colourless solid (238 mg, 86%). $C_{81}H_{155}N_9O_{23}$ requires 1622.1 Found ES$^+$: MH$_2^{2+}$, 812.4, MHNa$^{2+}$, 823.7, ES$^-$: MCl$^-$, 1657.3. $\delta_H$ (CD$_3$OD) 1.28 (46H, br, (CH$_2$)$_{19}$(CH$_2$)$_2$CO, (CH$_2$)$_4$CH), 1.44 (50H, m, (Me)$_3$C, CH$_2$CH$_2$N), 2.03 (1H, br, CH), 2.16 (2H, t, (CH$_2$)$_{22}$CH$_2$CO), 2.49 (2H, t, CH$_2$CONH), 2.70 (2H, m, CH$_2$CON), 3.0-3.3 (16H, m, CH$_2$NBOC), 3.4-3.6 (8H, m, N(CH$_2$)$_2$N), 3.6-3.85 (8H, m, CHOH), 4.11 (2H, m, CH$_2$OH), 4.19, 4.22 (2H, 2×d, CH$_2$OH).

(H15) N-[8-(aminobutylamino)-7-(aminobutylaminomethyl)octylaminocarbonyltricosanyl]-N',N'-bis(glucuronylaminoethyl)succinamide tetra(trifluoroacetate) salt

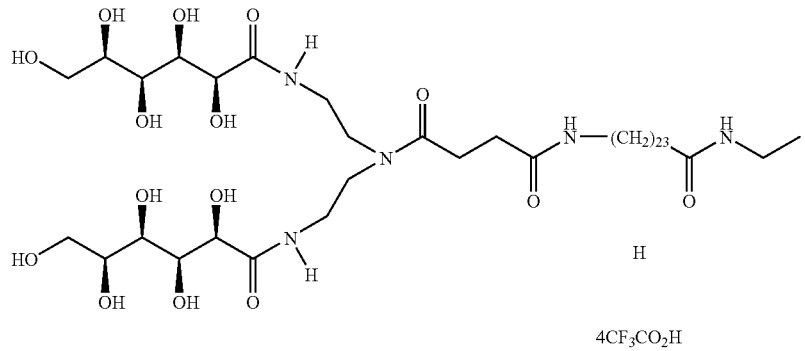

4CF$_3$CO$_2$H

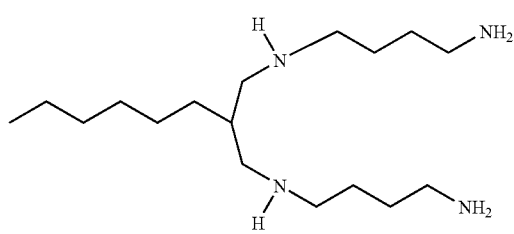

To H14 (234 mg) was added 96:4 trifluoroacetic acid: dichloromethane (10 ml). The solution was left for 20 minutes at room temperature, the solvents removed and the residues taken up into MilliQ water. The solution was filtered (0.45 mm polypropylene) and freeze dried to give a white solid. This was suspended in diethyl ether, left for 20 minutes and the ether decanted off. The remaining white solids were dried under vacuum to give the title compound as a white, hydroscopic solid (226 mg). $C_{61}H_{123}N_9O_{15}$ requires 1221.9 Found ES$^+$: MH$_2^{2+}$, 612.0, MH$^{+,}$ 1222.9. $\delta_H$ (D$_2$O) 1.29 (44H, br, (CH$_2$)$_{19}$(CH$_2$)$_2$CO, (CH$_2$)$_3$CH$_2$CH), 1.49 (8H, brm, CH$_2$CH, CH$_2$CH$_2$CO, CH$_2$CH$_2$NHCO), 1.78 (8H, br, NCH$_2$(CH$_2$)$_2$CH$_2$N), 2.21 (3H, br, CH), 2.51, 2.72 (4H, 2×t, CO(CH$_2$)$_2$CO), 3.0-3.3 (16H, m, CH$_2$N), 3.3-3.65 (8H, m, N(CH$_2$)$_2$N), 3.65-3.95 (8H, m, CHOH), 4.10, 4.30 (4H, 2×br, CH$_2$OH).

CARBOHYDRATE LIPID HEXAMINES

C24 Hexamine (H16) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-24-(peracetylglucuronylamino)tetracosanamide

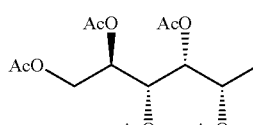
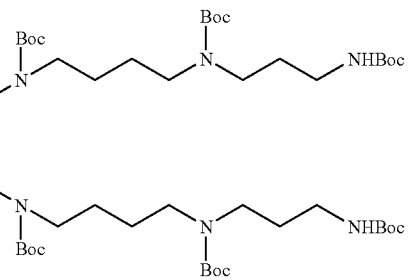

N-Methylmorpholine (0.06 ml, 0.57 mmol) was added to a stirred solution of F2 (400 mg, 0.52 mmol) in dry dichloromethane (10 ml) at room temperature under argon. After a few minutes N-hydroxysuccinimide (66 mg, 0.57 mmol) was added followed by EDC (109 mg, 0.57 mmol), the reaction was stirred overnight (tlc showed conversion to the active ester). A solution of B16 (640 mg, 0.622 mmol) and triethylamine (0.36 ml, 2.6 mmol) in dry dichloromethane (5 ml) was added dropwise and stirring continued for two hours. Tlc showed the active ester had been converted to a slower moving product (silica—60% ethyl acetate in hexane). The solvent was removed and the product chromatographed (silica—66% ethyl acetate in hexane) to yield the title compound (400 mg, 58%). $C_{93}H_{170}N_8O_{24}$ requires 1783.23. Found ES+: MH$^+$ 1785.4. $C_{93}H_{170}N_8O_{24}$ requires C: 63.33%, H: 10.24%, N: 7.12%. Found: C: 63.41%, H: 10.57%, N: 6.98%. $\delta_H$ (CDCl$_3$) 6.07 (1H, brt, CONH), 5.6 (1H, brt, CONH), 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m AcOCH$_2$(OAc)CH), 4.31 (1H, dd[J$_1$=4 Hz, J$_2$=12 Hz] AcOCH$_2$(OAc), 4.13 (1H, dd[J$_1$=6 Hz, J$_2$=12 Hz] AcOCH$_2$(OAc), 2.9-3.4 (24H, m, NCH$_2$), 2.0-2.3 (17H, m, CH$_2$CO+5×acetate), 2.23 (1H, m, CH$_2$CH(CH$_2$)$_2$), 1.2-1.8 (118 H, dm, CH$_2$+Me).

(H17) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-24-(glucuronylamino)tetracosanamide

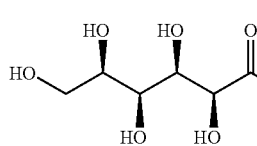
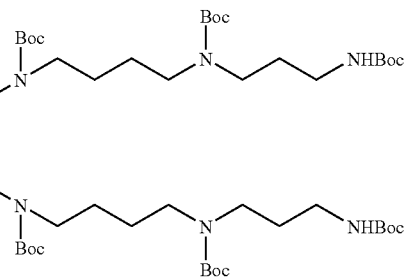

A solution of potassium carbonate (186 mg, 1.26 mmol) in water (1 ml) was added dropwise to a stirred solution of H16 (380 mg, 0.21 mmol) in methanol (7 ml) at room temperature. The flask was stirred for 30 mins whereupon tlc showed no starting material was present. Water (20 ml) was added and the precipitate filtered, washed and dried. The product was purified by chromatography (Reverse phase silica, Merck Lichroprep-15% methanol in dichloromethane) to yield the title compound (445 mg, 57%). $C_{83}H_{160}N_8O_{14}$ requires C: 63.33%, H: 10.24%, N: 7.12%. Found: C: 63.41%, H: 10.57%, N: 6.98%. $C_{67}H_{130}N_6O_{15}$ requires 1573.18. Found ES+: MH$^+$ 1574.3. $\delta_H$ (CD$_3$OD) 3.6-4.2 (6H, m, sugar), 3.0-3.4 (24H, m, CH$_2$N), 2.15 (3H, t, CH$_2$CO), 2.05 (1H, m, CH$_2$CH(CH$_2$)$_2$), 1.2-1.7 (118H, m, CH$_2$+Me), (H18) N-[8-(Aminopropylaminobutylamino)-7-(aminopropylaminobutylaminomethyl)octyl]-24-(glucuroylamino)tetracosanamide hexa(trifluoroacetate) salt

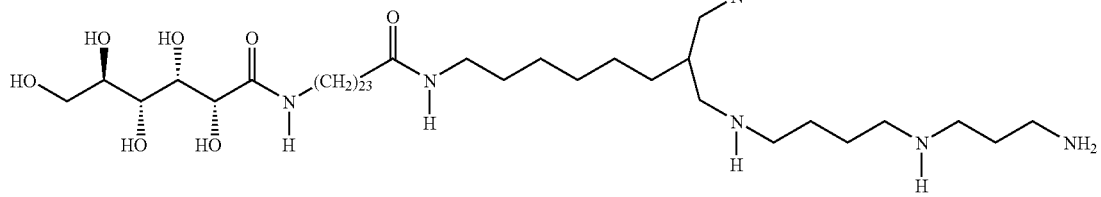

6CF$_3$CO$_2$H

A solution of H17 (245 mg, 0.353 mmol) in 96% TFA (10 ml, 4% water) was stirred for 30 min at room temperature. The TFA was removed under vacuum, and traces removed by evaporation of water. The title compound was cobtained as a colourless hygroscopic solid (400 mg, 86%) by lyophilisation. $C_{65}H_{118}N_8O_{19}F_{18}.2CF_3CO_2H$ requires C: 43.95%, H: 6.42%, N: 5.94%. Found: C: 47.10%, H: 7.18%, N: 6.76%. The free base $C_{53}H_{112}N_8O_7$ requires 972.86. Found ES+: MH$^+$ 973.9. $\delta_H$ (CD$_3$OD) 3.6-4.2 (6H, m, sugar), 3.0-3.4 (24H, m, CH$_2$N), 2.0-2.2 (7H, m, CH$_2$CO+CH$_2$CH(CH$_2$)$_2$+CH$_2$CH$_2$NH$_2$), 1.2-1.7 (60H, m, CH$_2$).

C18 Hexamine (H19) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-18-(peracetylglucuronylamino)octadecanamide

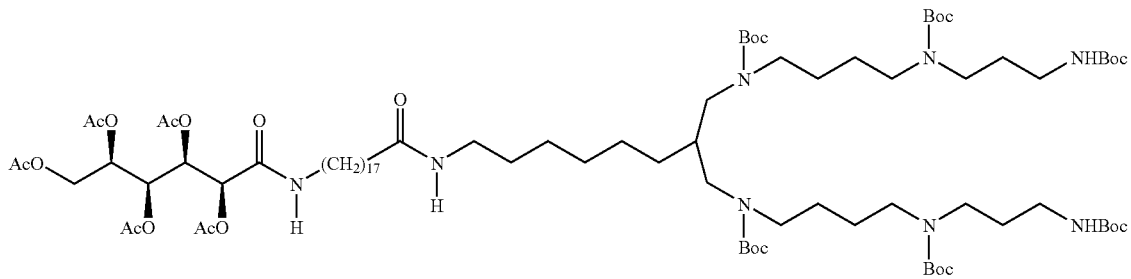

N-Methylmorphine (0.05 ml, 0.42 mmol) was added to a stirred solution of F4 (260 mg, 0.38 mmol) in dry dichloromethane (8 ml) at room temperature under argon. A few minutes later N-hydroxysuccinimide (48 mg, 0.42 mmol) was added followed by EDC (100 mg, 0.42 mmol), the reaction was stirred overnight (tlc showed conversion to the active ester). A solution of B16 (506 mg, 0.49 mmol) and triethylamine (0.3 ml, 1.89 mmol) in dry dichloromethane (6 ml) was added dropwise and stirring continued for two hours. Tlc showed the active ester had been converted to a slower moving product (silica—60% ethyl acetate in hexane). The solvent was removed and the product chromatographed (silica—70% ethyl acetate in hexane) to yield the title compound (420 mg, 65%). $C_{87}H_{158}N_8O_{24}.2H_2O$ requires C: 60.18%, H: 9.41%, N: 6.45%. Found: C: 60.18%, H: 9.25%, N: 6.55%, $\delta_H$ (CDCl$_3$) 6.07 (1H, brt, CONH), 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m AcOCH$_2$(OAc)CH), 4.31 (1H, dd[J$_1$=4 Hz, J$_2$=12 Hz] AcOCH$_2$(OAc), 4.13 (1H, dd[J$_1$=6 Hz, J$_2$=12 Hz] AcOCH$_2$(OAc), 2.9-3.4 (24H, m, NCH$_2$), 2.0-2.3 (17H, m, CH$_2$CO+ 5×acetate), 1.95 (1H, m, CH$_2$CH(CH$_2$)$_2$), 1.2-1.8 (106H, tm, CH$_2$+Me).

(H20) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-18-(glucuronylamino)octadecanamide

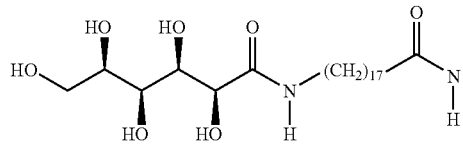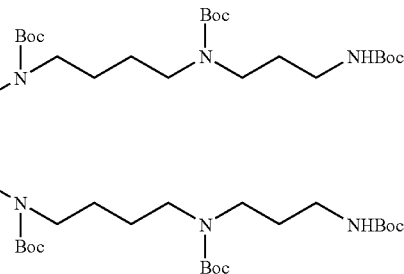

A solution of potassium carbonate (178 mg, 1.28 mmol) in water (1 ml) was added dropwise to a stirred solution of H19 (420 mg, 0.25 mmol) in methanol (7 ml) at room temperature. The flask was stirred for 30 min whereupon tlc showed no starting material was present. Water (20 ml) was added and the precipitate filtered, washed and dried. The product was purified by chromatography (Reverse phase silica, Merck Lichroprep—dichloromethane/methanol/water [2:6:1]) to yield, after trituration, with ether the title compound (220 mg, 60%). $C_{67}H_{130}N_6O_{15}$ requires 1489. Found ES+: MH$^+$ 1490

(H21) N-[8-(aminopropylaminobutylamino)-7-(aminopropylaminobutylaminomethyl)octyl]-18-(glucuronylamino)octadecanamide. hexa(trifluoroacetate) salt

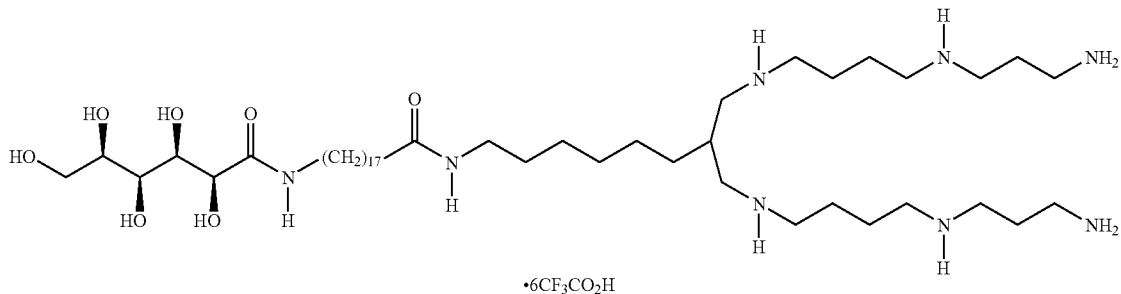

A solution of H20 (200 mg, 0.134 mmol) in 96% TFA (10 ml, 4% water) was stirred for 30 min at room temperature. The TFA was removed under vacuum, and traces removed by evaporation of toluene/methanol, then high vacuum. The compound was dissolved in water (8 ml) and filtered through a 0.45 μm filter (Whatman PP), the compound was converted to a colourless solid by lyophilisation. The product was triturated with ether to give the title compound as a hygroscopic white solid (183 mg, 88%). $C_{59}H_{106}N_8O_{19}F_{18} \cdot 2H_2O$ (anhydrous M.Wt 1572) requires C: 44.03%, H: 6.89%, N: 6.96%. Found: C: 43.99%, H: 6.67%, N: 6.89%. The free base $C_{47}H_{100}N_8O_7$ requires 888.7. Found ES+: MH+ 890. $\delta_H$ (CD$_3$OD) 3.6-4.2 (6H, m, sugar), 3.0-3.4 (24H, m, CH$_2$N+ CH$_2$NH$_2$), 2.0-2.2 (7H, m, CH$_2$CO+CH$_2$CH(CH$_2$)$_2$+ CH$_2$CH$_2$NH$_2$), 1.2-1.7 (48H, m, CH$_2$).

Bixin Hexamine (H22) N-{8-[t-Butyloxycarbonylaminopropyl(t-butyloxycarbonyl)-aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-N'-(peracetylglucuronylaminoethyl)-4,8,13,17-tetramethyl-1,20-docosadiamide

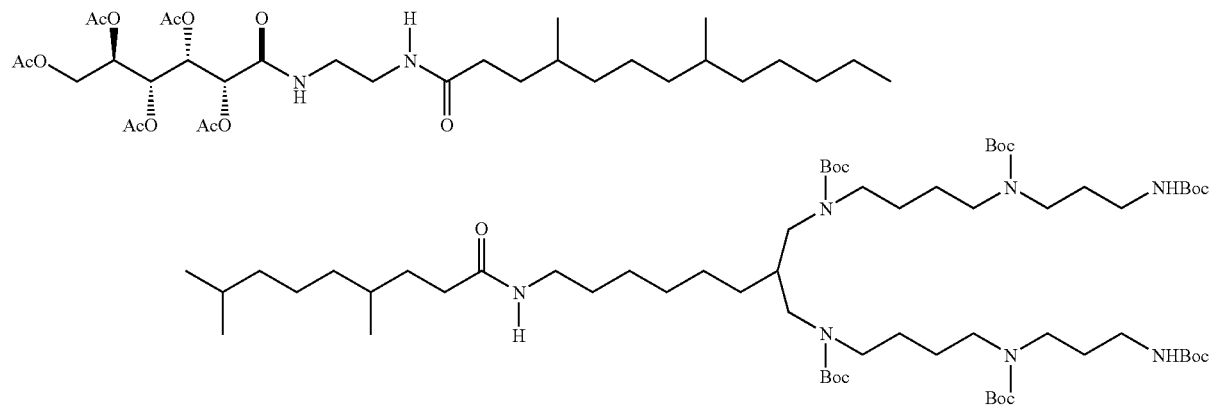

N-Methylmorpholine (0.04 ml, 0.34 mmol) was added to a stirred solution of F5 (282 mg, 0.34 mmol) in dry dichloromethane (10 ml) at room temperature under argon. After a few minutes N-hydroxysuccinimide (39 mg, 0.34 mmol) was added followed by EDC (65 mg, 0.34 mmol), the reaction was stirred overnight (tlc showed conversion to the active ester). A solution of B16 (318 mg, 0.34 mmol) and triethylamine (0.237 ml, 1.7 mmol) in dry dichloromethane (10 ml) was added dropwise and stirring continued for two hours. Tlc showed the active ester had been converted to a slower moving product (silica—10% methanol in dichloromethane). The solvent was removed and the product chromatographed (silica—5% methanol in dichloromethane) to yield the title compound (430 mg, 69%). $C_{95}H_{173}N_9O_{25}$ requires 1840.25. Found ES+: MH+ 1841.2. $\delta_H$ (CDCl$_3$) 7.10 (1H, br, CONH), 6.27 (1H, br, CONH), 5.75 (1H, br, CONH), 5.67 (1H, t, CH(OAc)CH(OAc)CONH), 5.43 (1H, t, CH(OAc)CH(OAc) CH(OAc) CONH), 5.30 (1H, m, CH(OAc)CONH), 5.05 (1H, m AcOCH$_2$(OAc)CH), 4.31 (1H, dd[J$_1$=4 Hz, J$_2$=12 Hz] AcOCH$_2$(OAc), 4.13 (1H, dd[J$_1$=6 Hz, J$_2$=12 Hz] AcOCH$_2$ (OAc), 2.9-3.5 (26H, m, NCH$_2$), 2.0-2.3 (15+9H, m, MeCO+ CH$_2$CO+CH$_2$CH(CH$_2$)$_2$+MeCH), 1.0-1.8(54+12+30H, ms, CH$_2$), 0.84-0.91(12H, 4×x, Me).

(H23) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)aminobutyl(t-butyloxycarbonyl)aminomethyl]octyl}-N'-(glucuronylaminoethyl)-4,8,13,17-tetramethyl-1,20-docosadiamide

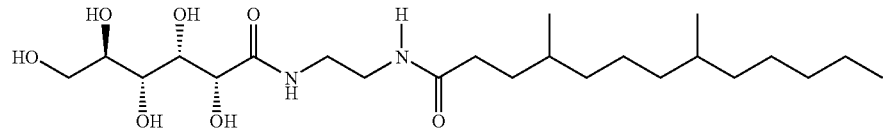

-continued

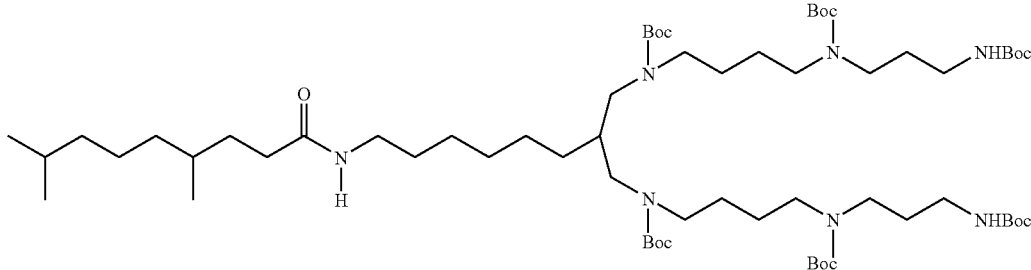

Ammonia solution (0.880, 7 ml) was added to a stirred solution of H22 (600 mg, 0.33 mmol) in methanol (15 ml, or until in solution when ammonia added) at room temperature. The flask was stirred for 1 hr whereupon tlc showed no starting material was present. The reaction was evaporated to dryness and the product purified by chromatography (Reverse phase silica, Merck-Lichroprep—dichloromethane/methanol/water [2:6:1]) to yield the title compound (416 mg, 78%). $C_{85}H_{163}N_9O_{20} \cdot 3/4H_2O$ (anhydrous M.Wt 1630) requires C: 62.07%, H: 10.08%, N: 7.66%. Found: C: 62.08%, H: 10.14%, N: 7.69%. $C_{85}H_{163}N_9O_{20}$ requires 1630. Found ES+: MH+ 1631.2. $\delta_H$ (CD$_3$OD) 3.6-4.3 (6H, ms, sugar), 2.9-3.5 (26H, m, NCH$_2$), 2.0-2.3 (9H, m, CH$_2$CO+CH$_2$CH(CH$_2$)$_2$+4×CH$_3$CH), 1.0-1.8(54+12+30H, ms, Me+CH$_2$), 0.84-0.91(12H, 4×x, Me).

(H24) N-[8-(aminopropylaminobutylamino)-7-(aminopropylaminobutylaminomethyl)octyl]-N'-(glucuronylaminoethyl)-4,8,13,17-tetramethyl-1,20-docosadiamide hexa (trifluoroacetate) salt

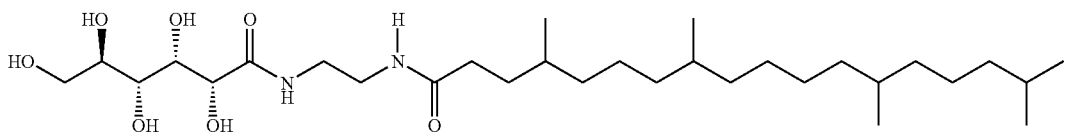

•6CF$_3$CO$_2$H

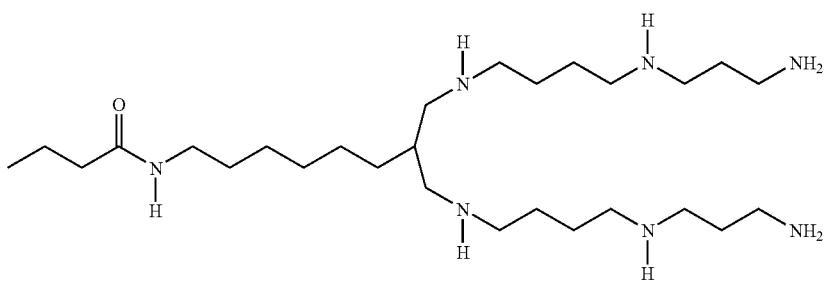

A solution of H23 (400 mg, 0.25 mmol) in 96% TFA (10 ml, 4% water) was stirred for 30 min at room temperature. The TFA was removed under vacuum, and traces removed by evaporation of water. The title compound was obtained as to a colourless hygroscopic solid (382 mg, 90%) by lyophilisation. $C_{55}H_{115}N_9O_8 \cdot C_{12}H_6F_{18}O_{12} \cdot 2.5H_2O$ (anhydrous M.Wt 1713 requires C: 45.73%, H: 7.22%, N: 7.16%. Found: C: 45.73%, H: 7.14%, N: 6.86%. The free base $C_{49}H_{101}N_7O_8$ requires 1029.89. Found ES+: MH+ 1031.0. $\delta_H$ (CD$_3$OD) 3.6-4.3 (6H, ms, sugar), 2.9-3.5 (26H, m, NCH$_2$), 2.0-2.3 (9H, m, CH$_2$CO+CH$_2$CH(CH$_2$)$_2$+4×MeCH), 1.01-1.8(12+30H, ms, CH$_2$), 0.84-0.91(12H, 4×s, Me).

C24 Amide Hexamine (H25) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)butyl(tbutyloxycarbonyl)aminomethyl]octyl}-12-(peracetylglucuronylaminododecanoylamino)dodecanamide

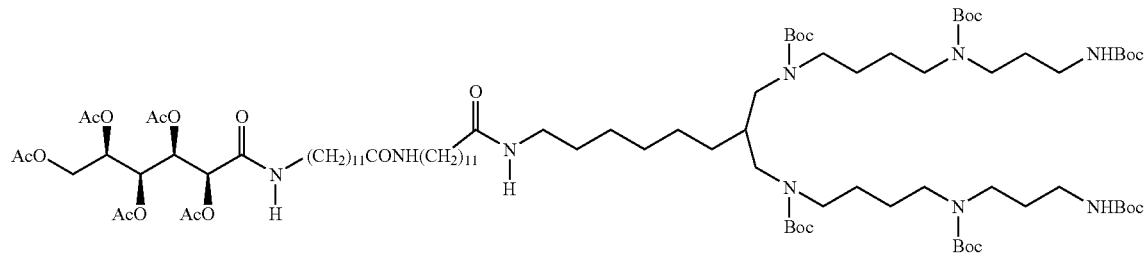

DBU (0.06 ml, 0.4 mmol) was added to a stirred suspension of F6 (320 mg, 0.4 mmol) in dry dichloromethane (5 ml) at room temperature under argon. A few minutes later N-hydroxysuccinimide (46 mg, 0.4 mmol) was added followed by EDC (76 mg, 0.4 mmol), the reaction was stirred overnight (tlc showed conversion to the active ester). A solution of B16 (411 mg, 0.4 mmol) and DBU(0.12 ml, 0.4 mmol) in dry dichloromethane (5 ml) was added dropwise and stirring continued for five hours. Tlc showed the active ester had been converted to a slower moving product (silica—60% ethyl acetate in hexane). The reaction was poured into 10% citric acid and extracted with dichloromethane, washed with brine, dried, and the solvent removed. The product was purified by chromatography (silica—2% to 5% methanol in dichloromethane) to yield the title compound (538 mg, 74%). $C_{93}H_{169}N_9O_{25}$. 3/4$H_2O$ requires C: 61.14%, H: 9.41%, N: 6.90%. Found: C: 61.16%, H: 9.37%, N: 6.82%. $C_{93}H_{169}N_9O_{25}$ requires 1812.2. Found ES+: MH$^+$ 1814.3 $\delta_H$ (CDCl$_3$) 6.13 (1H, brt, CONH), 5.93 (1H, br, CONH), 5.75 (1H, br, CONH), 5.67 (1H, t, CH(OAc)CH(OAc)CONH), 5.43 (1H, t, CH(OAc)CH(OAc)CH(OAc)CONH), 5.30 (1H, m, CH(OAc)CONH), 5.05 (1H, m AcOCH$_2$(OAc)CH), 4.31 (1H, dd[J$_1$=4 Hz, J$_2$=12 Hz] AcOCH$_2$(OAc), 4.13 (1H, dd[J$_1$=6 Hz, J$_2$=12 Hz] AcOCH$_2$(OAc), 2.9-3.3 (26H, m, NCH$_2$), 2.0-2.3 (20H, m, MeCO+CH$_2$CO+CH$_2$CH(CH$_2$)$_2$), 1.2-1.7 (112H, dm, CH$_2$+Me).

(H26) N-{8-[t-Butyloxycarbonylaminopropyl(t-butyloxycarbonyl)aminobutyl(t-butyloxycarbonyl)amino]-7-[t-butyloxycarbonylaminopropyl(t-butyloxycarbonyl)butyl(t-butyloxycarbonyl)aminomethyl]octyl}-12-(glucuronylaminododecanoylamino)dodecanamide

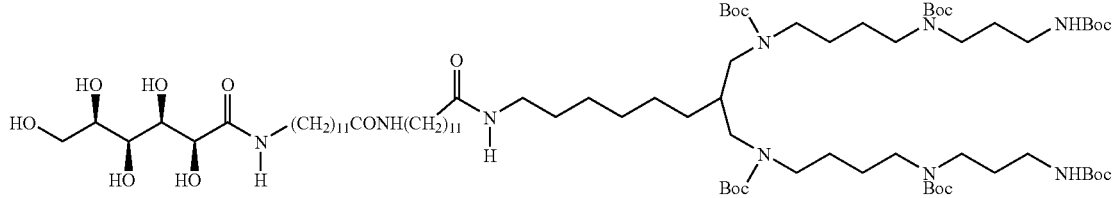

Ammonia solution (10 ml, 0.880) was added to a stirred solution of H25 (530 mg, 0.3 mmol) in methanol (10 ml) at room temperature, (extra methanol can be added to ensure a solution). The flask was stirred for 1 hr and evaporated to dryness. The white solid was suspended in water, filtered off and dried. The product was purified by chromatography (Reverse phase silica, Merck-Lichroprep eluted with dichloromethane/methanol/water [2:6:1]) The product was evaporated to dryness, suspended in water, filtered off, dried and triturated with ether. High vacuum yielded the title compound (368 mg, 77%) as a white solid. $C_{83}H_{159}N_9O_{20}$ requires C: 62.18%, H: 10.00%, N: 7.86%. Found: C: 62.04%, H: 9.93%, N: 7.77%. $C_{83}H_{159}N_9O_{20}$ requires 1602.17. Found ES+: MH$^+$ 1603.4. $\delta_H$ (CD$_3$OD) 3.5-4.2 (6H, m, sugar), 2.9-3.3 (26H, m, NCH$_2$), 2.15 (4H, t, CH$_2$CO), 2.07 (1H, br, CH$_2$CH(CH$_2$)$_2$), 1.2-1.8 (112H, dm, CH$_2$+Me).

(H27) N-[8-(Aminopropylaminobutylamino)-7-(aminopropylbutylaminomethyl)octyl]-12-(glucuronylaminododecanoylamino)dodecanamidehexa(trifluoroacetate) salt

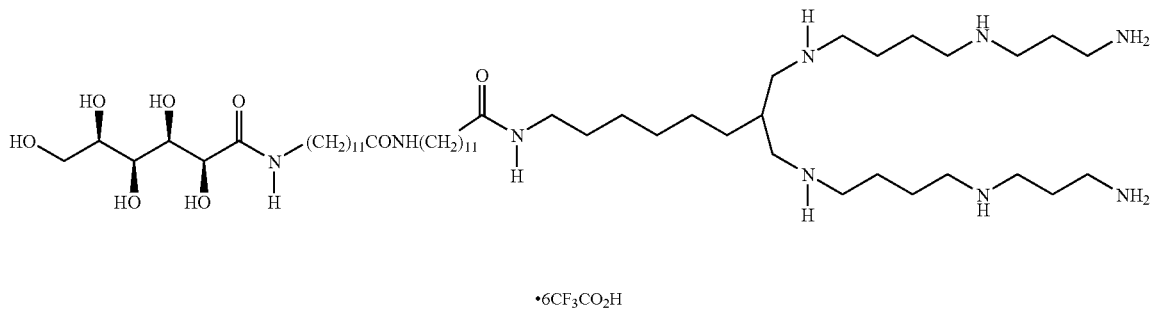

·6CF$_3$CO$_2$H

A solution of H26 (360 mg, 0.23 mmol) in 96% TFA (6 ml, 4% water) was stirred for 30 min at room temperature. The TFA was removed under vacuum, and traces removed by evaporation of toluene/methanol. The compound was subjected to high vacuum overnight, dissolved in water (5 ml) and filtered through a 0.45 μM (Whatman PP) filter The compound was converted to a colourless solid by lyophilisation. The lyophilised hygroscopic solid was triturated with ether and dried in vacuo to yield the title compound (370 mg, 98%). $C_{53}H_{111}N_9O_{20}$. $C_{12}H_6O_{12}F_{18}$. 2.8 H$_2$O (Mwt anhydrous=1686.67) requires C: 44.94%, H: 7.11%, N: 7.26%. Found: C: 44.93%, H: 6.92%, N: 7.12%. The free base $C_{53}H_{111}N_9O_8$ requires 1001.86. Found ES+: MH$^+$ 1003.9. $\delta_H$ (CD$_3$OD) 7.92 (1H, br, CONH), 7.80 (1H, br, CONH), 3.6-4.25 (6H, m, sugar), 2.9-3.4 (26H, m, CH$_2$N), 2.0-2.3 (9H, m, CH$_2$CO+CH$_2$CH(CH$_2$)$_2$+CH$_2$CH$_2$NH$_2$), 1.2-1.9 (50H, m, CH$_2$).

DISUGAR HEXAMINE (H28) N-{8-[Methyl(t-butyloxycarbonyl)aminopropyl(t-butyloxycarbonyl)aminobutyl(t-butyloxycarbonylamino]-7-[methyl(t-butyloxycarbonyl)aminopropyl(t-butyloxycarbonyl)aminobutyl(t-butyloxycarbonyl)aminomethyl]octylaminocarbonyltricosanyl}-N',N'-bis(peracetylglucuronylaminoethyl)succinamide

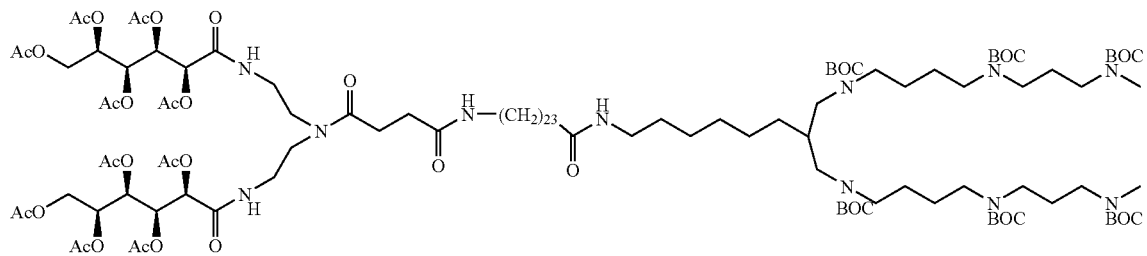

C4 (197 mg, 0.201 mmol), EDC hydrochloride (77 mg, 0.401 mmol) and N-hydroxysuccinimide (35 mg, 0.301 mmol) were dissolved in anhydrous dichloromethane (30 ml) and activated ester formation left at room temperature for two hours under argon. To the solution was added E4 (300 mg, 0.211 mmol) and triethylamine (61 mg, 0.602 mmol) and the reaction left overnight at room temperature under argon. The solvents were removed, and the resulting residues purified by gradient silica column chromatography (3-7% methanol in dichloromethane) to yield the title compound as a colourless solid (378 mg, 78%). $C_{119}H_{209}N_{11}O_{37}$ requires 2384.5. Found ES$^+$: MH$_2^{2+}$, 1193.9, MH$_3^{3+}$, 796.4. $\delta_H$ (CDCl$_3$) 1.23 (46H, (CH$_2$)$_{19}$(CH$_2$)$_2$CO, (CH$_2$)$_4$CH), 1.44 (72H, br+m, (Me)$_3$C, CH$_2$CH$_2$N, CH$_2$CH$_2$CO), 1.95 (1H, br, CH), 2.02-2.23 (30H, 10×s, MeCO), 2.17 (2H, t, (CH$_2$)$_{22}$CH$_2$CO), 2.4-2.8 (4H, brm, CO(CH$_2$)$_2$CO), 2.83 (6H, s, MeN), 2.9-3.5 (32H, m, CH$_2$N), 4.12 (2H, m, CH$_2$OAc), 4.30 (2H, dt, CH$_2$OAc), 5.20, 5.25 (2H, 2×d, CHOAcCO), 5.43, 5.60 (4H, 2×m, (CHOAc)$_2$CHOAcCO), 5.71 (1H, br, (CH$_2$)$_{23}$CONH), 6.11 (1H, br, CO(CH$_2$)$_2$CONH), 7.18, 7.65 (2H, 2×t, N(CH$_2$CH$_2$NH)$_2$).

(H29) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl(aminomethyl]octylaminocarbonyltricosanyl}-N',N'-bis(glucuronylaminoethyl)succinamide

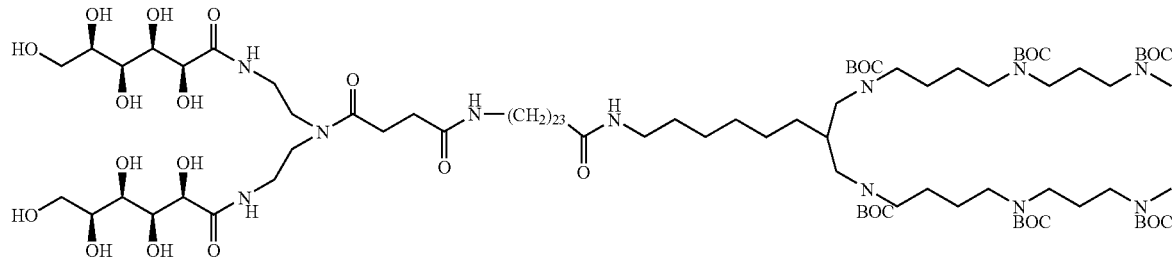

To H28 (377 mg) in methanol (15 ml) was added concentrated ammonium hydroxide (5 ml). The cloudy solution/suspension was rapidly stirred for two hours whereupon the solvent was removed and the resulting residues purified by reverse phase silica chromatography eluting with 2:6:1 dichloromethane:methanol:water to yield the title compound as a colourless solid (266 mg, 86%). $C_{99}H_{189}N_{11}O_{27}$ requires 1964.4 Found ES$^+$: MH$_2^{2+}$, 983.7. $\delta_H$ (CD$_3$OD) 1.28 (46H, br, (CH$_2$)$_{19}$(CH$_2$)$_2$CO, (CH$_2$)$_4$CH), 1.46 (68H, br, (Me)$_3$C, CH$_2$CH$_2$N, CH$_2$CH$_2$CO), 1.76 (4H, p, NCH$_2$CH$_2$CH$_2$N), 2.10 (1H, br, CH), 2.16 (2H, t, (CH$_2$)$_{22}$CH$_2$CO), 2.49, 2.70 (4H, t+dt, CO(CH$_2$)$_2$CO), 2.85 (6H, s, NMe), 3.0-3.4 (24H, m, CH$_2$N), 3.4-3.65 (8H, m, N(CH$_2$)$_2$N, 3.65-3.85 (8H, m, CHOH), 4.11, 4.20 (4H, brs+dd, CH$_2$OH). n (H30) N-[8-(Methylaminopropylaminobutylamino)-7-(methylaminopropylaminobutylaminomethyl)octylaminocarbonyl tricosanyl)-N',N'-bis(glucuronylaminoethyl)succinamide

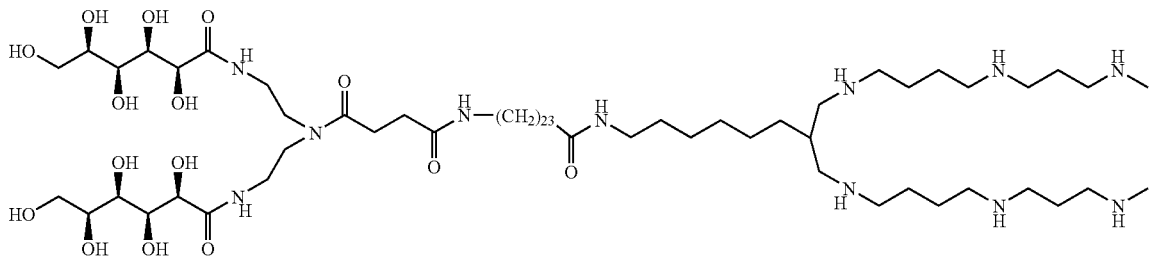

•6CF$_3$CO$_2$H

To H29 (266 mg) was added 96:4 trifluoroacetic acid:dichloromethane (10 ml). The solution was left for 20 minutes at room temperature, the solvents removed and the residues taken up into MilliQ water. The solution was filtered (0.45 mm polypropylene) and freeze dried to give a white solid. This was suspended in diethyl ether, left for 20 minutes and the ether decanted off. The remaing white solids were dried under vacuum to give the title compound as a white, hydroscopic solid (269 mg). $C_{69}H_{141}N_{11}O_{15}$ requires 1364.1 Found ES$^+$: MH$_2^{2+}$, 683.4, MH$^+$, 1365.4. $\delta_H$ (CD$_3$OD) 1.28 (44H, br, (CH$_2$)$_{19}$(CH$_2$)$_2$CO, (CH$_2$)$_3$CH$_2$CH), 1.50 (8H, m, CH$_2$CH, CH$_2$CH$_2$NH, CH$_2$CH$_2$CO), 1.82 (8H, br, NCH$_2$(CH$_2$)$_2$CH$_2$N), 2.05-2.25 (6H, m, CH$_2$CO, NCH$_2$CH$_2$CH$_2$N), 2.28 (1H, m, CH), 2.49, 2.72 (4H, 2×t, CO(CH$_2$)$_2$(CO), 2.73 (6H, s, NMe), 3.05-3.30 (24H, m, CH$_2$N), 3.35-3.65 (8H, m, NCH$_2$CH$_2$N), 3.65-3.85 (8H, m, CHOH), 4.10, 4.22 (4H, brs+dd, CH$_2$OH).

(H31) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-24-(peracetylglucuronylamino)tetracosanamide

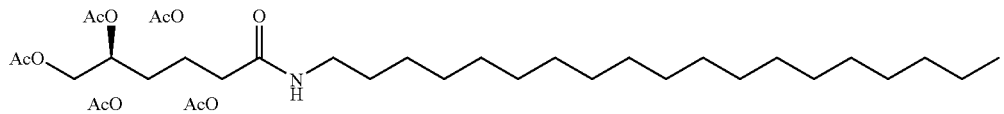

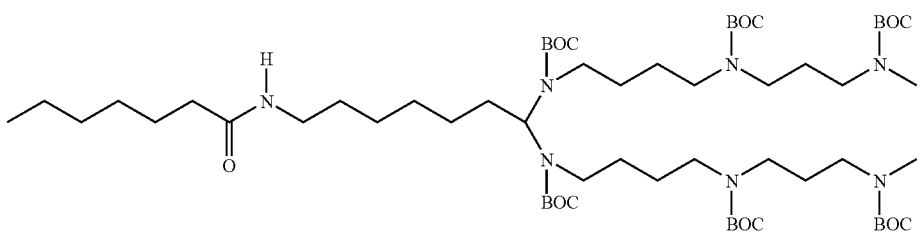

To F2 (131 mg, 0.170 mmol) in anhydrous dichloromethane (15 ml) were added EDC hydrochloride (46 mg, 0.238 mmol), N-hydroxysuccinimide (27 mg, 0.238 mmol) and the reaction left overnight. To the reaction were then added B21 (198 mg, 0.187 mmol) and triethylamine (68 mg, 0.679 mmol) and the reaction left for 3 hours at which point the solvent was removed. The residues were purified by gradient silica chromatography eluting with 60-80% ethyl acetate in hexane to yield the title compound as a colourless gum, (241 mg, 78%). $C_{95}H_{174}N_8O_{24}$ requires 1811.3 Found ES$^+$: MH$_2^{2+}$, 907.0. $\delta_H$ (CDCl$_3$) 1.24 (48H, br, (CH$_2$)$_{19}$(CH$_2$)$_2$N, CH$_2$CH$_2$CO, (CH$_2$)$_4$CH), 1.3-1.8 (70H, m, (Me)$_3$C, CH$_2$CH$_2$N), 2.0 (1H, br, CH), 2.04-2.19 (15H, 5xs, MeCO), 2.22 (2H, t, CH$_2$CO), 2.83 (6H, s, NMe), 2.9-3.35 (24H, m, CH$_2$N), 4.10-4.40 (2H, m, CH$_2$OAc), 5.03 (1H, m, CHOAcCH$_2$OAc), 5.28 (1H, d, CHOAcCO), 5.43, 5.67 (2H, 2xt, (CHOAc)$_2$CHOAcCH$_2$OAc), 6.05 (2H, 2xt, NHCO).

(H32) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-24-(glucuronylamino)tetracosanamide

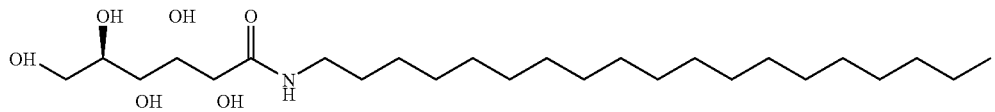

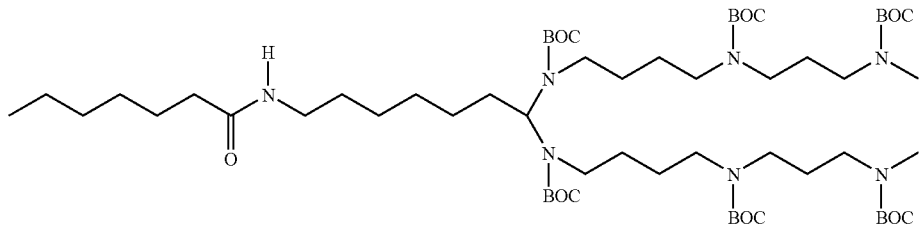

To H31 (235 mg) dissolved in methanol (10 ml) was slowly added with stirring NH$_4$OH (4 ml) until the solution started to become cloudy. After approximately 20 minutes an additional 3 ml of methanol was added to dissolve some of the forming white precipitate. The solution/suspension was stirred for a total of one hour at which point all solvents were removed. The residues were purified by reverse phase chromatography eluting with 2:6:1 CH$_2$Cl$_2$:MeOH:NH$_4$OH to yield the title compound as a colourless solid, (206 mg, 99%).

C$_{85}$H$_{164}$N$_8$O$_{19}$ requires 1601.2 Found ES$^+$: MH$^+$, 1601.9. δ$_H$ (CDCl$_3$) 1.24 (46H, br, (CH$_2$)$_{19}$(CH$_2$)$_2$N, (CH$_2$)$_4$CH), 1.35-1.80 (72H, brm, (Me)$_3$C, CH$_2$CH$_2$N, CH$_2$CH$_2$CO), 2.05 (1H, br, CH), 2.14 (2H, t, (CH$_2$)$_{22}$CH$_2$CO), 2.82 (6H, s, NMe), 3.0-3.4 (24H, brm, NCH$_2$), 3.5-4.1 (4H, br, CHOH), 4.17, 4.30 (2H, 2×br, CH$_2$OH), 5.85, 7.21 (2H, 2×br, NHCO).

(H33) N-[8-(methylaminopropylaminobutylamino)-7-(methylaminopropylaminobutylaminomethyl)octyl]-24-(glucuronylamino)tetracosanamide

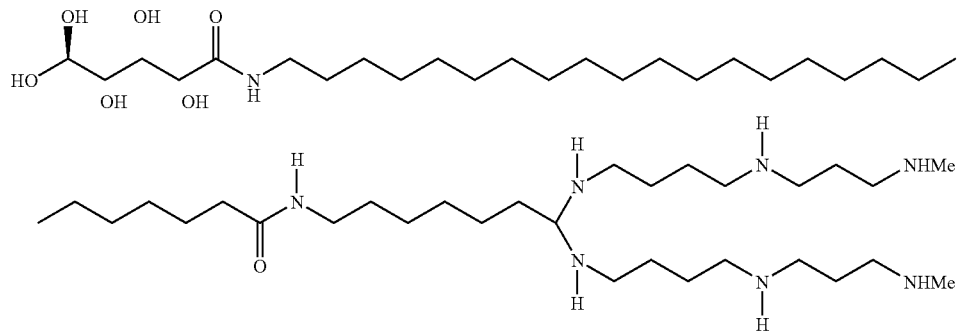

H32 (185 mg) was dissolved in 96:4 TFA:DCM and left for 20 minutes. The solvent was removed and the residues taken up in MilliQ water, filtered through a 0.2 mm filter, and the solution freeze dried to quantitatively give the title compound as a white solid. C$_{55}$H$_{116}$N$_8$O$_7$ requires 1000.9 Found ES$^+$: MH$^+$, 1001.9. δ$_H$ (CD$_3$OD) 1.32 (44H, br, (CH$_2$)$_{19}$(CH$_2$)$_2$CO, (CH$_2$)$_3$CH$_2$CH), 1.52 (8H, m, CH$_2$CH, CH$_2$CH$_2$N, CH$_2$CH$_2$CO), 1.82 (8H, m, NCH$_2$(CH$_2$)$_2$CH$_2$N), 2.08 (1H, br, CH), 2.12 (4H, m, NCH$_2$CH$_2$CH$_2$N), 2.23 (2H, m, CH$_2$CO), 2.73 (6H, s, NMe), 3.0-3.3 (24H, m, CH$_2$N), 3.58-3.82 (4H, m, CHOH), 4.08, 4.22 (2H, 2×m, CH$_2$OH).

(H34) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-24-(peracetylglucuronylaminododecanoylamino)tetracosanamide

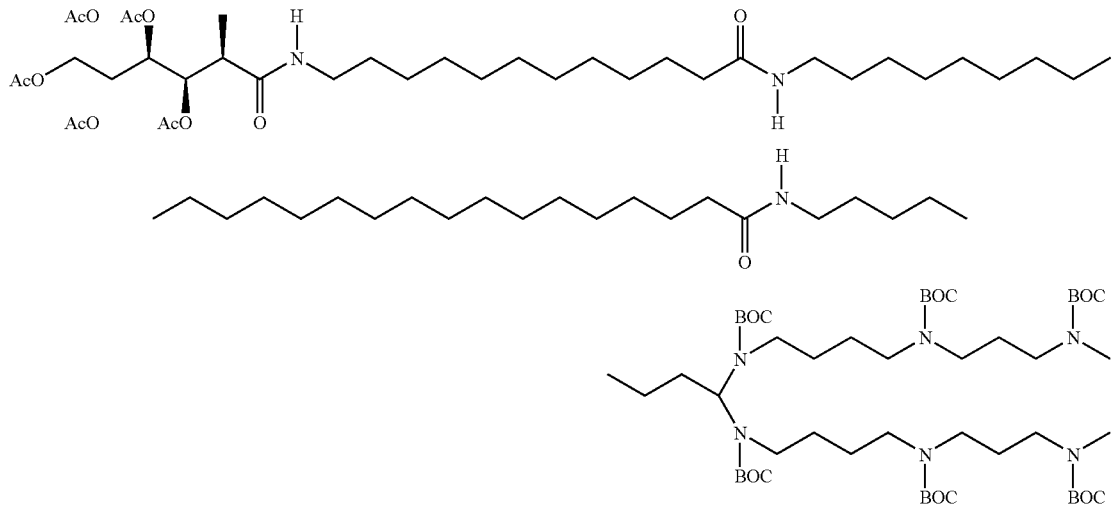

To F8 (67 mg, 0.111 mmol) in anhydrous dichloromethane (20 ml) were added EDC hydrochloride (30 mg, 0.155 mmol), N-hydroxysuccinimide (18 mg, 0.155 mmol) and the reaction left overnight. To this were then added E4 (174 mg, 0.122 mmol) and triethylamine (45 mg, 0.444 mmol) and the reaction left for a further four hours. The solvent was removed and the residues purified by gradient silica chromatography eluting with 50-90% ethyl acetate in hexane to yield the title compound, (90 mg, 40%) as a colourless gum. $C_{107}H_{197}N_9O_{25}$ requires 2008.4 Found ES$^+$: MNH$_4^+$, 2027.8. $\delta_H$ (CDCl$_3$) 1.25 (56H, br, NH(CH$_2$)$_2$(CH$_2$)$_{20}$, NH(CH$_2$)$_2$(CH$_2$)$_8$), 1.3-1.8 (72H, brm, (Me)$_3$C, CH$_2$CH$_2$N), 1.96 (1H, br, CH), 2.04, 2.05, 2.09, 2.20, 2.20 (15H, 5×s, MeCO), 2.23 (4H, m, CH$_2$CO), 2.84 (6H, s, NMe), 3.0-3.3 (26H, m, NCH$_2$), 4.14, 4.31 (2H, m, CH$_2$OAc), 5.04 (1H, dt, CH$_2$CHOAc), 5.29 (1H, d, CHOAcCO), 5.44, 5.66 (2H, 2×t, (CHOAc)$_2$CHOAcCO), 5.92, 6.09, 6.29 (3H, br+t+br, NHCO).

(H35) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-24 (glucuronylaminododecanoylamino)tetracosanamide

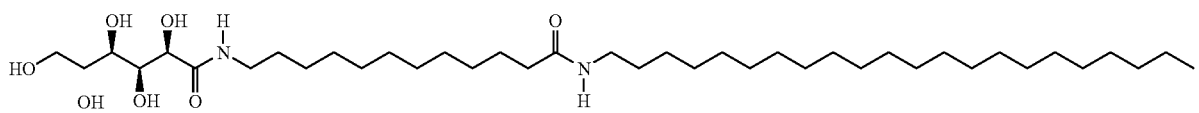

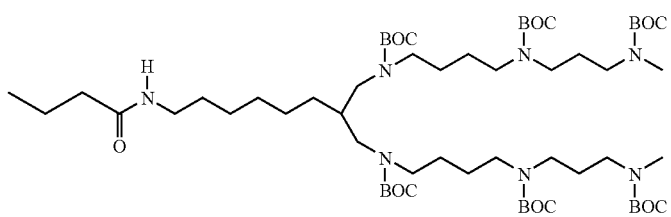

To a solution of H34 (90 mg) in methanol (12 ml) was added NH$_4$OH (4 ml) and the reaction left for 1 hour at which point the solvent was removed. The residues were purified by reverse phase silica chromatography eluting with 2:6:1 DCM:MeOH:H$_2$O to yield the title compound (80 mg, 99%) as a white solid. $C_{97}H_{187}N_9O_{20}$ requires 1798.4 Found ES$^+$: MH$_2^{2+}$, 900.9, MH$^+$, 1799.6. $\delta_H$ (CDCl$_3$) 1.25 (52H, br, N(CH$_2$)$_2$(CH$_2$)$_{19}$, N(CH$_2$)$_2$(CH$_2$)$_7$), 1.40-1.85 (76H, brm, (Me)$_3$C, CH$_2$CH$_2$N, CH$_2$CH$_2$CO), 1.95 (1H, br, CH), 2.16 (2H, t, CH$_2$CO), 2.84 (6H, s, NMe), 2.9-3.4 (26H, m, NCH$_2$), 3.82 (4H, br, CHOH), 4.17, 4.32 (2H, 2×br, CH$_2$OH), 5.92, 6.55, 7.22 (3H, 3×br, NHCO).

(H36) N-[8-(Methylaminopropylaminobutylamino)-7-(methylaminopropylaminobutylaminomethyl)octyl]-24-(glucuronylaminododecanoylamino)tetracosanamide

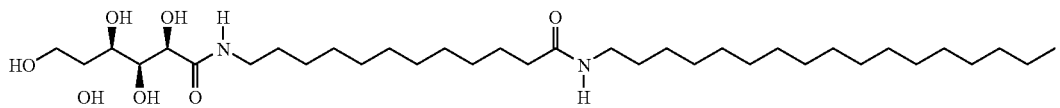

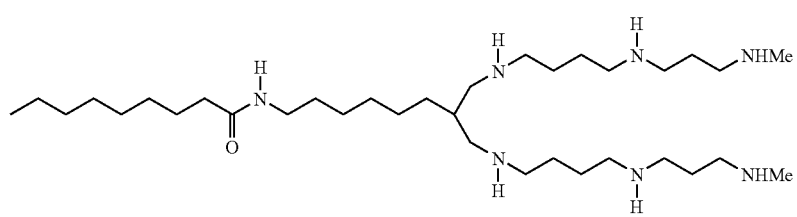

H35 (80 mg) was treated as in the synthesis of H33 to give the title compound in quantitative yield as a white solid. $C_{67}H_{139}N_9O_8$ requires 1198.1 Found ES$^+$: $MH_2^{2+}$, 600.2, MH$^+$, 1198.8. $\delta_H$ (CD$_3$OD) 28 (58H, br, (CH$_2$)$_7$(CH$_2$)$_2$CO, (CH$_2$)$_{19}$(CH$_2$)$_2$CO, (CH$_2$)$_3$CH$_2$CH), 1.51 (12H, m, CH$_2$CH, CH$_2$CH$_2$N, CH$_2$CH$_2$CO), 1.83 (8H, m, NCH$_2$(CH$_2$)$_2$CH$_2$N), 2.14 (9H, m, CH$_2$CO, NCH$_2$CH$_2$CH$_2$N, CH), 2.73 (6H, s, NMe), 3.0-3.3 (26H, m, NCH$_2$), 3.6-3.8 (4H, m, CHOH), 4.07, 4.19 (2H, 2×m, CH$_2$OH).

(H37) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-36-(glucuronylamino)hexatriacontanamide

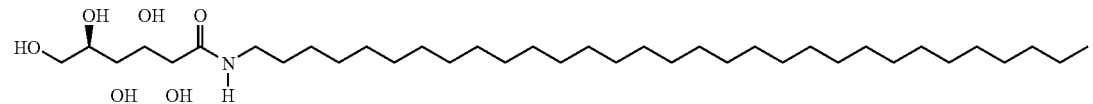

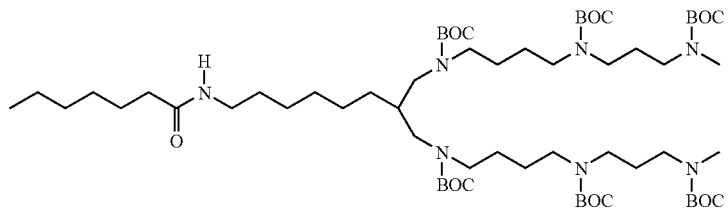

To E8 (612 mg, 0.038 mmol) in anhydrous methanol (15 ml) were added d-gluconolactone (14 mg, 0.077 mmol) and triethylamine (16 mg, 0.153 mmol) and the reaction stirred overnight at ambient temperature under argon. The solvents were removed and the residues purified by reverse phase chromatography eluting with 2:6:1 then 2:6:0.5 DCM:MeOH:H$_2$O to give the title compound (34 mg, 51%) as a colourless solid. $C_{97}H_{188}N_8O_{19}$ requires 1769.4 Found ES$^+$: MNa$^+$, 1793.2. $\delta_H$ (CDCl$_3$) 1.24 (72H, br, (CH$_2$)$_{32}$CH$_2$CONH(CH$_2$)$_2$(CH$_2$)$_4$), 1.44 (66H, m, (Me)$_3$C, CH$_2$CH$_2$N), 1.72 (4H, p, NCH$_2$CH$_2$CH$_2$N), 2.0 (1H, br, CH), 2.14 (2H, t, CH$_2$CO), 2.83 (6H, s, NMe), 3.0-3.4 (24H, m, CH$_2$N), 3.6-3.9 (4H, br, CHOH), 4.10, 4.25 (2H, 2×br, CH$_2$OH), 5.80 (1H, br, CONH(CH$_2$)$_6$(CH)), 7.30 (1H, br, CONH).

(H38) N-[8-(Methylaminopropylaminobutylamino)-7-(methylaminopropylaminobutylaminomethyl)octyl]-36-(glucuronylamino)hexatriacontanamide

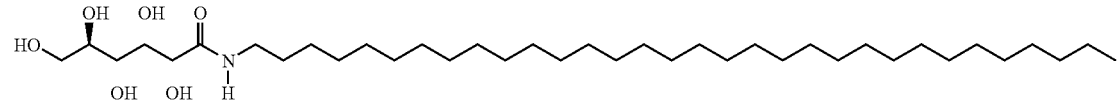

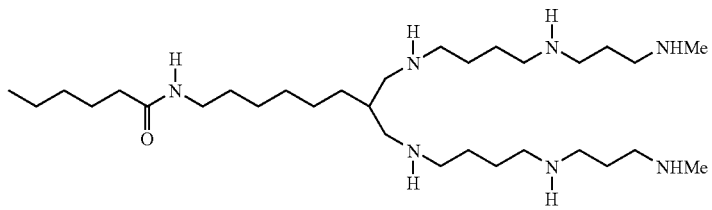

H37 (34 mg) was treated as in the synthesis of H33 to give the title compound in quantitative yield as a white solid. $C_{67}H_{140}N_8O_7$ requires 1169.1 Found ES$^+$: MH$_2^{2+}$, 585.7, MH$^+$, 1169.7. $\delta_H$ (CD$_3$OD) 1.29 (68H, br, (CH$_2$)$_{31}$(CH$_2$)$_2$CO, (CH$_2$)$_3$CH$_2$CH), 1.51 (8H, m, CH$_2$CH, CH$_2$CH$_2$N, CH$_2$CH$_2$CO), 1.83 (8H, brm, NCH$_2$(CH$_2$)$_2$CH$_2$N), 2.16 (7H, m, CH$_2$CO, NCH$_2$CH$_2$CH$_2$N, CH), 2.73 (6H, s, NMe), 3.0-3.3 (24H, m, NCH$_2$), 3.05-3.35 (4H, m, CHOH), 4.08-4.20 (2H, m+d, CH$_2$OH), 7.8-7.9 (2H, 2×br, NHCO).

I. PEG LIPIDS

This section contains the synthesis of:

(I2) N-[8-(Aminobutylamino)-7-(aminobutylaminomethyl)octyl]-24-[methoxypoly(ethyleneoxy)propanoylamino]tetracosanamide tetra(trifluoroacetate) salt

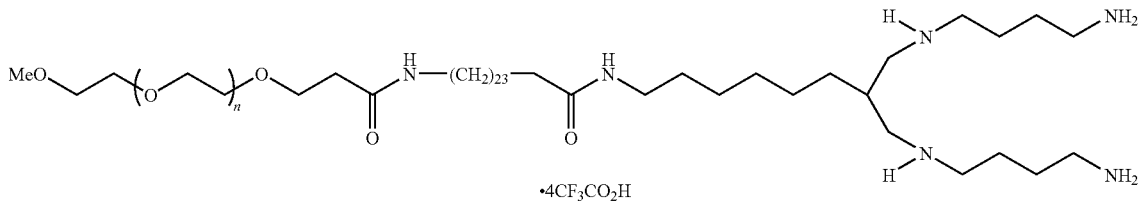

(I4) N-[8-(Methylaminopropylaminobutylamino)-7-(methylaminopropylaminobutylaminomethyl)octyl]-24-[methoxypoly(ethyleneoxy)propanoylamino]tetracosanamide hexa(trifluoroacetate) salt

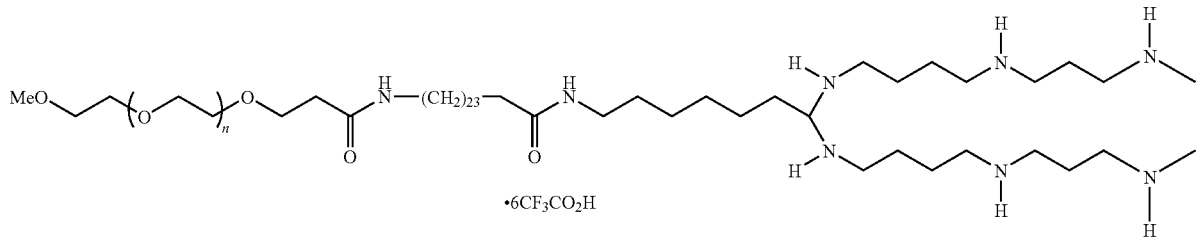

(I1) N-{8-[t-Butyloxycarbonylaminobutyl(t-butyloxycarbonyl)amino]-7-[t-butyloxycarbonylaminobutyl(t-butyloxycarbonyl)aminomethyl]octyl}-24-[methoxypoly(ethyleneoxy)propanoylamino]tetracosanamide

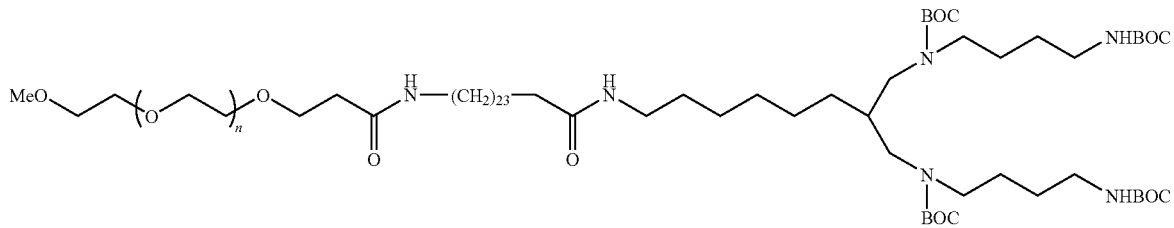

To methoxyPEGpropionic acid (MW approx 1800) (282 mg, 0.157 mmol) in anhydrous dichloromethane (20 ml) were added EDC hydrochloride (38 mg, 0.199 mmol) and N-hydroxysuccinimide (23 mg, 0.199 mmol) and the reaction left overnight under argon at room temperature. To this was added E2 (154 mg, 0.142 mmol) and triethylamine (57 mg, 0.570 mmol) and the reaction left for a further six hours. To this was then added water (0.2 ml) and the hydrolysis of any remaining activated ester left overnight. The solvent was removed and the residues purified by gradient silica chromatography (5-10% methanol in dichloromethane) to yield the title compound (369 mg, 90%) as a white solid. For n=38 $C_{143}H_{282}H_6O_{50}$ requires 2884.0 Found ES$^+$: MNa$_2^{2+}$, 1465.6. $\delta_H$ (CDCl$_3$) 1.24 (44H, br, (CH$_2$)$_{19}$(CH$_2$)$_2$CO, (CH$_2$)$_3$CH$_2$CH), 1.43 (52H, m, (Me)$_3$C, CH$_2$CH, CH$_2$CH$_2$N, CH$_2$CH$_2$CO, NCH$_2$(CH$_2$)$_2$CH$_2$N), 1.97 (1H, br, CH), 2.22 (2H, t, (CH$_2$)$_{22}$CH$_2$CO), 2.60 (2H, t, OCH$_2$CH$_2$CO), 3.05-3.15 (16H, m, NCH$_2$), 3.37 (3H, s, OMe), 3.63 (~170H, m, OCH$_2$).

(I2) N-[8-(Aminobutylamino)-7-(aminobutylaminomethyl)octyl]24-[methoxypoly(ethyleneoxy)propanoylamino]tetracosanamide tetra(trifluoroacetate) salt

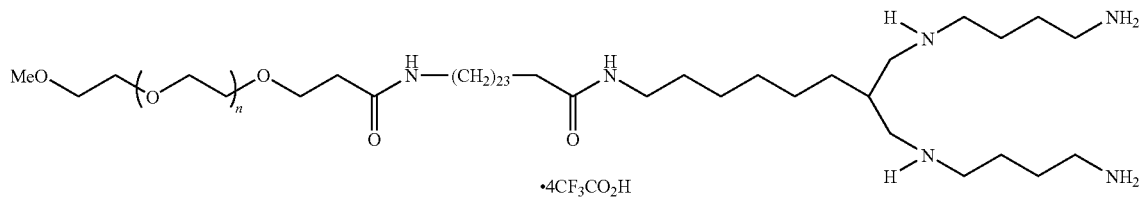

I1 (369 mg) was dissolved in 96:4 trifluoroacetic acid:dichloromethane (9 ml) and left for 15 minutes at room temperature. The solvent was removed, the residues taken up into water, filtered (0.45 mm polypropylene) and freeze dried to give the title compound a pale yellow viscous oil (370 mg). For n=38 $C_{123}H_{250}N_6O_{42}$ requires 2483.8. Found $ES^+$: $MH_2^{2+}$, 1243.5. $d_H$ (CDCl$_3$) 1.24 (52H, brm, (CH$_2$)$_{21}$CH$_2$CO, (CH$_2$)$_5$CH), 1.85 (8H, br, NCH$_2$(CH$_2$)$_2$CH$_2$N), 2.21 (2H, t, (CH$_2$)$_{22}$CH$_2$CO), 2.35 (1H, br, CH), 2.51 (2H, t, OCH$_2$CH$_2$CO), 2.8-3.35 (16H, brm, NCH$_2$), 3.37 (3H, s, OMe), 3.63 (~170H, br, OCH$_2$).

(I3) N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-24-[methoxypoly(ethyleneoxy)propanoylamino]tetracosanamide

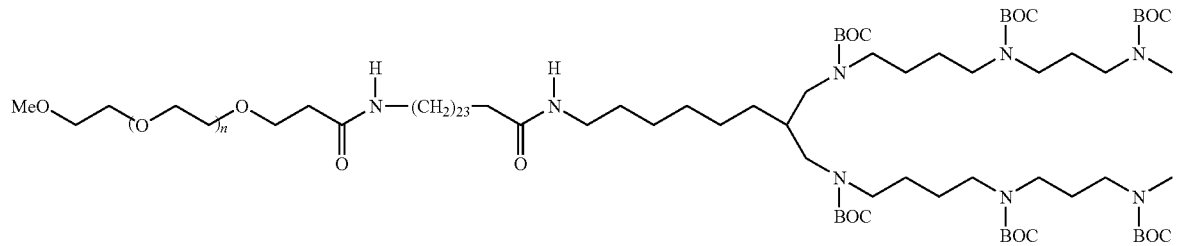

To methoxyPEGpropionic acid (MW approx 1800) (210 mg, 0.117 mmol) in anhydrous dichloromethane (20 ml) were added hydrochloride (29 mg, 0.148 mmol) and N-hydroxysuccinimide (17 mg, 0.148 mmol) and the reaction left overnight under argon at room temperature. To this was added E4 (151 mg, 0.106 mmol) and triethylamine (32 mg, 0.318 mmol) and the reaction left for a further six hours. To this was then added water (0.2 ml) and the hydrolysis of any remaining activated ester left overnight. The solvent was removed and the residues purified by gradient silica chromatography (5-10% methanol in dichloromethane) to yield the title compound (205 mg, 60%) as an off white solid. For n=38 $C_{161}H_{316}N_8O_{54}$ requires 3226.2 Found $ES^+$: $MNa_2^{2+}$, 1636.8. $\delta_H$ (CDCl$_3$) 1.24 (48H, brs, (CH$_2$)$_{20}$CH$_2$CO, (CH$_2$)$_4$CH), 1.43 (70H, brs+m, (Me)$_3$C, CH$_2$CH$_2$N), 1.98 (1H, br, CH), 2.19 (2H, t, (CH$_2$)$_{22}$CH$_2$CO), 2.54 (2H, t, OCH$_2$CH$_2$CO), 2.83 (6H, s, NMe), 3-3.5 (24H, brm, NCH$_2$), 3.36 (3H, s, OMe), 3.6 (~170H, s, OCH$_2$), 5.95, 6.95 (2H, br, CONH).

(I4) N-[8-(Methylaminopropylaminobutylamino)-7-(methylaminopropylaminobutylaminomethyl)octyl]-24-[methoxypoly(ethyleneoxy)propanoylamino]tetracosanamide hexa(trifluoroacetate) salt

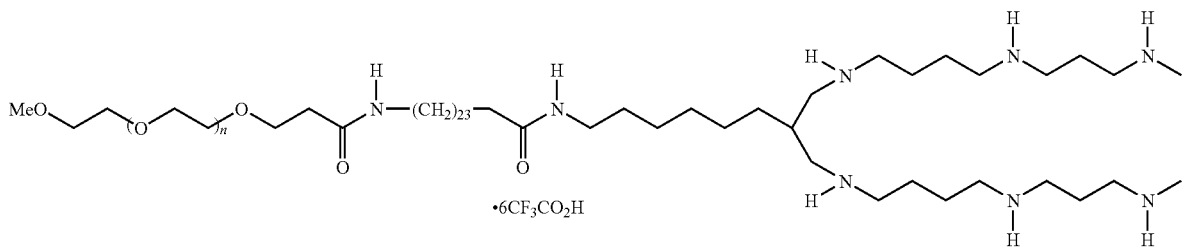

I3 (206 mg) was dissolved in 96:4 trifluoroacetic acid: dichloromethane (8 ml) and left for 15 minutes at room temperature. The solvent was removed, the residues taken up into water, filtered (0.45 mm polypropylene) and freeze dried to give the title compound as an off white solid (213 mg). For n=38 $C_{131}H_{268}N_8O_{42}$ requires 2625.9 Found ES+: $MH_2^{2+}$, 1314.5. $\delta_H$ (D$_2$O) 1.87 (44H, br, (CH$_2$)$_{19}$(CH$_2$)$_2$CO, (CH$_2$)$_3$CH$_2$CH), 2.06 (8H, br, CH$_2$CH, CH$_2$CH$_2$NH, CH$_2$CH$_2$CO, 2.38 (8H, br, NCH$_2$(CH$_2$)$_2$CH$_2$N), 2.72 (7H, br, (CH$_2$)$_{22}$CH$_2$CO, NCH$_2$CH$_2$CH$_2$N, CH), 3.05 (2H, t, OCH$_2$CH$_2$CO), 3.34 (6H, s, NMe), 3.72 (24H, br, CH$_2$N), 3.95 (3H, s, OMe), 4.25 (~170H, br, OCH$_2$).

SECTION 2

INTERMEDIATE 1

N-(Benzyloxycarbonyl)ethylenediamine

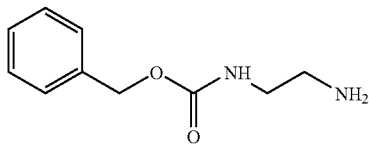

Benzyl chloroformate (2.55 g, 0.015 mmol) dissolved in 100 cm$^3$ of DCM was added dropwise to a rapidly-stirred solution of ethylenediamine (8.99 g, 0.15 mmol) in DCM (80 cm$^3$). After the mixture was left stirring overnight at room temperature under argon, the volatiles were removed on a rotary evaporator and the residue poured into water and filtered to remove insoluble precipitates. The aqueous solution was first acidified to pH 1 and washed with DCM, then the acidic solution basified to pH 12 with sodium hydroxide and extracted three times with DCM. These organic phases were combined, dried (K$_2$CO$_3$) and evaporated to dryness to yield the title compound without further purification (2.34 g). $C_{10}H_{14}N_2O_2$ requires 194.1. Found ES+: MH$^+$ 194.9. $\delta_H$ (CDCl$_3$) 7.26 (5H, s, aryl H), 5.50 (1H, br, CONH), 5.01 (2H, s, CH$_2$Ar), 3.12 (2H, q, OCONHCH$_2$), 2.69 (2H, t, CH$_2$NH$_2$).

INTERMEDIATE 2

Methyl N-(benzyloxycarbonylaminoethyl)-4,8,13,17tetramethyl-1,20-dodecanamoate

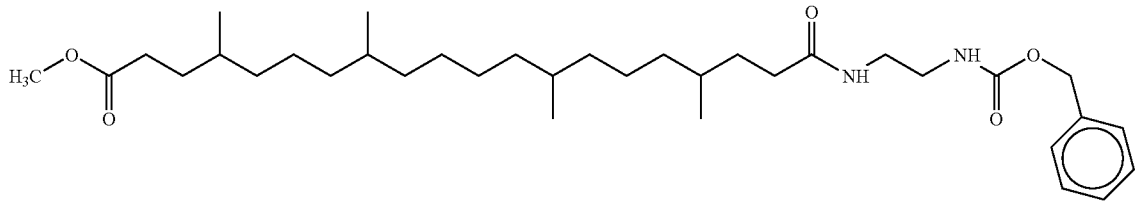

To a solution of D11 (Section 1) (5.94 g, 14.4 mmol) in DCM (100 cm$^3$) was added intermediate 1 (3.40 g, 17.6 mmol), HOBt (1.95 g, 14.4 mmol), DMAP (1.75 g, 14.4 mmol) and DCC (6.0 g, 28.8 mmol). After 24 h, precipitated matter was filtered off, and the solution was washed with citric acid (10%), water, and saturated sodium bicarbonate solution. After drying (MgSO$_4$), the solvent was removed in vacuo and the residue purified on silica (5% methanol/DCM) to give the title compound (4.80 g, 57%) as a pale yellow gum. $C_{35}H_{60}N_2O_5$ requires 588.5. Found ES+: MH$^+$ 589.3, MNa$^+$ 611.4. $\delta_H$ (CDCl$_3$) 0.7-0.9 (12H, m, CHCH$_3$), 0.8-1.8 (28H, br m, CHCH$_3$, CH$_2$), 2.15 (2H, m, CH$_2$CONH), 2.27 (2H, m, CH$_2$CO$_2$Me), 3.15-3.35 (4H, m, CH$_2$NH), 3.60 (3H, s, OCH$_3$), 5.0 (2H, s, CH$_2$Ph), 5.8 (1H, br t, NH), 6.75 (1H, br t, NH), 7.26 (5H, s, aryl H).

INTERMEDIATE 3

N-(benzyloxycarbonylaminoethyl)-4,8,13,17-tetramethyl-1, 20-dodecananoic acid

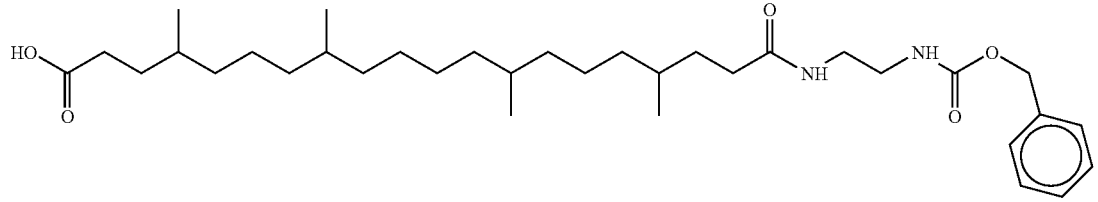

To intermediate 2 (4.8 g, 8.15 mmol) in methanol/water (2:1, 150 cm³) was added lithium hydroxide (4.8 g, 115 mmol). This was stirred vigourously for 24 h then poured into 2M hydrochloric acid (500 cm³) and extracted three times with DCM. These organic fractions were combined, dried (MgSO$_4$) and the solvent removed on a rotary evaporator to give the title compound as a yellow gum, 3.9 g, 84%. $C_{34}H_{58}N_2O_5$ requires 574.5. Found ES+: MH$^+$ 575.4 MNa$^+$ 597.4 $\delta_H$ (CDCl$_3$) 0.85-1.0 (12H, m, CH$_3$), 1.0-1.8 (28H, br m, CH$_2$, CH), 2.20 (2H, m, CH$_2$CONH), 2.36 (2H, m, CH$_2$CO$_2$), 3.2-3.4 (4H, m, CH$_2$N), 5.0 (2H, s, CH$_2$Ph), 5.5 (1H, t, NH), 6.5 (1H, t, NH), 7.26 (5H, s, aryl H). $\delta_C$ (CDCl$_3$) 19.3, 19.7, 24.2, 24.3, 24.35, 27.3, 31.7, 31.8, 32.3, 32.6, 32.7, 34.3, 36.9, 37.0, 37.1, 37.2 (22 CH$_2$, CHCH$_3$), 40.1, 40.8 (2C, CH$_2$N), 66.6 (1C, OCH$_2$), 127.9, 128.1, 128.5, 136.3 (6C, aryl C), 157.6 (1C, NHCO$_2$), 174.8 (1C, CONH), 178.6 (1C, CO$_2$H).

INTERMEDIATE 4

N-{N,N'-bis(t-Butyloxycarbonyl)-7-[N,N'-bis(t-butyloxycarbonyl)aminobutylaminomethyl]aminobutylaminooctyl}-N'-(benzyloxycarbonylaminoethyl)-4,8,13,17-tetramethyl-1,20-docosadiamide

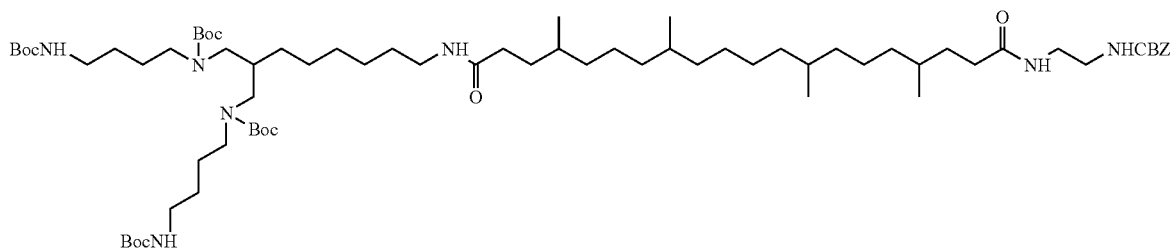

To a solution of Intermediate 3 (0.152 g, 0.26 mmol) in DCM (30 cm³) at 0° C. was added B8 (Section 1) (0.250 g, 0.34 mmol), HOBt (0.033 g, 0.26 mmol) and EDC (0.056 g, 0.29 mmol). After 24 h, the solution was washed with water, saturated sodium bicarbonate solution, the organic fraction was dried (MgSO$_4$) and the solvent evaporated in vacuo. Purification on silica (5% methanol/DCM) yielded the title compound as a colourless gum, 0.300 g, 91%, silica TLC rf 0.4 (5% methanol/DCM). $C_{71}H_{129}N_7O_{12}$ requires 1272. Found ES+: MH$^+$ 1273, MLi$^+$ 1279 $\delta_H$ (CDCl$_3$) 0.85-1.0 (12H, m, CH$_3$), 1.0-1.8 (83H, br m, CH$_2$, CH, CH$_3$), 2.20 (4H, m, CH$_2$CONH), 2.8-3.4 (18H, m, CH$_2$N), 4.8 (2H, t, NH), 5.0 (2H, s, CH$_2$Ph), 5.7 (1H, t, NH), 5.8 (1H, t, NH), 6.4 (1H, t, NH), 7.26 (5H, s, aryl H). $\delta_C$ (CDCl$_3$) 19.2, 19.5, 24.2, 24.3, 25.0, 25.4, 26.3, 26.6, 27.2, 28.3, 29.4, 29.5, 29.8, 32.4, 32.5, 32.8, 34.2, 34.4, 37.0, 37.2, 39.3, 40.0, 40.1, 40.9 (2C, CH$_2$N), 46.9, 49.2, 53.3, 66.5 (1C, OCH$_2$), 78.8, 79.2 (4C, (CH$_3$)$_3$), 127.8, 128.0, 128.3, 136.3 (6C, aryl C), 155.6, 155.9, 157.6 (1C, NHCO$_2$), 173.3, 174.2 (2C, CONH).

INTERMEDIATE 5

N-{N,N'-bis(t-Butyloxycarbonyl)-7-[N,N'-bis(t-butyloxycarbonyl)aminobutylaminomethyl]aminobutylaminooctyl}-N'-(aminoethyl)-4,8,13,17-tetramethyl-1,20-docosadiamide

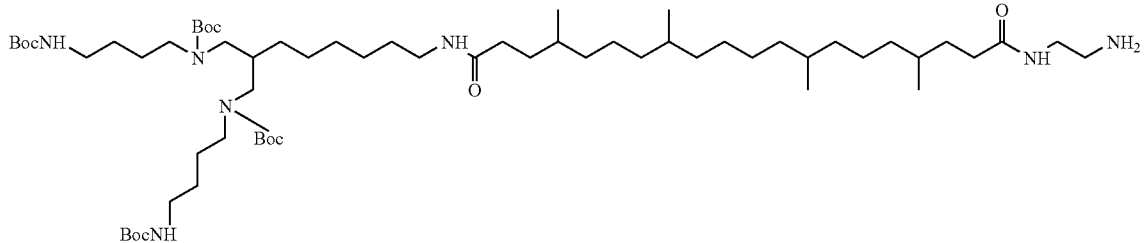

To a solution of Intermediate 4 (0.079 g, 0.062 mmol) in tert-butanol (20 cm³) at 40° C. was added ammonium formate (0.3 g), palladium on carbon (5%) (0.035 g) and Pearlman's catalyst (0.035 g). After 18 h of vigorous stirring under an argon atmosphere, the solid matter was filtered off and the solvent removed in vacuo to yield the title compound as a glassy solid. (0.058 g, 82%). $C_{63}H_{126}N_7O_{10}$ requires 1138. Found ES+: MH⁺1139; $\delta_H$ (CDCl₃) 0.85-1.0 (12H, m, CH₃), 1.0-1.8 (83H, br m, CH₂, CH, CH₂), 2.20 (4M, m, CH₂CONH), 2.8-3.4 (18H, m, CH₂N), 4.8 (2H, t, NH), 5.8 (1H, t, NH), 6.7 (1H, t, NH).

INTERMEDIATE 6
N-{N,N'-bis(t-Butyloxycarbonyl)-7-[N,N'-bis(t-butyloxycarbonyl)aminobutylaminomethyl]aminobutylaminooctyl}-N'-(maleimidobutanoylaminoethyl)-4,8,13,17-tetramethyl-1,20-docosadiamide

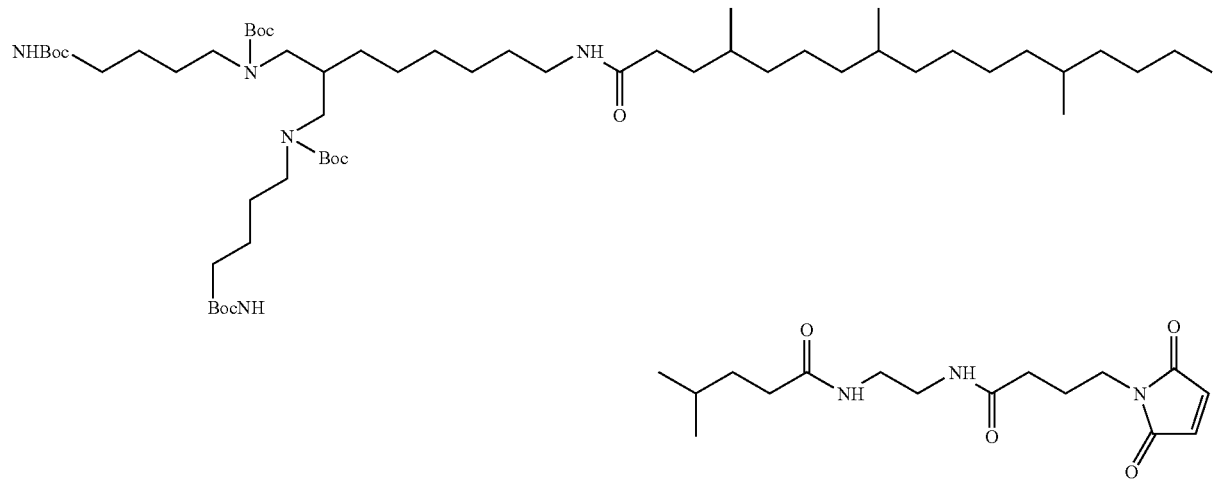

To a solution of 4-maleimidobutyric acid (0.030 g, 0.165 mmol) in DCM (5 cm³) in a salted ice bath was added HOBt (0.022 g, 0.165 mmol) and EDC (0.031 g, 0.165 mmol). After 2 h Intermediate 5 (0.058 g, 0.051 mmol) in DCM (5 cm³) was added dropwise to the active ester solution cooled in a salted ice bath. After 2.5 h the reaction mixture was washed once with water, dried (MgSO₄), filtered and the solvent removed. The compound was purified by chromatography (silica, 5% methanol/DCM) to give the title compound as a glassy solid (0.031 g, 47%). $C_{71}H_{130}N_8O_{13}$ requires 1303. Found ES+: MH⁺ 1304, MNa⁺ 1326; $\delta_H$ (CDCl₃) 0.85-1.0 (12H, m, CH₂), 1.0-1.8 (83H, br m, CH₂, CH, CH₂), 1.90 (2H, CH₂CH₂maleimide), 2.20 (6H, m, CH₂CONH), 2.8-3.4 (18H, m, CH₂N), 3.55 (2H, t, CH₂maleimide), 4.7 (2H, br s, NH), 5.6 (1H, br s, NH), 6.4 (2H, br s, NH), 6.7 (2H, s, maleimide).

INTERMEDIATE 7
N-[7-(Aminobutylaminomethyl)aminobutylaminooctyl]-N'-(maleimidobutanoylaminoethyl)-4,8,13,17-tetramethyl-1,20-docosadiamide tetra(trifluoroacetate) salt

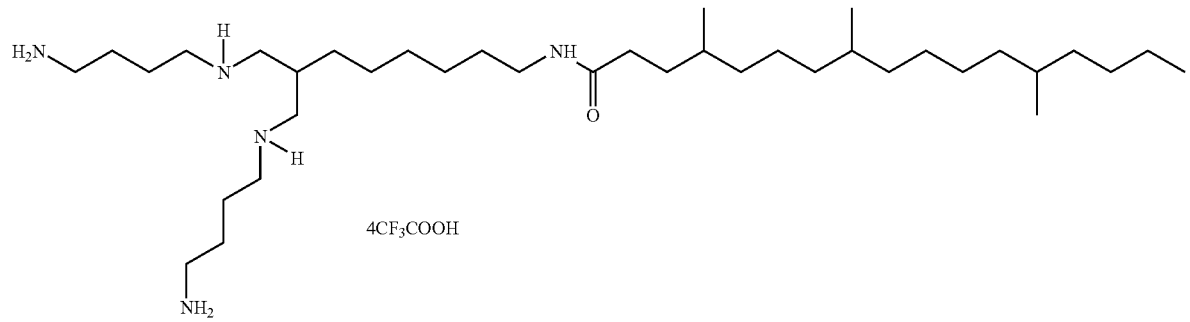

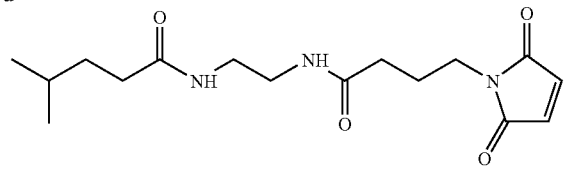

Intermediate 6 (0.035 g, 0.027 mmol) was dissolved with stirring in 96% trifluoroacetic acid (aqueous, 3 cm³). After 20 min the acid was removed quickly under high vacuum and azeotroped with toluene and finally methanol. The residue was dissolved in water, filtered (Whatman syringe filters 0.45 μm PP) and lyophilised to produce the title compound as a white fluffy solid (0.037 g, 100%). $C_{51}H_{98}N_8O_5$ requires 902.8. Found ES+: MH⁺ 903.4, $[MH_2]^{2+}$ 452.6; $\delta_H$ (CD₃OD) 0.85-1.0 (12H, m, CH₃), 1.0-1.8 (47H, br m, CH₂, CH, CH₃), 2.20 (8H, m, CH₂CONH, CH₂CH₂maleimide), 2.8-3.4 (18H, m, CH₂N), 3.55 (2H, t, CH₂-maleimide), 6.80 (2H, s, maleimide) $\delta_C$ (CD₃OD) 173, 175.6, 176.9, 177.3 (4C, CONH).

INTERMEDIATE 8

N¹-{N,N',N''-tri(t-Butyloxycarbonyl)-7-[N,N',N'''-tri(t-butyloxycarbonyl)aminopropylaminobutylaminomethyl]aminopropylaminobutylaminooctyl}-N'-(benzyloxycarbonylaminoethyl)-4,8,13,17-tetramethyl-1,20-docosadiamide

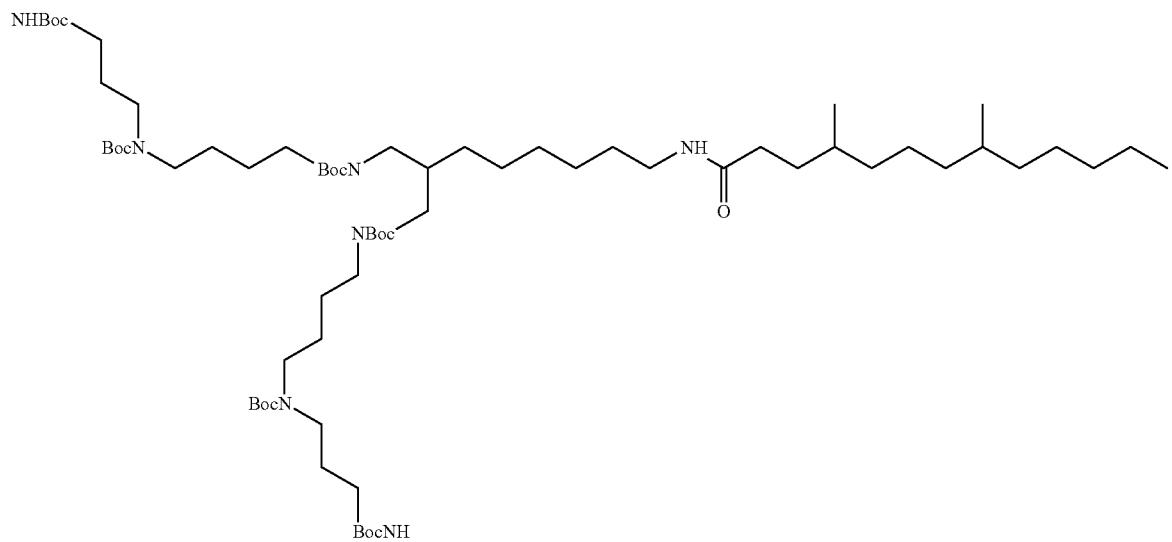

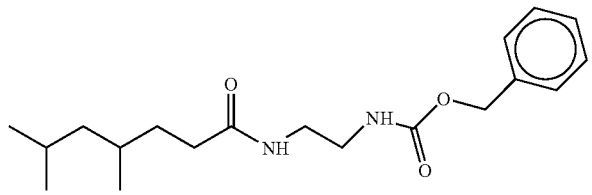

To a solution of Intermediate 3 (0.095 g, 0.165 mmol) in DCM (5 cm³) at 0° C. was added B16 (Section 1) (0.150 g, 0.145 mmol), HOBt (0.022 g, 0.17 mmol) and EDC (0.032 g, 0.165 mmol). After 24 h, the solution was washed with water then saturated sodium bicarbonate solution, and the organic fraction dried (MgSO₄) and the solvent evaporated in vacuo. Purification on silica (3% methanol/DCM) yielded the title compound as a colourless gum, 0.215 g, 93%, silica TLC rf 0.2 (5% MeOH/DCM). $C_{87}H_{159}N_9O_{16}$ requires 1586. Found ES+: MH⁺ 1587 MNa⁺ 1609 $\delta_H$ (CDCl₃) 0.85-1.0 (12H, m, CH₃), 1.0-1.8 (105H, br m, CH₂, CH, CH₃), 2.20 (4H, m, CH₂CONH), 2.8-3.4 (26H, m, CH₂N), 5.0 (2H, s, CH₂Ph), 5.4 (1H, t, NH), 5.6 (1H, t, NH), 6.2 (1H, t, NH), 7.38 (5H, s, aryl H).

INTERMEDIATE 9

N¹-{N,N',N''-tri(t-Butyloxycarbonyl)-7-[N,N',N''-tri(t-butyloxycarbonyl)aminopropylaminobutylaminomethyl]aminopropylaminobutylaminooctyl}-N'-(aminoethyl)-4,8,13,17-tetramethyl-1,20-docosadiamide

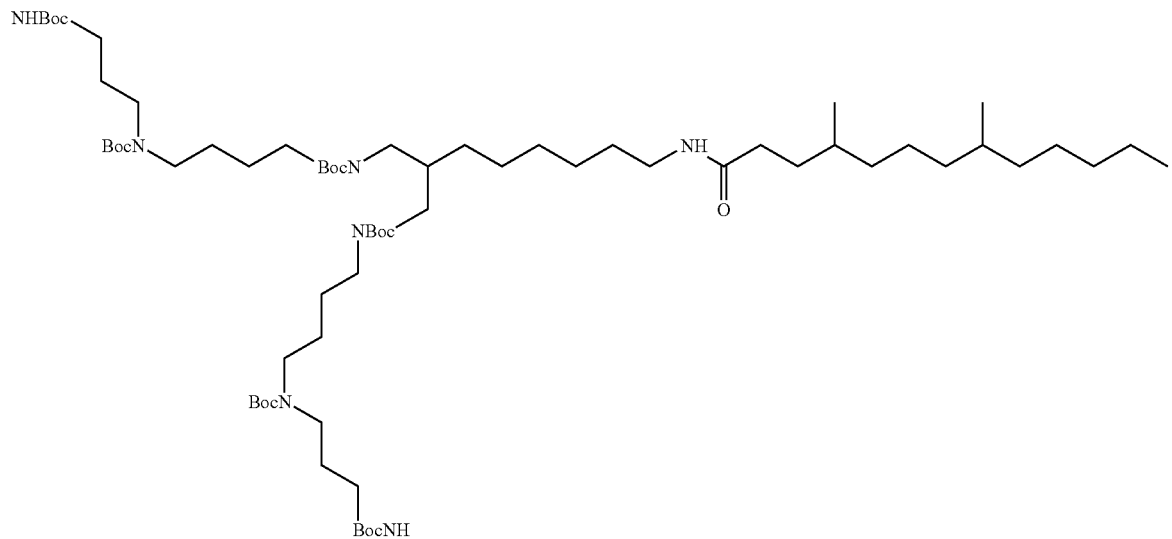

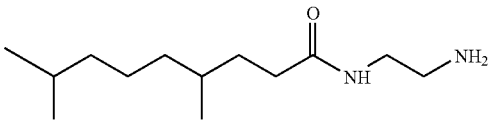

To a solution of Intermediate 8 (0.137 g, 0.086 mmol) in t-butanol (20 cm³) at 40° was added ammonium formate (0.5 g), palladium on carbon (5%) (0.060 g) and Pearlman's catalyst (0.060 g). After 24 h on vigorous stirring under an argon atmosphere, the solid matter was filtered off using gravity filtration followed by a syringe filter and the solvent removed in vacuo to yield the title compound as a glassy solid (0.109 g, 87%). $C_{79}H_{153}N_9O_{14}$ requires 1452 Found ES+: MH⁺ 1453, [MH₂]²⁺; $\delta_H$ (CDCl₃) 0.85-1.0 (12H, m, CH₃), 1.0-1.8 (105H, br m, CH₂, CH, CH₃), 2.20 (4H, m, CH₂CONH), 2.8-3.4 (26H, m, CH₂N), 5.4 (1H, t, NH), 5.75 (2H, t, NH), 6.3 (1H, t, NH).

INTERMEDIATE 10

N¹-{N,N',N''-tri(t-Butyloxycarbonyl)-7-[N,N',N''-tri(t-butyloxycarbonyl)aminopropylaminobutylaminomethyl]aminopropylaminobutylaminooctyl}-N'-(maleimidobutanoylaminoethyl)-4,8,13,17-tetramethyl-1,20-docosadiamide

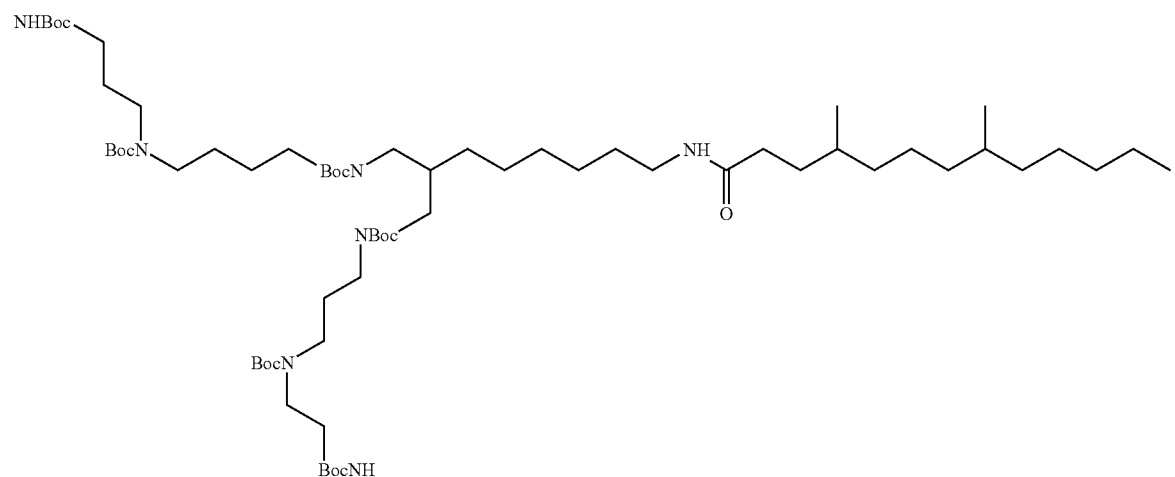

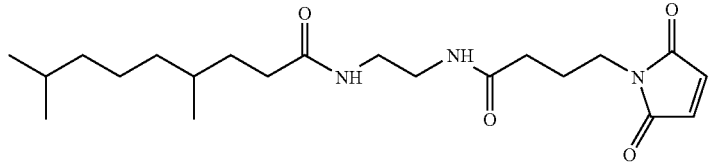

To a solution of 4-maleimidobutyric acid (0.050 g, 0.275 mmol) in DCM (10 cm$^3$) in a salted ice bath was added HOBt (0.037 g, 0.275 mmol) and EDC (0.052 g, 0.275 mmol). After 2 h Intermediate 9 (0.109 g, 0.075 mmol) in DCM (10 cm$^3$) was added dropwise to the active ester solution cooled in a salted ice bath. After 2 h, the reaction mixture was washed twice with water and then dried (MgSO$_4$). After filtration and removal of solvent, the compound was purified by chromatography (silica, 5% MeOH/DCM) to give the title compound as a glassy solid (0.94 g, 77%). C$_{87}$H$_{160}$N$_{10}$O$_{17}$ requires 1617. Found ES+: [MH$_2$]$^{2+}$ 820.6, MNa$^+$ 1640; $\delta_H$ (CDCl$_3$) 0.85-1.0 (12H, m, CH$_3$), 1.0-1.8 (105H, br m, CH$_2$, CH, CH$_3$), 1.90 (2H, CH$_2$CH$_2$maleimide), 2.20 (6H, m, CH$_2$CONH), 2.8-3.4 (26H, m, CH$_2$N), 3.55 (2H, t, CH$_2$-maleimide), 5.7 (1H, br s, NH), 6.5 (2H, br s, NH), 6.68 (2H, s, maleimide). $\delta_C$ (CD$_3$OD) 20.1, 20.5, 25.8, 25.9, 28.2, 28.8, 29.1, 30.7, 31.3, 31.5, 34.1, 34.2, 34.3, 34.6, 35.2, 38.3, 38.5, 38.7, 40.3, 80.2, 81.2 (6C, (CH$_3$)$_3$), 135.7 (2C, maleimide), 156.0, 157.7, 158.6 (6C, NHCO$_2$), 172.8, 175.5, 176.6, 177.1 (4C, CONH).

INTERMEDIATE 11

N$^1$-[7-(Aminopropylaminobutylaminomethyl)aminopropylaminobutylaminooctyl](maleimidobutanoylaminoethyl)-4,8,13,17-tetramethyl-1,20-docosadiamide hexa(trifluoroacetate) salt

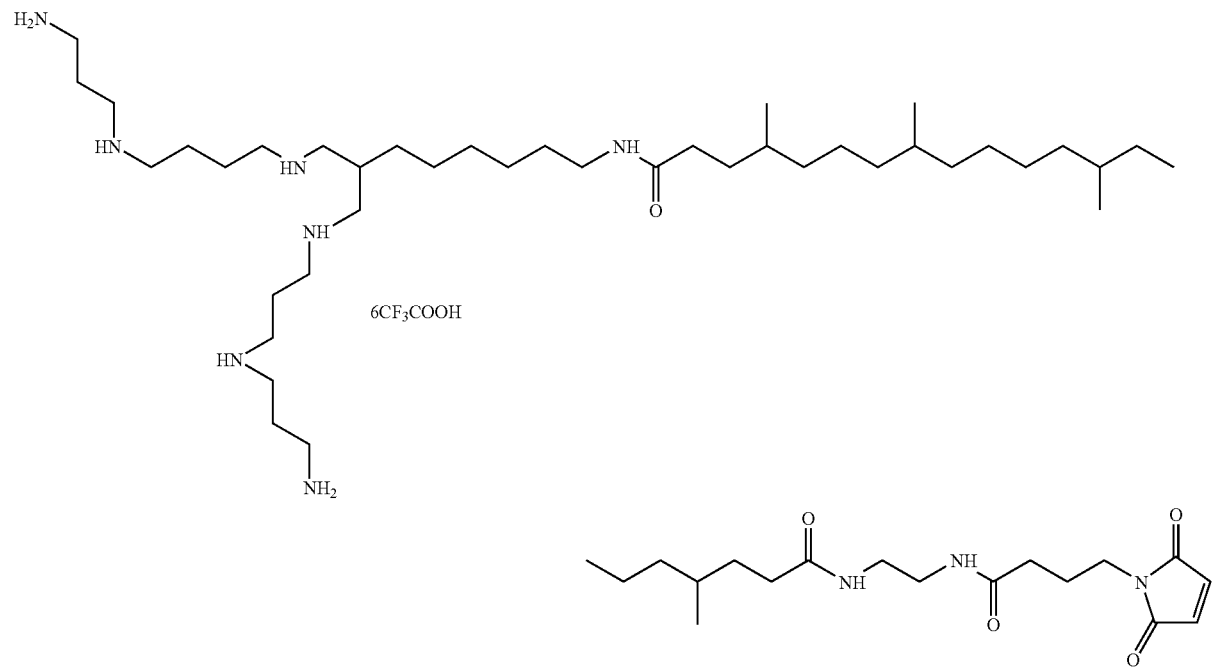

Intermediate 10 (0.047 g, 0.027 mmol) was dissolved with stirring in 96% trifluoroacetic acid (aqueous, 2 cm$^3$). After 20 min the acid was removed quickly under high vacuum and azeotroped with toluene and finally methanol. The residue was dissolved in water, filtered (Whatman syringe filters 0.45 μm PP) and lyophilised to produce the title compound as a white fluffy solid (0.049 g, 100%). C$_{57}$H$_{112}$N$_{10}$O$_5$ requires 1017. Found ES+: [MH$_3$]$^{3+}$ 340.1 [MH$_2$]$^{2+}$ 509.7; $\delta_H$ (CD$_3$OD) 0.85-1.0 (12H, m, CH$_3$), 1.0-1.8 (60H, br m, CH$_2$, CH, CH$_3$), 2.20 (8H, m, CH$_2$CONH, CH$_2$CH$_2$maleimide), 2.8-3.4 (26H, m, CH$_2$N), 3.55 (2H, t, CH$_2$-maleimide), 6.80 (2H, s, maleimide) $\delta_C$ (CD$_3$OD) 20.2, 20.6, 24.4, 24.6, 25.8, 25.9, 26.0, 27.4, 28.2, 28.8, 30.6, 30.8, 31.1, 34.2, 34.4, 34.7, 35.4, 38.2, 38.6, 38.8, 40.4, 40.6, 46.3, 118.2 (6C, m, CF$_3$), 135.8 (2C, maleimide), 163.3 (6C, m, CF$_3$CO$_2$), 172.9, 175.6, 176.9, 177.3 (4C, CONH).

INTERMEDIATE 12

$N^1$-{N,N'-di(t-Butyloxycarbonyl)-7-[N,N'-di(t-butyloxycarbonyl)aminobutylaminomethyl]aminobutylaminooctyl}-24-(maleimidobutanoylamino)tetracosanamide

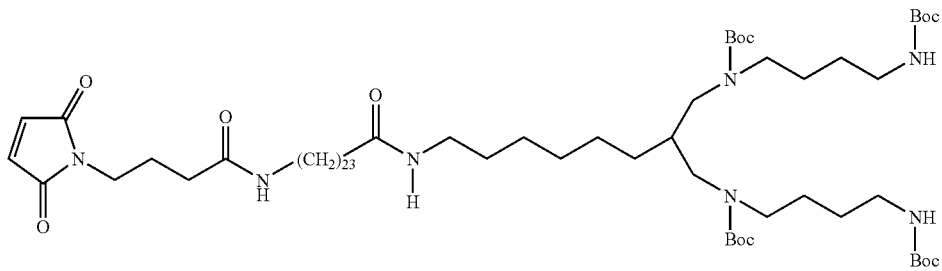

4-Maleimidobutyric acid N-hydroxysuccinimide ester (200 mg, 0.8 mmol) was dissolved in DCM (20 cm$^3$) and E2 (Section 1) (412 mg, 0.38 mmol) added dropwise in 5 cm$^3$ of DCM. After 2 h the reaction was complete and it was evaporated to small bulk before chromatography (silica—20% hexane in ethyl acetate). The solvent was removed under high vacuum and the residue dissolved in ether before evaporation to dryness to yield the title compound as a white solid (39 mg, 84%). $C_{69}H_{127}N_7O_{12}$ requires 1246. Found ES+: MH$^+$ 1246.8. $C_{69}H_{127}N_7O_{12}$ requires C: 66.47%, H: 10.27%, N: 7.86%. Found: C: 66.33%, H: 10.31%, N: 7.85% $\delta_H$ (CDCl$_3$) 6.70 (2H, s, maleimide), 5.9 (1H, br, CONH), 4.65 (1H, br, CONH), 3.57 (2H, t, CH$_2$ maleimide), 2.9-3.4 (24H, m, NCH$_2$), 2.17 (2H, m, (CH$_2$)$_{22}$CH$_2$CONH)), 2.15 (2H, t, (malNCH$_2$CH$_2$CH$_2$CONH), 1.94 (2+1H, m, (malNCH$_2$CH$_2$CH$_2$CONH+bridgehead), 1.8-1.0 (96H, m, CH$_2$).

INTERMEDIATE 13

$N^1$-[7-(Aminobutylaminomethyl)aminobutylaminooctyl]-24-(maleimidobutanoylamino)tetracosanamide tetra(trifluoroacetate) salt

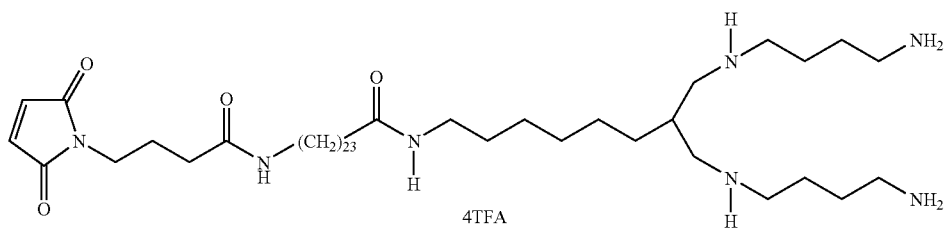

Intermediate 12 (398 mg, 0.32 mmol) was dissolved with stirring in 96% trifluoroacetic acid (aqueous, 10 cm$^3$). After 30 min the acid was removed quickly under high vacuum and azeotroped with toluene and finally methanol. The residue was dissolved in water, filtered (Whatman syringe filters 0.45 μm PP) and lyophilised. The white fluffy solid was triturated with anhydrous ether, filtered off and subjected to high vacuum to yield the title compound as a white solid which was dissolved in water and lyophilised again (330 mg, 80%). $C_{49}H_{95}N_7O_4$ requires 845.75. Found ES+: MH$^+$ 846.9. $C_{49}H_{95}N_7O_4$. 4.5TFA requires C: 51.24%, H: 7.38%, N: 7.21%. Found: C: 51.25%, H: 7.42%, N: 7.31%. $\delta_H$ (CD$_3$OD) 6.80 (2H, s, maleimide), 3.52 (2H, t, CH$_2$ maleimide), 3.0-3.3 (12H, m, NCH$_2$), 2.97 (4H, t, CH$_2$NHCO), 2.20 (1H, m, bridgehead), 2.16 (4H, dt, (CH$_2$CONH), 1.86 (2H, m, malNCH$_2$CH$_2$CH$_2$CONH), 1.9-1.2 (60H, m, CH$_2$).

INTERMEDIATE 14

N$^1$-{N,N',N"-tri(t-Butyloxycarbonyl)-7-[N,N',N"-tri(t-butyloxycarbonyl)aminopropylaminobutylaminomethyl]aminopropylaminobutylaminooctyl}-24-(benzyloxycarbonylamino)tetracosanamide

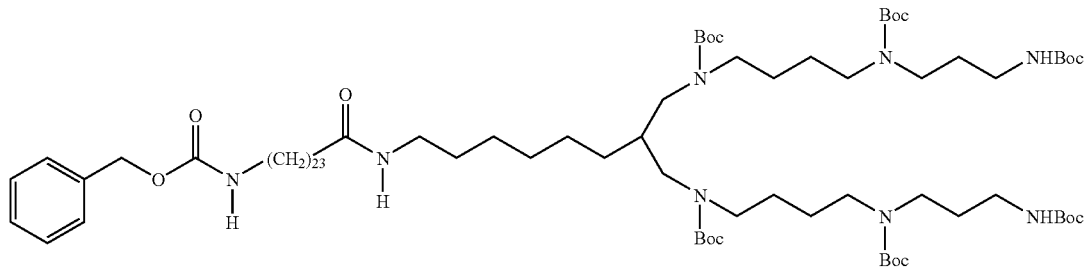

D19 (Section 1) (380 mg, 0.735 mmol) was dissolved in DCM (6 cm$^3$) containing DBU (223 mg, 1.47 mmol) and N-hydroxysuccinimide (169 mg, 1.47 mmol) to give a clear solution. EDC was added (210 mg, 1.1 mmol) and after 3 h B16 (Section 1) (580 mg, 0.56 mmol) was added and the stirred reaction left 18 h. The product was purified by chromatography (silica—60% ethyl acetate in hexane) to yield the title compound as a glassy product (678 mg, 79%). C$_{85}$H$_{156}$N$_8$O$_{15}$ requires 1529.17. Found ES+: MH$^+$ 1530.2. $\delta_H$ (CDCl$_3$) 7.33 (5H, m, ArH), 6.00 (1H, br, CONH), 5.08 (2H, s, CH$_2$Ph), 4.7 (1H, br, CONH), 2.9-3.4 (24H, m, NCH$_2$), 2.19 (2H, t, CH$_2$CO$_2$H), 1.8-1.0 (118H, m, CH$_2$).

INTERMEDIATE 15

N$^1$-{N,N',N"-tri(t-Butyloxycarbonyl)-7-[N,N',N"-tri(t-butyloxycarbonyl)aminopropylaminobutylaminomethyl]aminopropylaminobutylaminooctyl}-24-aminotetracosanamide

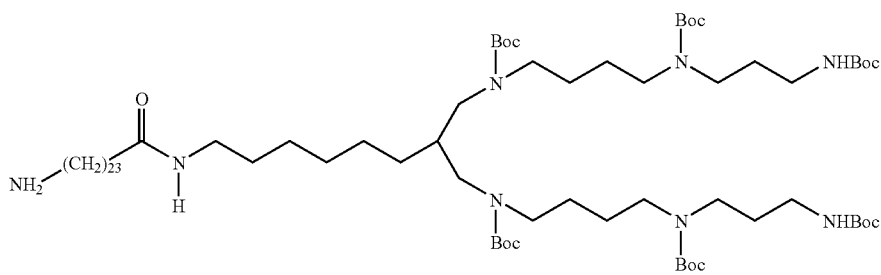

Intermediate 14 (432 mg, 0.28 mmol) was dissolved in t-butanol (50 cm$^3$) at 40° C. containing Raney nickel (500 mg), Pearlman's catalyst (500 mg) and ammonium formate (3 g) under a hydrogen atmosphere. There was a vigorous hydrogen evolution and the reaction was complete after 5 h. The catalyst was removed by filtration and the reaction evaporated to dryness. The product was purified by chromatography (silica—10% methanol in DCM containing 0.1% triethylamine) to yield the title compound as a glassy product (350 mg, 89%). C$_{77}$H$_{150}$N$_8$O$_{13}$ requires 1395.1. Found ES+: MH$^+$ 1396.0. $\delta_H$ (CDCl$_3$) 5.65 (1H, br, CONH), 2.9-3.4 (24H, m, NCH$_2$), 2.19 (2H, t, CH$_2$CO$_2$H), 1.8-1.0 (118H, m, CH$_2$).

INTERMEDIATE 16

$N^1$-{N,N',N''-tri(t-Butyloxycarbonyl)-7-[N,N',N''-tri(t-butyloxycarbonyl)aminopropylaminobutylaminomethyl]aminopropylaminobutylaminooctyl}-24-(maleimidobutanoylamino)tetracosanamide

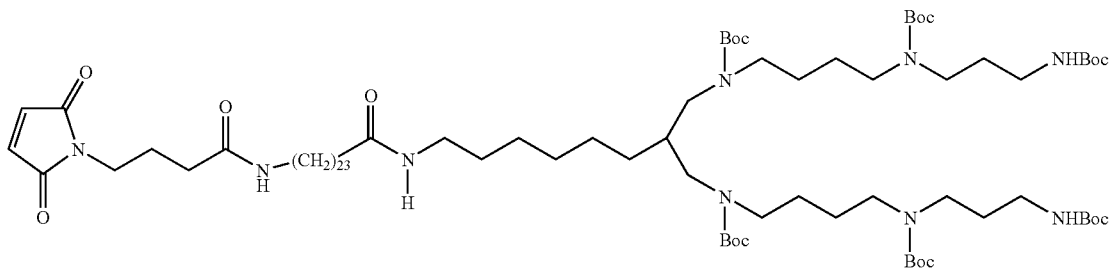

4-Maleimido butyric acid N-hydroxysuccinimide ester (200 mg, 1.25 mmol) was dissolved in DCM (20 cm$^3$). Intermediate 15 (344 mg, 0.25 mmol) was added dropwise in 5 cm$^3$ of DCM. After 2 h the reaction was complete and it was evaporated to small bulk before chromatography (silica—10% hexane in ethyl acetate). The solvent was removed under high vacuum and the residue dissolved in ether before evaporation to dryness to yield the title compound as a white solid (216 mg, 55%). $C_{85}H_{157}N_9O_{16}$ requires 1560.2. Found ES+: MH$^+$ 1561. $\delta_H$ (CDCl$_3$) 6.70 (2H, s, maleimide), 6.2 (1H, br, CONH), 5.9 (1H, br, CONH), 3.57 (2H, t, CH$_2$ maleimide), 2.9-3.4 (24H, m, NCH$_2$), 2.23 (2H, t, (CH$_2$)$_{22}$CH$_2$CONH)), 2.16 (2H, t, (malNCH$_2$CH$_2$CH$_2$CONH), 1.94 (2+1H, m, (malNCH$_2$CH$_2$CH$_2$CONH+bridgehead), 1.8-1.0 (118H, m, CH$_2$).

INTERMEDIATE 17

$N^1$-[7-(Aminopropylaminobutylaminomethyl)aminopropylaminobutylaminooctyl]-24-(maleimidobutanoylamino)tetracosanamide hexa(trifluoroacetate) salt

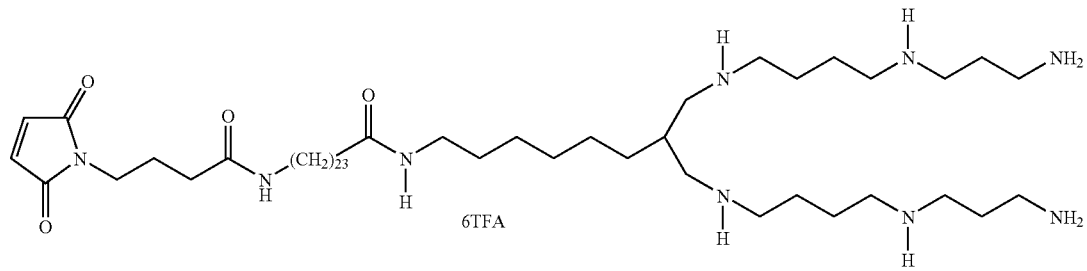

Intermediate 16 (216 mg, 0.14 mmol) was dissolved with stirring in 96% trifluoroacetic acid (aqueous, 10 cm$^3$). After 30 min the acid was removed quickly under high vacuum and azetroped with toluene and finally methanol. The residue was dissolved in water, filtered (Whatman syringe filters 0.45 μm PP) and lyophilised. The white fluffy solid was triturated with anhydrous ether, filtered off and subjected to high vacuum to yield the title compound as a white solid (233 mg, 100%). $C_{55}H_{109}N_9O_4$ requires 959.9. Found ES+: MH$^+$ 961.0. $C_{67}H_{115}N_9O_{16}F_{18}$· 2H$_2$O requires C: 47.88%, H: 7.14%, N: 7.50%. Found: C: 47.86%, H: 6.86%, N: 7.35%, $\delta_H$ (CD$_3$OD) 6.80 (2H, s, maleimide), 3.52 (2H, t, CH$_2$ maleimide), 3.0-3.3 (24H, m, NCH$_2$), 2.16 (2H, t, (CH$_2$)$_{22}$CH$_2$CONH), 2.07 (2H, t, malNCH$_2$CH$_2$CH$_2$CONH), 1.86 (2+1H, m, malNCH$_2$CH$_2$CH$_2$CONH+bridgehead), 1.9-1.2 (64H, m, CH$_2$).

INTERMEDIATE 18

24-[maleimidopropanoylaminopoly(ethyleneoxy)propanoylamino]-N-{8-[Methyl(t-butyloxycarbonyl)aminopropyl(t-butyloxycarbonyl)aminobutyl(t-butyloxycarbonyl)amino]-7-[methyl(t-butyloxycarbonyl)aminopropyl(t-butyloxycarbonyl)aminobutyl(t-butyloxycarbonyl)aminomethyl]octyl}-tetracosanamide

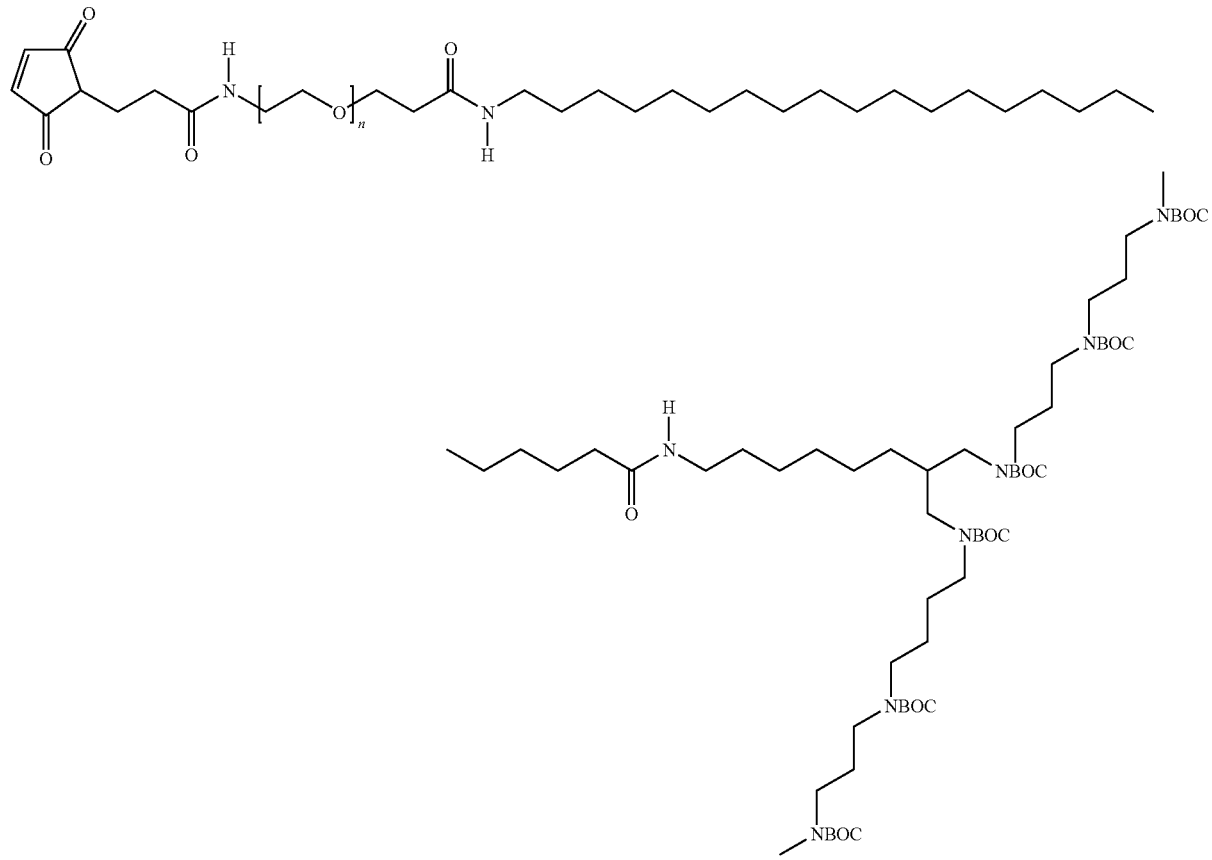

To NHS-PEG-MAL MW 2000 (Shearwater) (169 mg, 0.078 mmol) in anhydrous DCM (10 cm³) were added 50 (117 mg, 0.092 mmol) and triethylamine (16 mg, 0.157 mmol) and the reaction left overnight under argon. The solvent was removed and the residues purified by silica column chromatography (eluting with 5-10% methanol in DCM) to yield the title compound as a white solid, 205 mg, 76%. $C_{171}H_{328}N_{10}O_{58}$ (n=41) requires 3450.3. Found ES⁺: MNa⁺, 3474.0, MNa₂²⁺, 1748.7. $\delta_H$ (CDCl₃) 1.24 (46H, br, (CH₂)₄CH, (CH₂)₁₉(CH₂)₂₂CO), 1.38-1.80 (72H, m, (CH₃)₃C, CH₂CH₂CH₂NH, CH₂CH₂CH₂CO, NCH₂(CH₂)₂CH₂N, NCH₂CH₂CH₂N), 1.97 (1H, br, CH), 2.20 (2H, t, (CH₂)₂₂CH₂CO), 2.4-2.7 (4H, m, NCH₂CH₂O, PEGCH₂CO), 2.83 (6H, s, NCH₃), 2.90-3.35 (26H, m, NCH₂, 3.35-3.9 (~176H, br, OCH₂), 6.03 (1H, br, (CH₂)₂₃CONH), 6.30, 6.93 (2H, 2×br, CONH).

INTERMEDIATE 19

(52) 24-[maleimidopropanoylaminopoly(ethyleneoxy)propanoylamino]-N-{8-[Methylaminopropylaminobutylamino]-7-[methylaminopropylaminobutylaminomethyl]octyl}tetracosamamide

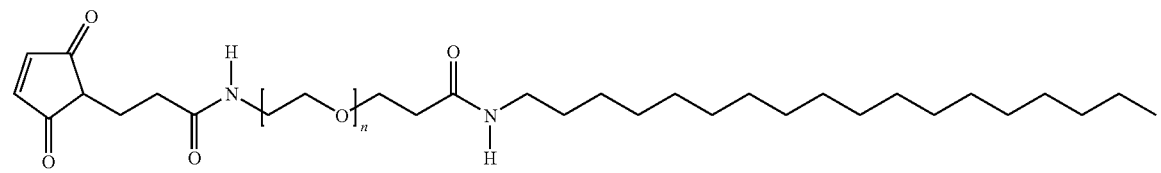

-continued

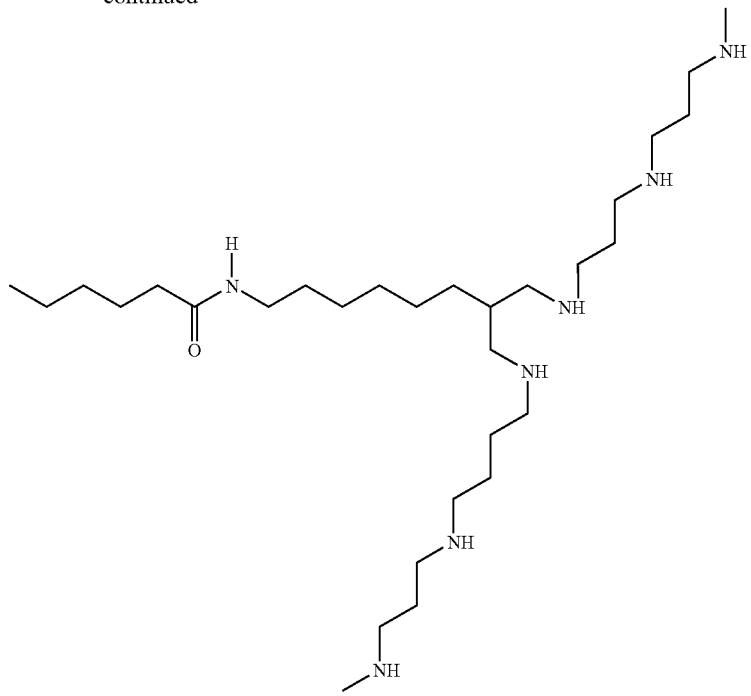

(51) (205 mg) was dissolved in 96:4 trifluoroacetic acid: water (4 cm³) and left at room temperature for 25 minutes. The solvent was removed, the residues taken up into MilliQ water (10 cm³) and filtered through a 0.2 μm polypropylene filter. The solution was freeze dried to yield the title compound as a colourless gum/solid in quantitative yield. $C_{147}H_{292}N_{10}O_{49}$ (n=44) requires 2982.1. Found ES+: $MH_2^{2+}$, 1470.3. $\delta_H$ (CD$_3$OD) 1.20-1.45 (44H, m, (CH$_2$)$_3$CH$_2$CH, (CH$_2$)$_{19}$CH$_2$CO), 1.45-1.70 (8H, m, CH$_2$CH, CH$_2$CH$_2$CH$_2$NH, CH$_2$CH$_2$CH$_2$CO), 1.83 (8H, m, NCH$_2$(CH$_2$)$_2$CH$_2$N), 2.11 (2H, m, CH$_2$CO), 2.15 (4H, m, NCH$_2$CH$_2$CH$_2$N), 2.23 (1H, m, CH), 2.42 (2H, t, OCH$_2$CH$_2$CO), 2.47 (2H, t, NCH$_2$CH$_2$CO), 2.74 (6H, s, NCH$_3$), 3.0-3.25 (26H, m, NCH$_2$), 3.50 (2H, t, NCH$_2$CH$_2$CO), 3.55-3.90 (~180 H, m, OCH$_2$), 6.82 (2H, s, CH=CH).

SECTION 3

The following gives details for the preparation of a targeted bipolar lipid of the invention using an anti-CD3 antibody (OKT3) and a pegylated lipid (Intermediate 19). It will be appreciated that the procedure described will give other targeted lipids of the invention by simple substitution of the antibody and/or lipid with other targeting molecules and bipolar lipids as generally and specifically described herein.

A. Site Specific Attached of OKT3 Fab' to Intermediate 19

1. Selective Reduction of F(ab')$_2$ to Fab':

OKT3 F(ab')$_2$ (900 ul, 5 mg/ml) was incubated with 2-mercaptoethylamine (100 ul: 100 mM) at 37° C. for 30 minutes. Excess reducing agent was removed by application to a pre-packed, pre-equilibrated (0.1M sodium acetate, 2 mM EDTA, pH 5.80) G25 column (PD-10, Pharmacia). The concentration of the eluted protein was determined by absorbance at 280 nm (Extinction coefficient 1.43).

The extent of reduction from F(ab')$_2$ to Fab' was established by HPLC gel filtration analysis. (DuPont GF250; 0.2M sodium phosphate, pH 7.0).

2. Incubation of Fab' with Intermediate 19

OKT3 Fab' (2 mg, 0.04 uml) in 0.1M sodium acetate, 2 mM EDTA, pH 5.80 was added to a lyophilised powder of Intermediate 19 (1 mg, 0.3 umol). The mixture was vortexed and maintained at 37° C. for 30 minutes and 4° C. overnight.

The reaction mix was then applied to a pre-primed (1% PEG$_{2000}$), pre-equilibrated (0.2M sodium phosphate, pH 7.0) Sephacryl S-300 column (30 cm×0.9 cm) to remove excess Intermediate 19 and to buffer exchange for further purification.

The fractions were pooled by OD at 280 nm and analysed by SDS PAGE (Novex 4-20% gradient).

3. Removal of Unreacted Fab' by Hydrophobic Interaction Chromatography

SDS PAGE (reducing conditions) had shown that there was unreacted Fab' as evidenced by the presence of non-derivatised heavy chain. The buffer containing the S-300 purified material was adjusted to the composition of the equilibration buffer in the column step. This was then applied to the pre-equilibrated (1.5M ammonium sulphate, 50 mM sodium phosphate, pH 7.0) Porous PE (50 um) column (1.66 mm dia×10 cm) and eluted with a linear gradient of 1.5M ammonium sulphate/50 mM sodium phosphate, pH 7.0 to 50 mM sodium phosphate, pH7.0 over 20 column volumes at a flow rate of 5 mlmin$^{-1}$.

The eluted fractions were analysed by SDS PAGE (Novex; 4-20% gradient) and the concentration determined by absorbance at 280 nm (extinction coefficient 1.43).

The unreacted Fab'/F(ab')$_2$ was eluted in the void volume and at approximately 1M ammonium sulphate and the required product eluted as a broad peak from 0.6M to zero ammonium sulphate. Total step recovery of required product was 29%.

Fab'-conjugated Intermediate 19 was concentrated via an Amicon stirred cell (Millipore: 10K cut off). A FACS competition assay using FITC-labelled OKT3 IgG showed that there was no change to the binding ability of the Intermediate 19 derivatised material compared to the parent Fab'.

B Random Modification of OKT3 IgG with Intermediate 19

1. Introduction of Thiol groups onto IgG with N-Succinimidyl S-Acetylthioacetate (SATA)

OKT3 IgG antibody (1.0 ml, 6 mg) was incubated with SATA/DMSO (3.3 ul, 20 mM) at room temperature for 30 minutes.

Excess SATA was removed by application of the mix to a pre-packed, pre-equilibrated (50 mM sodium phosphate/1 mM EDTA, pH 7.50) G25 column (PD-10, Pharmacia).

Protein concentration was determined by measuring the absorbance at 280 nm (extinction coefficient 1.43).

The thiol groups on the SATA-derivatised IgG (900 ul) were activated with 50 mM sodium phosphate/1 mM EDTA buffer containing 0.5M hydroxylamine hydrochloride for 2 h at room temperature. Titration with 4,4' dithidipyridine showed that 1.5 thiols had been introduced per antibody molecule.

2. Incubation of Thiolated IgG with Intermediate 19

Thiolated antibody (3.0 mg, 0.02 nmol) in 50 mM sodium phosphate/1 mM EDTA, pH 7.50 was incubated with Intermediate 19 (solution in water, 0.5 mg, 0.14 umol) at 37° C. for 30 min at 4° C. overnight.

The reaction mix was then applied to a pre-primed (1% $PEG_{2000}$) pre-equilibrated (0.2M sodium phosphate, pH 7.0) Sephacryl S-300 column (30 cm×0.9 cm) to remove excess Intermediate 19 and to buffer exchange. The pooled fractions were anlysed by SDS PAGE (Novex 4-20% gradient) and the concentration determined by absorbance at 280 nm (extinction coefficient 1.43).

A change in the banding pattern of the heavy chain (as observed on a reducing gel) provided evidence that modification of the IgG had occurred.

SECTION 4

PREPARATION OF NON-LIPOSOMAL TARGETED BIPOLAR LIPID PARTICLES FOR DELIVERY OF DNA TO CELLS AND SPECIFIC TRANSFECTION THEREOF

The following gives a general procedure for the preparation of particles according to the invention. Where particular targeted and other bipolar lipids are mentioned it will be appreciated that these may be substituted by any equivalent targeted and/or bipolar lipids as generally and particularly described herein.

Materials

| | |
|---|---|
| Diluent (G5H): | 5% glucose in HEPES was prepared from 8 volumes 10 mM HEPES pH 8 and one volume 45% glucose (Sigma, sterile aqueous solution). The diluent was sterile filtered to 0.2μ. |
| DNA: | Plasmid DNA (pCMVβ encoding the β-galactosidase reporter gene) was prepared using a Qiagen kit according to the manufacturer's instruction and was formulated at approximately 1 mg/ml in 10 mM TRIS/10 mM EDTA buffer pH 8.0 and sterile filtered to 0.45μ. Plasmid DNA was diluted in G5H to 62 μg/ml working solution (equivalent to 0.2 mM DNA phosphate). |
| 1st bipolar lipid: | A 10 mg/ml solution of the TFA salt of H33 (Section 1) was prepared in water and sterile filtered to 0.02μ, (for H33 equivalent to 35.59 mM $N^+$). |
| 2nd bipolar lipid: | A 10 mg/ml solution of the TFA salt of I4 (Section 1) was prepared in water and sterile filtered to 0.02μ (for I4 equivalent to 17.89 mM $N^+$). Working solutions of each bipolar lipid were prepared in G5H at 1.2 mM ($N^+$ equivalents). |
| Test Targeted Lipid: | Anti-CD3 (IgG or Fab' fragment) antibody-Intermediate 19 conjugate as described in Section 3. |
| Control lipid: | Isotype matched control (IgG2a or Fab' fragment thereof) antibody-Intermediate 19 conjugate as prepared in a similar manner to the Test lipid. Test and control lipids were diluted in G5H to 1 μM with respect to antibody binding site concentration. |
| Co-lipid: | A 25 mM solution of the following lipid mixture was prepared in 0.5 M octyl glucoside: cholesterol: dioleyl phosphatidylethanolamine: cholesterol hemisuccinate (molar ratio 40:40:20). The solution was sterile filtered to 0.02μ. |

Method 1

All reagents and procedures were carried out under sterile conditions.

To prepare 1 ml quantities of particles of the invention at 20 μg/ml DNA containing a desired percentage of either bipolar lipid, the working solutions of each bipolar lipid were mixed in the respective proportion by volume to give 162 μl. For example for a 33 mol % 1st bipolar lipid/67 mol % 2nd bipolar lipid mixture 54 μl of first-bipolar lipid (1.2 mM) were mixed with 108 μl of the second bipolar lipid. The mixture was diluted with 494 ul of G5H in a 7 ml vial, then 323 μl diluted DNA added drop-wise with vortexing. The test or control lipids were added to separate mixtures as single 21 μl aliquots with vortexing. The transfection mixtures were left for at least 30 min at room temperature before use or stored at 4° C. for longer periods.

Method 2

All reagents and procedures were carried out under sterile conditions.

To prepare 1 ml quantities of particles of the invention at 20 μg/ml DNA containing a desired percentage of either bipolar lipid, the working solutions of each bipolar lipid were mixed in the respective proportion by volume to give 162 μl. The test or control conjugates were added to separate mixtures as single 21 μl aliquots with vortexing. The mixture was diluted with 494 ul of G5H in a 7 ml vial, then 323 μl diluted DNA added drop-wise with vortexing. The transfection mixtures were left for at least 30 min at room temperature before use or stored at 4° C. for longer periods.

Method 3

All reagents and procedures were carried out under sterile conditions.

To prepare 1 ml quantities of particles of the invention at 20 μg/ml DNA containing a desired percentage of either bipolar lipid, the working solutions of each bipolar lipid were mixed in the respective proportion by volume to give 162 μl. The mixture was diluted with 494 ul of G5H in a 7 ml vial. The test or control conjugates, as single 21 μl aliquots, were added to separate 323 μl portions of diluted DNA with vortexing, then added drop-wise to the diluted bipolar lipid mixture with vortexing. The transfection mixtures were left for at least 30 min at room temperature before use or stored at 4° C. for longer periods.

The above preparations from Methods 1, 2 and 3 resulted in a bipolar lipid cation: DNA anion charge ratio of 3:1 and 5 antibody binding sites per plasmid. Either parameter could be varied by changing the volume of the respective reagent by the desired proportion and by making an equivalent change to the volume of G5H addition by the converse amount. Charge ratios were varied from 0.5:1 to 6:1 and the antibody binding sites per plasmid were varied from 0.5 to 100. The molar percentage of the first bipolar lipid relative to the total bipolar lipid was varied from 0% to 100%.

Method 4

All reagents and procedures were carried out under sterile conditions.

DNA was diluted in G5H to 248 µg/ml working solution (equivalent to 0.8 mM DNA phosphate). Working solutions of each bipolar lipid were prepared in G5H at 4 mM ($N^+$ equivalents).

To prepare 1 ml quantities of condensed DNA mixture, at 60 µg/ml DNA, containing a desired percentage of either bipolar lipid; the working solutions of each bipolar lipid were mixed in the respective proportion by volume to give 194 µl. For example for a 33 mol % 1st bipolar lipid/67 mol % 2nd bipolar lipid mixture 64 µl of 1st bipolar lipid (1.2 mM) were mixed with 130 µl of the 2nd bipolar lipid.

A 63 µl aliquot of either test or control conjugate and 377 µl of G5H were added to the bipolar lipid mixture.

The co-lipid solution (124 µl) was added to 242 µl of DNA and the mixture added drop-wise to the bipolar lipid mixture with vortexing. The mixture was left at room temperature for at least 30 min, after which time it became slightly turbid.

Octyl glucoside was removed from the preparation by gel filtration, using a Sephadex G25 PD10 column equilibrated with 35 ml 10 mM HEPES pH 8 under sterile conditions. A void volume fraction of 2 ml was collected to which 0.25 ml of 45% glucose was added. For transfection the preparation was further diluted to 20 µg/ml DNA with G5H.

Method 5

As for Method 4 except that 194 µl of the bipolar lipid mixture, 63 µl of test or control conjugate, 377 µl of G5H and 124 µl of the co-lipid solution were pre-mixed then added drop-wise to 242 µl of DNA with vortexing.

The above preparations from Methods 4 and 5 resulted in a bipolar lipid cation: DNA (phosphate) anion charge ratio of 4:1 and 5 antibody binding sites per plasmid. The ratio of total co-lipid to DNA was 16:1 moles per DNA phosphate. All three parameters could be varied by changing the volume of the respective reagent by the desired proportion and by making an equivalent change to the volume of G5H addition by the converse amount. Charge ratios were varied from 0.5:1 to 6:1 and the antibody binding sites per plasmid were varied from 0.5 to 100. Lipid: DNA ratios were varied from 1:1 to 50:1. The molar percentage of the first bipolar lipid relative to the total bipolar lipid was varied from 0% to 100%.

SPECIFIC TRANSFECTION OF JURKAT CELLS USING ANTIBODY TARGETED BIPOLAR LIPID PARTICLES

Aim

Specific transfection efficacy of anti-CD3 targeted bipolar lipid particles prepared in Section 3 above was tested on a human T-cell line that was positive for the CD3 surface marker. Paired transfection experiments where anti-CD3 targeted particles were compared against particles associated with an irrelevant antibody specificity, as provided by the control lipid, would therefore give a direct measure of the benefit of this form of targeting.

Bipolar lipid particles prepared in the absence of co-lipid (Methods 1, 2 and 3) were primarily tested under serum free conditions (Protocol 1), whereas bipolar lipid particles containing co-lipid (Methods 4 and 5) were also tested in the presence of serum (Protocol 2).

Successful transfection was quantified after culturing for 24 h by assay of the expressed reporter gene, β-galactosidase, in cell supernatants following lysis and centrifugation to remove cell debris. Supernatant protein concentrations were also measured in order to normalise β-galactosidase levels to account for any variations in cellular mass.

Preparation of Cells

A human T-cell line, Jurkat E6.1, was obtained from ECACC and cell culture materials from Gibco. Cells were cultured in Dulbecco's Modified Eagles medium (DMEM) containing 10% fetal calf serum (FCS) and supplemented with 2 mM glutamine, 50 units/ml penicillin and 50 µg/ml streptomycin. Cells were harvested for transfection experiments by centrifugation at 1300 rpm for 5 minutes, supernatants were discarded and the pellets washed twice in 50 ml serum free DMEM and re-suspended at 2×106 per ml in serum free DMEM containing supplements.

Protocol 1: Serum Free Transfection

Transfections were carried out in 24 well culture dishes; 200 µl of transfection complexes prepared as above containing 20 µg/ml DNA was transferred into triplicate wells. Jurkat cells in serum free medium were added to the wells in 500 µl aliquots. The culture dish was gently agitated to ensure adequate mixing and incubated for 60 min at 37° C. in 5% CO2. Aliquots of 300 µl of 33% FCS in DMEM with supplements were added to each culture well and incubation conditions maintained for a total of 24 h.

Protocol 2 : Transfection in the Presence of Serum

Transfections were carried out as above except that after addition of the 200 µl of transfection complex, 300 µl of 33% FCS in DMEM with supplements were added to each culture well, before addition of the cells instead of after the addition of the cells.

For both protocols cells were harvested by transferring suspensions to tubes and centrifugation at 1300 rpm for 5 min. Supernatants were aspirated and pellets washed twice with 2 ml cold Dulbeccois phosphate buffered saline. Cells were lysed by the addition of 400 µl of lysis buffer and vigorous agitation on an orbital shaker for 20 min. Cell debris was pelleted by centrifugation of the tubes at 1500 rpm for 20 min. Supernatants were recovered by carefully transferring 400 µl to clean tubes. The concentration of the expressed reporter gene, β-galactosidase in the supernatants was determined using a β-Gal ELISA kit (supplied by Boehringer-Mannheim) and supernatant protein concentration was determined using a BCA protein assay kit (supplied by Pierce and Warriner). If these assays were not carried out immediately, the supernatants were stored at −70° C.

β-Gal ELISA

The following fits components were used:

lysis buffer, sample buffer, wash buffer (×10), anti-β-galactosidase antibody coated 96-well microwell plate, digoxin conjugated anti-β-galactosidase antibody (anti-β-Gal DIG), peroxidase conjugated anti-digoxin antibody (anti-DIG-POD), β-galactosidase standard at 1024 pg/ml.

Lyophilised reagents and wash buffer were reconstituted in de-ionised water as per manufactureris instructions. Lysis buffer was diluted 3 volumes to 10 volumes PBS. The TMB reagent A+B pack (supplied by Pierce and Warriner) was used in place of the kit substrate; equal volumes of reagent A and B were mixed just prior to use. Eight doubling dilutions of the β-galactosidase standard were prepared in lysis buffer. The anti-β-Gal-DIG reagent was diluted: 20 µl per 10 ml sample buffer and the anti-DIG-POD diluted: 40 µl per 10 ml sample buffer.

The microplate was blocked by incubation for 1 h with 300 μl per well of 20% new-born bovine serum, then washed twice with wash buffer and 100 μl sample buffer added per well.

The first ELISA stage involved adding 100 μl of sample or standard per well in triplicate and incubating for 1.5 h at room temperature with orbital agitation at 300 rpm. The wells were washed 4 times with 400 μl wash buffer per well.

The second ELISA stage required 200 μl of diluted anti-β-Gal-DIG per well and incubation for 1 h as above followed by the same wash regimen. The third ELISA stage required 200 μl of diluted anti-DIG-POD per well and incubation for 1 h and wash as above.

The final stage required the addition of 200 μl per well TMB substrate reagent and incubating for 30 min at room temperature, with agitation at 300 rpm. Colour intensity in the wells was measured at 630 nm using a plate reader with a reference wavelength set to 490 nm.

BCA Protein Assay

Standards were prepared from a 2 mg/ml stock of bovine serum albumin by diluting in lysis buffer to give a series at 12.5, 25, 50, 100, 200, 400, 600, 800 and 1000 μg/ml. Triplicate 100 μl aliquots of sample or standard and 200 μl of working BCA reagent per well were added to a blank microwell plate and incubated at 37° C. for 30 minutes. Colour development was measured at 592 nm using a plate reader.

Results of various successful high levels of transfections with targeted particles of the invention are shown in the accompanying FIGS. 1-4. In these experiments targeted controls showed zero or low levels of transfection.

In the Figures the words "bolasome" or "targeted bolasome" are used to describe particles according to the invention.

In the Figures:

FIG. 1

Shows mass of reporter gene, β-galactosidase, in lysed Jurkat cell supernatants, following 24 h in culture after transfection with anti-human CD3 antibody (OKT3) coupled particles of the invention. Levels for control particles coupled with an irrelevant isotype matched antibody (IgG2a) are also shown. Values given are mean and standard deviations of triplicate transfections and have been normalised against supernatant protein mass.

In this experiment the proportion of antibody-lipid has been varied relative to a constant amount of both total bipolar lipid and of DNA; the former being expressed as antibody binding sites per plasmid.

FIG. 2

Shows mass of reporter gene, β-galactosidase, in lysed Jurkat cell supernatants, following 24 h in culture after transfection with anti-human CD3 antibody (OKT3) coupled particles of the invention. Levels for control particles coupled with an irrelevant isotype matched antibody (IgG2a) are also shown. Values given are mean and standard deviations of triplicate transfections and have been normalised against supernatant protein mass.

In this experiment the proportion of 2nd bipolar lipid (containing PEG) has been varied as a percentage of the total amount of bipolar lipid in the system (1st bipolar lipid+2nd bipolar lipid+antibody-lipid). Total bola and DNA remain constant at a charge ratio of 4:1 and antibody-lipid is incorporated at 3 antibody binding sites per plasmid.

Surprisingly a peak of transfection was observed at 33 mol % and 2nd bipolar lipid with much lower levels seen at higher or lower concentrations.

FIG. 3

Shows mass of reporter gene, β-galactosidase, in lysed Jurkat cell supernatants, following 24 h in culture after transfection with anti-human CD3 antibody (OKT3) coupled particles of the invention that have been prepared in the presence of co-lipid. Levels for equivalent particles coupled with an irrelevant isotype matched antibody (IgG2a) are also shown. Values given are mean and standard deviations of triplicate transfections and have been normalised against supernatant protein mass.

In this experiment serum sensitives of the particles have been challenged by pre-incubation with either foetal calf serum or human serum at 20% (v/v) for 15 minutes compared to the absence of serum, prior to transfection. Serum did not have a significant inhibitory effect on the level of transfection.

FIG. 4

Shows mass of reporter gene, β-galactosidase, in cell supernatants of lysed peripheral blood monomorphonuclear cells (PBMCs), following 24 h in culture after transfection with anti-human CD3 antibody (OKT3) particles of the invention that have been prepared in the presence of co-lipid. Levels for equivalent particles coupled with an irrelevant isotype matched antibody (IgG2a) are also shown. Values given are mean and standard deviations of triplicate transfections and have been normalised against supernatant protein mass.

In this experiment PBMCs from two different human donors have been compared with similar levels of transfection observed in each donor. In either case specificity of targeting has been demonstrated by the zero or low level of transfection seen for the control particles.

Figure 5:
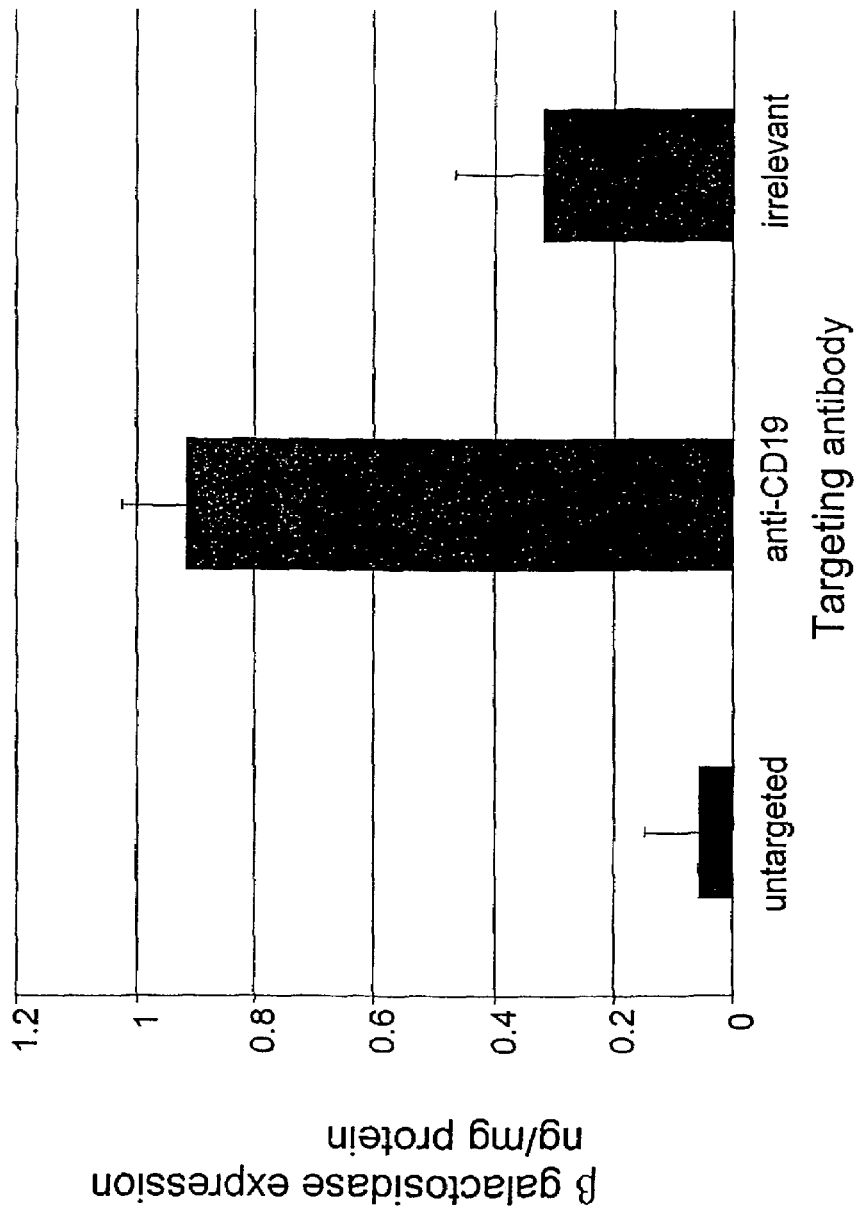
Figure 6:
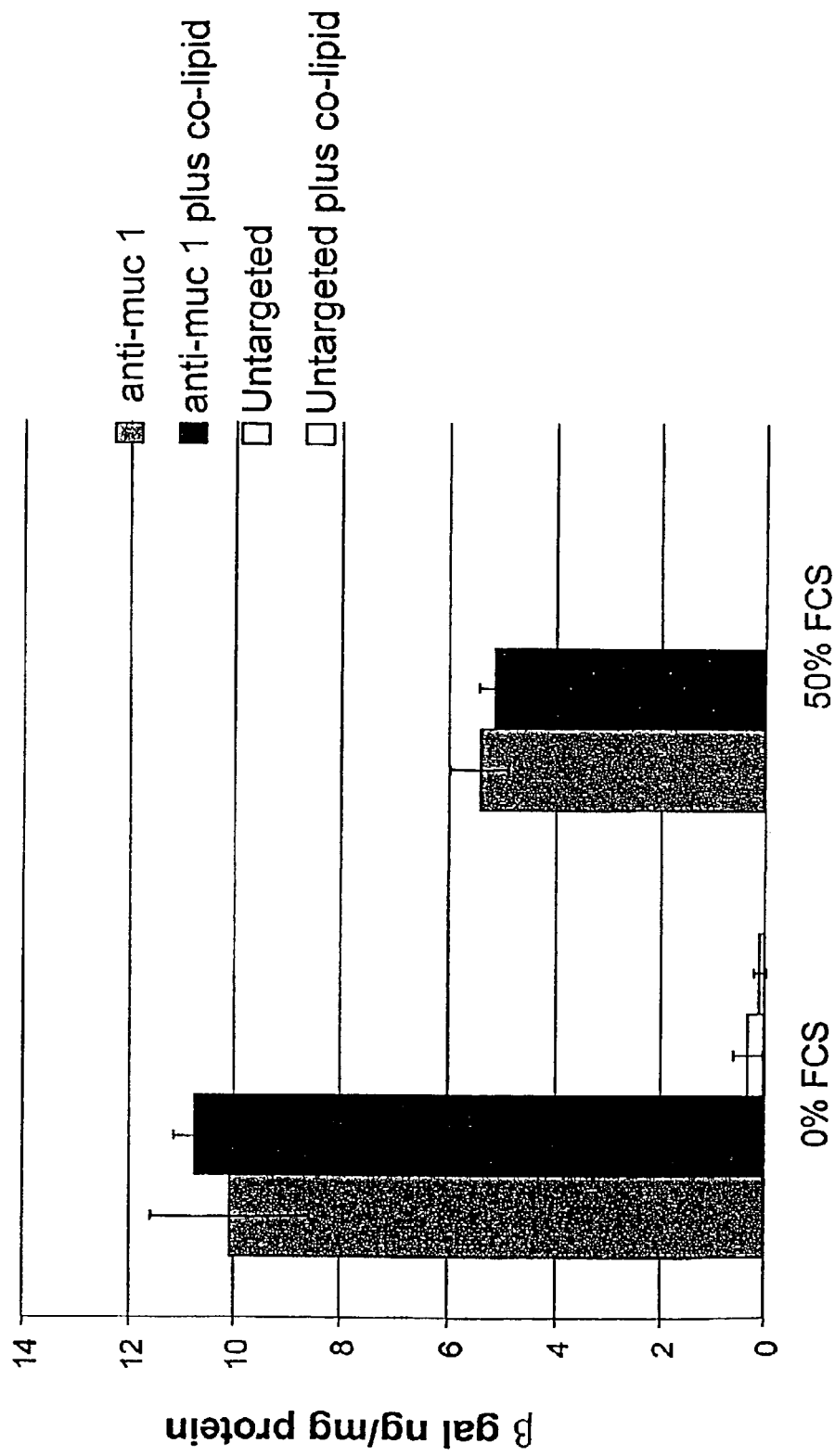
Figure 7:
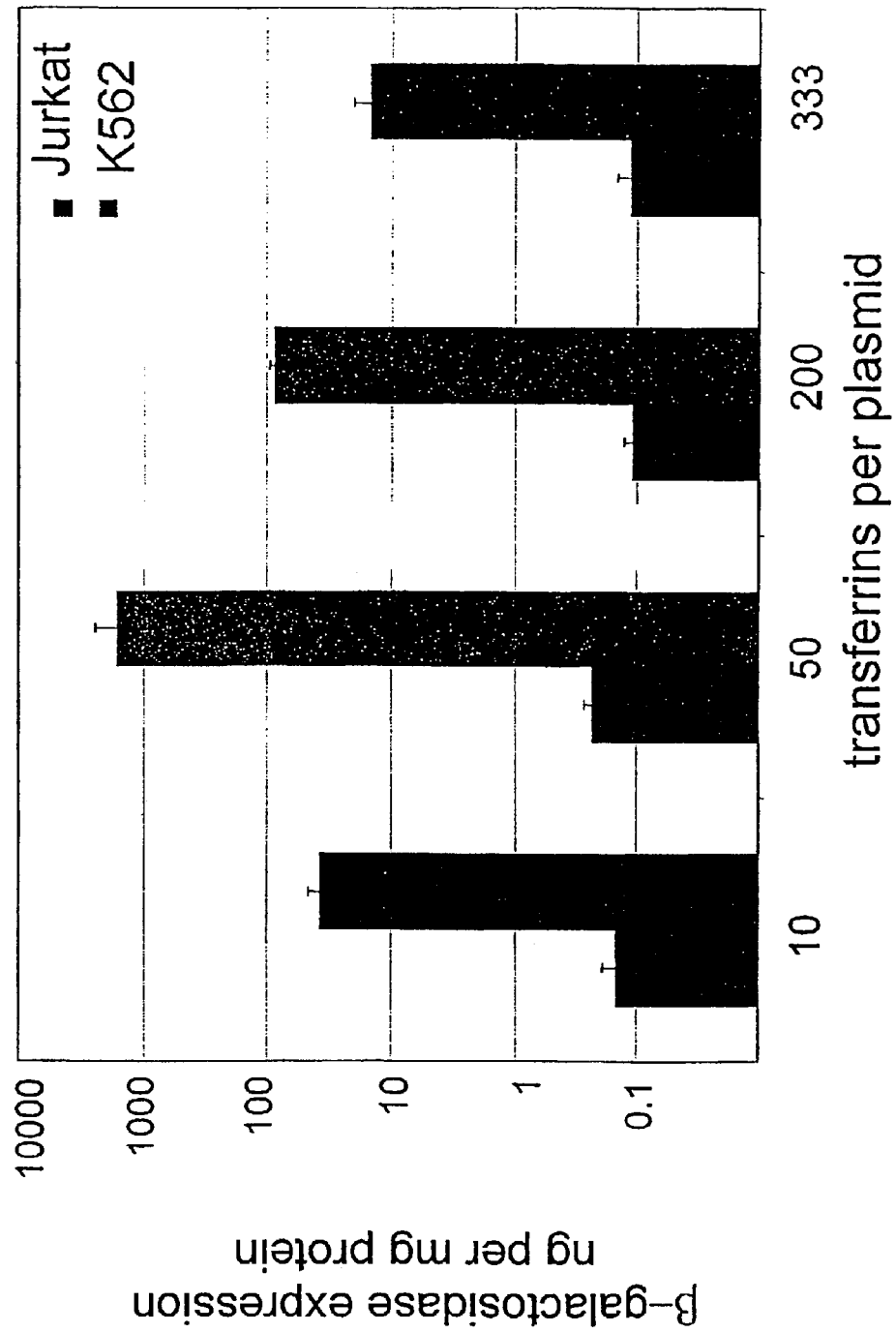

Similar experiments were performed using targeted particles of the invention in which the anti-CD3 targeting molecule was replaced by an anti-CD19 or anti-muc1 antibody or transferrin. The particles were prepared using the appropriate antibody or transferrin and Intermediate 19 with other bipolar lipids and co-lipids as described in Sections 3 and 4 above. Transfection of cell lines and quantification of transfection were carried out as described above and the results are shown in the accompanying FIGS. 5-7:

In the Figures:

FIG. 5

Shows mass of reporter gene, β-galactosidase, in lysed JY B-cells, following 24 h in culture after transfection with anti-CD19 antibody coupled particles of the invention.

The figure clearly shows a high level of transfection with the anti-CD19 particle of the invention when compared to untargeted or irrelevant controls.

FIG. 6

Shows mass of reporter gene, β-galactosidase, in lysed MCF-7 cell supernatants, following 24 h in culture after transfection with anti-muc1 antibody particles of the invention prepared in the absence or presence of co-lipid.

In this experiment serum sensitivities of the particles have been challenged by pre-incubation with 50% foetal calf serum. Transfection levels were high when compared to untargeted particules, even in the presence of serum.

FIG. 7

Shows mass of reporter gene, in lysed K562 or Jurkat cells, following 24 h in culture after transfection with transferrin coupled particles of the invention.

In each experiment tansfection was obtained with the transferrin targeted particle.

The invention claimed is:

1. A lipid represented by formula (2a):

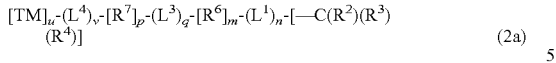
$$[TM]_u\text{-}(L^4)_v\text{-}[R^7]_p\text{-}(L^3)_q\text{-}[R^6]_m\text{-}(L^1)_n\text{-}[\text{—}C(R^2)(R^3)(R^4)] \quad (2a)$$

wherein:
TM is an antibody or an antigen binding fragment or derivative thereof,
u is an integer 1 or 2,
$L^4$ is -(Alk$^1$)$_r$(X$^1$)$_s$(Alk$^2$)$_t$-,
wherein X$^1$ is an —O— atom; a —S— atom; —C(O)—; —C(O)O—; —C(S)—; —S(O); —S(O)$_2$—; —N(R$^5$)—; —CON(R$^5$)—; —OC(O)N(R$^5$)—; —CSN (R$^5$)—; —N(R$^5$)CO—; N(R$^5$)C(O)O—; —N(R$^5$)CS—; —S(O)N(R$^5$)—; —S(O)$_2$N(R$^5$)—; —N(R$^5$)S(O)—; —N(R$^5$)S(O)$_2$; —N(R$^5$)CON(R$^5$)—; or —N(R$^5$)SO$_2$N (R$^5$)—,
wherein R$^5$ is a hydrogen atom, a straight or branched alkyl group or an -Alk$^1$X$^1$-chain;
wherein in any of the groups containing two R$^5$ substituents each R$^5$ may be the same or different;
wherein Alk$^1$ and Alk$^2$, which may be the same or different, is each an optionally substituted straight or branched C$_{1-10}$alkylene, C$_{2-10}$alkenylene or C$_{2-10}$alkynylene chain optionally interrupted or terminated by at least one carbocyclic or heterocarbocyclic groups and/or heteroatoms or heteroatom containing groups X$^1$; and
r, s, and t, which may be the same or different, is each zero or the integer 1, provided that when one of r, s or t is zero at least one of the remainder is the integer 1,
v is zero or the integer 1,
L$^1$ is —X$^1$Alk$^2$- or —[X$^1$]$_2$Alk$^1$X$^1$Alk$^2$-,
wherein X$^1$ is an —O— atom; a —S—atom; —C(O)—; —C(O)O—, —C(S)—; —S(O); —S(O)$_2$—; —N(R$^5$)—; —CON(R$^5$)—; —OC(O)N(R$^5$)—; —CSN (R$^5$)—; —N(R$^5$)CO—; N(R$^5$)C(O)O—; —N(R$^5$)CS—; —S(O)N(R$^5$)—; —S(O)$_2$N(R$^5$)—; —N(R$^5$)S(O)—; —N(R$^5$)S(O)$_2$—; —N(R$^5$)CON(R$^5$)—; or —N(R$^5$)SO$_2$N(R$^5$)—;
wherein R$^5$ is a hydrogen atom, a straight or branched alkyl group or an -Alk$^1$X$^1$— chain,
wherein in any of the groups containing two R$^5$ substituents each R$^5$ may be the same or different;
wherein Alk$^1$ and Alk$^2$, which may be the same or different, is each an optionally substituted straight or branched C$_{1-6}$alkylene, C$_{2-6}$alkenylene or C$_{2-6}$alkynylene chain optionally interrupted or terminated by at least one carbocyclic or heterocarbocyclic groups and/or heteroatoms or heteroatom containing groups X$^1$,
m is an integer of from 1 to 6,
n is zero or the integer 1;
R$^7$ is a hydrophilic hydrocarbon containing at least two atoms or groups capable of being solvated by water;
p is an integer of from 1 to 6;
L$^3$ is —X$^1$—, —X$^1$Alk$^1$X$^1$— or [X$^1$Alk$^1$]$_1$X$^1$Alk$^2$X$^1$,
wherein X$^1$ is an —O— atom; a —S— atom; —C(O)—; —C(O)O—; —C(S)—; —S(O); —S(O)$_2$—; —N(R$^5$)—; —CON(R$^5$)—; —OC(O)N(R$^5$)—; —CSN (R$^5$)—; —N(R$^5$)CO—; N(R$^5$)C(O)O—; —N(R$^5$)CS—; —S(O)N(R$^5$)—; —S(O)$_2$N(R$^5$)—; —N(R$^5$)S(O)—; —N(R$^5$)S(O)$_2$; —N(R$^5$)CON(R$^5$)—; or —N(R$^5$)SO$_2$N (R$^5$)— group;
wherein R$^5$ is a hydrogen atom, a straight or branched alkyl group or an -Alk$^1$X$^1$— chain;
wherein in any of the groups containing two R$^5$ substituents each R$^5$ may be the same or different;
wherein Alk$^1$ and Alk$^2$, which may be the same or different, is each an optionally substituted straight or branched C$_{1-6}$alkylene, C$_{2-6}$alkenylene or C$_{2-6}$alkynylene chain optionally interrupted or terminated by at least one carbocyclic or heterocarbocyclic groups and/or heteroatoms or heteroatom containing groups X$^1$;
q is zero or an integer of from 1 to 6;
R$^6$ is a hydrocarbon chain;
R$^2$ is a hydrogen atom or an optionally substituted aliphatic, cycloaliphatic, heteroaliphatic, heterocycloaliphatic, aromatic or heteroaromatic group optionally containing one or more cationic centers; and
R$^3$ and R$^4$, which may be the same or different, is each an optionally substituted aliphatic, cycloaliphatic, heteroaliphatic, heterocycloaliphatic, aromatic or heteroaromatic group containing one or more cationic centers or R$^3$ and R$^4$ together with the carbon atom to which they are attached form a cycloaliphatic, heterocycloaliphatic, aromatic or heteroaromatic group containing two or more cationic centers.

2. The lipid according to claim 1, wherein u is the integer 1.

3. The lipid according to claim 1, wherein:
v is the integer 1.

4. The lipid according to claim 1, wherein v is the integer 1 and L$^4$ is an —NHCO(Alk$^2$)$_t$- group in which Alk$^2$ is a straight or branched C$_{1-10}$ alkylene chain and t is zero or the integer 1.

5. The lipid according to claim 1, wherein R$^2$ is a hydrogen atom; and R$^3$ and R$^4$ are each Sp$^1$[WSp$^2$]$_b$WSp$^3$ or -Sp$^1$[WSp$^2$]$_b$WH, wherein Sp$^1$, Sp$^2$ and Sp$^3$, which may be the same or different, is each a spacer group, W is a cationic center and b is zero or an integer from 1 to 6.

6. The lipid according to claim 5, wherein Sp$^1$, Sp$^2$ and Sp$^3$ is each an optionally substituted aliphatic, cycloaliphatic, heteroaliphatic, heterocycloaliphatic, aromatic or heteroaromatic group.

7. The lipid according to claim 6, wherein Sp$^1$, Sp$^2$ and Sp$^3$ is each an optionally substituted C$_{1-6}$alkylene chain.

8. The lipid according to claim 5, wherein W is a —NH— group.

9. The lipid according to claim 5, wherein b is an integer of from 1 to 3.

10. The lipid according to claim 1, wherein —C(R$^2$)(R$^3$)(R$^4$) is —CH[Sp$^1$NHSp$^2$NH$_2$]$_2$, —CH[Sp$^1$NHSp$^2$NHSp$^2$NH$_2$]$_2$ or —CH[SP$^1$NHSp$^2$NHSp$^2$NHCH$_3$]$_2$, wherein Sp$^1$ is —CH$_2$— and each Sp$^2$ is —(CH$_2$)$_3$- or —(CH$_2$)$_4$—.

11. The lipid according to claim 1, wherein n in -(L$^2$)$_n$- is the integer 1.

12. The lipid according to claim 11, wherein X$^1$ is a —CONH— group, Alk$^1$ is a —CH$_2$—CH$_2$ chain and Alk$^2$ is a —(CH$_2$)$_4$— chain, —(CH$_2$)$_5$— chain or —(CH$_2$)$_6$— chain.

13. The lipid according to claim 1, wherein m is an integer 1 or 2.

14. The lipid according to claim 1, wherein R$^6$ is an optionally substituted C$_{10-60}$aliphatic chain.

15. The lipid according to claim 14, wherein R$^6$ is a linear, optionally substituted C$_{16-38}$alkylene chain.

16. The lipid according to claim 1, wherein q is the integer 1 and p is the integer 1 or 2.

17. The lipid according to claim 1, wherein L$^3$ is a —NHCO—, —CONH—, —CONH(CH$_2$)$_2$NHCO—, or —[CONH(CH$_2$)$_2$—]$_2$NCO(CH$_2$)$_2$CONH group.

18. The lipid according to claim 1, wherein R$^7$ is a synthetic or naturally occurring polyol or a poly(alkylene oxide) or a derivative thereof.

19. The lipid according to claim 18, wherein $R^7$ is a poly(alkylene oxide) or a derivative thereof.

20. The lipid according to claim 19, wherein $R^7$ is a poly(ethylene oxide).

21. The lipid according to claim 3, wherein $R^5$ is a methyl or ethyl group.

22. The lipid according to claim 11, wherein $R^5$ is a methyl or ethyl group.

23. The lipid according to claim 1, wherein $R^5$ is a methyl or ethyl group.

* * * * *